United States Patent
Dietrich et al.

(10) Patent No.: US 8,524,691 B2
(45) Date of Patent: Sep. 3, 2013

(54) PHOSPHONATED RIFAMYCINS AND USES THEREOF FOR THE PREVENTION AND TREATMENT OF BONE AND JOINT INFECTIONS

(75) Inventors: Evelyne Dietrich, St. Laurent (CA); Ranga Reddy, St. Laurent (CA); Kelly Tanaka, St. Laurent (CA); Ting Kang, St. Laurent (CA); Yanick LaFontaine, St. Laurent (CA); Adel Rafai Far, St. Laurent (CA)

(73) Assignee: The Medicines Company, Parsippany, NJ (US)

( * ) Notice: Subject to any disclaimer, the term of this patent is extended or adjusted under 35 U.S.C. 154(b) by 214 days.

(21) Appl. No.: 13/058,518

(22) PCT Filed: Aug. 10, 2009

(86) PCT No.: PCT/US2009/053295
§ 371 (c)(1),
(2), (4) Date: Apr. 7, 2011

(87) PCT Pub. No.: WO2010/019511
PCT Pub. Date: Feb. 18, 2010

(65) Prior Publication Data
US 2011/0178001 A1 Jul. 21, 2011

Related U.S. Application Data

(60) Provisional application No. 61/088,626, filed on Aug. 13, 2008.

(51) Int. Cl.
*A01N 57/00* (2006.01)
*A61K 31/66* (2006.01)
*C07D 225/04* (2006.01)

(52) U.S. Cl.
USPC ............... 514/102; 514/80; 514/81; 540/453; 540/457; 540/458

(58) Field of Classification Search
None
See application file for complete search history.

(56) References Cited

U.S. PATENT DOCUMENTS

| 5,854,227 | A | 12/1998 | Hartmann et al. |
| 7,300,924 | B2 | 11/2007 | Boojamra et al. |
| 2003/0045746 | A1 | 3/2003 | Jomaa |

FOREIGN PATENT DOCUMENTS

| WO | 2007-096703 | 8/2007 |

OTHER PUBLICATIONS

Lehoux, D., Bisphosphonated Rifamycin Prodrugs for the Treatment of Osteomyelitis, Cambridge Healthtech Institute's Second Annual—The Challenge of Antibacterial Drug Development: Edited by Zhongping Huang et al. AMRI Technical Report, published in Apr. 23-24, 2008.
International Search Report for PCT/US2009/053295, dated Apr. 21, 2010.
Reddy, R. et al., Bisphosphonated Benzoxazinorifamycin Prodrugs for the Prevention and Treatment of Osteomyelitis, ChemMedChem, 2008, vol. 3, No. 12, pp. 1863-1868.
Extended European Search Report dated May 15, 2012, from the European Patent Office in corresponding European Application No. 09807130.1.

*Primary Examiner* — Jeffrey S. Lundgren
*Assistant Examiner* — Michael Schmitt
(74) *Attorney, Agent, or Firm* — Roylance, Abrams, Berdo & Goodman, L.L.P.

(57) ABSTRACT

The present invention relates to phosphonated Rifamycins, and methods of making and using such compounds. These compounds are useful as antibiotics for prophylaxis and/or the treatment of bone and joint infections, especially for the prophylaxis and/or treatment of osteomyelitis.

19 Claims, No Drawings

PHOSPHONATED RIFAMYCINS AND USES THEREOF FOR THE PREVENTION AND TREATMENT OF BONE AND JOINT INFECTIONS

BACKGROUND OF THE INVENTION

Osteomyelitis is an inflammation of bone caused by a variety of microorganisms, mainly *Staphylococcus aureus* (Carek et al., American Family Physician (2001), Vol 12, 12:2413-2420). This painful and debilitating disease occurs more commonly in children. Within the adult population, diabetics and kidney dialysis patients are also vulnerable. The acute form of the disease is treatable with antibiotics, but requires a lengthy period of daily therapy. It can, however, revert to a recurrent or chronic form requiring repeated hospital stays and heavy treatment regimens.

The Rifamycins are a class of semisynthetic antibacterial ansamycins, several members of which are currently used clinically or are under clinical evaluation (Burman et al, Clin. Pharmacokinet. (2001), 40:327-341). Rifamycins target the bacterial DNA-dependent RNA polymerase with 2-4 orders of magnitude greater affinity than for the equivalent eukaryotic enzymes (Floss and Yu, Chem Rev. (2005), 105:621-632). Rifamycins act by binding a well defined site on the β subunit of the RNA polymerase holoenzyme, and as a result, interfere with and inhibit the initial phase of RNA synthesis. The common structural scaffold of these inhibitors presents a well defined position which allows for the modulation of their pharmacokinetic and pharmacodynamic properties without substantially altering their mode of binding. This has resulted in a number of well investigated compounds within the class, including Rifampicin (U.S. Pat. No. 3,342,810), Rifapentin (U.S. Pat. No. 4,002,752), Rifandin (U.S. Pat. No. 4,353,826), Rifabutin (U.S. Pat. No. 4,219,478), Rifalazil (U.S. Pat. No. 4,983,602) and Rifaximin (U.S. Pat. No. 4,341,785). Recently, a number of 25-deacetyl analogs have also been demonstrated to be attractive antibacterials (US patent application 2005/043298). Rifamycins are extremely potent against Gram positive pathogens, less so against the Gram negative ones, and display side effects generally only at high dose or in the presence of Cytochrome P3A inhibitors. Their unique ability to affect bacteria in a quiescent state, which may stem from their need for short bursts of RNA synthesis even in the absence of growth, makes them prime candidates for chronic infections, often in combination so as to avoid a relatively high frequency of resistance. In this respect, Rifampicin, generally in combination with other antibacterials, has resulted in attractive outcomes in the treatment of bone and joint infections (Darley and McGowan, J. Antimicrob. Chemother. (2004) 53, 928-935; Widmer et al, Clin. Infect. Dis. (1992) 14, 1251-1253)

Bisphosphonates are well-characterized bone-seeking agents. These compounds are recognized for having a high affinity to the bones due to their ability to bind the $Ca^{2+}$ ions found in the hydroxyapatite forming the bone tissues (Hirabayashi and Fujisaki, Clin. Pharmacokinet. (2003) 42(15): 1319-1330). Therefore, many different types of bisphosphonate-conjugated compounds have been made for targeting drugs selectively to the bone, including proteins (Uludag et al., Biotechnol Prog. (2000) 16:1115-1118), vitamins (U.S. Pat. No. 6,214,812, US 2003/0129194 and WO 02/083150), tyrosine kinase inhibitors (WO 01/44258 and WO 01/44259), hormones (U.S. Pat. No. 5,183,815 and US 2004/0116673) and bone scanning agents (U.S. Pat. No. 4,810,486). These and other bisphosphonate derivatives have been used as therapeutic agents for bone diseases such as arthritis (U.S. Pat. No. 4,746,654), osteoporosis (U.S. Pat. No. 5,428,181 and U.S. Pat. No. 6,420,384), hypercalcemia (U.S. Pat. No. 4,973,576), and bone cancers (U.S. Pat. No. 6,548,042). Despite the progress which has been made in the past years, bone-specific delivery is still limited by the unique anatomical features of the bones.

In view of the above, there is a need for better administrable drugs for the prevention and treatment of bone and joint infections. More particularly, there is a need for highly active phosphonated derivatives of Rifamycins capable of achieving both time-controlled (or sustained) and spatially controlled (or targeted) drug delivery to the bones.

The present invention fulfills these needs and also other needs as will be apparent to those skilled in the art upon reading the following specification.

SUMMARY OF THE INVENTION

The present invention is directed to antimicrobial compounds which have an affinity for binding bone. More particularly, the invention is directed to phosphonated Rifamycins. These compounds are useful as antibiotics for the prophylaxis and/or treatment of bone and joint infections, especially for the prophylaxis and/or treatment of osteomyelitis.

In a first embodiment, the present invention is directed to compounds represented by Formula (I), and to pharmaceutically acceptable salts, metabolites, solvates and prodrugs thereof:

wherein:

A is a Rifamycin or a Rifamycin derived antibiotic molecule;

L is a cleavable linker for coupling A to B;

B is a phosphonated group; and n is 1, 2, 3, 4, 5, 6 or 7.

In preferred aspects of the first embodiment, each -L-B is independently described by Formula (Ia)

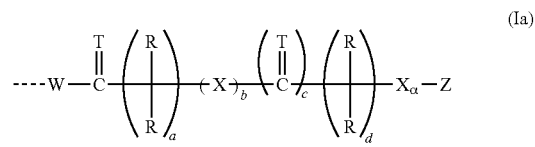

wherein:

each T is independently oxygen or sulfur;

each R is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, substituted aryloxy, and $-R^a-Y-R^b-Y-R^b-B$;

W is a covalent bond or is selected from the group of
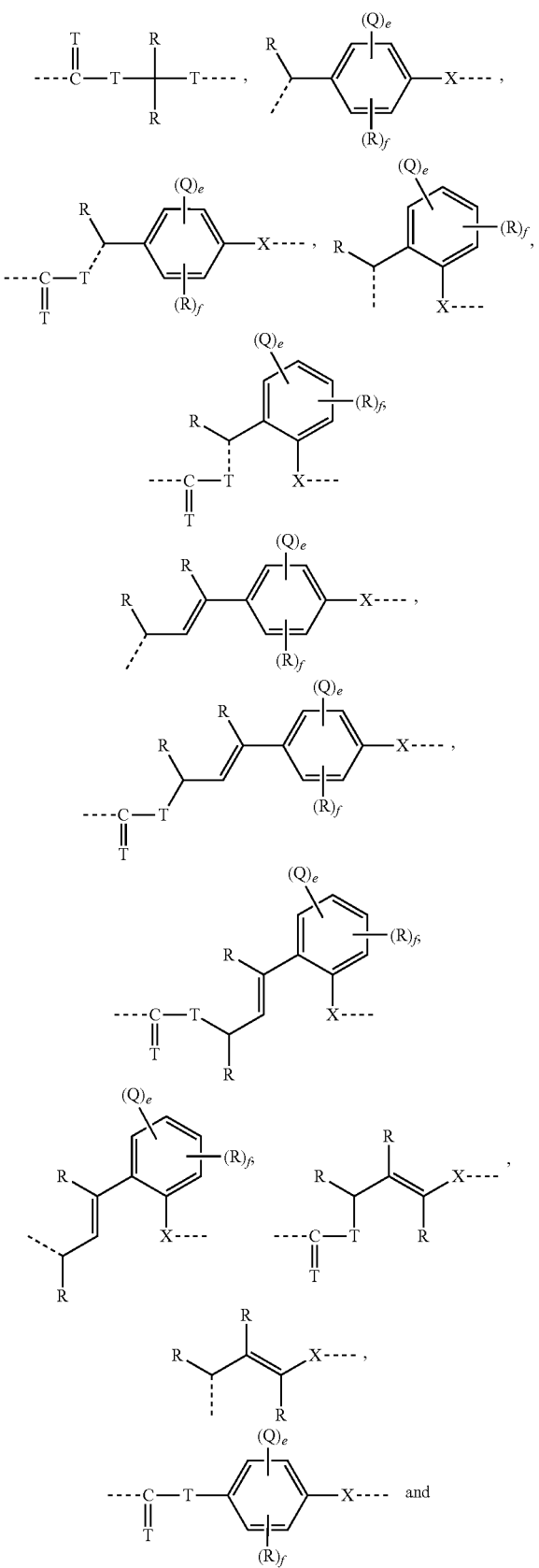
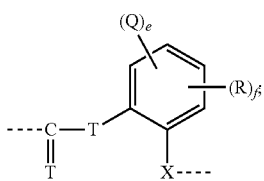
each X is independently —O—, —S— or —N(R)—;
each Q is independently nitro, chloro, bromo, iodo or fluoro;
Z is selected from the group consisting of hydrogen, acyl, substituted acyl, aroyl, substituted aroyl, alkoxycarbonyl, substituted alkoxycarbonyl, aryloxycarbonyl, substituted aryloxycarbonyl,
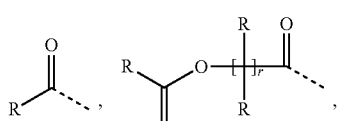
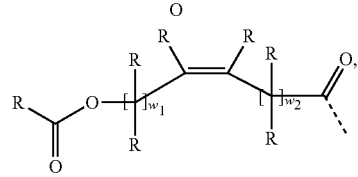
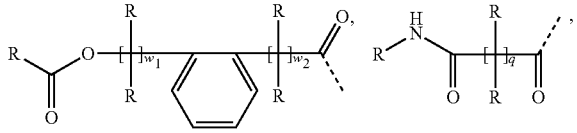
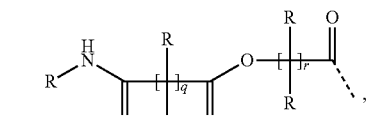
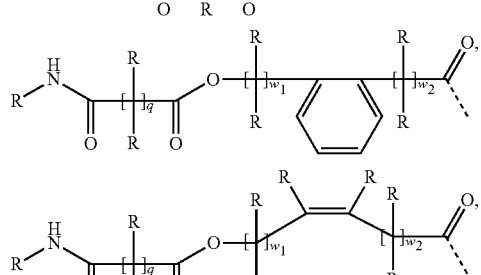
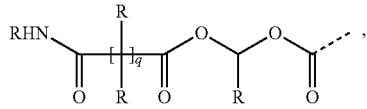
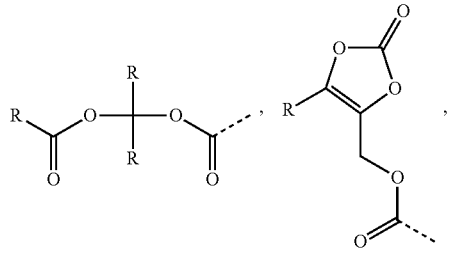

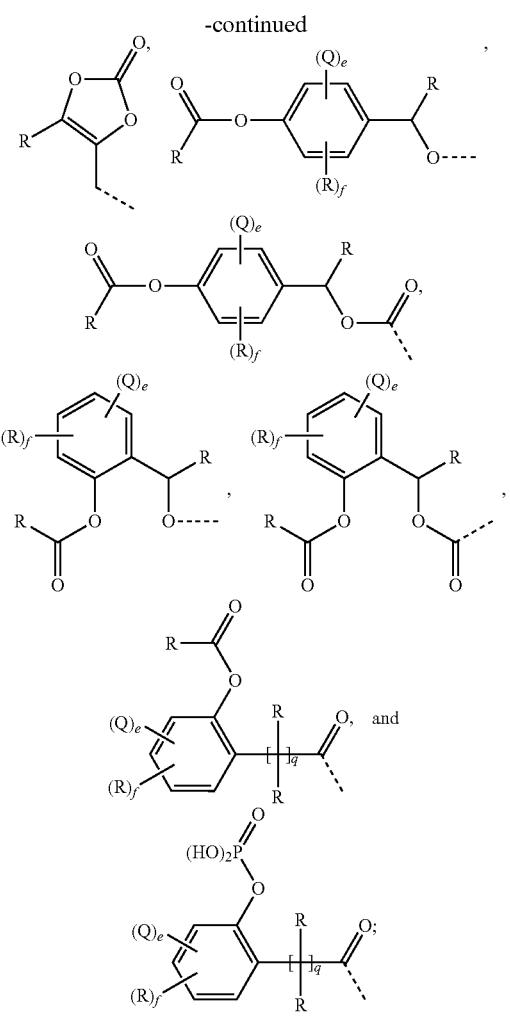

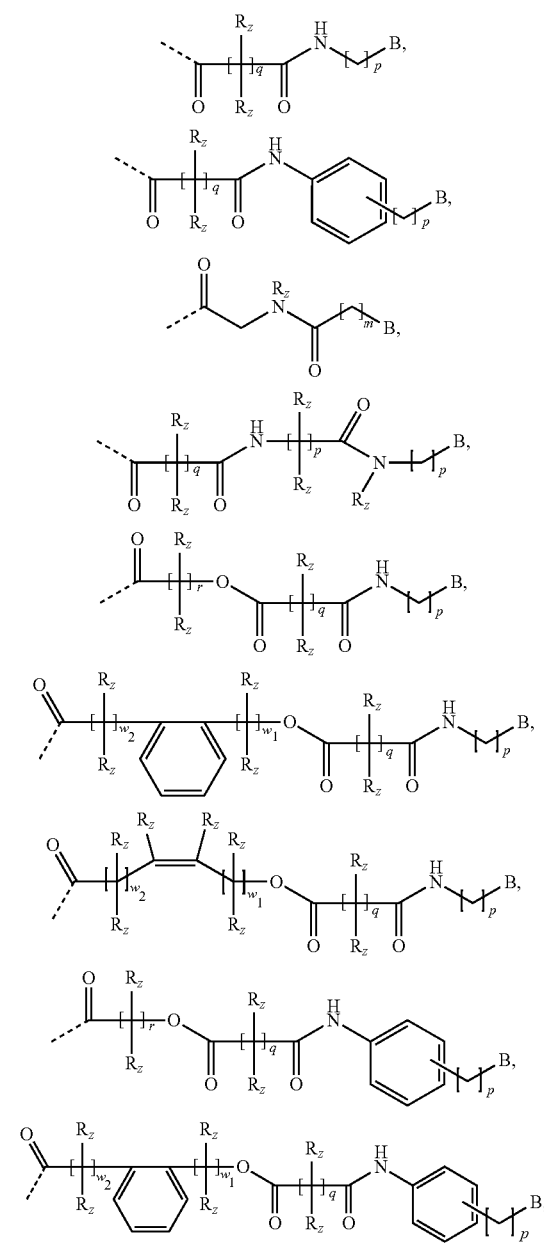

alkynyl, substituted alkynyl, cycloalkyl, substituted cycloalkyl, cycloalkenyl, substituted cycloalkenyl, aryl, heteroaryl and heterocyclic;

q is 2 or 3;

r is 1, 2, 3, 4 or 5;

$w_1$ and $w_2$ are each integers $\geq 0$ such that their sum ($w_1+w_2$) is 1, 2 or 3;

a, b, c, d are each integers $\geq 0$ such that a+b+c+d 57;

e and f are each integers $\geq 0$ such that e+f=4; and $\alpha$ is 0 or 1;

with the proviso that at least one R in Formula (Ia) is —$R^a$—Y—$R^b$—Y—$R^b$—B; and with the further proviso that -L-B is not any of the following structures:

each $R^a$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each $R^b$ is independently selected from the group consisting of a covalent bond, alkylene, substituted alkylene, alkenylene, substituted alkenylene, alkynylene, substituted alkynylene, arylene and substituted arylene;

each Y is independently selected from the group consisting of a covalent bond, —$CH_2$—, —O—, —S—, —S—S—, —$NR^c$—, —S(O)—, —$SO_2$—, —$NR^cC(O)$—, —$OSO_2$—, —OC(O)—, —$N(R^c)SO_2$—, —$C(O)NR^c$—, —C(O)O—, —$SO_2NR^c$—, —$SO_2O$—, —$P(O)(OR^c)O$—, —$P(O)(OR^c)NR^c$—, —$OP(O)(OR^c)O$—, —$OP(O)(OR^c)NR^c$—, —OC(O)O—, —$NR^cC(O)O$—, —$NR^cC(O)NR^c$—, —$OC(O)NR^c$—, —C(O)—, and —$N(R^c)SO_2NR^c$—;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$C(O)R^d$;

each $R^d$ is independently selected from the group consisting of alkyl, substituted alkyl, alkenyl, substituted alkenyl,

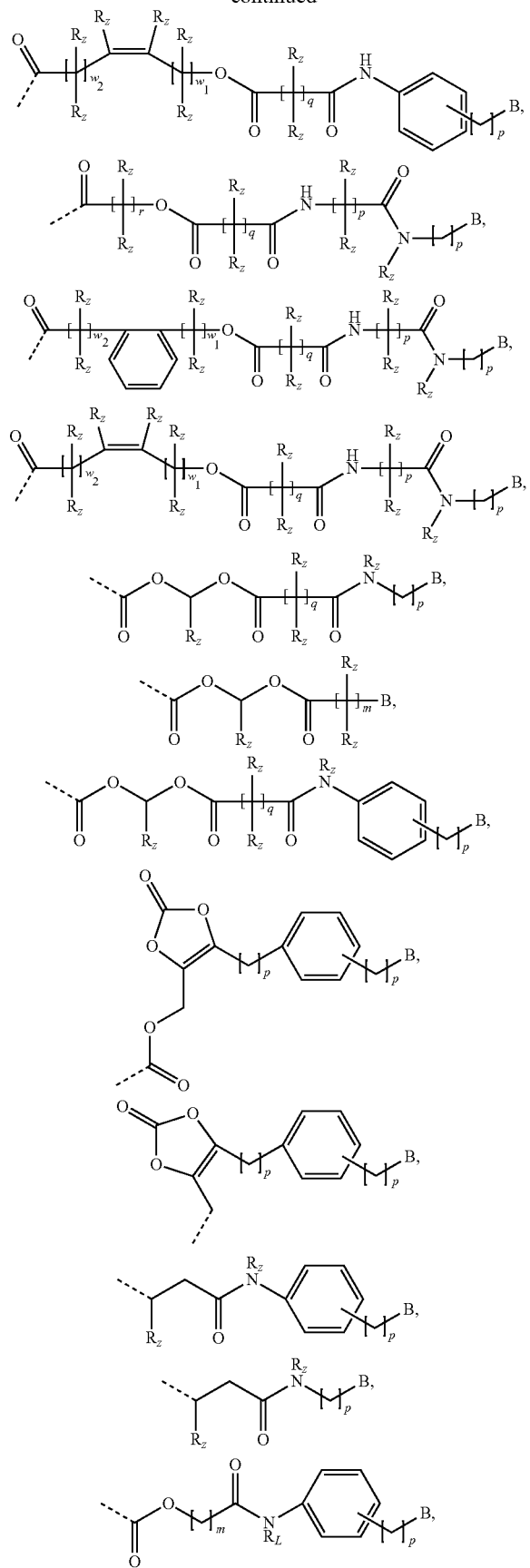

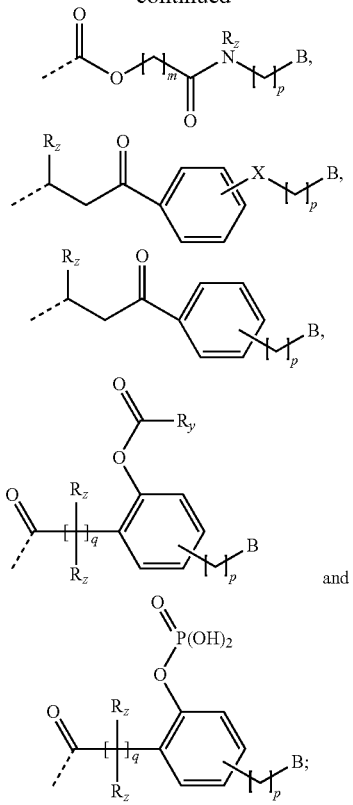

wherein:
X, B, r, q, $w_1$ and $w_2$ are defined as above;
each p is independently 0 or an integer $\leq 10$;
each $R_Z$ is independently H, ethyl or methyl;
each $R_L$ is independently H, ethyl or methyl;
$R_Y$ is represented by $C_iH_j$, where i is an integer $\leq 20$ and j is an integer $\leq 2i+1$; and
m is an integer $\leq 10$.

Preferably, n is an integer of 1 to 3 in the first embodiment.
Preferably, B is a bisphosphonate in the first embodiment. More preferably, B is a bisphosphonate selected from the group consisting of:

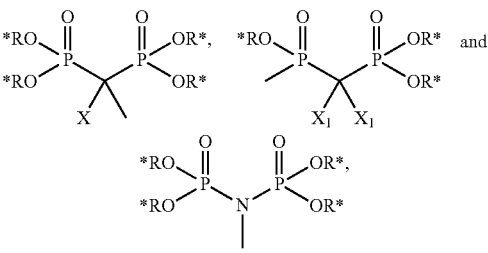

wherein:
each R* is independently selected from the group consisting of H, lower alkyl, cycloalkyl, aryl and heteroaryl, with the proviso that at least two R* are H;
X is H, OH, $NH_2$, or a halo group; and
$X_1$ are both H, or each is independently selected from the group consisting of H, OH, $NH_2$, and a halo group.

Preferably, L is a cleavable linker for covalently and reversibly coupling B to A in the first embodiment. More preferably, L couples B to A through one or more hydroxyl groups on A, through one or more nitrogen atoms on A, or through one or more hydroxyl groups and one or more nitrogen atoms on A.

In a first aspect of the first embodiment, each B-L- is independently selected from the group consisting of:

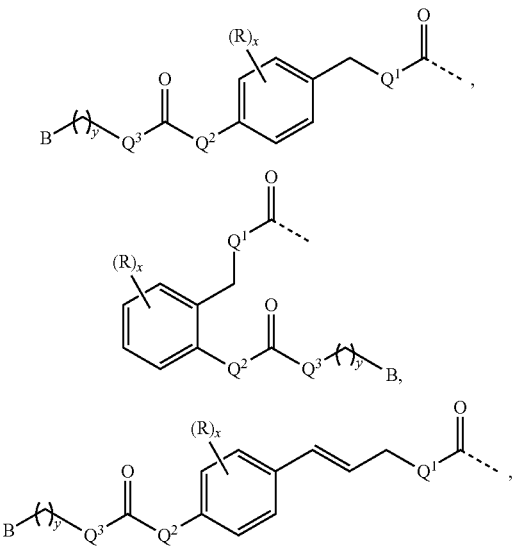

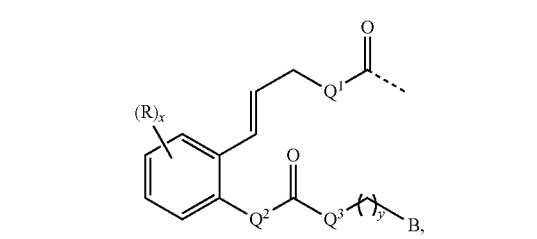

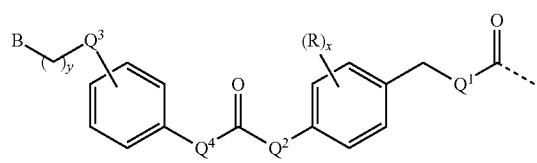

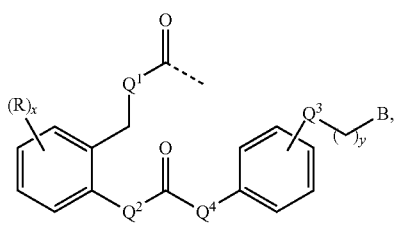

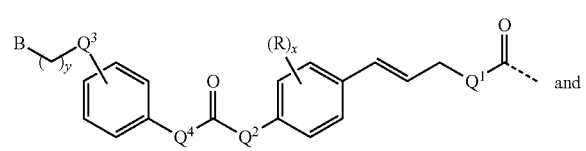

and

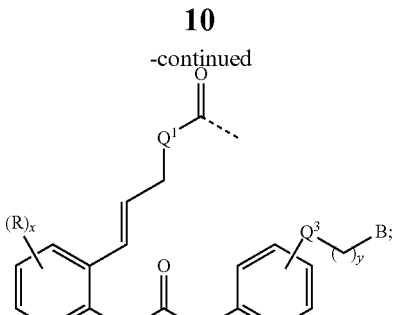

wherein,
B is a phosphonated group;
$Q^1$ is —O— or —S—;
$Q^2$ is —O—, —S— or —N($R_L$)—;
$Q^3$ is —O—, —S—, —N($R_L$)— or —CH$_2$—;
$Q^4$ is —O—, —S—, —N($R_L$)—, —CH$_2$— or a covalent bond;
each R is independently selected from the group consisting of chloro, bromo, fluoro, iodo, nitro, trifluoromethyl and $C_mH_l$, where m is an integer such that $0 \leq m \leq 6$ and l is an integer $\leq 2m+1$;
each $R_L$ is $C_mH_l$, where m is an integer such that $0 \leq m \leq 6$ and l is an integer $\leq 2m+1$;
x is 1, 2, 3 or 4; and
y is an integer $\leq 10$.

In a second aspect of the first embodiment, each B-L- is independently represented by the following Formula (BL$_1$):

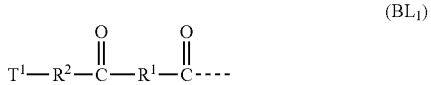
(BL$_1$)

wherein each

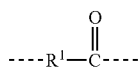

and

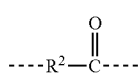

is independently selected from the group consisting of:

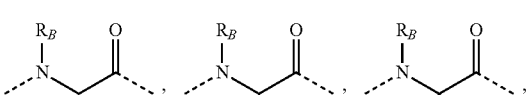

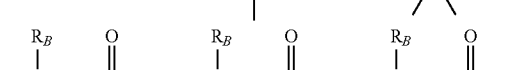

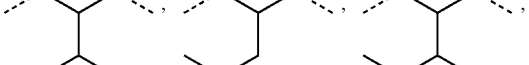

-continued
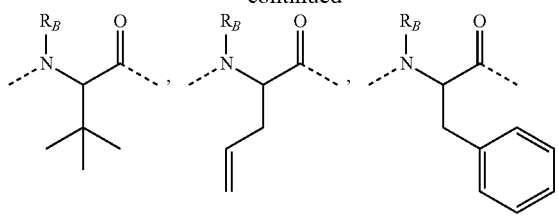
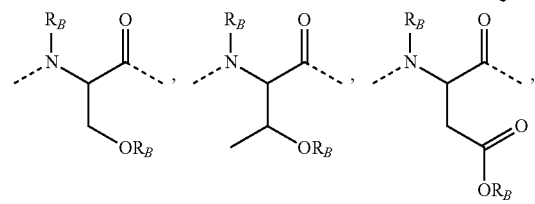
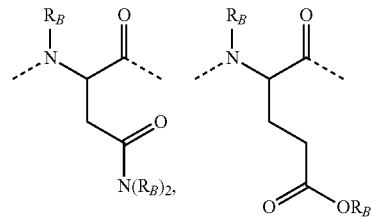
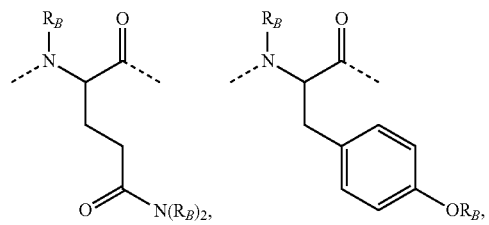
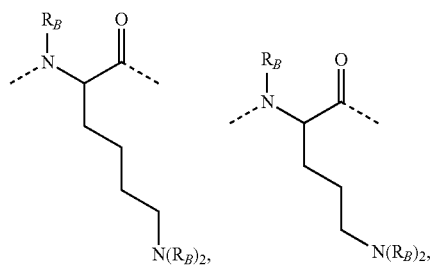
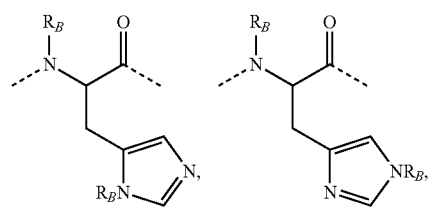
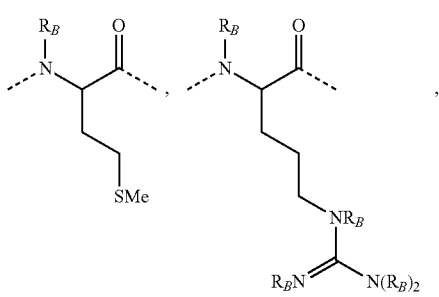
-continued
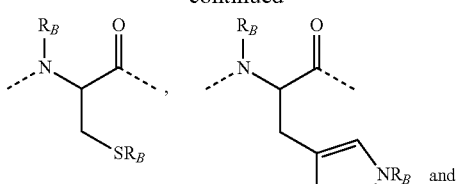
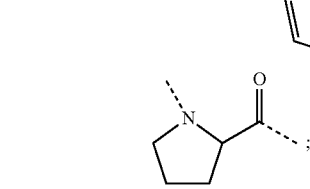
$T^1$ is selected from the group consisting of:
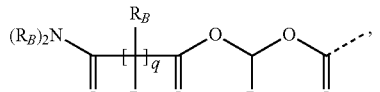
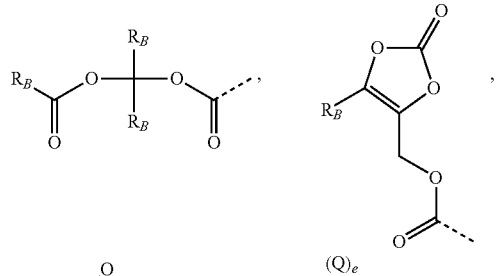
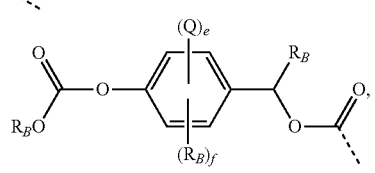
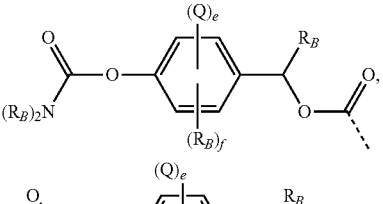
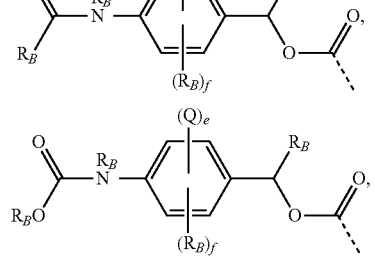

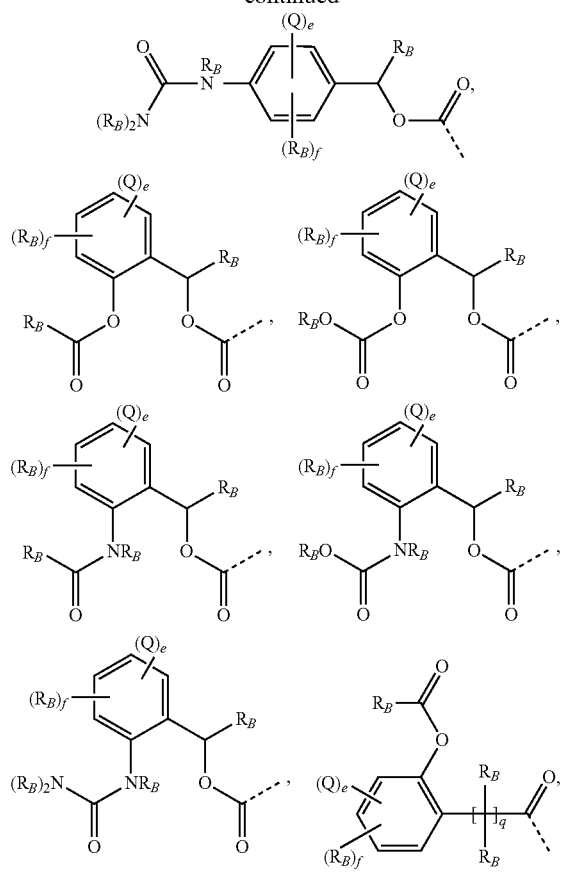

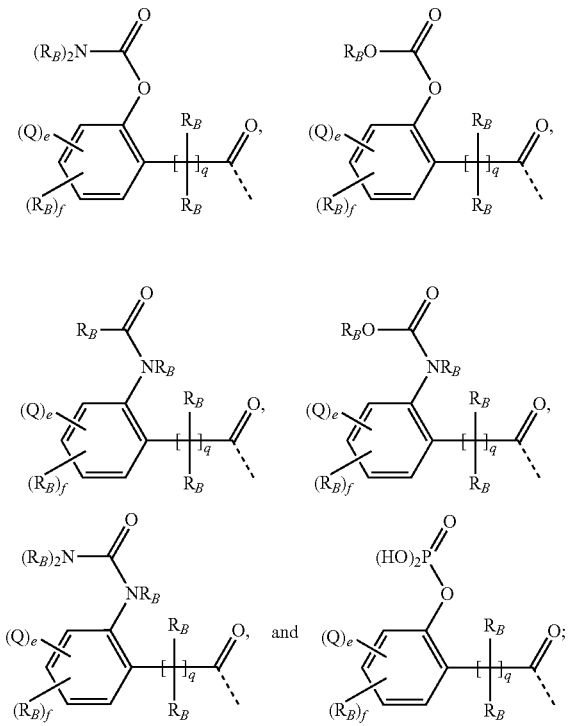

each $R_B$ is independently selected from the group consisting of hydrogen,

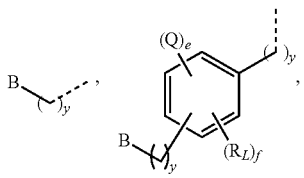

and $C_mH_l$, where m is an integer such that $0 \leq m \leq 6$ and l is an integer $\leq 2m+1$;

B is a phosphonated group;

each Q is independently nitro, chloro, bromo, iodo or fluoro;

each $R_L$ is $C_mH_l$, where m is an integer such that $0 \leq m \leq 6$ and l is an integer $\leq 2m+1$;

q is 2 or 3;

y is an integer $\leq 10$; and e and f are integers $\geq 0$ such that e+f=4.

In a third aspect of the first embodiment, each B-L- is independently represented by the following Formula (BL$_2$):

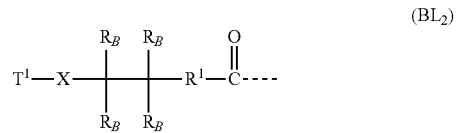

wherein

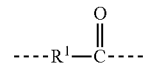

is selected from the group consisting of:

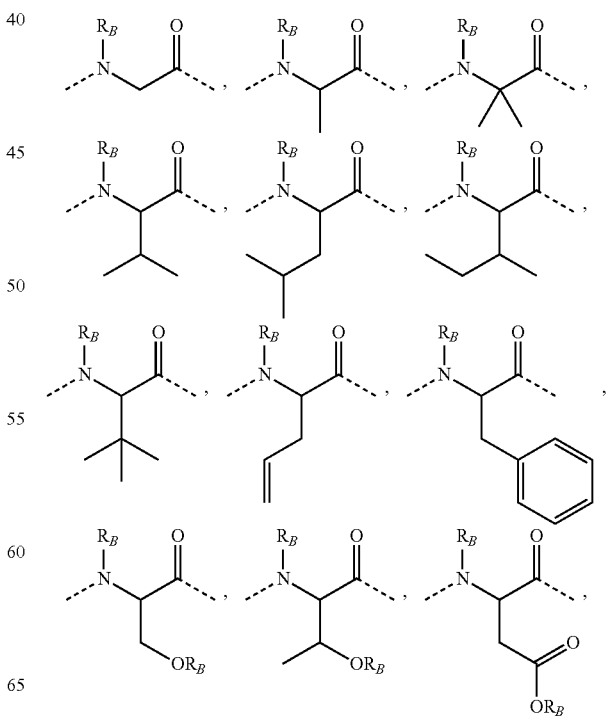

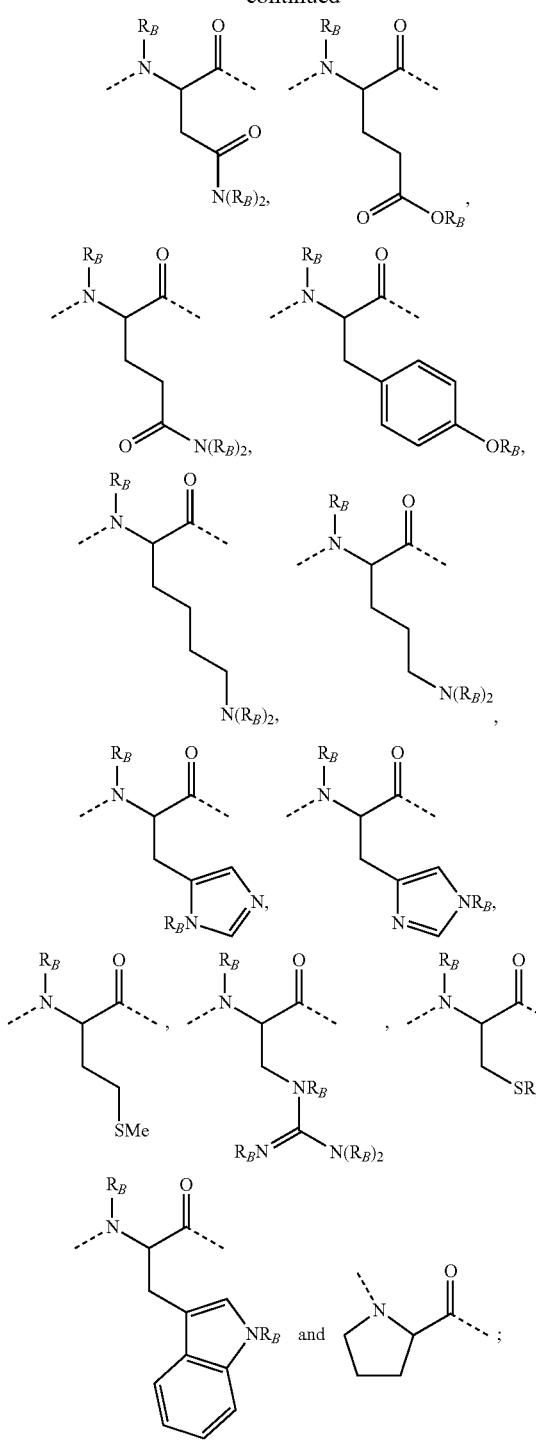
T₁ is selected from the group consisting of:
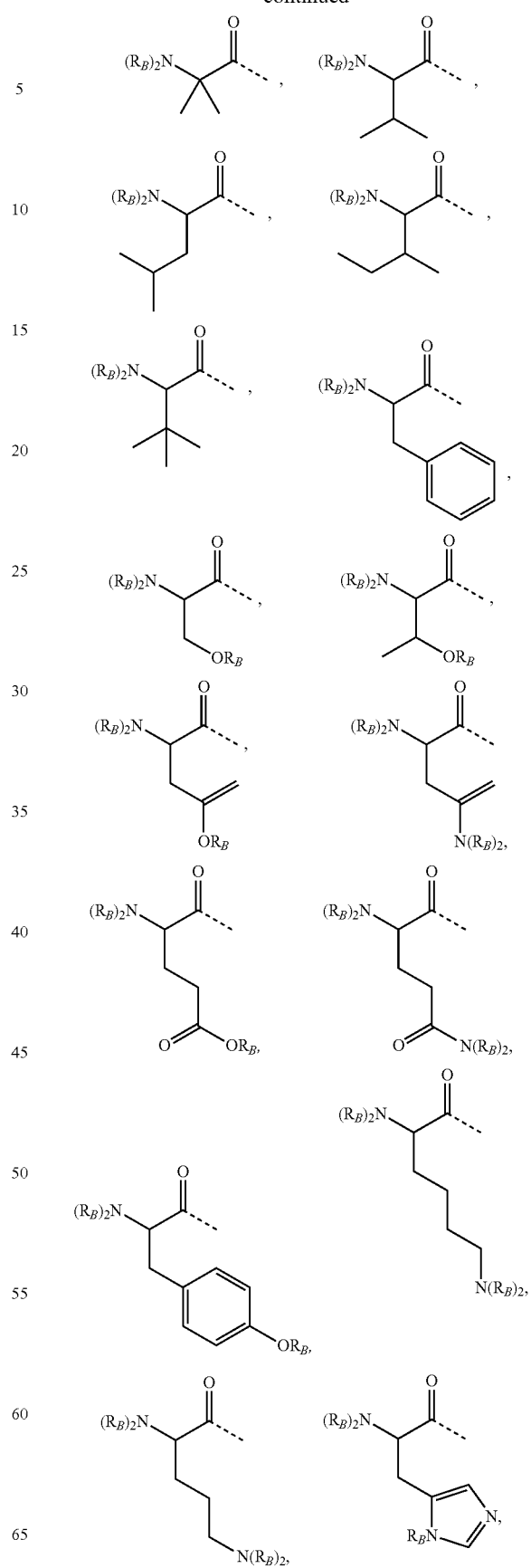

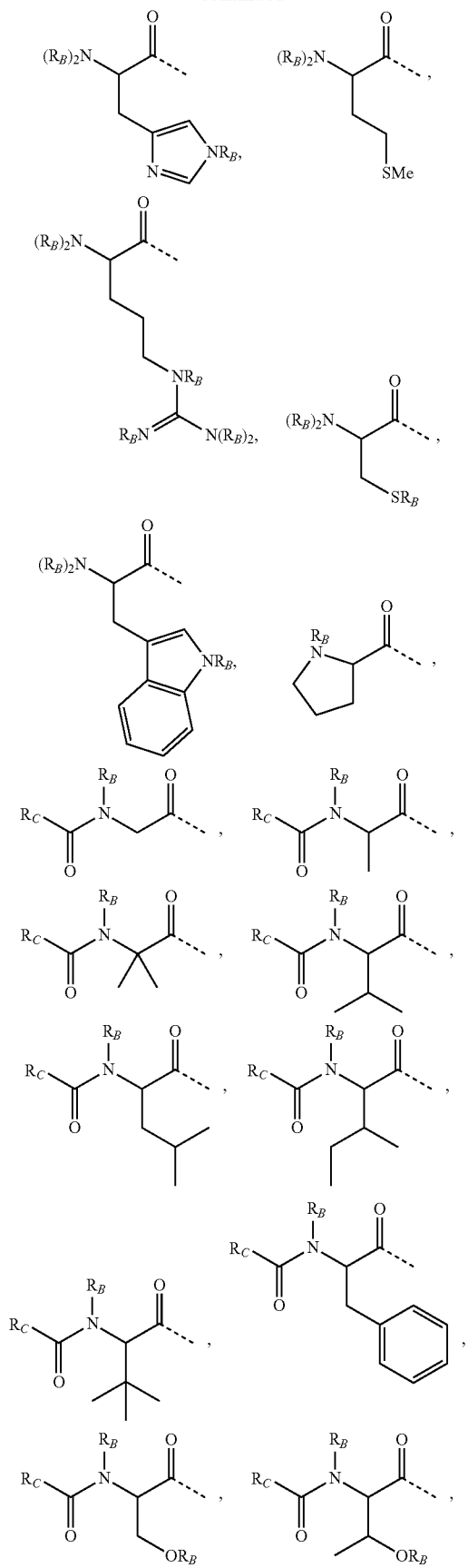
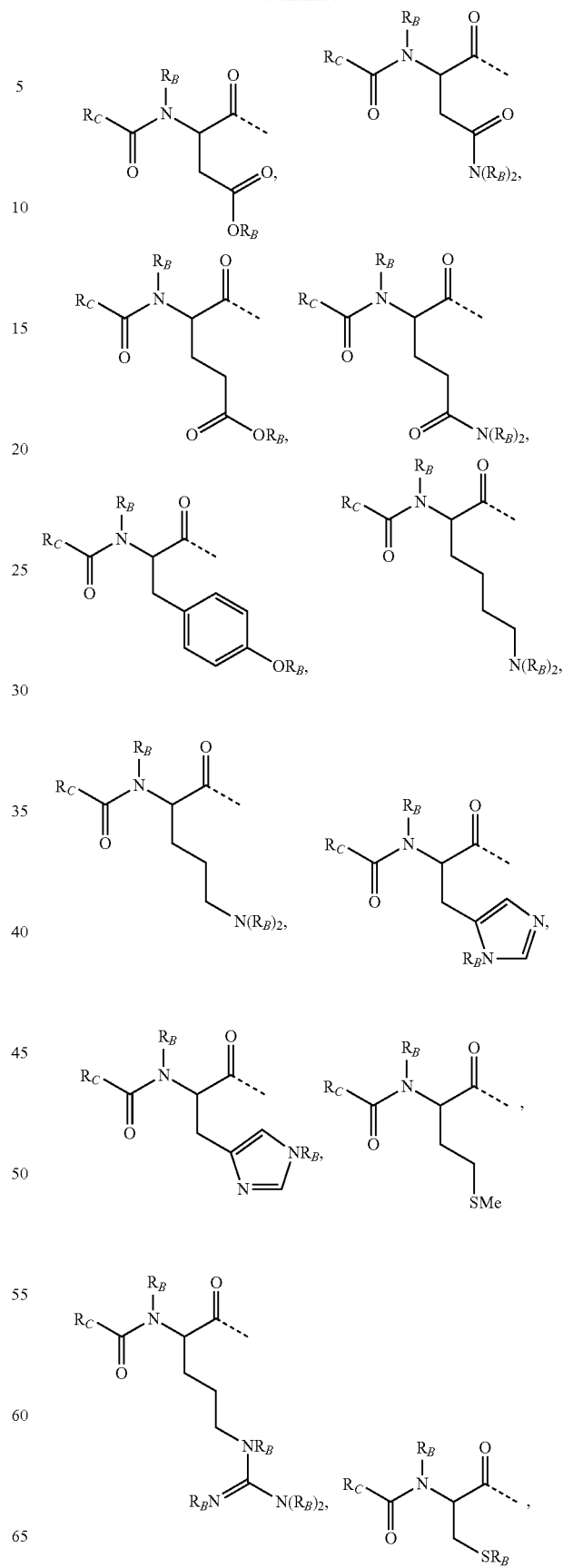

-continued

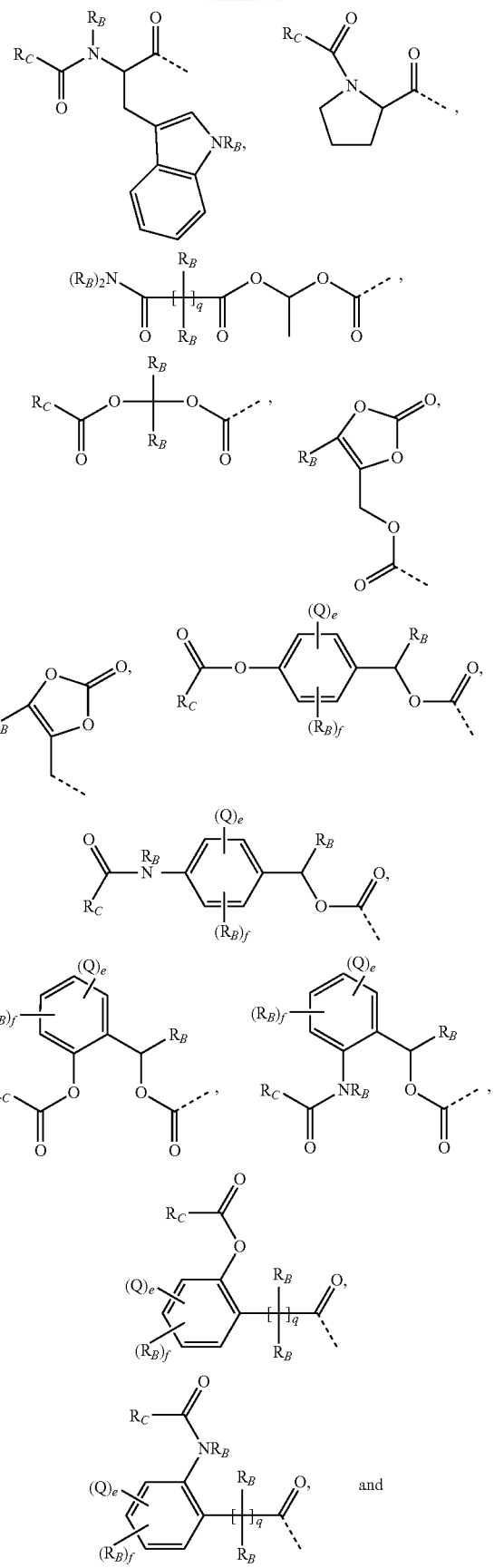

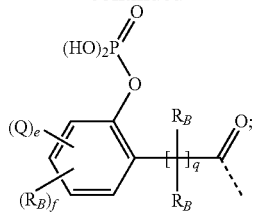

$R_C$ is $R_B$, $OR_B$ or $N(R_B)_2$;
X is —O—, —S— or —N($R_B$)—;
each $R_B$ is independently selected from the group consisting of hydrogen,

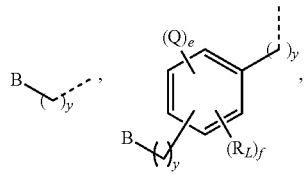

and $C_mH_l$, where m is an integer such that $0 \leq m \leq 6$ and l is an integer $\leq 2m+1$;
B is a phosphonated group;
each Q is independently nitro, chloro, bromo, iodo or fluoro;
each $R_L$ is $C_mH_l$, where m is an integer such that $0 \leq m \leq 6$ and l is an integer $\leq 2m+1$;
q is 2 or 3;
y is an integer $\leq 10$; and
e and f are integers $\geq 0$ such that e+f=4.

In a fourth aspect of the first embodiment, each B-L- is independently represented by the following Formula ($BL_3$):

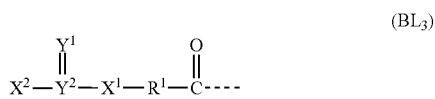

(BL$_3$)

wherein

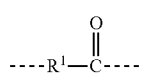

is independently selected from the group consisting of:

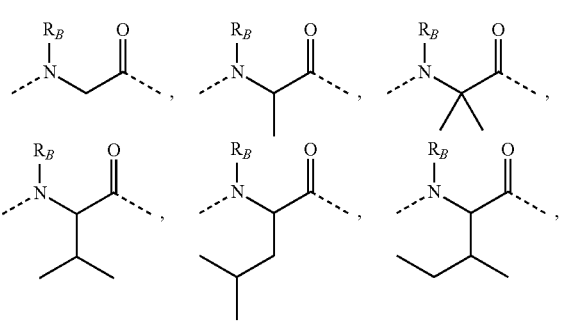

21
-continued
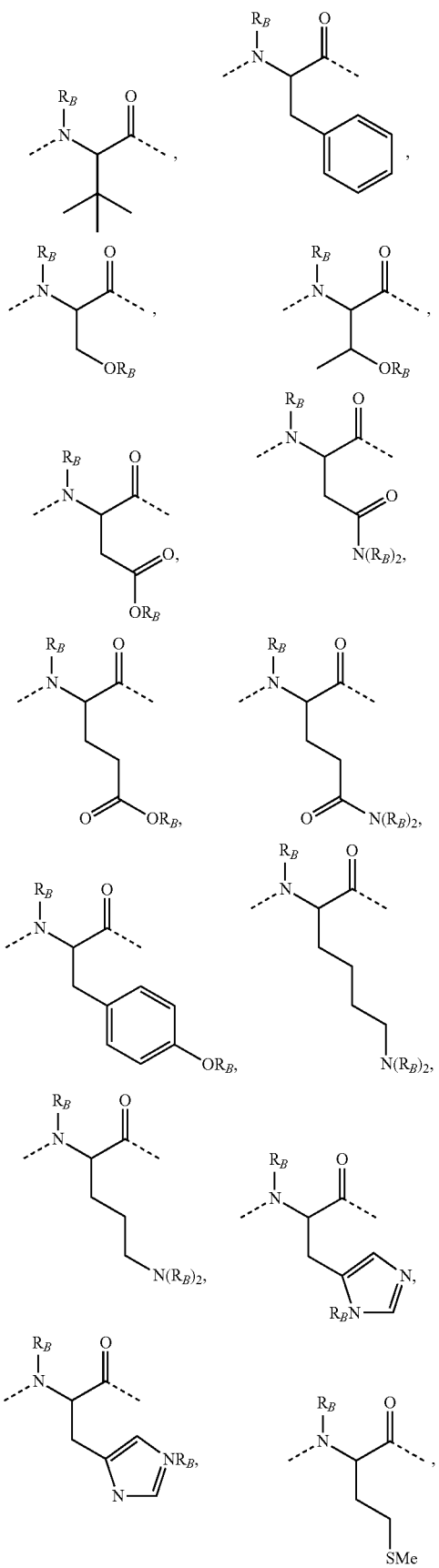
22
-continued
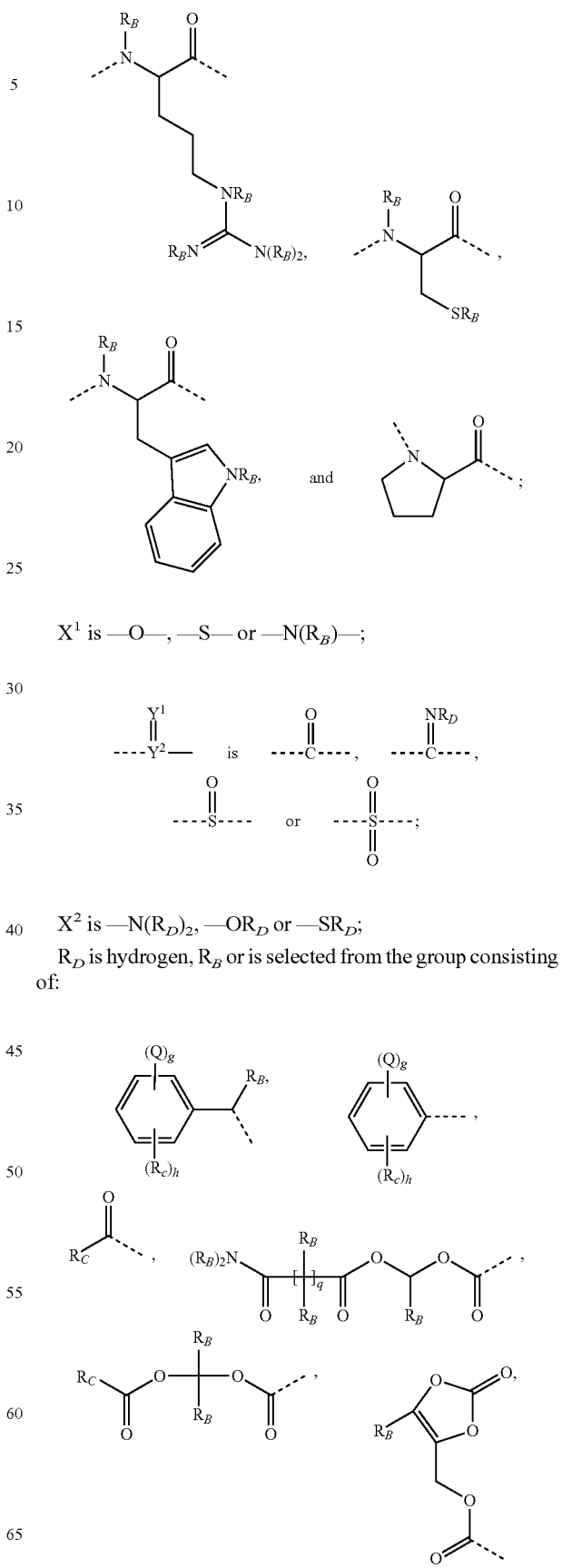
$X^1$ is —O—, —S— or —N($R_B$)—;
$\overset{Y^1}{\underset{Y^2}{\text{---}}}$ is $\overset{O}{\underset{}{\text{---C---}}}$, $\overset{NR_D}{\underset{}{\text{---C---}}}$, $\overset{O}{\underset{}{\text{---S---}}}$ or $\overset{O}{\underset{O}{\text{---S---}}}$;
$X^2$ is —N($R_D$)$_2$, —O$R_D$ or —S$R_D$;
$R_D$ is hydrogen, $R_B$ or is selected from the group consisting of:

-continued

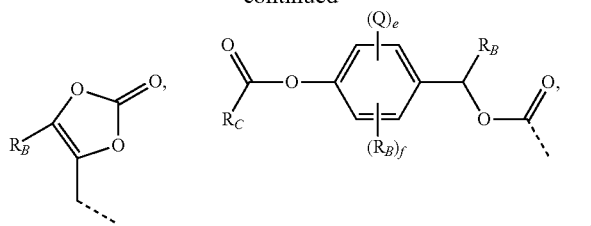

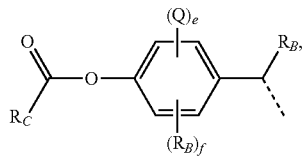

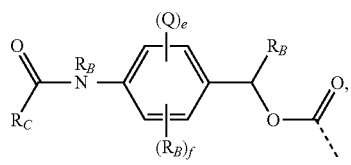

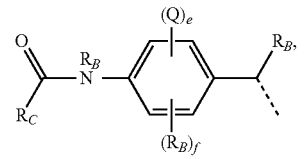

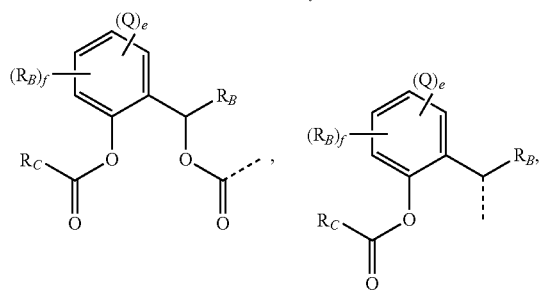

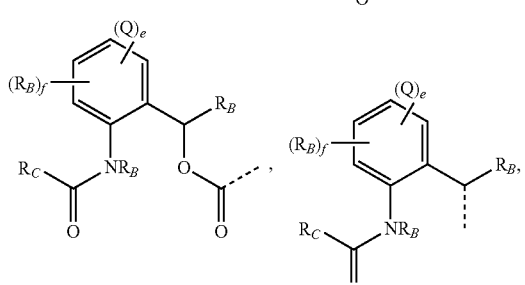

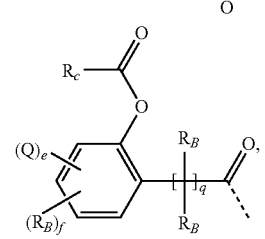

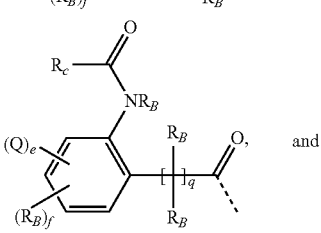

-continued

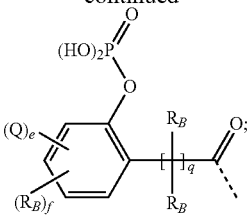

$R_C$ is $R_B$, $OR_B$ or $N(R_B)_2$;
each $R_B$ is independently selected from the group consisting of hydrogen,

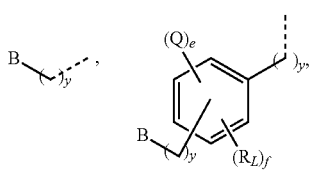

and $C_mH_l$, where m is an integer such that $0 \leq m \leq 6$ and l is an integer $\leq 2m+1$;

B is a phosphonated group;
each Q is independently $-SR_c$, $-S(O)R_c$, $-S(O)_2R_c$, $-COR_c$, nitro, chloro, bromo, iodo or fluoro;
each $R_L$ is $C_mH_l$, where m is an integer such that $0 \leq m \leq 6$ and l is an integer $\leq 2m+1$;
q is 2 or 3;
y is an integer $\leq 10$;
e and f are integers $\geq 0$ such that e+f=4; and
g and h are integers $\geq 0$ such that g+h=5.

In a fifth aspect of the first embodiment, each B-L- is independently represented by Formula ($BL_4$) or Formula ($BL_5$):

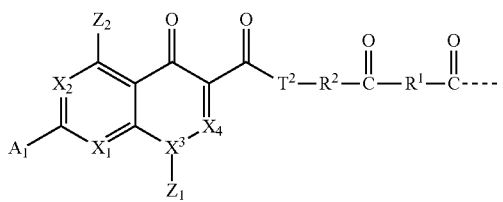

(BL4)

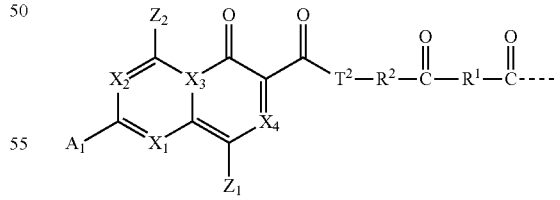

(BL5)

wherein
each

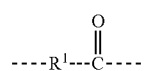

and
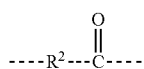
is independently selected from the group consisting of:
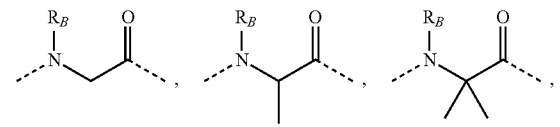
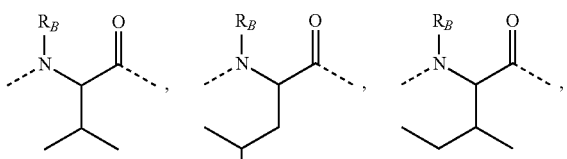
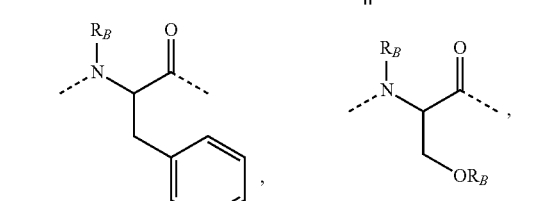
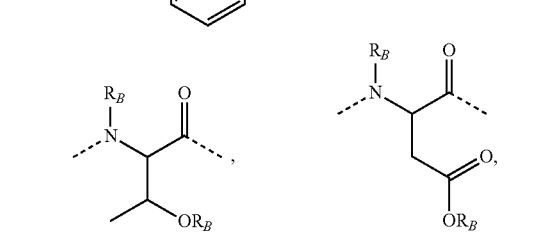
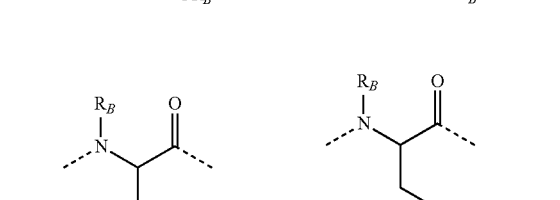
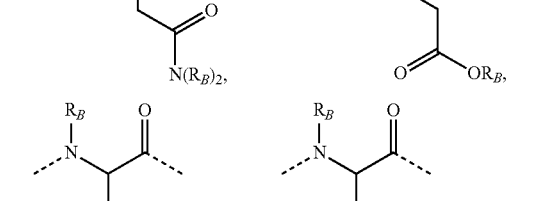
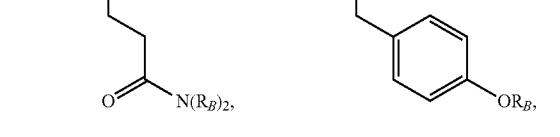
-continued
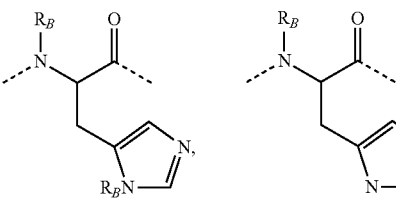
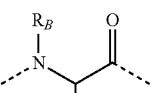
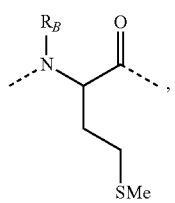
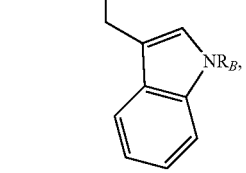
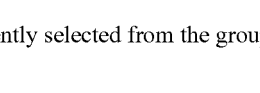
and
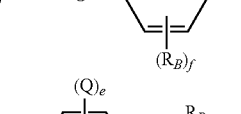
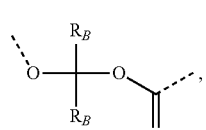
each T² is independently selected from the group consisting of:
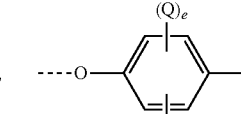
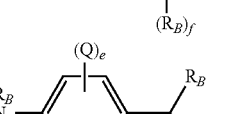
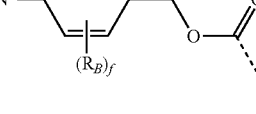

-continued

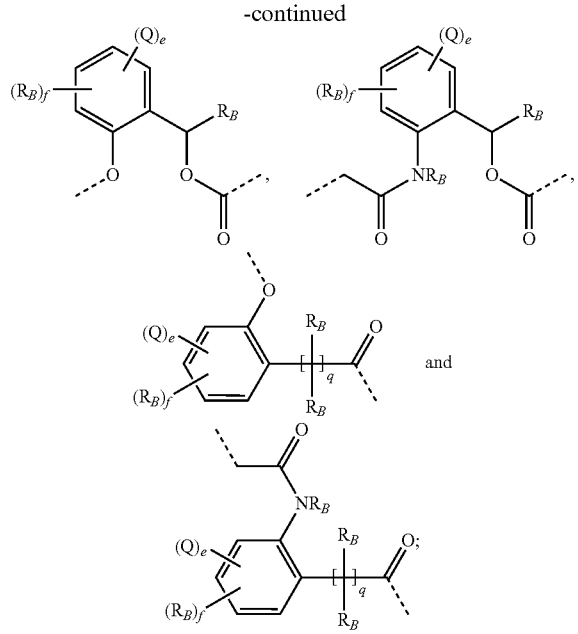

each $R_B$ is independently selected from the group consisting of hydrogen,

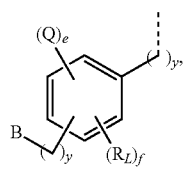

and $C_mH_l$, where m is an integer such that $0 \leq m \leq 6$ and l is an integer $\leq 2m+1$;

each $A_1$ is independently hydrogen, halogen, alkyl, aryl, pyridinyl, —O-alkyl or an amino radical;

each $Z_1$ is independently alkyl, aryl or —O-alkyl;

each $Z_2$ is independently hydrogen, halogen or an amino radical;

each $X_1$ is independently N or —$CY_1$—, wherein $Y_1$ is hydrogen, halogen, alkyl, —O-alkyl or —S-alkyl, or $X_1$ forms a bridge with $Z_1$;

each $X_2$ is independently N or —$CY_2$—, wherein $Y_2$ is hydrogen, halogen, alkyl, —O-alkyl or —S-alkyl, or $X_2$ forms a bridge with $A_1$;

each $X_3$ is independently N or CH;

each $X_4$ is independently N or CH;

B is a phosphonated group;

each Q is independently nitro, chloro, bromo, iodo or fluoro;

each $R_L$ is $C_mH_l$, where m is an integer such that $0 \leq m \leq 6$ and l is an integer $\leq 2m+1$;

q is 2 or 3;

y is an integer $\leq 10$; and e and f are integers $\geq 0$ such that e+f=4.

In a sixth aspect of the first embodiment, each B-L- is independently represented by Formula ($BL_6$) or Formula ($BL_7$):

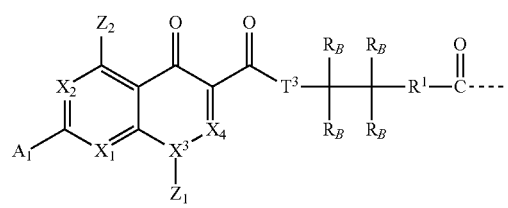

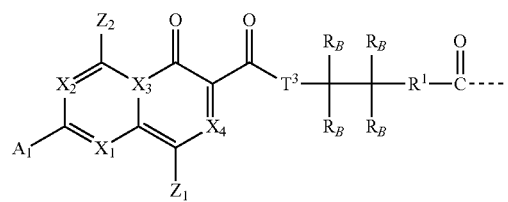

wherein each

is independently selected from the group consisting of:

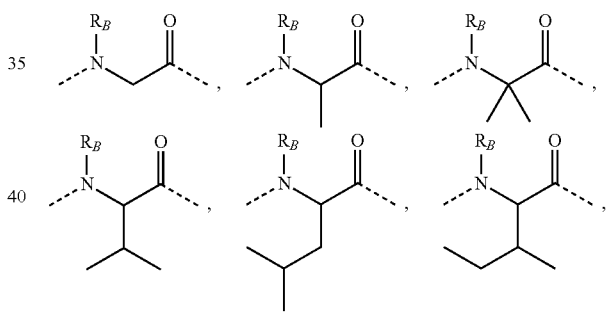

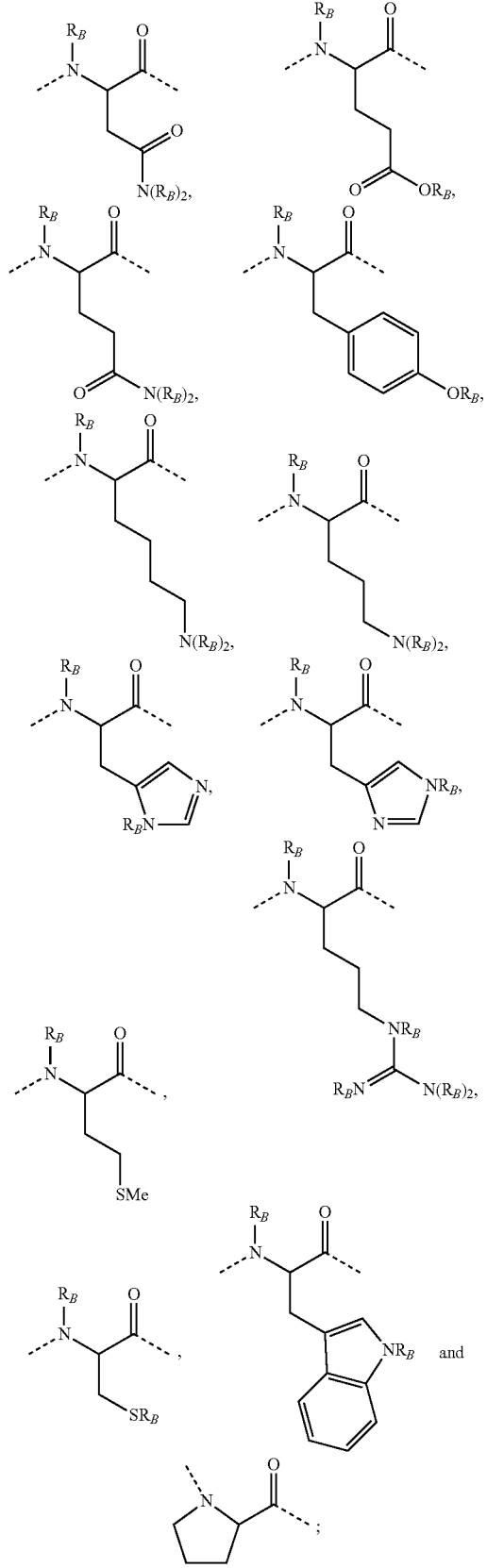
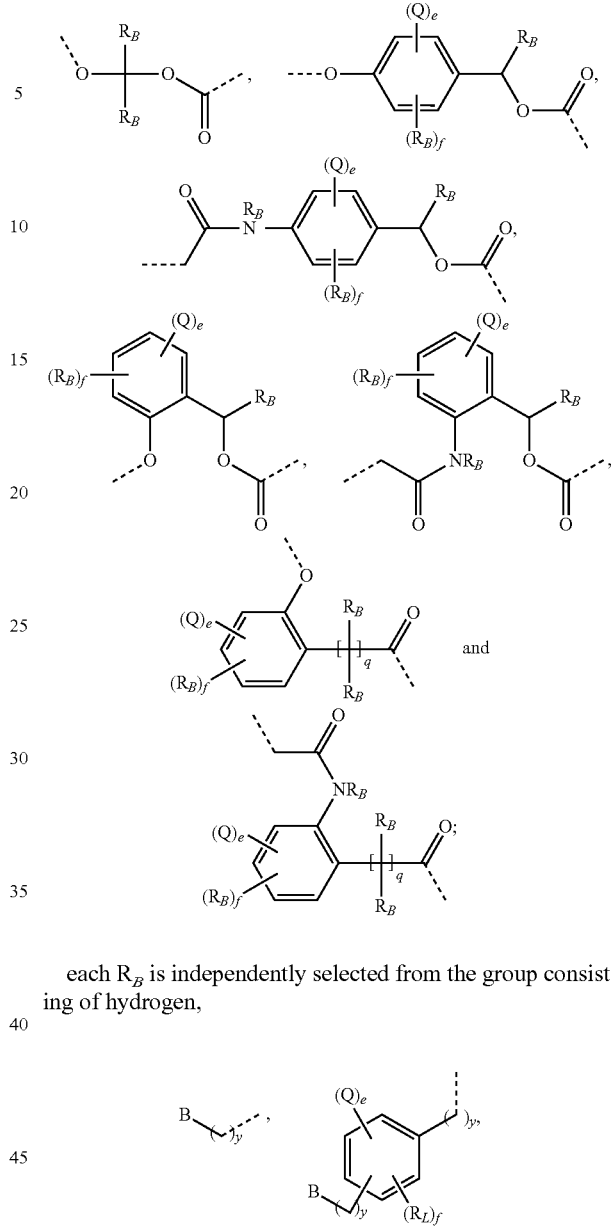

each $T^3$ is selected from the group consisting of oxygen, sulfur, or is selected from the group of each $R_B$ is independently selected from the group consisting of hydrogen, and $C_mH_l$, where m is an integer such that $0 \leq m \leq 6$ and l is an integer $\leq 2m+1$;

each $A_1$ is independently hydrogen, halogen, alkyl, aryl, pyridinyl, —O-alkyl or an amino radical;

each $Z_1$ is independently alkyl, aryl or —O-alkyl;

each $Z_2$ is independently hydrogen, halogen or an amino radical;

each $X_1$ is independently N or —$CY_1$—, wherein $Y_1$ is hydrogen, halogen, alkyl, —O-alkyl or —S-alkyl, or $X_1$ forms a bridge with $Z_1$;

each $X_2$ is independently N or —$CY_2$—, wherein $Y_2$ is hydrogen, halogen, alkyl, —O-alkyl or —S-alkyl, or $X_2$ forms a bridge with $A_1$;

each $X_3$ is independently N or CH;

each $X_4$ is independently N or CH;

B is a phosphonated group;

each Q is independently nitro, chloro, bromo, iodo or fluoro;

each $R_L$ is $C_mH_l$, where m is an integer such that $0 \leq m \leq 6$ and l is an integer $\leq 2m+1$;

q is 2 or 3;

y is an integer $\leq 10$; and e and f are integers $\geq 0$ such that e+f=4.

In the first embodiment, the Rifamycin or Rifamycin derived antimicrobial molecule A may have a structure represented by the following Formula (IA):

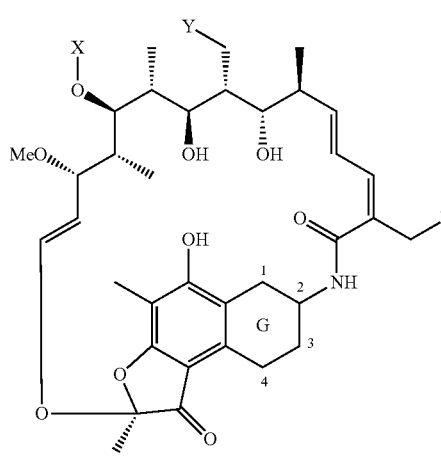

wherein:

X is H— or $R_1CO$—, wherein $R_1$ is a substituted or unsubstituted alkyl chain of 1-6 carbons;

each Y is independently selected from the group consisting of H— and RO—, wherein R is H—, $R_1$—, or $R_1CO$—, with $R_1$ defined as above;

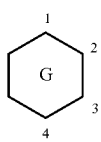

is selected from the group consisting of Formulae IA1-1A9:

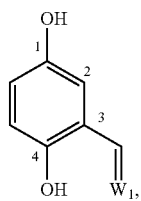 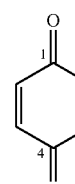 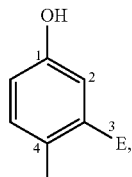

IA1　　　IA2　　　IA3

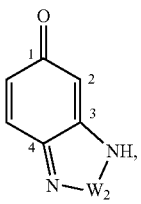 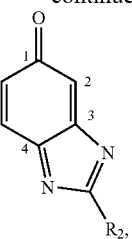 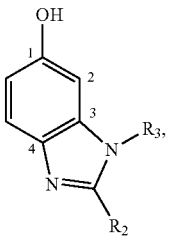

IA4　　　IA5　　　IA6

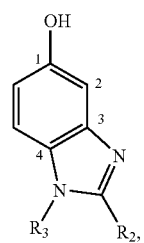 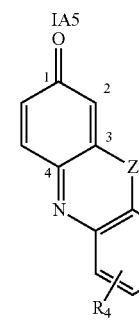

IA7　　　IA8　　　and

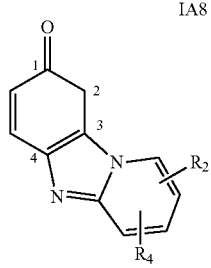

IA9 wherein $R_2$ is H—, a substituted or unsubstituted alkyl chain of 1-10 carbons, or a dialkyl amino group, wherein said dialkyl amino group may be a substituted piperidine, a substituted morpholine or a substituted piperazine;

$R_3$ is H— or a substituted or unsubstituted alkyl chain of 1-7 carbons;

$R_4$ is a hydroxyl group, a sulfhydryl group or a substituted or unsubstituted alkyl chain of 1-3 carbons;

$W_1$ is oxygen or —$NR_2$ with $R_2$ defined as above;

$W_2$ is a substituted or unsubstituted methylene, including:

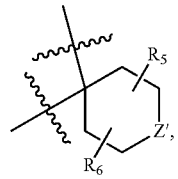

wherein $R_5$ and $R_6$ are independently H— or a substituted or unsubstituted alkyl chain of 1-5 carbons, and Z' is an oxygen atom, a sulfur atom, a substituted methylene, a carbonyl, —$NR_1$, or —$N(O)R_1$, where $R_1$ is defined as above;

E is a halogen or $R_2$, where $R_2$ is defined as above; and

Z is O, S or $NR_3$, where $R_3$ is defined as above.

In a preferred aspect, the Rifamycin or Rifamycin derived antimicrobial molecule A has a structure represented by one of the following formulas or an antimicrobial derivative thereof:
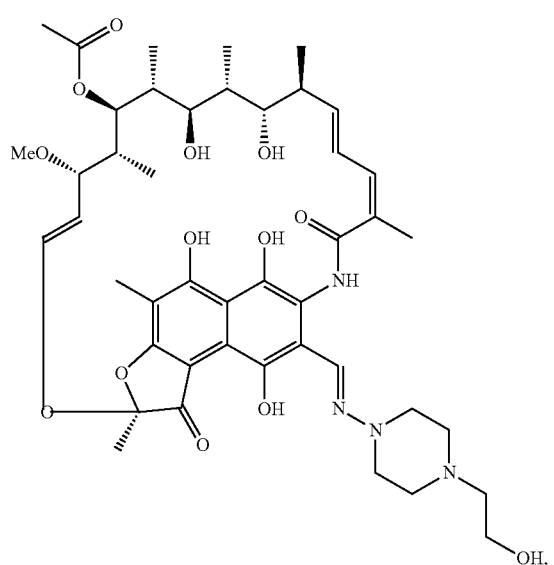
(IB)
(IC)
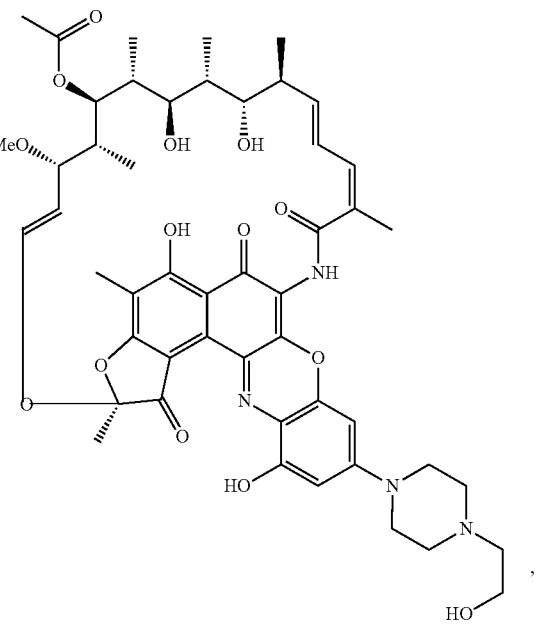
(ID)
(IE)
and -continued

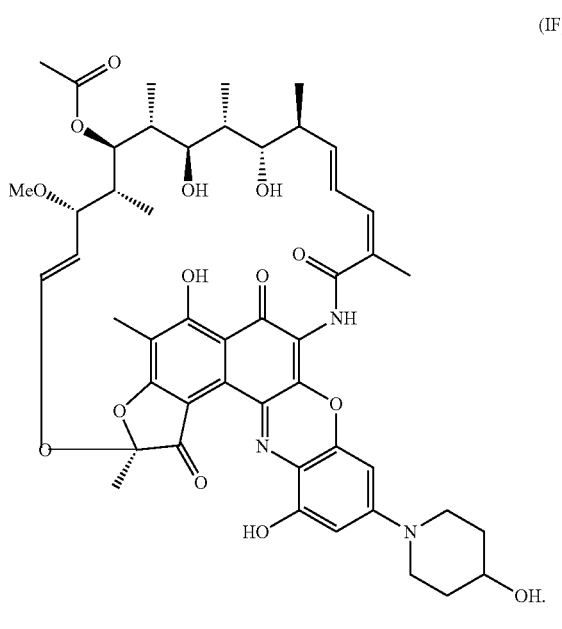
(IF)

In particular preferred aspect of the first embodiment, the Rifamycin or Rifamycin derived antimicrobial molecule A is Rifampicin, Rifapentin, Rifabutin, Rifalazil, Rifaximin, Rifandin, or an antimicrobial derivative of one of these compounds.

In a further aspect of the first embodiment, the compounds of the invention are represented by Formula (II), and pharmaceutically acceptable salts, metabolites, solvates and prodrugs thereof:

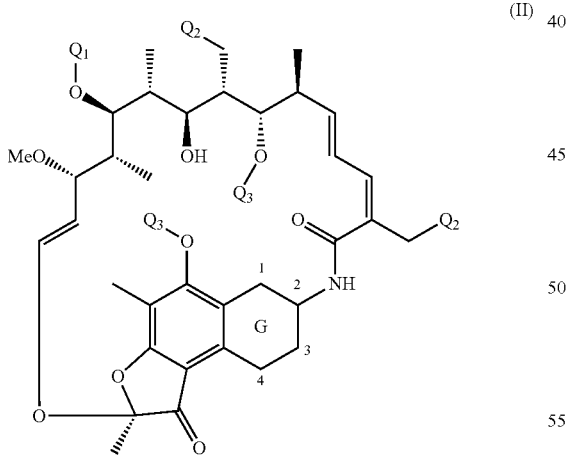
(II)

wherein:

$Q_1$ is H—, $R_1$CO— or $L_1$-, wherein $R_1$ is a substituted or unsubstituted alkyl chain of 1-6 carbons;

each $Q_2$ is independently selected from the group consisting of H—, $R_x$O— and $L_2$O—, wherein $R_x$ is H—, $R_1$— or $R_1$CO—, with $R_1$ defined as above;

each $Q_3$ is independently selected from the group consisting of H— and $L_3$-;

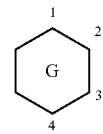

is selected from the group consisting of Formulae IA1-1A9:

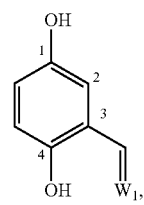
IA1

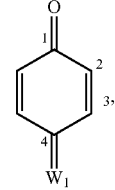
IA2

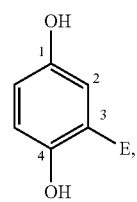
IA3

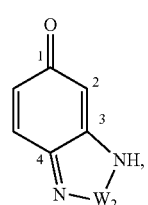
IA4

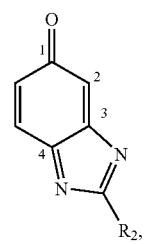
IA5

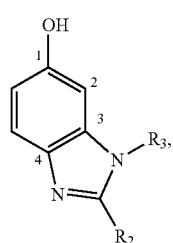
IA6

-continued

IA7
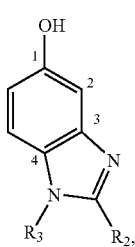

IA8
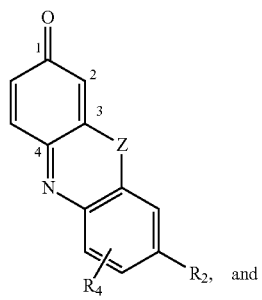

IA9
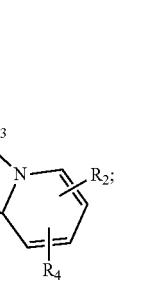

wherein

R$_2$ is H—, a substituted or unsubstituted alkyl chain of 1-10 carbons or a dialkyl amino group, wherein said dialkyl amino group may be a substituted piperidine, a substituted morpholine or a substituted piperazine, wherein the substituent is one member selected from the group consisting of L$_4$O—, L$_5$S— and L$_6$NR$_7$—, wherein R$_7$ is a substituted or unsubstituted alkyl chain of 1-7 carbons;

R$_3$ is H—, a substituted or unsubstituted alkyl chain of 1-7 carbons or L$_7$-;

R$_4$ is a hydroxyl group, a sulfhydryl group or a substituted or unsubstituted alkyl chain of 1-3 carbons, L$_8$O— or L$_9$S—;

W$_1$ is oxygen or —NR$_2$, with R$_2$ defined as above;

W$_2$ is a substituted or unsubstituted methylene, including

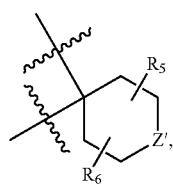

wherein R$_5$ and R$_6$ are independently H— or a substituted or unsubstituted alkyl chain of 1-5 carbons, and Z' is an oxygen atom, a sulfur atom, a substituted methylene, a carbonyl, —NR$_1$, or —N(O)R$_1$, where R$_1$ is defined as above;

E is a halogen or R$_2$, where R$_2$ is defined as above;

Z is O, S or NR$_3$, where R$_3$ is defined as above;

each L$_1$, L$_2$, L$_3$, L$_4$, L$_5$, L$_6$, L$_7$, L$_8$ and L$_9$ is a group of Formula (Ia):

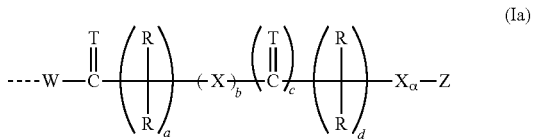

wherein:

each T is independently oxygen or sulfur;

each R is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, substituted aryloxy, and —R$^a$—Y—R$^b$—Y—R$^b$—B;

W is a covalent bond or is selected from the group of

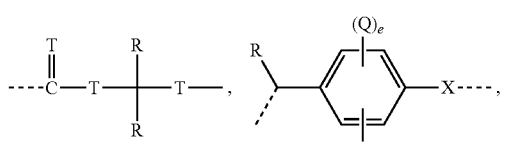

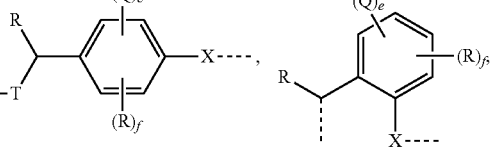

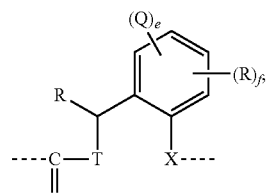

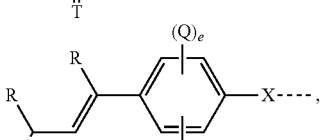

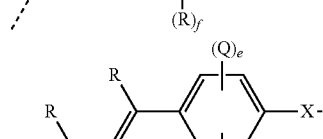

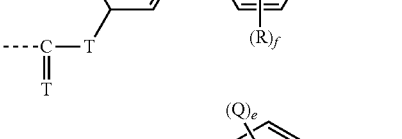

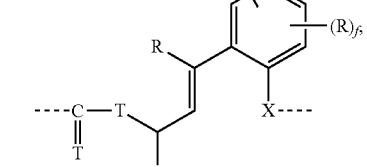

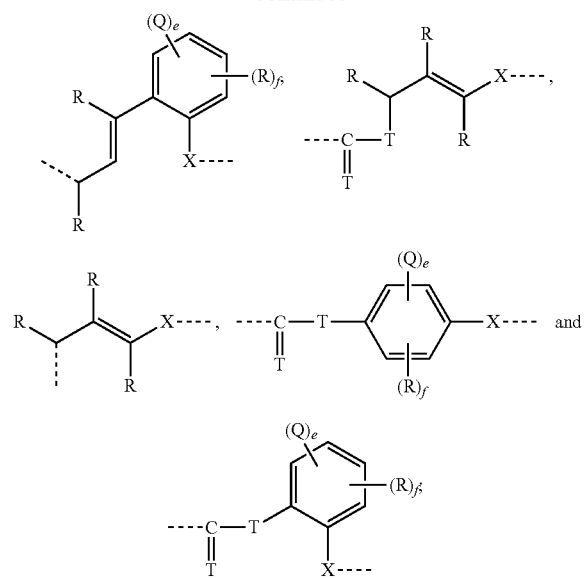

each X is independently —O—, —S— or —N(R)—;

each Q is independently nitro, chloro, bromo, iodo or fluoro;

Z is selected from the group consisting of hydrogen, acyl, substituted acyl, aroyl, substituted aroyl, alkoxycarbonyl, substituted alkoxycarbonyl, aryloxycarbonyl, substituted aryloxycarbonyl,

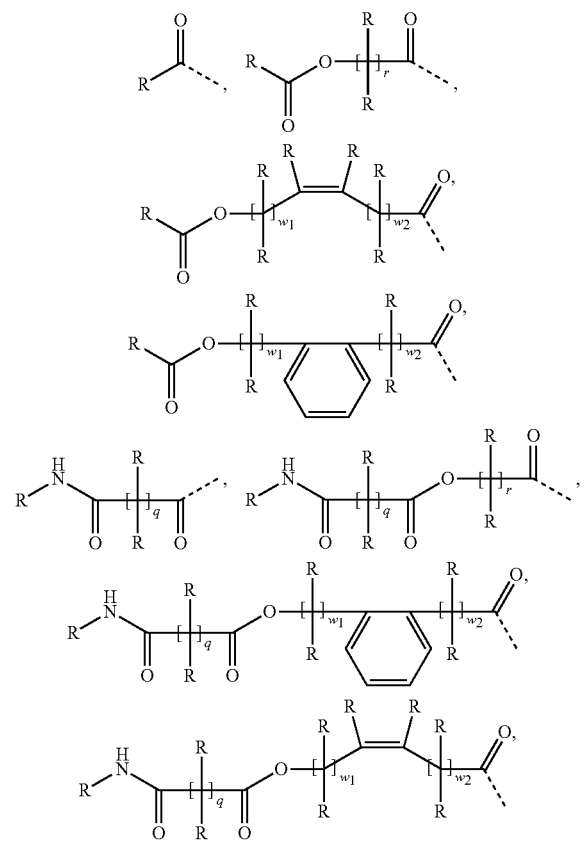

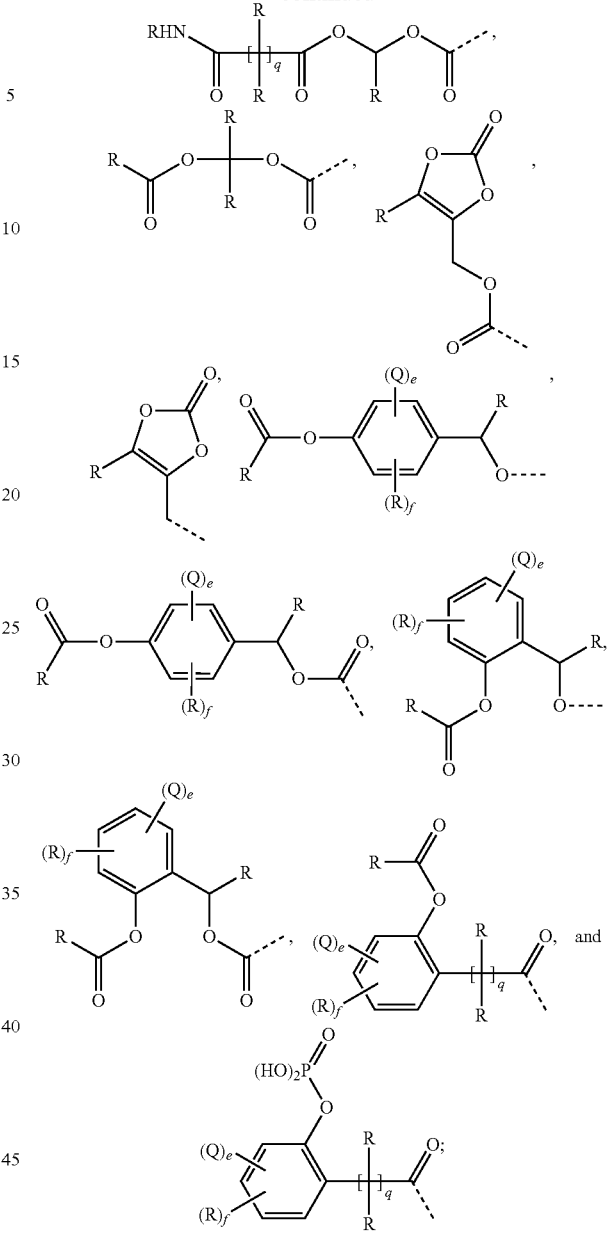

each $R^a$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each $R^b$ is independently selected from the group consisting of a covalent bond, alkylene, substituted alkylene, alkenylene, substituted alkenylene, alkynylene, substituted alkynylene, arylene and substituted arylene;

each Y is independently selected from the group consisting of a covalent bond, —$CH_2$—, —O—, —S—, —S—S—, —$NR^c$—, —S(O)—, —$SO_2$—, —$NR^cC(O)$—, —$OSO_2$—, —OC(O)—, —$N(R^c)SO_2$—, —C(O)$NR^c$—, —C(O)O—, —$SO_2NR^c$—, —$SO_2O$—, —P(O)(O$R^c$)O—, —P(O)(O$R^c$)$NR^c$—, —OP(O)(O$R^c$)O—, —OP(O)(O$R^c$)$NR^c$—, —OC (O)O—, —NR$^c$C(O)O—, —NR$^c$C(O)NR$^c$—, —OC(O)NR$^c$—, —C(O)—, and —N(R$^c$)SO$_2$NR$^c$—;

each R$^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;

each R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

q is 2 or 3;

r is 1, 2, 3, 4 or 5;

$w_1$ and $w_2$ are each integers $\geq 0$ such that their sum ($w_1 + w_2$) is 1, 2 or 3;

a, b, c, d are each integers $\geq 0$ such that a+b+c+d$\leq$7;

e and f are each integers $\geq 0$ such that e+f=4;

α is 0 or 1; and

B is a phosphonated group selected from the group consisting of:

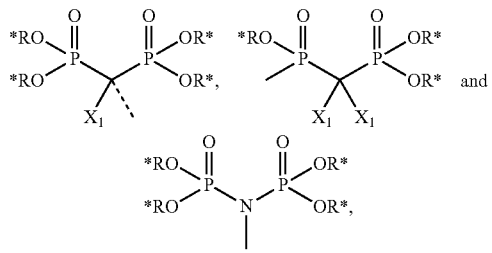

wherein:

each R* is independently selected from the group consisting of H, lower alkyl, cycloalkyl, aryl and heteroaryl, with the proviso that at least two R* are H;

each X$_1$ is independently selected from the group consisting of H, OH, NH$_2$, and a halo group;

with the proviso that at least one of R in Formula (Ia) is —R$^d$—Y—R$^b$—Y—R$^b$—B;

with the further proviso that at least one of L$_1$, L$_2$, L$_3$, L$_4$, L$_5$, L$_6$, L$_7$, L$_9$ and L$_9$ is present; and with the additional proviso that none of L$_1$, L$_2$, L$_3$, L$_4$, L$_5$, L$_6$, L$_7$, L$_8$ and L$_9$ is one of the following structures:

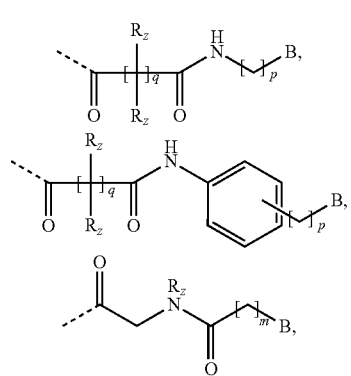

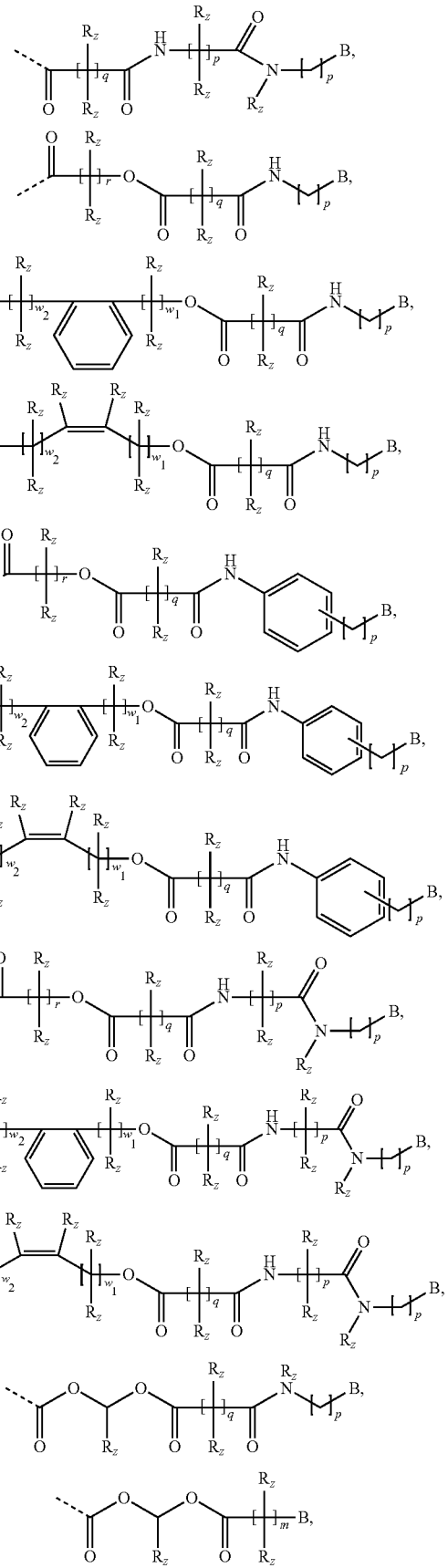

-continued

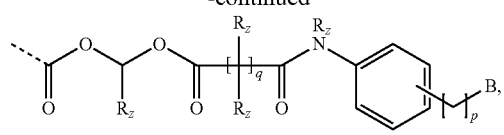
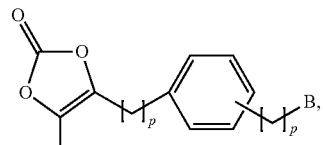
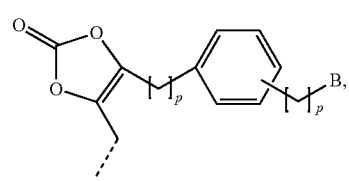
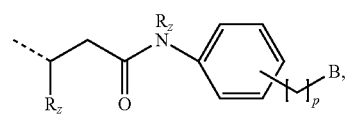
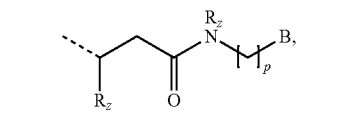
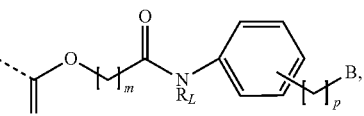

wherein:
X, B, q, r, $w_1$ and $w_2$ are defined as above;
each p is independently 0 or an integer $\leq 10$;
each $R_L$ independently H, ethyl or methyl;
each $R_Z$ is independently H, ethyl or methyl;
$R_Y$ is represented by $C_iH_j$, where i is an integer $\leq 20$ and j is an integer $\leq 2i+1$; and
m is an integer $\leq 10$.

Examples of the compounds of first embodiment include the following, along with pharmaceutically acceptable salts, metabolites, solvates, and prodrugs thereof:

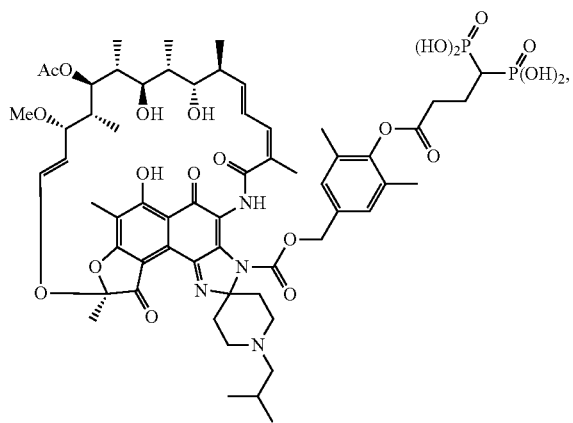

(19)

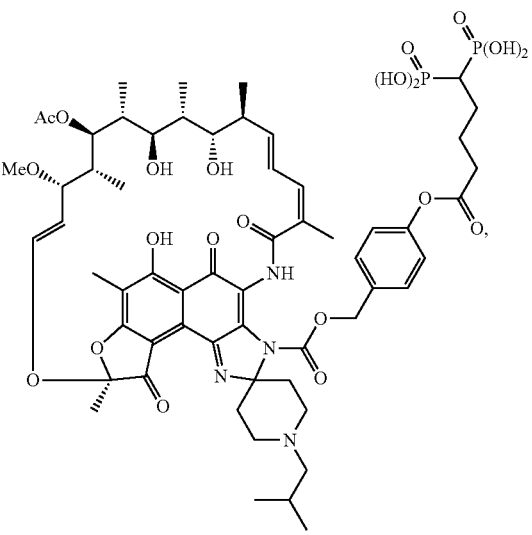

(18)

-continued
(28)
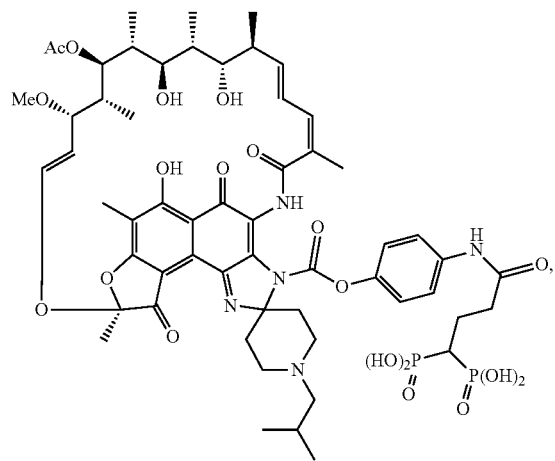
(36)
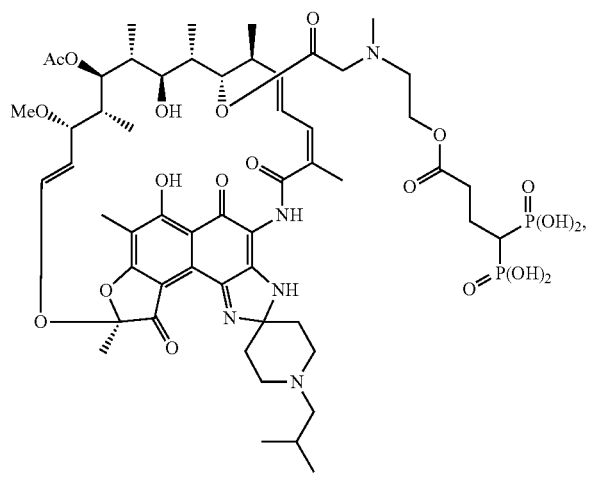
(42)
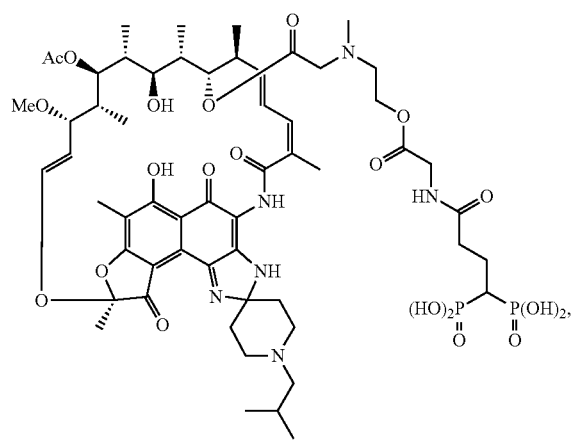
(48a)
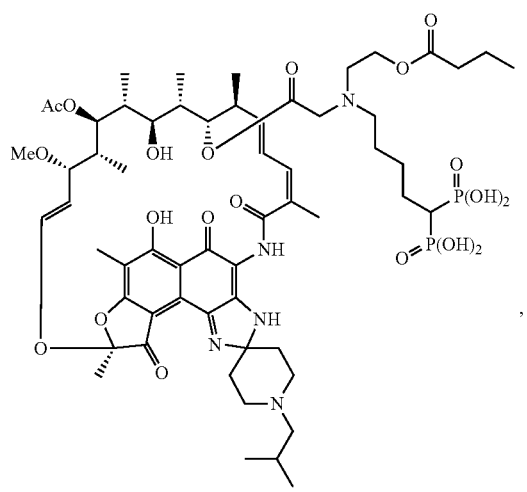
(48b)
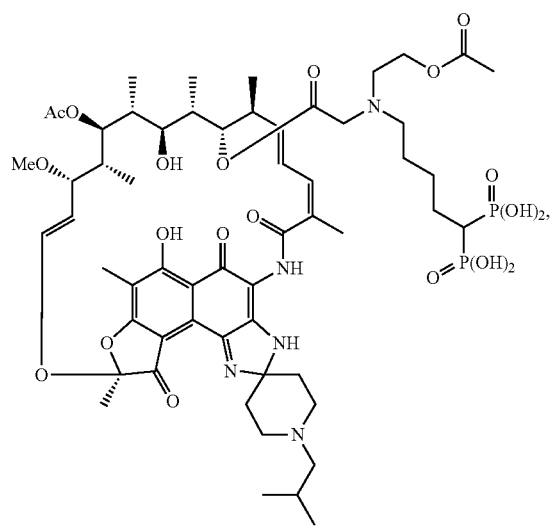
(52)
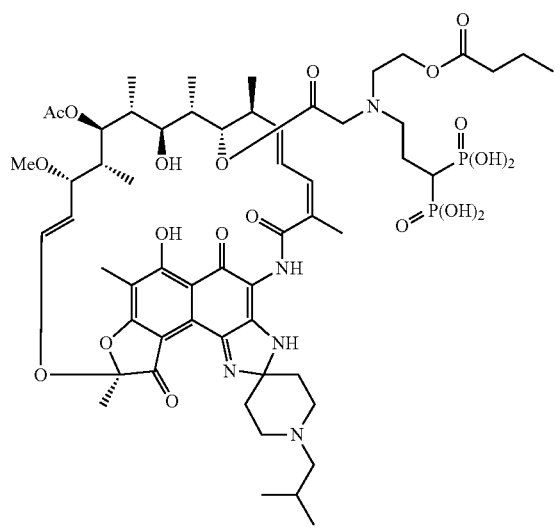

(59)
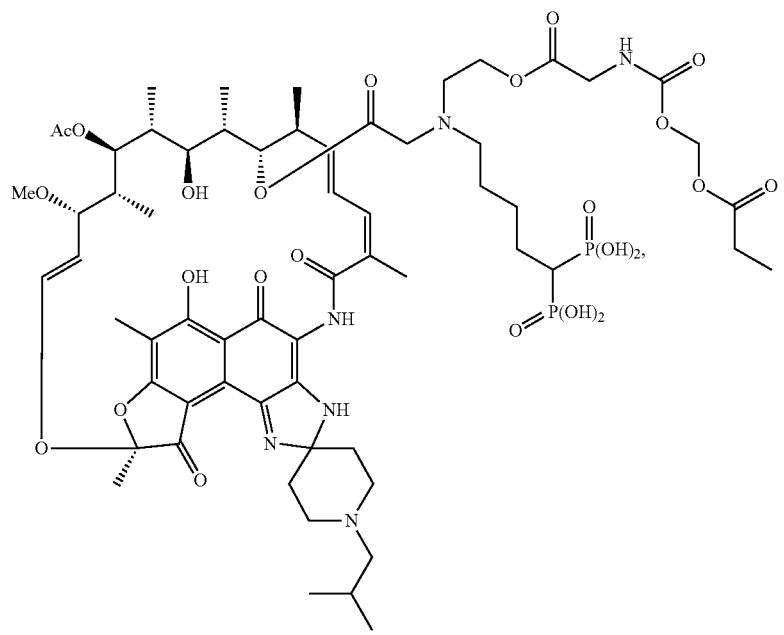
(66)
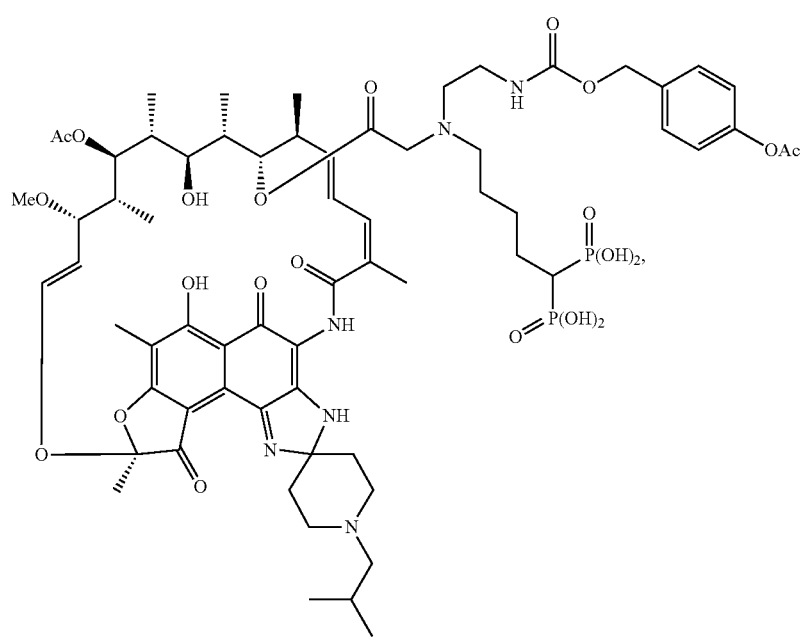

-continued
(71)
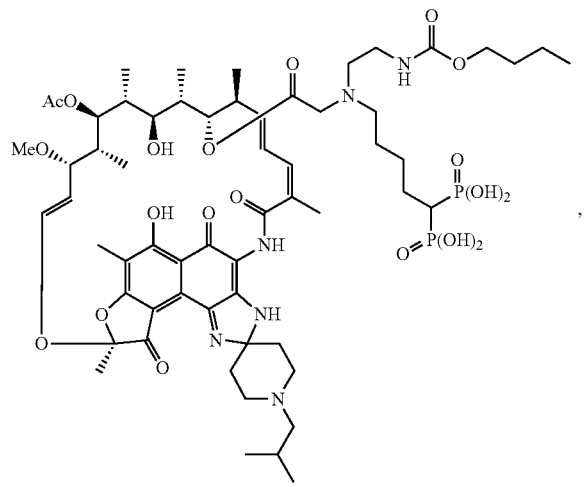
(79a)
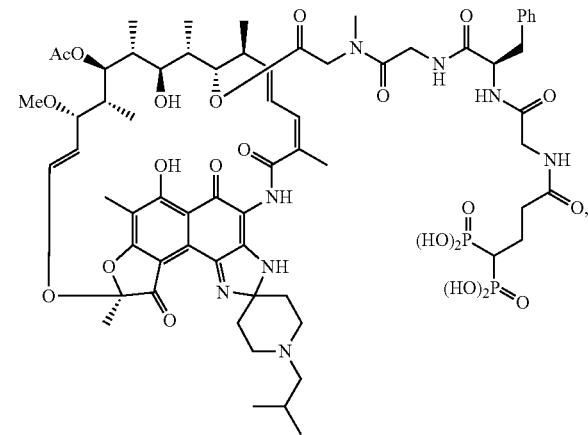
(79b)
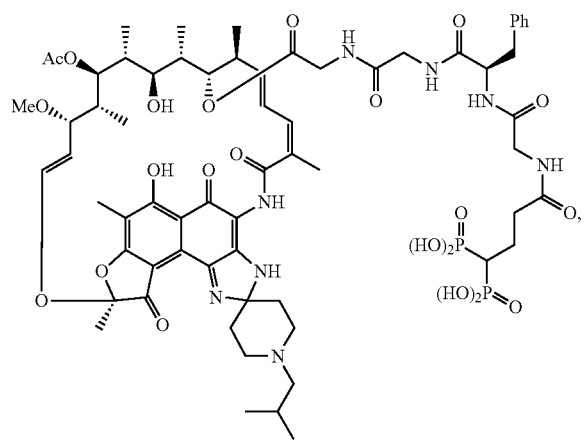
(89)
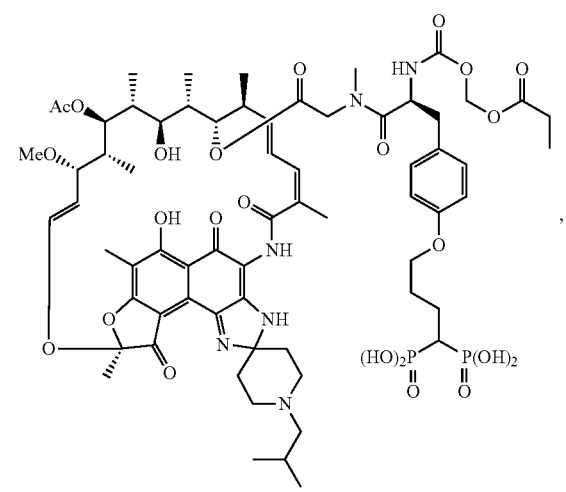
(95)
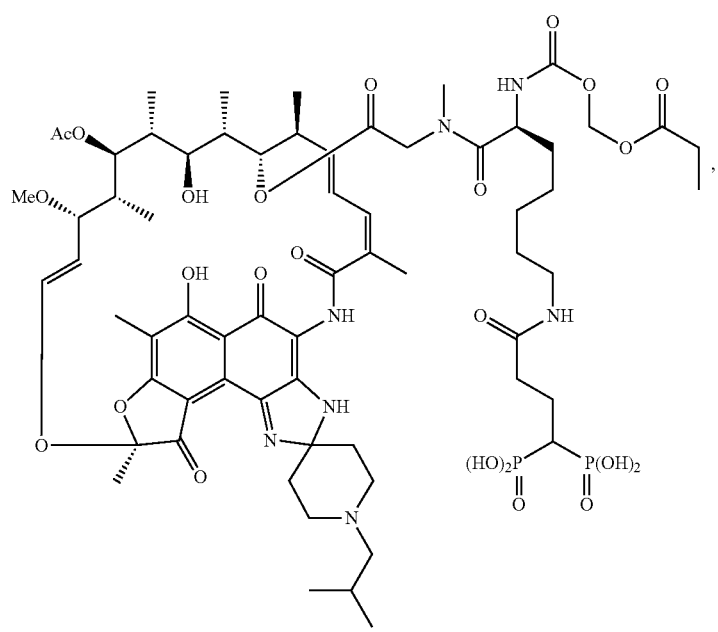

-continued
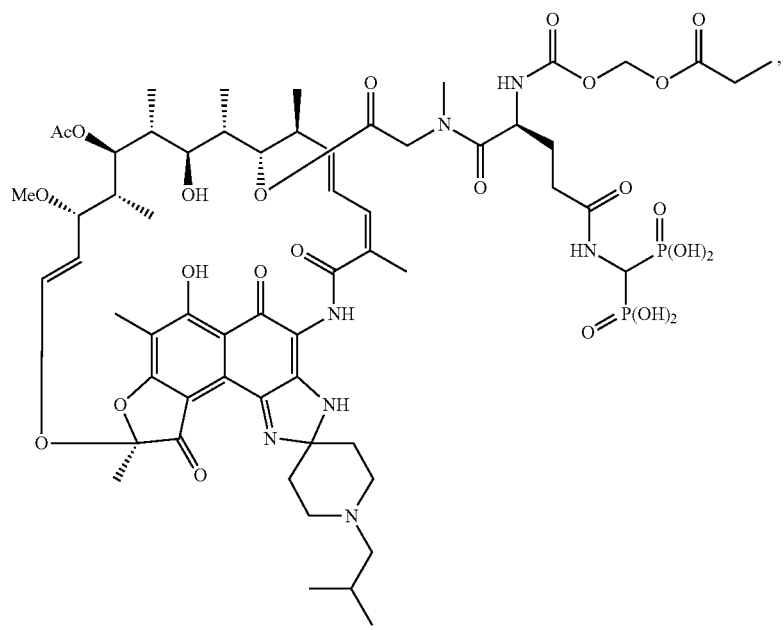
(102)
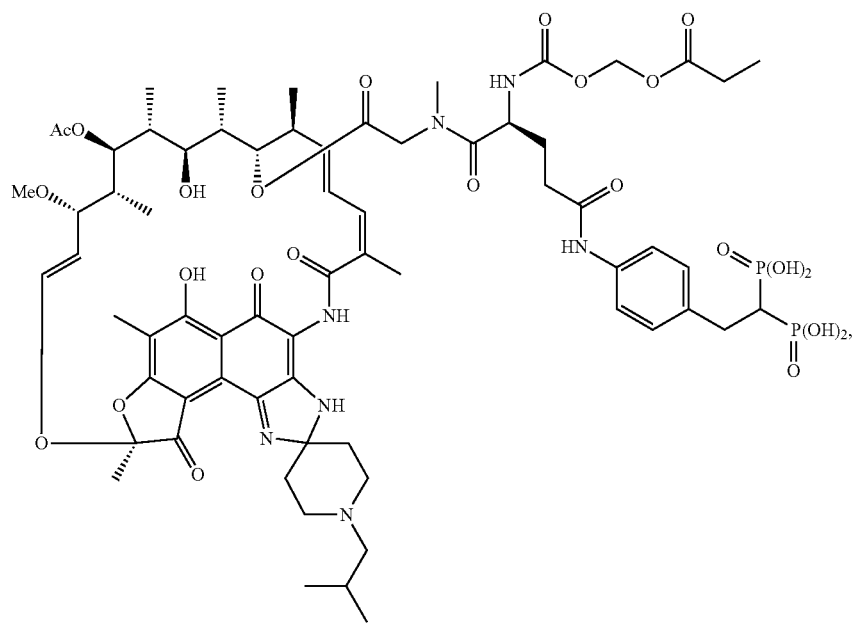
(110)

-continued
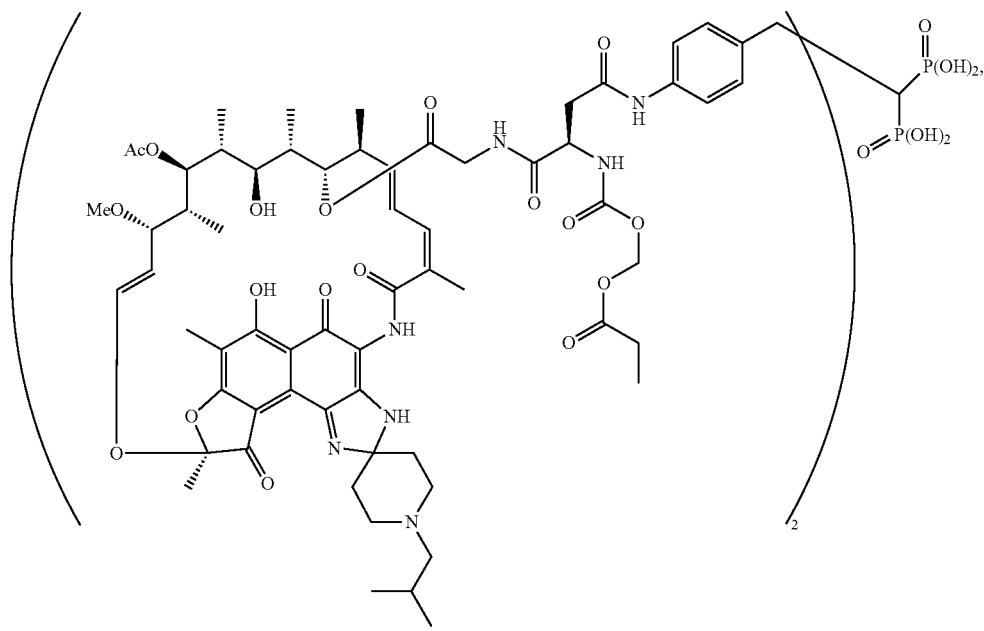
(118)
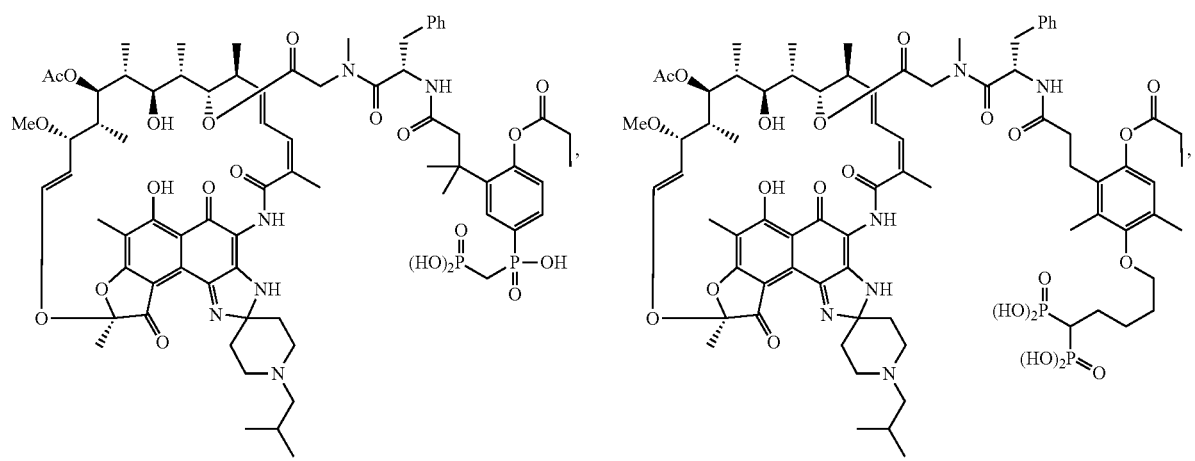
(128)
(138)
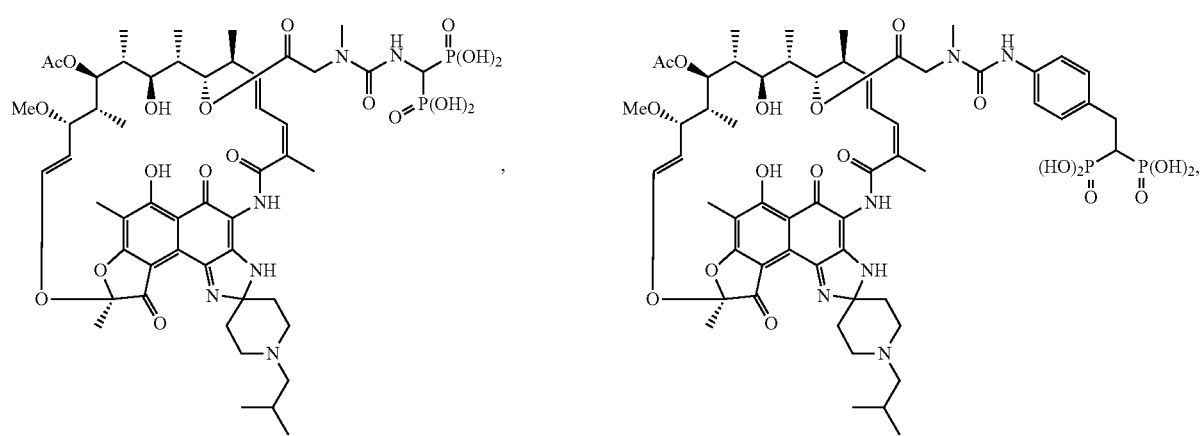
(140)
(142b)

(142a)

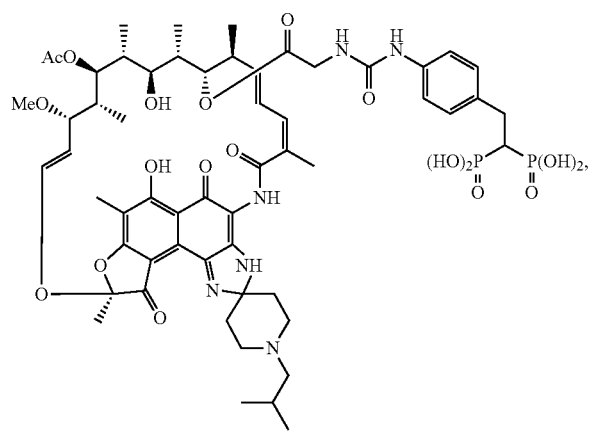

(147)

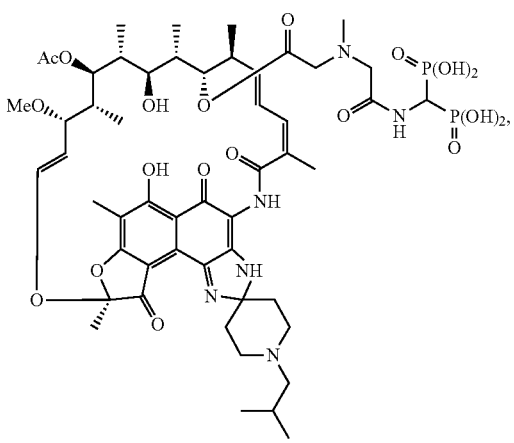

(150)

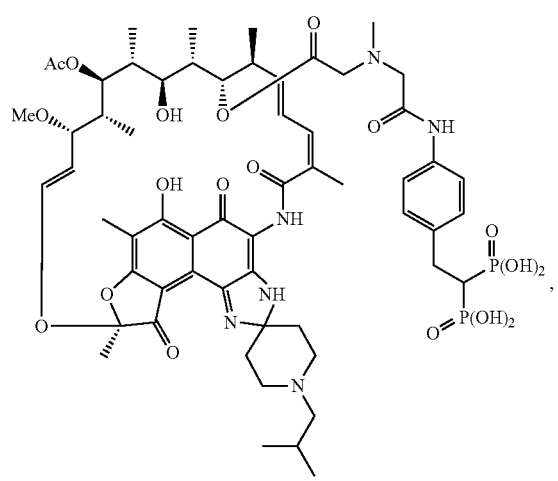

(155)

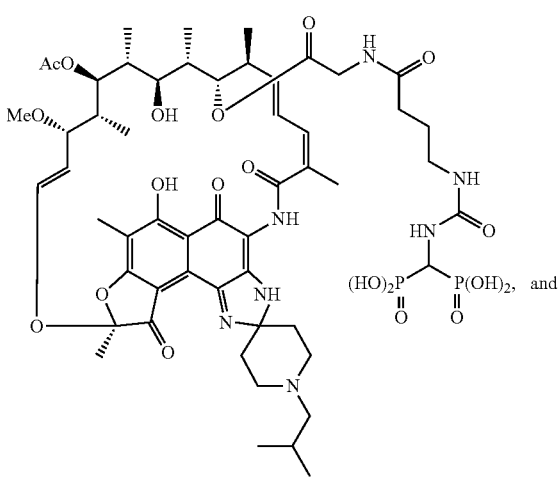

and (164)

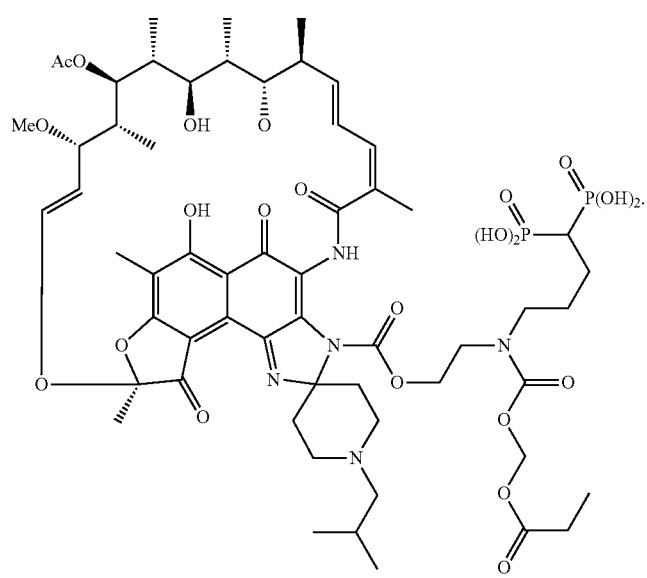

In a second embodiment, the present invention includes pharmaceutical compositions comprising (i) one or more of the compounds as defined herein and pharmaceutically acceptable salts, metabolites, solvates, and prodrugs thereof, and (ii) a pharmaceutically acceptable carrier or excipient.

For example, the invention includes a pharmaceutical composition comprising at least one compound of Formula (I) or (II), or a pharmaceutically acceptable salt, metabolite, solvate, or prodrug thereof, and a pharmaceutically acceptable carrier or diluent.

In a third embodiment, the present invention includes methods for treating a bacterial infection, such as osteomyelitis, in a subject using the compounds of the invention. In one aspect, the methods for treating a bacterial infection in a subject comprise administering to a subject in need of treatment a pharmaceutically effective amount of one or more of the compounds as defined herein, or a pharmaceutical composition as defined herein, thereby treating a bacterial infection in a subject. For example, the invention includes methods for treating a bacterial infection in a subject comprising administering to a subject in need of treatment a pharmaceutical composition comprising a pharmaceutically effective amount of at least one compound of Formula (I) or (II), or a pharmaceutically acceptable salt, metabolite, solvate, or prodrug thereof, and a pharmaceutically acceptable carrier or excipient, thereby treating a bacterial infection in a subject.

In a fourth embodiment, the present invention includes methods for preventing bacterial infections in a subject using the compounds of the invention. In one aspect, the methods for preventing a bacterial infection in a subject comprise administering to a subject in need of prevention a pharmaceutically effective amount of one or more of the compounds as defined herein, or a pharmaceutical composition as defined herein, thereby preventing a bacterial infection in a subject. For example, the invention includes methods for preventing a bacterial infection in a subject comprising administering to a subject in need of prevention a pharmaceutical composition comprising a pharmaceutically effective amount of at least one compound of Formula (I) or (II), or a pharmaceutically acceptable salt, metabolite, solvate, or prodrug thereof, and a pharmaceutically acceptable carrier or excipient, thereby preventing a bacterial infection in a subject.

In a fifth embodiment, the present invention includes methods of providing prophylaxis for a bacterial infection in a subject using the compounds of the invention. In one aspect, the methods of providing prophylaxis for a bacterial infection in a subject comprise administering to a subject in need of prophylaxis a pharmaceutically effective amount of one or more of the compounds as defined herein, or a pharmaceutical composition as defined herein, thereby providing prophylaxis for a bacterial infection in a subject. For example, the invention includes methods of providing prophylaxis for a bacterial infection in a subject comprising administering to a subject in need of prophylaxis a pharmaceutical composition comprising a prophylactically effective amount of at least one compound of Formula (I) or (II), or a pharmaceutically acceptable salt, metabolite, solvate, or prodrug thereof, and a pharmaceutically acceptable carrier or excipient, thereby providing prophylaxis for a bacterial infection in a subject.

In a sixth embodiment, the present invention includes methods for accumulating a Rifamycin or a Rifamycin derived antibacterial molecule in a bone of a subject using the compounds of the invention. In one aspect, the methods for accumulating a Rifamycin or a Rifamycin derived antibacterial molecule in a bone of a subject comprise administering to a subject in need of treatment a pharmaceutically effective amount of one or more of the compounds as defined herein, or a pharmaceutical composition as defined herein, thereby accumulating a Rifamycin or a Rifamycin derived antibacterial molecule in a bone of a subject. For example, the invention includes methods accumulating a Rifamycin or a Rifamycin derived antibacterial molecule in a bone of a subject comprising administering to a subject in need of treatment a pharmaceutical composition comprising a pharmaceutically effective amount of at least one compound of Formula (I) or (II), or a pharmaceutically acceptable salt, metabolite, solvate, or prodrug thereof, and a pharmaceutically acceptable carrier or excipient, thereby accumulating a Rifamycin or a Rifamycin derived antibacterial molecule in a bone of a subject.

In each of the methods of the invention, the subject may be an animal, preferably a mammal, more preferably a human.

In each of the methods of the invention, the methods may further comprise administering a second therapeutic agent in conjunction with administration of the compounds or pharmaceutical compositions. Preferably the second therapeutic agent is an antibiotic. More preferably the second therapeutic agent is an antibiotic selected from the group consisting of tetracycline, a tetracycline derived antibacterial agent, glycylcycline, a glycylcycline derived antibacterial agent, minocycline, aminocycline derived antibacterial agent, an oxazolidinone antibacterial agent, an aminoglycoside antibacterial agent, a quinolone antibacterial agent, vancomycin, a vancomycin derived antibacterial agent, a teicoplanin, a teicoplanin derived antibacterial agent, eremomycin, an eremomycin derived antibacterial agent, chloroeremomycin, a chloroeremomycin derived antibacterial agent, oritavancin, an oritavancin derived antibacterial agent, daptomycin, a daptomycin derived antibacterial agent, rifamycin, and a rifamycin derived antibacterial agent.

In a seventh embodiment, the present invention includes processes for the preparation of a phosphonated Rifamycin, preferably a phosphonated Rifamycin of Formula (I) and/or Formula (II) as defined herein.

An advantage of the invention is that it provides antimicrobial compounds having an increased binding affinity for bone. The invention also provides methods for the unmet medical need of prevention and treatment of bone and joint infections.

Additional objects, advantages and features of the present invention will become more apparent upon reading the following non-restrictive description of preferred embodiments which are exemplary and should not be interpreted as limiting the scope of the present invention.

DETAILED DESCRIPTION OF THE INVENTION

The present invention discloses phosphonated Rifamycins, in particular, those phosphonated compounds defined in Formula (I) and Formula (II) as defined above and hereinafter. These compounds are useful antimicrobial agents effective against a number of human and veterinary pathogens. A phosphonated group is reversibly coupled to a Rifamycin via a cleavable linker.

Phosphonated Rifamycins have been synthesized and demonstrated herein to have an increased affinity for osseous materials. The presence of Rifamycins in the bones can be prolonged by administering phosphonated Rifamycins according to the invention. In vivo, these phosphonated compounds accumulate in bones in amounts greater than amounts of non-phosphonated equivalents. In addition, significant in vivo protection against bone infection has been demonstrated for at least three days prior to infection for animals injected with phosphonated Rifamycins according to the invention. Accordingly, the compounds of the invention are particularly useful for the prophylaxis and/or treatment of bone and joint-related infections and bone-related diseases such as osteomyelitis.

A) Definitions

In order to provide an even clearer and more consistent understanding of the invention, including the scope given herein to particular terms, the following general definitions are provided:

The term "alkyl" refers to saturated aliphatic groups including straight-chain, branched-chain, cyclic groups, and combinations thereof, having the number of carbon atoms specified, or if no number is specified, having 1 to 12 carbon atoms (preferably 1 to 6). Examples of alkyl groups include, but are not limited to groups such as methyl, ethyl, n-propyl, isopropyl, n-butyl, isobutyl, sec-butyl, t-butyl, n-pentyl, neopentyl, cyclopropyl, cyclobutyl, cyclopentyl, cyclohexyl, cyclobutylmethyl, cyclobutylethyl, cyclopentylmethyl, cyclopentylethyl, and adamantyl. Cyclic alkyl groups (e.g. cycloalkyl or heterocycloalkyl) can consist of one ring, including, but not limited to, groups such as cycloheptyl, or multiple fused rings, including, but not limited to, groups such as adamantyl or norbornyl.

The term "alkylaryl" refers to an alkyl group having the number of carbon atoms designated, appended to one, two, or three aryl groups.

The term "N-alkylaminocarbonyl" refers to the radical —C(O)NHR where R is an alkyl group.

The term "N,N-dialkylaminocarbonyl" refers to the radical —C(O)NR$_a$R$_b$ where R$_a$ and R$_b$ are each independently an alkyl group.

The term "alkylthio" refers to the radical —SR where R is an alkyl group.

The term "alkoxy" as used herein refers to an alkyl, alkenyl, or alkynyl linked to an oxygen atom and having the number of carbon atoms specified, or if no number is specified, having 1 to 12 carbon atoms (preferably 1 to 6). Examples of alkoxy groups include, but are not limited to, groups such as methoxy, ethoxy, tert-butoxy, and allyloxy. The term "alkoxycarbonyl" refers to the radical —C(O)OR where R is an alkyl. The term "alkylsulfonyl" refers to the radical —SO$_2$R where R is an alkyl group.

The term "alkylene" means a saturated divalent aliphatic group including straight-chain, branched-chain, cyclic groups, and combinations thereof, having the number of carbon atoms specified, or if no number is specified, having 1 to 12 carbon atoms (preferably 1 to 6), e.g., methylene, ethylene, 2,2-dimethylethylene, propylene, 2-methyl-propylene, butylene, pentylene, cyclopentylmethylene, and the like.

The term "substituted alkyl" means an alkyl group as defined above that is substituted with one or more substituents, preferably one to three substituents, wherein the substituents are preferably selected from the group consisting of halogen, alkyl, aryl, alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents, wherein the substituents are preferably selected from the group consisting of halogen, alkyl, aryl, alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to —CF$_3$, —CF$_2$—CF$_3$, hydroxymethyl, 1- or 2-hydroxyethyl, methoxymethyl, 1- or 2-ethoxyethyl, carboxymethyl, 1- or 2-carboxyethyl, methoxycarbonylmethyl, 1- or 2-methoxycarbonyl ethyl, benzyl, pyrdinylmethyl, thiophenylmethyl, imidazolinylmethyl, dimethylaminoethyl and the like.

The term "substituted alkylene" means an alkylene group as defined above that is substituted with one or more substituents, preferably one to three substituents, wherein the substituents are preferably selected from the group consisting of halogen, alkyl, aryl, alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents, wherein the substituents are preferably selected from the group consisting of halogen, alkyl, aryl, alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to —CF$_2$—, —CF$_2$—CF$_2$—, hydroxymethylene, 1- or 2-hydroxyethylene, methoxymethylene, 1- or 2-ethoxyethylene, carboxymethylene, 1- or 2-carboxyethylene, and the like.

The term "alkenyl" refers to unsaturated aliphatic groups including straight-chain, branched-chain, cyclic groups, and combinations thereof, having the number of carbon atoms specified, or if no number is specified, having 1 to 12 carbon atoms (preferably 1 to 6), which contain at least one double bond (—C=C—). Examples of alkenyl groups include, but are not limited to allyl vinyl, —CH$_2$—CH=CH—CH$_3$, —CH$_2$—CH$_2$-cyclopentenyl and —CH$_2$—CH$_2$-cyclohexenyl where the ethyl group can be attached to the cyclopentenyl, cyclohexenyl moiety at any available carbon valence.

The term "alkenylene" refers to unsaturated divalent aliphatic groups including straight-chain, branched-chain, cyclic groups, and combinations thereof, having the number of carbon atoms specified, or if no number is specified, having 1 to 12 carbon atoms (preferably 1 to 6), which contain at least one double bond (—C=C—). Examples of alkenylene groups include, but are not limited to —CH=CH—, —CH$_2$—CH=CH—CH$_2$—, —CH$_2$—CH(cyclopentenyl)- and the like.

The term "alkynyl" refers to unsaturated aliphatic groups including straight-chain, branched-chain, cyclic groups, and combinations thereof, having the number of carbon atoms specified, or if no number is specified, having 1 to 12 carbon atoms (preferably 1 to 6), which contain at least one triple bond (—C≡C—). Examples of alkynyl groups include, but are not limited to acetylene, 2-butynyl, and the like.

The term "alkynylene" refers to unsaturated divalent aliphatic groups including straight-chain, branched-chain, cyclic groups, and combinations thereof, having the number of carbon atoms specified, or if no number is specified, having 1 to 12 carbon atoms (preferably 1 to 6), which contain at least one triple bond (—C≡C—). Examples of alkynylene groups include, but are not limited to —C≡C—, —C≡C—CH$_2$—, and the like.

The term "substituted alkenyl" or "substituted alkynyl" refers to the alkenyl and alkynyl groups as defined above that are substituted with one or more substituents, wherein the substituents are preferably selected from the group consisting of halogen, alkyl, aryl, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkenyl and alkynyl groups include, but are not limited to —CH=CF$_2$, methoxyethenyl, methoxypropenyl, bromopropynyl, and the like.

The term "substituted alkenylene" or "substituted alkynylene" refers to the alkenylene and alkynylene groups as defined above that are substituted with one or more substituents, wherein the substituents are preferably selected from the group consisting of halogen, alkyl, aryl, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

The term "aryl" or "Ar" refers to an aromatic carbocyclic group of 6 to 14 carbon atoms having a single ring (including but not limited to groups such as phenyl) or multiple condensed rings (including but not limited to groups such as naphthyl or anthryl), and includes both unsubstituted and substituted aryl groups. Substituted aryl is an aryl group that is substituted with one or more substituents, preferably one to three substituents, wherein the substituents are preferably selected from the group consisting of alkyl, aryl, alkenyl, alkynyl, halogen, alkoxy, acyloxy, amino, mono or dialkylamino, hydroxyl, mercapto, carboxy, benzyloxy, phenyl, aryloxy, benzyl, cyano, nitro, thioalkoxy, carboxaldehyde, carboalkoxy and carboxamide, or a functionality that can be suitably blocked, if necessary for purposes of the invention, with a protecting group. Representative examples include, but are not limited to naphthyl, phenyl, chlorophenyl, iodophenyl, methoxyphenyl, carboxyphenyl, and the like. The term "aryloxy" refers to an aryl group linked to an oxygen atom at one of the ring carbons. Examples of alkoxy groups include, but are not limited to, groups such as phenoxy, 2-, 3-, or 4-methylphenoxy, and the like. The term "arylthio group" refers to the radical —$SR_c$, where $R_c$ is an aryl group. The term "heteroarylthio group" refers to the radical —$SR_d$ where $R_d$ is a heteroaryl.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —$NH_2$.

The term "N-alkylamino" and "N,N-dialkylamino" means a radical —NHR and —NRR' respectively where R and R' independently represent an alkyl group as defined herein. Representative examples include, but are not limited to N,N-dimethylamino, N-ethyl-N-methylamino, N,N-di(1-methylethyl)amino, N-cyclohexyl-N-methylamino, N-cyclohexyl-N-ethylamino, N-cyclohexyl-N-propylamino, N-cyclohexylmethyl-N-methylamino, N-cyclohexylmethyl-N-ethylamino, and the like.

The term "thioalkoxy" means a radical —SR where R is an alkyl as defined above e.g., methylthio, ethylthio, propylthio, butylthio, and the like.

The term "acyl group" means a radical —C(O)R, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "thioacyl group" means a radical —C(S)R, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "sulfonyl group" means a radical —$SO_2R$, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "acyloxy" means a radical —OC(=O)R, where R is hydrogen, alkyl, aryl, heteroaryl or substituted alkyl wherein alkyl, aryl, heteroaryl, and substituted alkyl are as defined herein. Representative examples include, but are not limited to formyloxy, acetyloxy, cylcohexylcarbonyloxy, cyclohexylmethylcarbonyloxy, benzoyloxy, benzylcarbonyloxy, and the like.

The term "heteroalkyl," "heteroalkenyl," and "heteroalkynyl" refers to alkyl, alkenyl, and alkynyl groups respectively as defined above, that contain the number of carbon atoms specified (or if no number is specified, having 1 to 12 carbon atoms, preferably 1 to 6) which contain one or more heteroatoms, preferably one to three heteroatoms, as part of the main, branched, or cyclic chains in the group. Heteroatoms are independently selected from the group consisting of —NR—, —NRR, —S—, —S(O)—, —S(O)$_2$—, —O—, —SR, —S(O)R, —S(O)$_2$R, —OR—PR—, —PRR, —P(O)R— and —P(O)RR; (where each R is hydrogen, alkyl or aryl) preferably —NR where R is hydrogen or alkyl and/or O. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—$CH_3$, —$CH_2$—O—$CH_3$, —$CH_2$—$CH_2$—O—$CH_3$, —S—$CH_2$—$CH_2$—$CH_3$, —$CH_2$—CH($CH_3$)—S—$CH_3$, —$CH_2$—$CH_2$—NH—$CH_2$—$CH_3$, 1-ethyl-6-propylpiperidino, 2-ethylthiophenyl, piperazino, pyrrolidino, piperidino, morpholino, and the like. Examples of heteroalkenyl groups include, but are not limited to groups such as —CH=CH—$CH_2$—N($CH_3$)$_2$, and the like.

The term "heteroaryl" or "HetAr" refers to an aromatic monovalent monocyclic, bicyclic, or tricyclic radical containing 4, 5, 6, 7, 8, 9, 10, 11, 12, 13, 14, 15, 16, 17, or 18-member ring atoms, including 1, 2, 3, 4, or 5 heteroatoms, preferably one to three heteroatoms including, but not limited to, heteroatoms such as N, O, P, or S, within the ring. Representative examples include, but are not limited to, single ring such as imidazolyl, pyrazolyl, pyrazinyl, pyridazinyl, pyrimidinyl, pyrrolyl, pyridyl, thiophene, and the like, or multiple condensed rings such as indolyl, quinoline, quinazoline, benzimidazolyl, indolizinyl, benzothienyl, and the like.

The heteroalkyl, heteroalkenyl, heteroalkynyl and heteroaryl groups can be unsubstituted or substituted with one or more substituents, preferably one to three substituents, wherein the substituents are preferably selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, pyrrolidine, morpholine, or piperidine, substituted at a nitrogen or carbon by a phenyl or benzyl group, and attached to the remainder of the molecule by any available valence on a carbon or nitrogen, —NH—S(=O)$_2$-phenyl, —NH—(C=O)O-alkyl, —NH—C(=O)O-alkyl-aryl, and the like. The heteroatom(s) as well as the carbon atoms of the group can be substituted. The heteroatom(s) can also be in oxidized form.

The term "heteroarylene" refers to the diradical group derived from heteroaryl (including substituted heteroaryl), as defined above, and is exemplified by the groups 2,6-pyridinylene, 2,4-pyridinylene, 1,2-quinolinylene, 1,8-quinolinylene, 1,4-benzofuranylene, 2,5-pyridinylene, 2,5-indolenylene, and the like.

The term "heteroalkylene", "heteroalkenylene", and "heteroalkynylene" refers to the diradical group derived from heteroalkyl, heteroalkenyl, and heteroalkynyl (including substituted heteroalkyl, heteroalkenyl, and heteroalkynyl) as defined above.

The term "carboxaldehyde" means —CHO.

The term "carboalkoxy" means —C(=O)OR where R is alkyl as defined above and include groups such as methoxycarbonyl, ethoxycarbonyl, and the like.

The term "carboxamide" means —C(=O)NHR or —C(=O)NRR' where R and R' are independently hydrogen, aryl or alkyl as defined above. Representative examples include groups such as aminocarbonyl, N-methylaminocarbonyl, N,N-dimethylaminocarbonyl, and the like.

The term "carboxy" refers to the radical —C(O)OH.

The term "carbamoyl" refers to the radical —C(O)NH$_2$.

The term "halogen" or "halo" as used herein refer to Cl, Br, F or I substituents, preferably fluoro or chloro.

The term "hydroxy" refers to a —OH radical.

The terms "isomers" refers to compounds that have the same molecular formula (or elemental composition) but differ in the nature or sequence of bonding of their atoms or the arrangement of their atoms in space. Isomers in which the connectivity between atoms is the same but which differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example which is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (–)-isomers respectively). A chiral compound can exist as either an individual enantiomer or as a mixture thereof. A mixture containing equal proportions of the enantiomers is called a "racemic mixture".

The compounds of this invention may possess one or more asymmetric centers. Such compounds can therefore be produced as individual (R)- or (S)-stereoisomers or as mixtures thereof. For example, the carbons numbered 20, 22 and 24 in compounds 15, 25 and 30 as described in the Exemplification section are each linked to a hydrogen atom, a methyl group, and two different methylene groups, and therefore these carbons are asymmetric centers. The compounds 15, 25 and 30 can exist as stereoisomers. Unless indicated otherwise, the description or naming of a particular compound in the specification and claims is intended to include both individual enantiomers and mixtures, racemic or otherwise, thereof. The description is also intended to include all possible diastereomers and mixtures thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The term "optically pure" refers to a compound that is enantiomerically pure. As used herein, the term "optically pure" is intended to mean a compound which comprises at least a sufficient amount of a single enantiomer to yield a compound having the desired pharmacological activity. Preferably, "optically pure" is intended to mean a compound that comprises at least 90% of a single isomer (80% enantiomeric excess), preferably at least 95% (90% e.e.), more preferably at least 97.5% (95% e.e.), and most preferably at least 99% (98% e.e.). Preferably, the compounds of the invention are optically pure.

The term "protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Preferred amino protecting groups include, but are not limited to, benzyloxycarbonyl (CBz), t-butyloxycarbonyl (Boc), t-butyldimethylsilyl (TBDMS), 9-fluorenylmethyl-oxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Preferred hydroxyl protecting groups include acetyl (Ac), benzoyl (Bz), benzyl (Bn), Tetrahydropyranyl (THP), TBDMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxy-methyloxycarbonyl).

As used herein, the terms "bone", "bone tissues" or "osseous tissues" refer to the dense, semi rigid, porous, calcified connective tissue forming the major portion of the skeleton of most vertebrates. It also encompasses teeth, osteoarticular tissues and calcifications that are frequently seen in the walls of atherosclerotic vessels.

The term "antibacterial" refers to those compounds that inhibit, halt or reverse growth of bacteria, those compounds that inhibit, halt, or reverse the activity of bacterial enzymes or biochemical pathways, those compounds that kill or injure bacteria, and those compounds that block or slow the development of a bacterial infection.

The term "subject" is intended to mean an animal, such birds or mammals, including humans and animals of veterinary or agricultural importance, such as dogs, cats, horses, sheep, goats, and cattle.

B) Compounds of the Invention

As described above and hereinafter, the inventors have prepared phosphonated Rifamycins having a high binding affinity to osseous tissues.

Each of the compounds of the present invention is encompassed within Formula (I):

(I)

wherein:

A is a Rifamycin or a Rifamycin derived antibiotic molecule;

L is a cleavable linker for coupling A to B;

B is a phosphonated group; and n is 1, 2, 3, 4, 5, 6 or 7 as defined above in the summary of the invention as the first embodiment of the invention.

The present invention includes pharmaceutically acceptable salts, metabolites, solvates and prodrugs of the compounds of Formula (I).

In a preferred embodiment, n is an integer of 1 to 3.

The present invention is also directed to the compounds of Formula (II), and pharmaceutically acceptable salts, metabolites, solvates and prodrugs thereof, as shown and defined in the summary of the invention above. The compounds of Formula (II) are a subset of the compounds encompassed within the scope of Formula (I).

Rifamycins

Rifamycins are a well known class of semisynthetic antimicrobial agents. As used herein, the terms "Rifamycin" and "Rifamycins" mean both the compound identified as Rifamycin itself, as well as all derivative compounds having antimicrobial activity understood by the skilled artisan to fall within the Rifamycin class of compounds. Thus, the present invention is not restricted to a specific Rifamycin, but encompasses Rifamycin derived antimicrobial molecules having a suitable antimicrobial activity. These derivative compounds may be variously described herein as "Rifamycin derived antimicrobial molecules", "Rifamycin derived molecules", "Rifamycin derived antibacterial agents" and "Rifamycin derivatives." Such related terms have the same meaning and refer to antimicrobial agents which are part of the well known class of "Rifamycins" as described in more detail herein. Such derivative compounds are chemical analogs of Rifamycin that have antimicrobial (e.g., antibacterial) activity. These derivatives will be understood by the skilled artisan to be similar in structure to Rifamycin, but also include those chemical compounds not traditionally defined as a Rifamycin. Rifamycin derivatives include, but are not limited to, those compounds of Formula (IA) of the present invention. Specific examples include Rifampin (also commonly spelled as Rifampicin) (U.S. Pat. No. 3,342,810), Rifapentin (U.S. Pat. No. 4,002,752), Rifandin (U.S. Pat. No. 4,353,826), Rifabutin (U.S. Pat. No. 4,219,478), Rifalazil (U.S. Pat. No. 4,983,602) and Rifaximin (U.S. Pat. No. 4,341,785) as well as other Rifamycin derivatives and hybrids, such as those described in United States patent application publications 2003/0105086, 2005/0043298, 2005/0143374, 2005/0203076, 2005/0203085, 2005/0209210, 2005/0256096, 2005/0261262, 2005/0277633, 2006/0019985 and 2006/0019986, and those described in WIPO publications WO 03/045319, WO 03/051299, WO 2004/034961 and WO 2005/062882.

Examples of suitable Rifamycins and Rifamycin derived antimicrobial molecules A for use in the present invention include, but are not limited to, those Rifamycins and Rifamycin derived antimicrobial molecules encompassed within Formula (IA), as defined in the summary of the invention above. Further examples of suitable Rifamycins include the compounds of Formula (IB), Formula (IC), Formula (ID), Formula (IE), and Formula (IF) shown and defined in the summary of the invention above.

Additional Rifamycins and Rifamycin derived antimicrobial molecules A that may be used in the present invention include the following: Rifampicin, its quinone form, its deacetylated form and the deacetylated form of its quinone form; the hydrazone of 1-amino-4-(2-hydroxyethyl)piperazine and 3-formyl Rifamycin S, its quinone form, its deacetylated form and the deacetylated form of its quinone form; Rifabutin and its deacetylated form; Rifapentin, its quinone form, its deacetylated form and the deacetylated form of its quinone form; Rifalazil and its deacetylated form; Rifamixin and its deacetylated form; Rifandin, its quinone form, its deacetylated form and the deacetylated form of its quinone form; 1',4-Didehydro-1-deoxy-1,4-dihydro-3'-hydroxy-5'-[4-(2-hydroxyethyl)-1-piperazinyl]-1-oxorifamycin VIII and its deacetylated form; 1',4-Didehydro-1-deoxy-1,4-dihydro-3'-hydroxy-5'-[4-hydroxy-1-piperidinyl]-1-oxorifamycin VIII and its deacetylated form; 1',4-Didehydro-1-deoxy-1,4-dihydro-3'-hydroxy-5'-[4-piperazinyl]-1-oxorifamycin and its deacetylated form. The chemical structures of these molecules are illustrated hereinafter. Arrows indicate preferred sites for attachment of the phosphonated group.

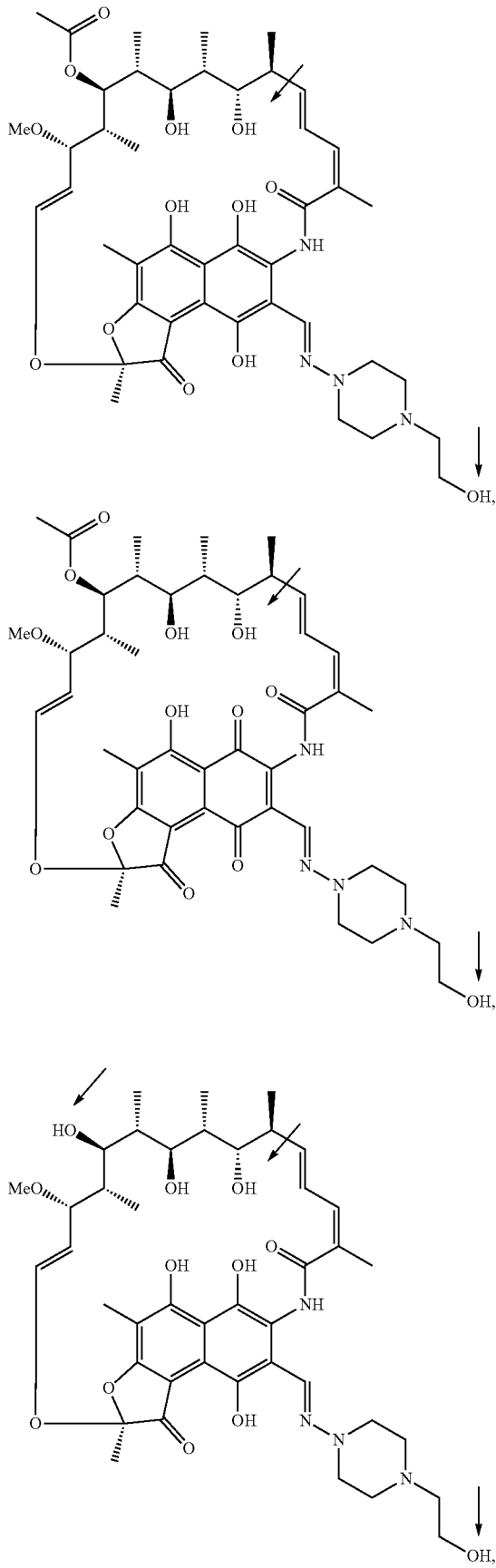

67
-continued
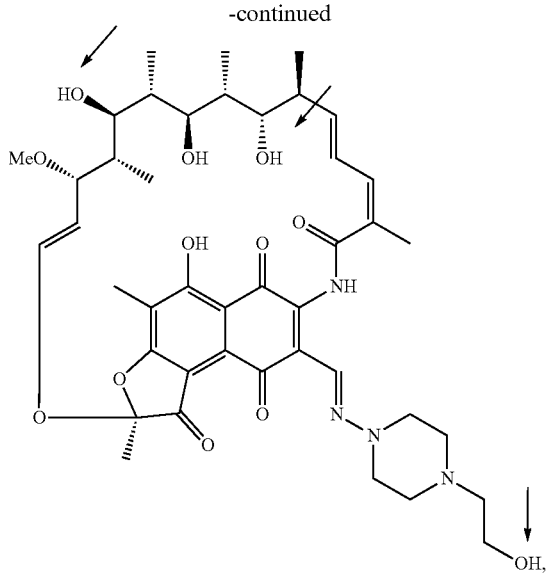
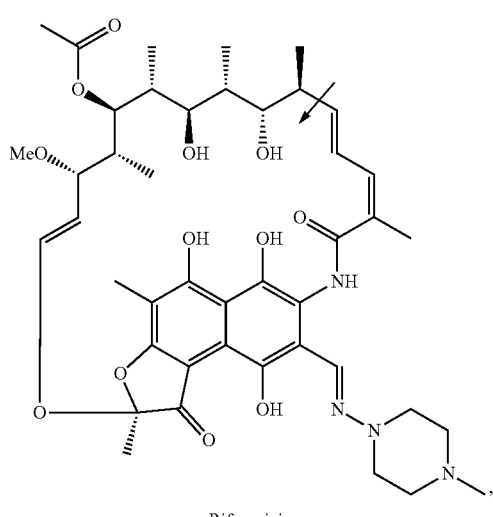
Rifampicin
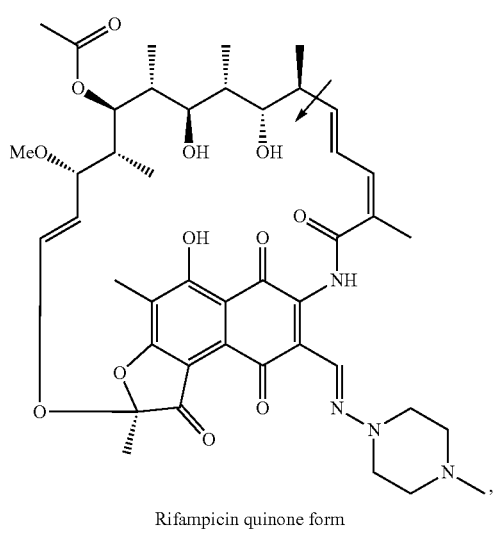
Rifampicin quinone form
68
-continued
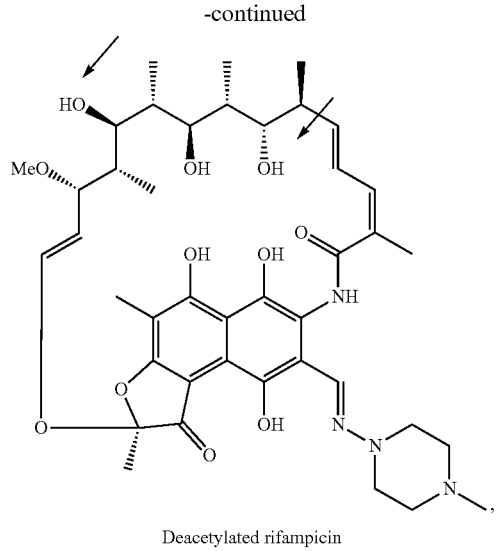
Deacetylated rifampicin
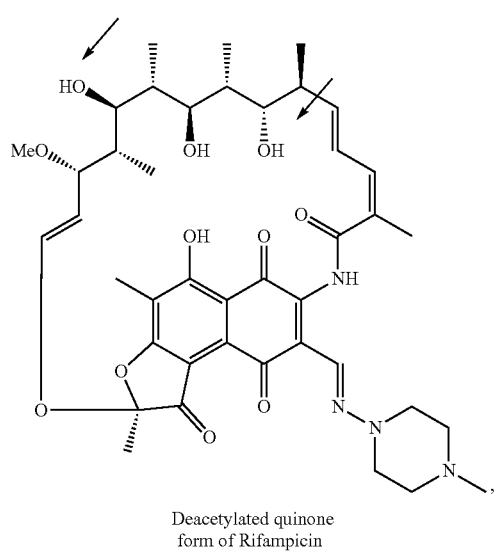
Deacetylated quinone
form of Rifampicin
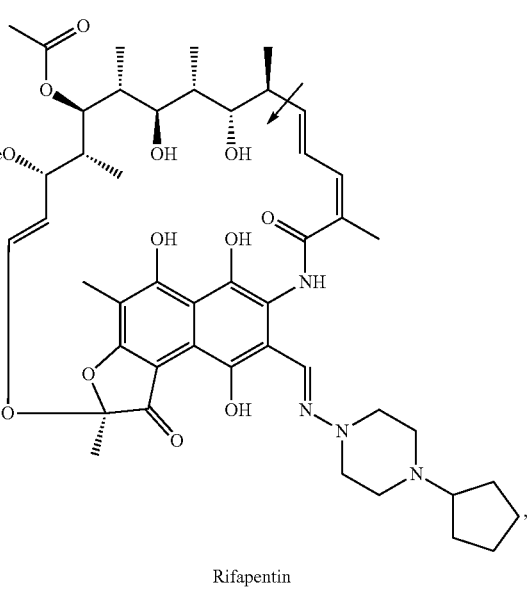
Rifapentin 69
-continued
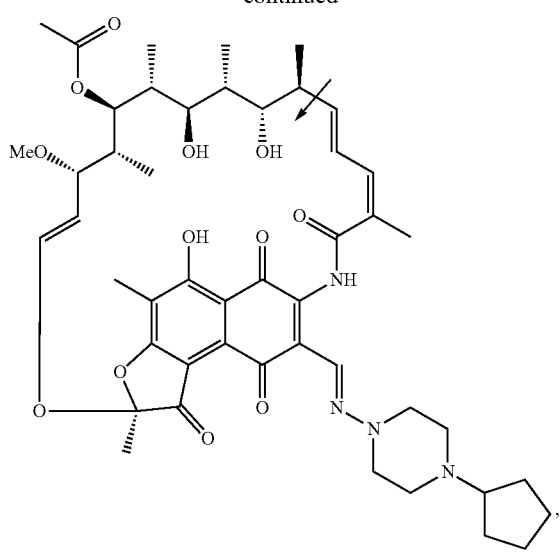
Rifapentin quinone form
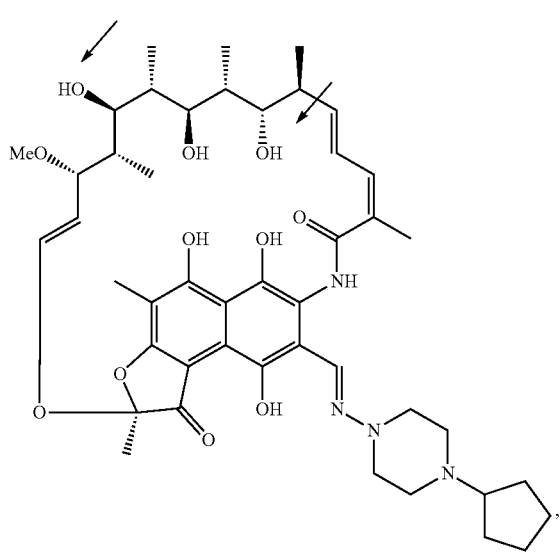
Deacetylated rifapentin
70
-continued
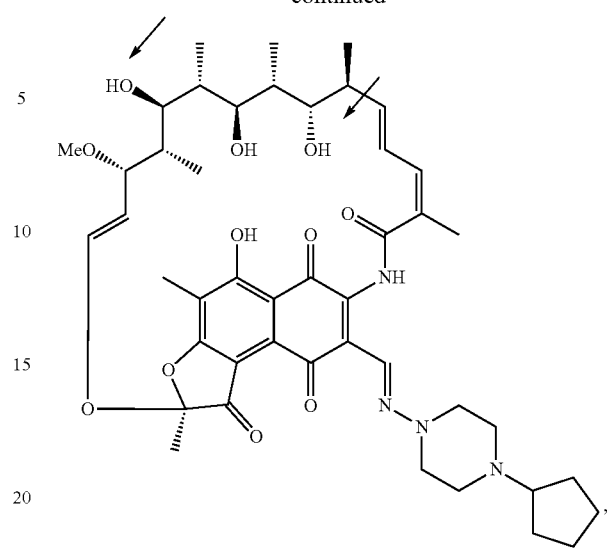
Deacetylated quinone
form of rifapentin
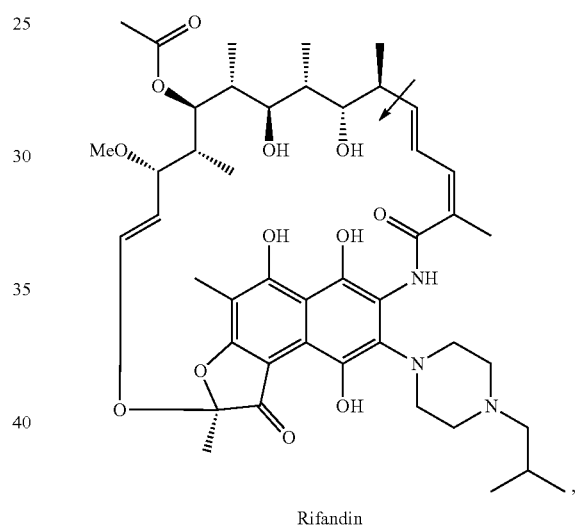
Rifandin
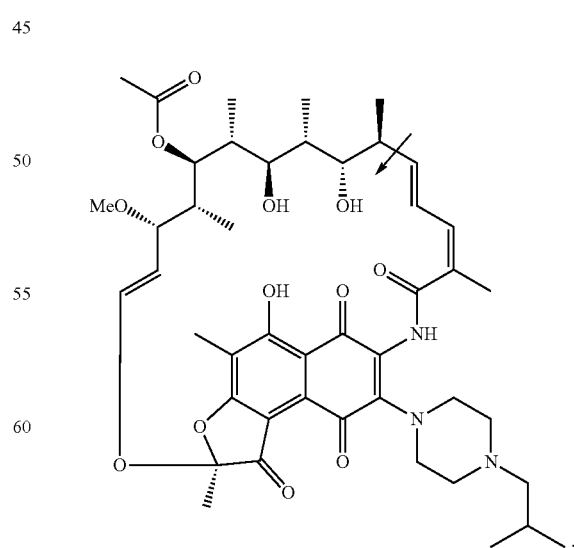
Rifandin quinone form 71
-continued
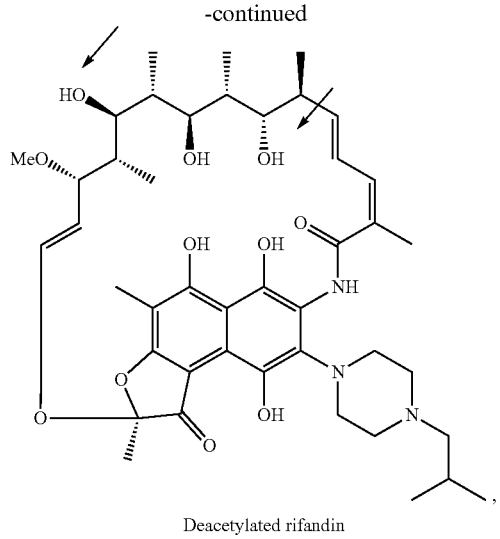
Deacetylated rifandin
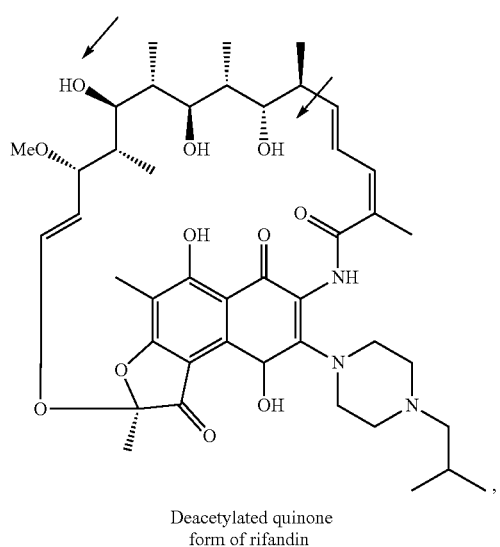
Deacetylated quinone form of rifandin
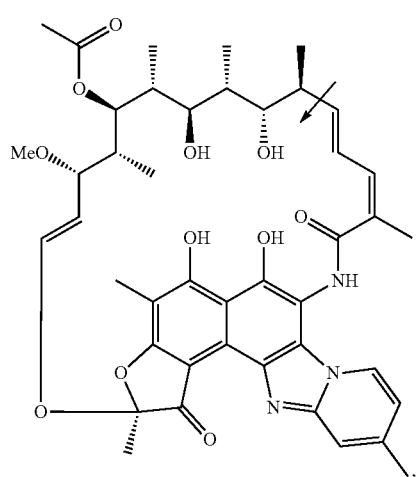
Rifamixin
72
-continued
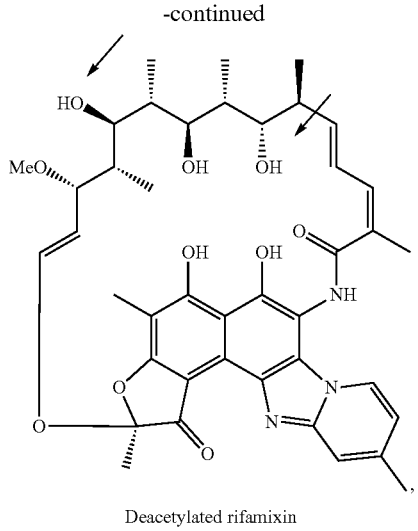
Deacetylated rifamixin
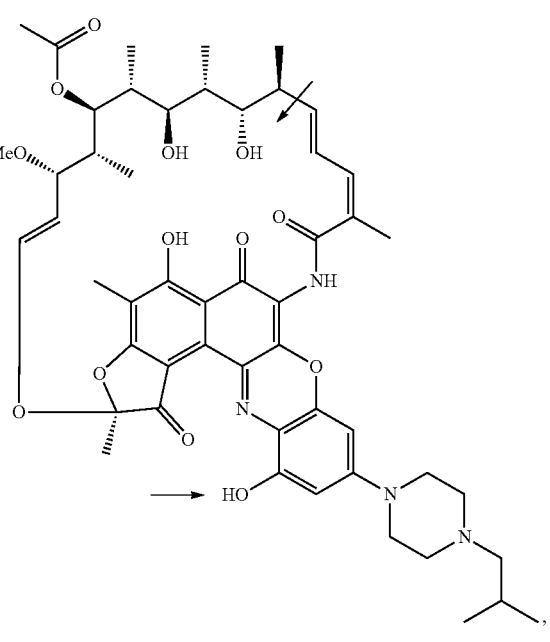
Rifalazil

73
-continued
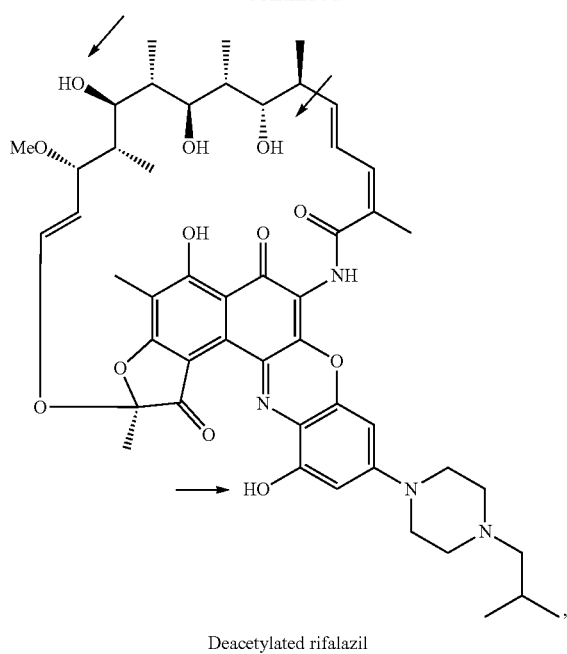
Deacetylated rifalazil
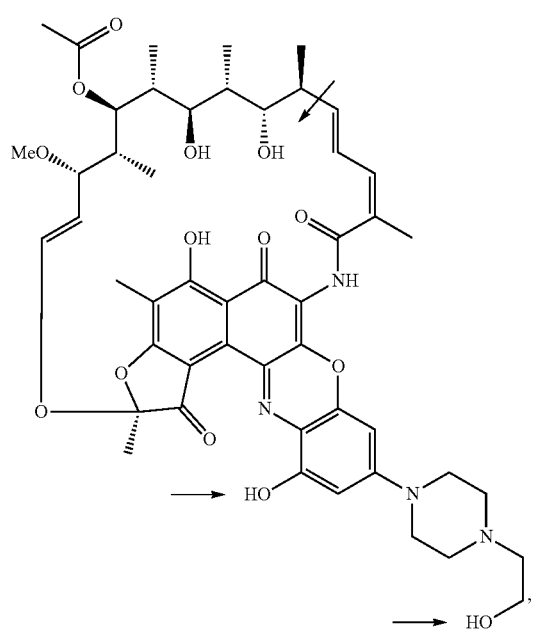
74
-continued
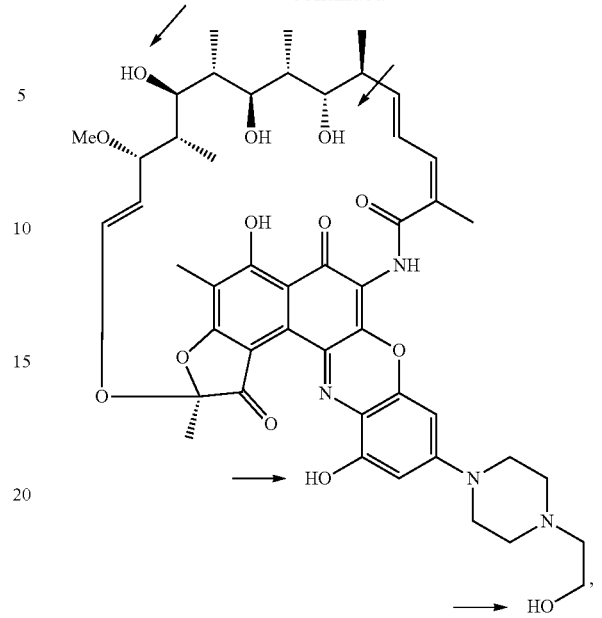
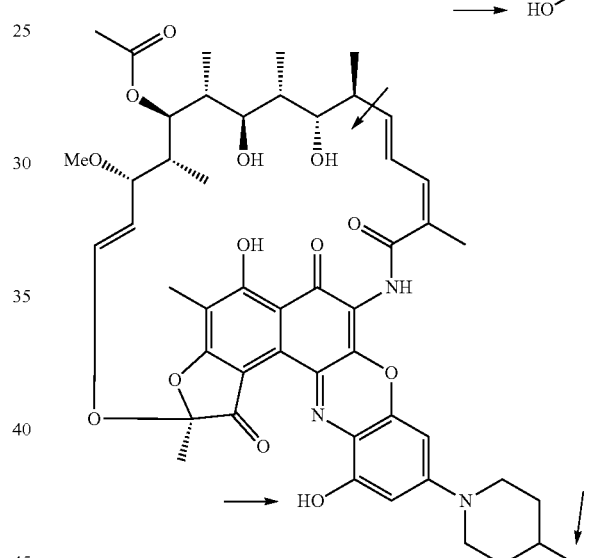
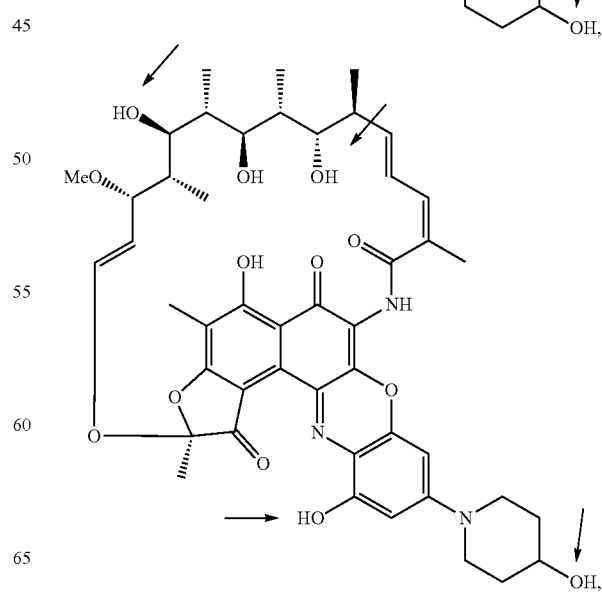

75
-continued

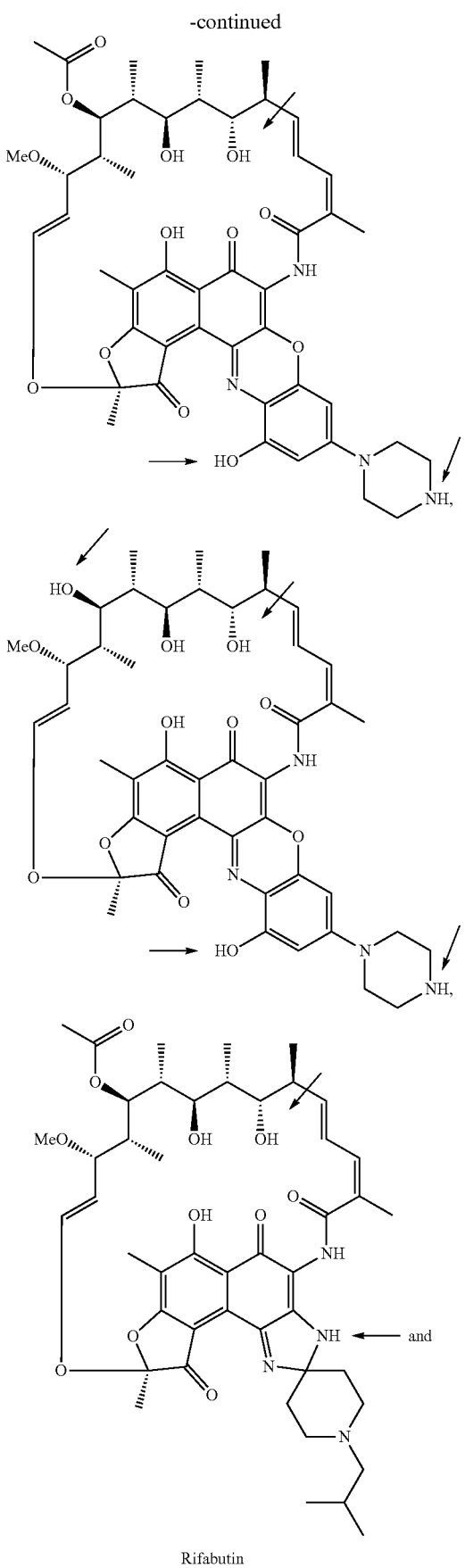

Rifabutin

76
-continued

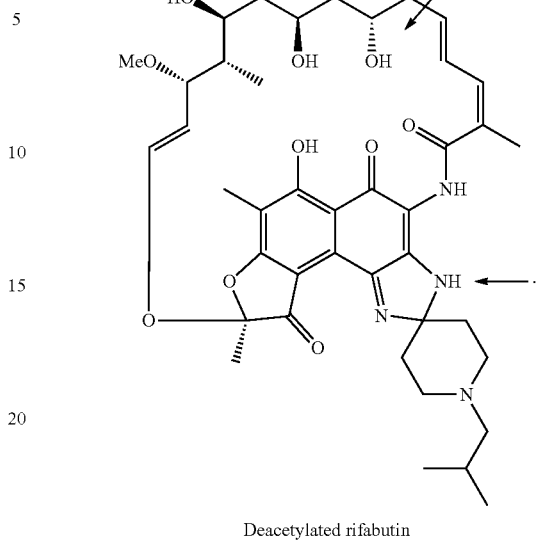

Deacetylated rifabutin

Specific examples of phosphonated Rifamycins according to the invention are also shown in the Exemplification section. Those skilled in the art will readily prepare the Rifamycin derived antimicrobial molecules according to the invention. If necessary, the skilled artisan may refer to the numerous literatures found in the art, including the US patents, PCT patent applications and scientific publications listed herein, and incorporated herein by reference.

The present invention also encompasses phosphonated Rifamycins having more than one phosphonated group. As mentioned previously, the above identified sites of attachment are only preferred sites for tethering a phosphonated group and all other potential sites (for instance on any of the hydroxyl groups of a Rifamycin) are covered by the present invention.

Linkers

As mentioned previously, the essence of the invention lies in the presence of a phosphonated group reversibly coupled to a Rifamycin via a cleavable linker for the purpose of increasing the affinity, binding, accumulation and/or retention time of the Rifamycin to or within the bones, while permitting its gradual release through the cleavage of the cleavable linker or release of the compound from the bone. The cleavage may not provide the parent rifamycin in a single step but may rely on the generation and decomposition of a transient intermediate molecular entity.

The phosphonated group B according to the present invention is reversibly and covalently coupled to the Rifamycin A through a cleavable linker L. As used herein, the term "cleavable" refers to a group that is chemically or biochemically unstable under physiological conditions. The chemical instability preferably results from spontaneous decomposition due to a reversible chemical process, an intramolecular chemical reaction or hydrolysis (i.e. splitting of the molecule or group into two or more new molecules or groups due to the net insertion of one or more water molecules) when it depends on an intermolecular chemical reaction. Preferably, the instability is triggered by a hydrolysis step, leading to a sequence of spontaneous chemical events eventually providing the parent Rifamycin A.

Cleavage may be very rapid or very slow. For instance, the half-life of the process may be of about 1 minute, about 15 minutes, about 30 minutes, about 1 hour, about 5 hours, about 10 hours, about 15 hours, about 1 day or about 48 hours. The chemical processes leading to cleavage may be enzyme-sensitive, that is, they rely only on selected specific enzymes (e.g. amidase, esterase, metalloproteinase, etc) or may rely on other chemical events, such as but not limited to acid/base catalysis, cyclizations, eliminations, substitutions or self-cleavage. For instance, an esterase-dependent event relying on bone-specific esterases (Goding et al. Biochim Biophys Acta (2003), 1638(1):1-19) or bone-specific metalloproteinase (MMP) (Kawabe et al., Clin Orthop. (1986) 211:244-51; Tuckermann et al., Differentiation (2001), 69(1):49-57; Sellers et al., Biochem J. (1978) 171(2):493-6) or on the action of alkaline phosphatases thereby releasing the Rifamycin at its desired site of action may be involved. Similarly, a cleavage process which does not readily occur in the plasma, thereby permitting a sufficient amount of the phosphonated Rifamycin to reach and accumulate within the osseous tissues before releasing the Rifamycin, may be involved.

As an example, the rate of cleavage may be selected such that only 1%, 5%, 10%, 15%, 20%, 25%, 30%, 35%, 40%, 50%, 60%, or 70% of the bone-bonded antibiotic is released through a time period extending to 1 minute, 15 minutes, 30 minutes, 1 hour, 5 hours, 10 hours, 15 hours, 1 day, 2 days, 3 days, 4 days, 5 days, 6 days 7 days, one week, two weeks, three weeks or more following administration of the compound of the invention. Preferably, the rate of cleavage is selected such that only about 1% to about 25% of the bone-bonded Rifamycin is released per day. The choice of the particular means of coupling the Rifamycin A to the phosphonated group B may vary according to factors such as (i) the site of attachment of the phosphonated group to the Rifamycin, (ii) the type of phosphonated group used; (iii) the type of Rifamycin used, and (iv) the desired ease of cleavage and associated release of the Rifamycin.

Preferably, the phosphonated group B is coupled to the Rifamycin A through one or more hydroxyl groups on A, through one or more nitrogen atoms on A, through one or more sulhydryl groups on A, or a combination of one or more hydroxyl groups, one or more nitrogen atoms, and/or one or more sulhydryl groups, on A.

The present invention includes the use of a pH-sensitive linker that is cleaved only at a predetermined range of pH. In one embodiment, the pH-sensitive linker is a base-sensitive linker that is cleaved at a basic pH ranging from about 7 to about 9. According to another embodiment, the linker is an acid-sensitive linker that is cleaved at an acidic pH ranging from about 7.5 to about 4, preferably from about 6.5 and lower. It is hypothesized that such an acid-sensitive linker would allow a specific release of the Rifamycin A mostly at a site of bacterial infection because it is known that acidification of tissues commonly occurs during infection (O'Reilley et al., Antimicrobial Agents and Chemotherapy (1992), 36(12): 2693-97).

For the sake of brevity, in some aspects the cleavable linkers L are described herein in the context of the linker and associated phosphonated group(s) B, i.e., as -L-B groups. Examples of -L-B groups suitable for use in conjunction with a Rifamycin or Rifamycin derived antibiotic molecule A to form the antimicrobial compounds of the present invention include, but are not limited to, those defined by and encompassed within Formula (Ia), Formula (BL$_1$), Formula (BL$_2$), Formula (BL$_3$), Formula (BL$_4$), Formula (BL$_5$), Formula (BL$_6$) and Formula (BL$_7$) shown and defined in the summary of the invention above.

Specific -L-B groups that are suitable for use in the present invention include:

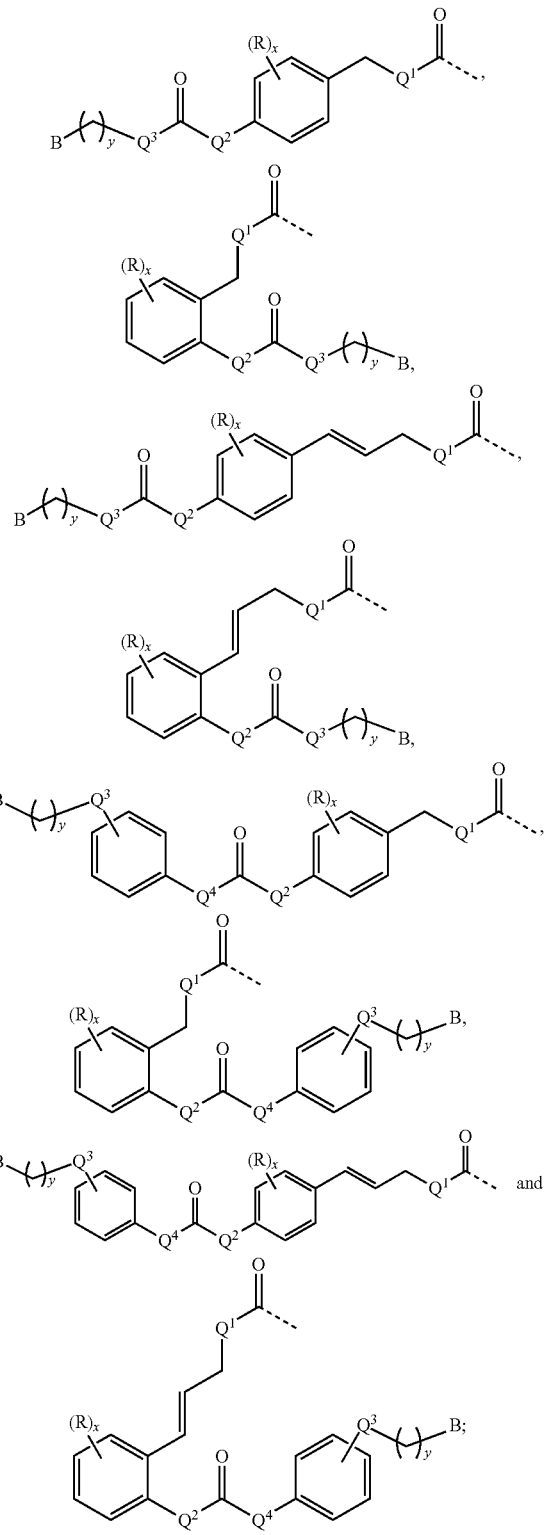

wherein,
B is a phosphonated group;
Q$^1$ is —O— or —S—;
Q$^2$ is —O—, —S— or —N(R$_L$)—;

$Q^3$ is —O—, —S—, —N($R_L$)— or —CH$_2$—;

$Q^4$ is —O—, —S—, —N($R_L$)—, —CH$_2$— or a covalent bond;

each R is independently selected from the group consisting of chloro, bromo, fluoro, iodo, nitro, trifluoromethyl and $C_mH_l$, where m is an integer such that $0 \leq m \leq 6$ and l is an integer $\leq 2m+1$;

each $R_L$ is $C_mH_l$, where m is an integer such that $0 \leq m \leq 6$ and l is an integer $\leq 2m+1$;

x is 1, 2, 3 or 4; and y is an integer $\leq 10$.

In certain embodiments of the invention, one or more, or all, of the following groups -L-B is specifically excluded from being used in conjunction with a Rifamycin or Rifamycin derived antibiotic molecule A to form an antimicrobial compound of the present invention:

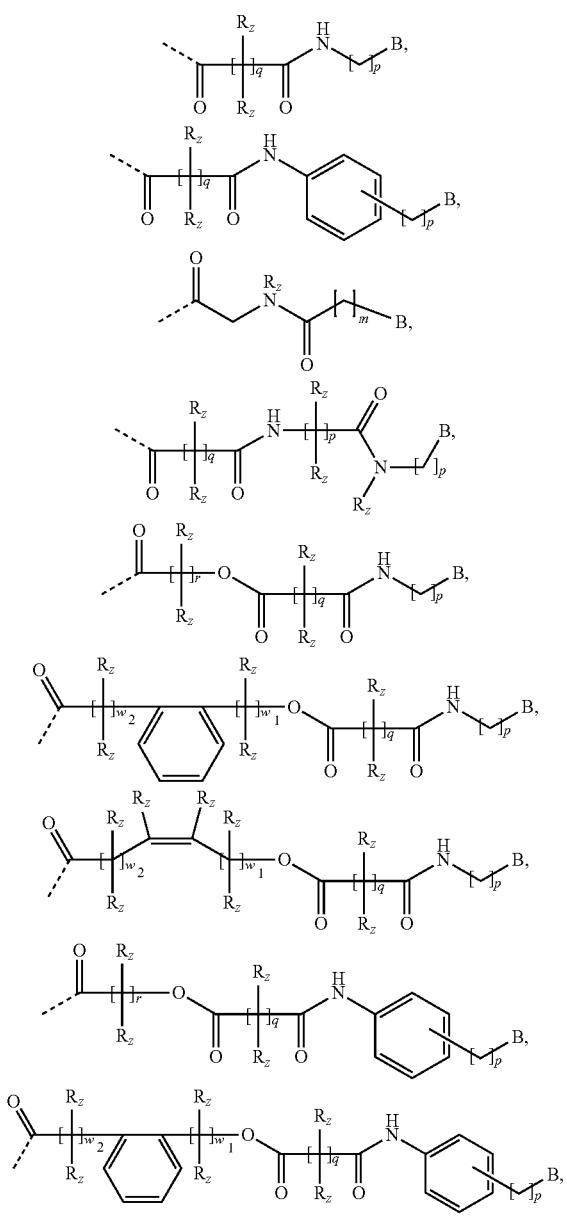

-continued

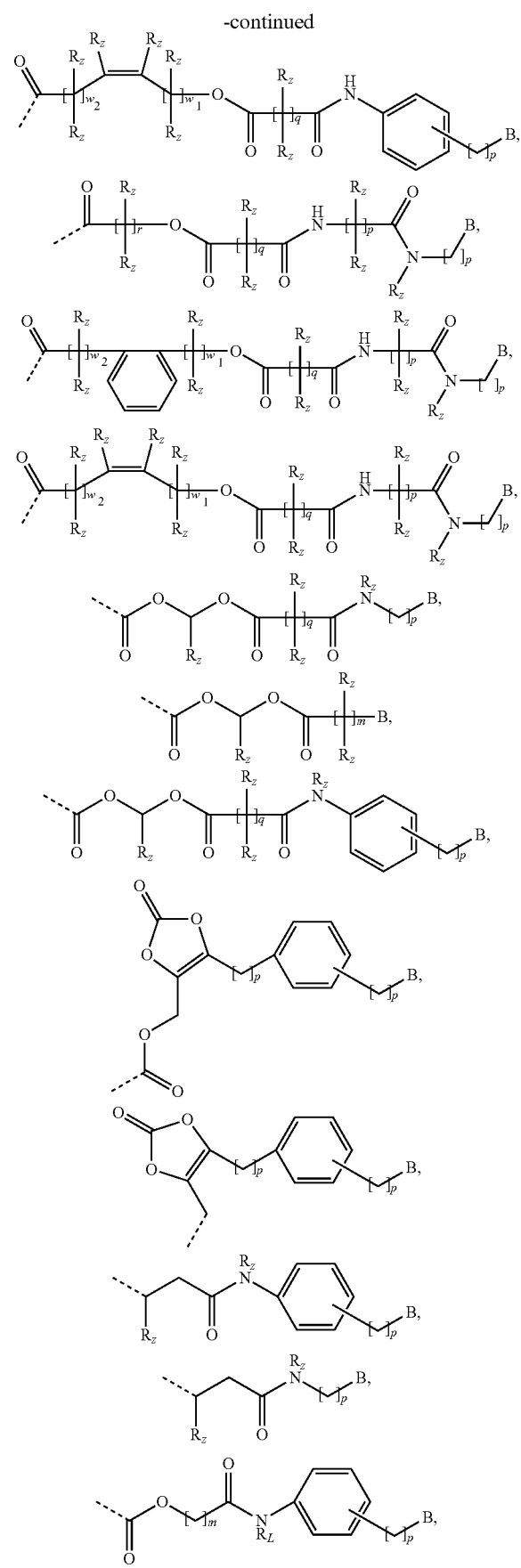

-continued

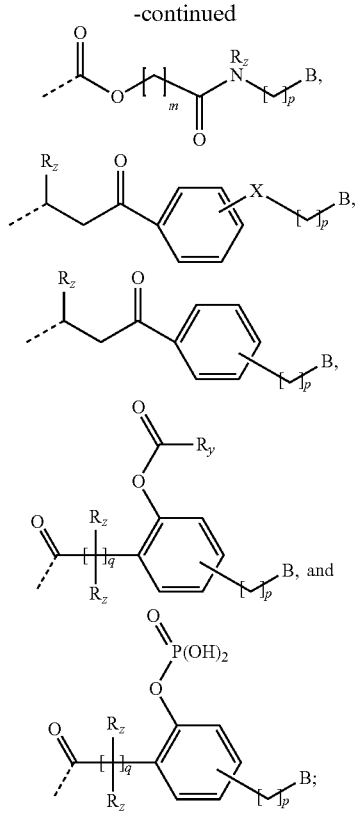

wherein:
each $R_Z$ is independently H, ethyl or methyl;
$R_L$ independently H, ethyl or methyl;
$R_Y$ is represented by $C_iH_j$, where i is an integer $\leq 20$ and j is an integer $\leq 2i+1$;
X is independently —O—, —S— or —N(R)—;
B is a phosphonated group selected from the group consisting of:

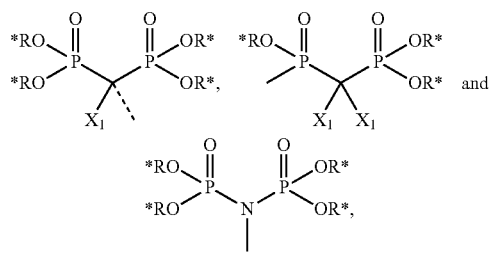

wherein:
each R* is independently selected from the group consisting of H, lower alkyl, cycloalkyl, aryl and heteroaryl, with the proviso that at least two R* are H;
each $X_1$ is independently selected from the group consisting of H, OH, $NH_2$, and a halo group;
each p is independently 0 or an integer $\leq 10$;
q is 2 or 3;
m is an integer $\leq 10$;
r is 1, 2, 3, 4 or 5; and
$w_1$ and $w_2$ are each integers $\geq 0$ such that their sum ($w_1 + w_2$) is 1, 2 or 3.

Phosphonates

As used herein, the term "phosphonated group" refers to any compound non-toxic to humans having at least one phosphorus atom bonded to at least three oxygen atoms and having a measurable affinity to osseous tissues as described herein. All non-toxic phosphonated groups having a high affinity to bone due to their ability to bind the $Ca^{2+}$ ions found in the hydroxyapatite forming the bone tissues are suitable according to the present invention. Suitable examples of phosphonated groups can be found in WO 04/026315 (Ilex Oncology Research), U.S. Pat. No. 6,214,812 (MBC Research), U.S. Pat. No. 5,359,060 (Pfizer), U.S. Pat. No. 5,854,227 and U.S. Pat. No. 6,333,424 (Elizanor Pharm.), U.S. Pat. No. 6,548,042 (Arstad and Skattelbol) and WO 2004/089925 (Semaphore Pharmaceuticals).

Although monophosphonates, bisphosphonates, and tris- or tetraphosphonates can be used, bisphosphonates are preferred. Preferably, the phosphonated group B is the bisphosphonate —CH(P(O)(OH)$_2$)$_2$. As shown in Example 3 hereinafter, Rifamycins possessing such a bisphosphonate group have a strong binding affinity for bone powder. Of course, other types of phosphonated groups could be selected and synthesized by those skilled in the art. For instance the phosphonated group may be an esterase-activated bisphosphonate radical (Vepsalainen J., Current Medicinal Chemistry, 9, 1201-1208, 2002) or be any other suitable prodrug thereof. These and other suitable phosphonated groups are encompassed by the present invention.

Examples of bisphosphonate and trisphosphonate groups suitable for use as the phosphonated group B of the present invention include but are not limited to those having the formula:

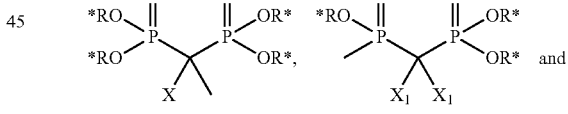

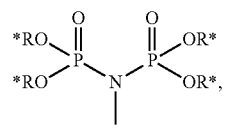

wherein:
each R* is independently selected from the group consisting of H, lower alkyl, cycloalkyl, aryl and heteroaryl, with the proviso that at least two, preferably three, R* are H;
X is H, OH, $NH_2$, or a halo group; and
$X_1$ are both H, or each is independently selected from the group consisting of H, OH, $NH_2$, and a halo group.

The present invention also includes the use of a single phosphonated group coupled to two or more antibacterial molecules. In such circumstances, the antibacterial molecules may be the same (e.g. two molecules of a Rifamycin) or different (e.g. one molecule of the fluoroquinolone antibacterial ciprofloxacin (Cipro®; U.S. Pat. No. 4,670,444) and one molecule of a Rifamycin). The phosphonated group may also be tethered to similar groups (e.g. the hydroxyl groups) or to different groups (e.g. the carboxyl group of one fluoroquinolone molecule and the hydroxyl group of a Rifamycin).

A non-limiting list of useful antibiotics with which the compounds of the present invention might be coupled through a single phosphonated group includes: sulfonamides, beta-lactams, tetracyclines, chloramphenicol, aminoglycosides, macrolides, glycopeptides, streptogramins, quinolones, fluoroquinolones, oxazolidinones and lipopeptides. In particular, tetracycline, tetracycline derived antibacterial agents, glycylcycline, glycylcycline derived antibacterial agents, minocycline, minocycline derived antibacterial agents, oxazolidinone antibacterial agents, aminoglycoside antibacterial agents, quinolone antibacterial agents, vancomycin, vancomycin derived antibacterial agents, teicoplanin, teicoplanin derived antibacterial agents, eremomycin, eremomycin derived antibacterial agents, chloroeremomycin, chloroeremomycin derived antibacterial agents, oritavancin, an oritavancin derived antibacterial agent, daptomycin, and daptomycin derived antibacterial agents are preferred.

Because of its high affinity to osseous tissues, the phosphonated group B will likely remain bound to the bones for an extended period of time (up to several years). Therefore, it is very important that the phosphonated group be endowed with low or preferably no measurable toxicity. According to another embodiment, the phosphonated group B and the linker L are selected such that the linker is hydrolyzed or cleaved in vivo (preferably mostly in osseous tissues) thereby releasing: (i) the Rifamycin A and (ii) a chosen non-toxic phosphonated molecule having a proven bone therapeutic activity. Such compounds would thus have a double utility that is to: 1) provide locally to the bones, for an extended period of time and/or at increased concentrations, an antibiotic useful in preventing and/or treating a bacterial bone infection, and 2) provide to the bones a drug stimulating bone regeneration or inhibiting bone resorption, thereby facilitating bone recovery from damages caused by an infection or other injury. Suitable phosphonated molecules with proven bone therapeutic activity useful according to the invention include but are not limited to risedronate and olpadronate (and others such as pamidronate, alendronate, incadronate, etidronate, ibandronate, zolendronate or neridronate), these molecules being well known bisphosphonate bone resorption inhibitors commonly used for the treatment of osteoporosis.

The scheme below illustrates the principles of that embodiment:

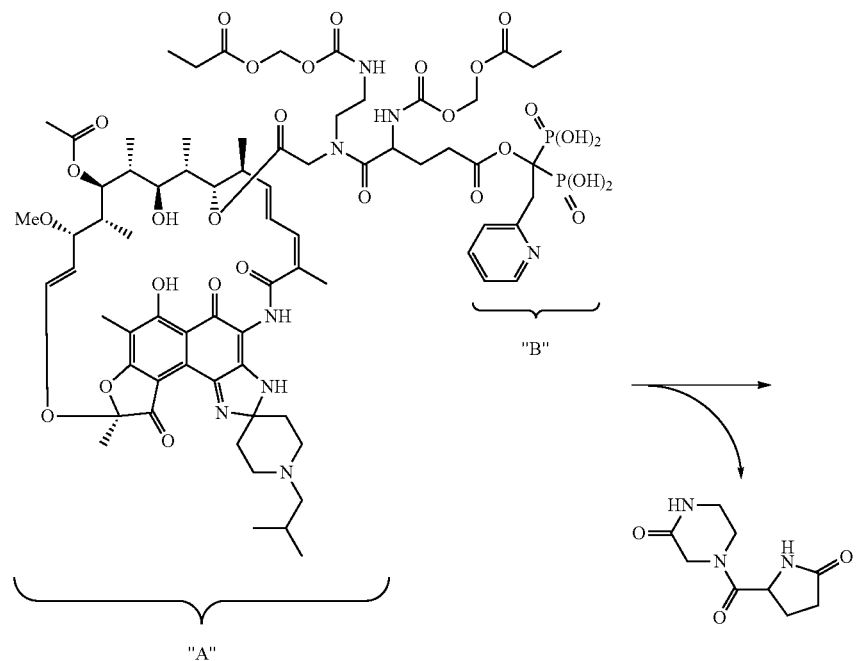

-continued

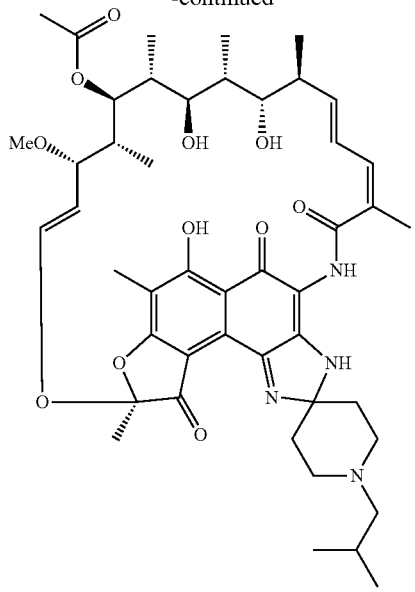

Rifabutin

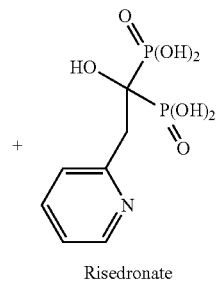

Risedronate

In addition to those compounds described hereinbefore and in the Exemplification section, including the compounds encompassed within Formula (I) and Formula (II), specific compounds encompassed within the scope of the invention (and within the scope of Formula (I)) include the compounds (18), (19), (28), (36), (42), (48a), (48b), (52), (59), (66), (71), (79a), (79b), (89), (95), (102), (110), (118), (128), (138), (140), (142a), (142b), (147), (150), (155) and (164) shown in the summary of the invention.

In addition to the compounds of Formula (I) and Formula (II), and compounds (18), (19), (28), (36), (42), (48a), (48b), (52), (59), (66), (71), (79a), (79b), (89), (95), (102), (110), (118), (128), (138), (140), (142a), (142b), (147), (150), (155) and (164), the invention encompasses pharmaceutically acceptable salts, metabolites, solvates and prodrugs of these compounds. While salts, metabolites, solvates and prodrugs are discussed below, the skilled artisan will understand that "pharmaceutically acceptable" means suitable for administration to a subject, such as a mammal, preferably a human.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such as p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum, and lithium.

In the case of compounds, salts, prodrugs or solvates that are solids, it is understood by those skilled in the art that the inventive compounds, salts, prodrugs and solvates may exist in different crystal forms, all of which are intended to be within the scope of the present invention.

A "pharmaceutically acceptable active metabolite" refers to a pharmacologically active product produced through metabolism in the body of a compound of Formula (I) or Formula (II) as defined herein.

A "pharmaceutically acceptable solvate" refers to a solvate that retains the biological effectiveness and properties of the biologically active components of compounds of Formula (I) and/or Formula (II). Examples of pharmaceutically acceptable solvates include, but are not limited to water, isopropanol, ethanol, methanol, DMSO, ethyl acetate, acetic acid, and ethanolamine.

A "prodrug" refers to a compound that can undergo processing to release an active drug molecule. Compounds of Formula (I) and Formula (II) according to the invention are prodrugs as the linker L may be cleaved to release a Rifamycin. In particular, prodrugs of the present invention include compounds which release, in vivo, an active parent drug (i.e., compounds of Formula (IA) as defined herein) when such prodrug is administered to a subject.

Prodrugs also include complex prodrug compounds that undergo two or more events in prodrug processing. According to this embodiment, complex prodrugs would release, upon processing, a compound of Formula (I) or Formula (II) (itself a prodrug) that in turn undergoes cleavage to release a desired Rifamycin.

Complex prodrug compounds according to the present invention may be prepared by modifying functional groups present in phosphonated Rifamycins, such as hydroxy and amino groups. Examples of complex prodrugs include, but are not limited to, esters (e.g., acetate, formate, and benzoate derivatives) and carbamates (e.g., N,N-dimethylaminocarbonyl) of hydroxy functional groups of phosphonated Rifamycins. Examples of prodrugs of the present invention thus include in vivo hydrolyzable esters of a compound of Formula (I) and/or of Formula (II).

An in vivo hydrolyzable ester of a compound of Formula (I) and/or of Formula (II) containing carboxy or hydroxy group is, for example, a pharmaceutically-acceptable ester which is hydrolyzed in the human or animal body to produce the parent acid or alcohol. Suitable pharmaceutically-acceptable esters for carboxy include (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolen-2-onylmethyl esters, for example 5-methyl-1,3-dioxolen-2-onylmethyl; and (1-6C)alkoxycarbonyloxyethyl esters, for example 1-methoxycarbonyloxyethyl, and may be formed at any carboxy group in the compounds of this invention.

An in vivo hydrolyzable ester of a compound of Formula (I) and/or of Formula (II) containing a hydroxy group includes inorganic esters such as phosphate esters and alpha-acyloxyalkyl ethers and related compounds which as a result of in vivo hydrolysis of the ester break down to give the parent hydroxy group. Examples of alpha-acyloxyalkyl ethers include acetoxymethoxy and 2,2-dimethylpropionyloxymethoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The inventive compounds of the invention may also exist as single stereoisomers, racemates and/or mixtures of enantiomers and/or diastereomers. All such single stereoisomers, racemates and mixtures thereof are intended to be within the scope of the present invention. Preferably, the inventive compounds are used in optically pure form.

C) Pharmaceutical Compositions

The compounds of the present invention may be formulated for administration to a subject, such as a human, as pharmaceutical compositions. The pharmaceutical compositions of the invention comprise at least one compound of Formula (I) or (II), or a pharmaceutically acceptable salt, metabolite, solvate or prodrug thereof, in combination with a pharmaceutically acceptable carrier or excipient. Preferably, the compound of the present invention in a pharmaceutical composition is a therapeutically effective amount of the compound.

Pharmaceutically acceptable carriers and excipient are those compounds, solutions, substances or materials that can be used to produce formulations of the antimicrobial compounds of the present invention that are suitable for administered to a subject. In particular, carriers and excipients of the present invention are those useful in preparing a pharmaceutical composition that is generally safe, non-toxic and neither biologically nor otherwise undesirable, and that may present pharmacologically favorable profiles, and includes carriers and excipient that are acceptable for veterinary use as well as human pharmaceutical use. Suitable pharmaceutically acceptable carriers and excipients are well known in art and can be determined by those of skill in the art as the clinical situation warrants. The skilled artisan will understand that diluents are included within the scope of the terms carriers and excipients.

Examples of suitable carriers and excipients include saline, buffered saline, dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717), hydrophilic and hydrophobic carriers, and combinations thereof. Hydrophobic carriers include, for example, fat emulsions, lipids, PEGylated phospholids, polymer matrices, biocompatible polymers, liposheres, vesicles, particles, and liposomes. The terms specifically exclude cell culture medium. More particularly: (1) Dulbecco's phosphate buffered saline, pH about 7.4, containing about 1 mg/ml to 25 mg/ml human serum albumin, (2) 0.9% saline (0.9% w/v NaCl), (3) 5% (w/v) dextrose, or (4) water, may be used.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

The particular carrier, diluent or excipient used will depend upon the means and purpose for which the active ingredient is being applied.

Pharmaceutically acceptable excipients also include tonicity agents that make the pharmaceutical composition compatible with blood. Tonicity agents are particularly desirable in injectable formulations.

Acceptable methods for preparing the pharmaceutical compositions according to the invention are known to those skilled in the art. For example, pharmaceutical compositions may be prepared following conventional techniques of the pharmaceutical chemist involving steps such as mixing, granulating, and compressing when necessary for tablet forms, or mixing, filling, and dissolving the ingredients as appropriate, to give the desired products for various routes of administration.

D) Methods for Inhibiting Bacterial Growth

According to a related aspect, the present invention concerns methods of inhibiting bacterial growth. The method comprises contacting the bacteria for the purpose of such inhibition with an effective amount of a phosphonated Rifamycin compound according to the invention or a pharmaceutical composition comprising one or more compounds according to the invention (or a pharmaceutically acceptable salt, metabolite, solvate or prodrug thereof). For example, one can inhibit bacterial RNA polymerase, bacterial RNA polymerase dependent DNA transcription and/or bacterial translation by contacting a bacterium with a compound of the invention.

The contacting may be carried out in vitro (e.g., in laboratory tissue cultures, in biochemical and/or cellular assays), in vivo in a non-human animal, in vivo in mammals, including humans and/or ex vivo (e.g. for sterilization purposes).

The activity of the inventive compounds as inhibitors of DNA transcription and/or translation may be measured by any of the methods available to those skilled in the art, including in vivo and in vitro assays. Examples of assays of bacterial RNA polymerase enzymes have been described in U.S. Pat. No. 5,635,349 and by Sawadogo and coworkers (Proc. Natl. Acad. Sci. USA (1985), 82:4394-4398), Doan and coworkers (FEMS Microbiol. Lett. (2001), 196:135-139) and Wu and coworkers (Anal. Biochem. (1997), 245:226-230).

E) Methods of Treatment

A related aspect of the invention concerns the use of a compound of the invention as an active ingredient in a pharmaceutical, therapeutic or anti-bacterial composition for treatment purposes. Thus the invention includes methods of treating bacterial infections through the administration of a pharmaceutically effective amount of at least one compound of the invention (i.e., the compounds of Formula (I) and (II)) to a subject in need of treatment. Preferably, the compounds of the invention are administered to the subject in the form of a pharmaceutical composition, as defined herein. The terms "treating" and "treatment" mean at least the mitigation of a disease condition or symptom associated with a bacterial infection in a subject, including mammals such as a human, that is achieved by a reduction of growth, replication, and/or propagation of any bacterium, such as Gram-positive or Gram-negative organisms, and includes curing, healing, inhibiting, relieving from, improving and/or alleviating, in whole or in part, the disease condition. The mitigation may be about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. Non-limiting examples of the methods of the invention are provided above in the summary of the invention.

The invention also includes methods of preventing bacterial infections in a subject through the administration of a pharmaceutically effective amount of at least one compound of the invention (i.e., the compounds of Formula (I) and (II)) to a subject in need of prevention. Preferably, the compounds of the invention are administered to the subject in the form of a pharmaceutical composition, as defined herein. The terms "prevent" and "prevention" mean blocking or stopping a disease condition associated with a bacterial infection from developing in a mammal, preferably a human. Such methods may be practiced, for example, on subjects having a higher risk for bacterial infection than the general population, including patients undergoing treatment for bacterial infections whereby normal gut flora is inhibited by antimicrobial therapy, patients with impaired immune function (e.g., immunoglobulin deficiency, splenic dysfunction, splenectomy, HIV infection, impaired leukocyte function, hemoglobinopathies), the elderly (Loo et al., 2005. NEJM 353:2442), people with certain malignancies (e.g., multiple myeloma, chronic lympocytic leukemia, lymphoma), people at increased occupational risk (e.g., public services workers, such a fire, water, sanitary, police, medical, and laboratory workers, hospital workers), people in closed populations (e.g., prisons, military, nursing homes) and others that have immunological deficiencies that might enhance their susceptibility to bacterial infection. The prevention may be protection of about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. The prevention lasts at least about 0.5, 1, 2, 3, 4, 5, 6, 7, 8, 9, 10, 12, 14, 16, 18, 20, 25, 30, 35, 40, 45, 50 or more days after administration of a pharmaceutical composition.

In order to prevent infection, the compound(s) of the invention could be administered once, twice, thrice or more, from 1, 2, 3, 4, 5, 6, 7 days or more, up to 10, 9, 8, 7, 6, 5, 4, 3, 2, or 1 hour or less before the subject has the potential to be exposed to the bacteria. Non-limiting examples of the methods of the invention are provided above in the summary of the invention.

An additional use that is particularly contemplated for the compounds of the invention is for prophylaxis purposes. Indeed, many surgeons consider that humans should be considered for antibiotic prophylaxis before a medical procedure to mitigate the potential for an infection resulting from ineffective sterility during the procedure. Deep infection is a serious complication sometimes requiring subsequent medical intervention and it is accompanied by significant morbidity and mortality. The compounds and compositions of the invention may therefore be used as a replacement for, or in addition to, prophylactic antibiotics in this situation. For instance, the compounds and/or compositions of the invention may be administered by injection to achieve a systemic and/or local effect against relevant bacteria shortly before an invasive medical treatment, such as surgery or insertion of an in-dwelling device (e.g. joint replacement (hip, knee, shoulder, etc.)). Treatment may be continued after invasive medical treatment, such as post-operatively or during the in-body time of the device. In addition, the compounds and/or pharmaceutical compositions may also be administered before the invasive medical treatment to permit the accumulation of the compound into the bone tissues prior to the treatment.

Thus, the invention also includes methods of providing propylaxis for bacterial infections in a subject through the administration of a prophylactically effective amount of at least one compound of the invention (i.e., the compounds of Formula (I) and (II)) to a subject in need of propylaxis. Preferably, the compounds of the invention are administered to the subject in the form of a pharmaceutical composition, as defined herein. Non-limiting examples of the methods of the invention are provided above in the summary of the invention.

The term "prophylaxis" is intended to mean at least a reduction in the likelihood that a disease condition associated with a bacterial infection will develop in a mammal, preferably a human. In particular, the term is related to the treatment of a mammal to reduce the likelihood of the occurrence of a bacterial infection, such as bacterial infection that may occur during or following a surgery involving bone reparation or replacement. The term also includes reducing the likelihood of a bacterial infection when the mammal is found to be predisposed to having a disease condition but not yet diagnosed as having it. For example, one can reduce the likelihood of a bacterial infection in a mammal by administering a compound of Formula (I) or (II), or a pharmaceutically acceptable salts, metabolites, solvates and prodrug thereof, before occurrence of such infection. The prophylaxis may be about a reduction of about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. The prophylaxis lasts at least about 0.5, 1, 2, 3, 4, 5, 6, 7, 8, 9, 10, 12, 14, 16, 18, 20, 25, 30, 35, 40, 45, 50 or more days after administration of a pharmaceutical composition.

In each instance, the compounds and/or pharmaceutical compositions of the present invention may be administered once, twice, thrice or more, from 1, 2, 3, 4, 5, 6, 7 days or more, to 10, 9, 8, 7, 6, 5, 4, 3, 2, or 1 hour or less before surgery for permitting an advisable systemic or local presence of the compounds, and/or accumulation in the bones, preferably in the areas potentially exposed to bacterial contamination during the surgical procedure. Even more preferably, phosphonated compounds and/or pharmaceutical compositions of the invention may be administered such that they can reach a local concentration of about 5, 10, 20, 30, 40, 50, 75, 100, 500 or even 1000 fold higher concentration than the concentration that would normally be achieved during the administration of the unmodified parent Rifamycin, i.e. a non-phosphonated equivalent. The compound(s) may be administered after the invasive medical treatment for a period of time, such as 1, 2, 3, 4, 5 or 6 days, 1, 2, 3 or more weeks, or, for example, for the entire time an in-dwelling medical device is present in the body.

The present invention also provides a method of inducing accumulation of Rifamycin in bones of a subject, such as mammal, wherein a phosphonated Rifamycin having high affinity to osseous tissues is administered to a subject. The phosphonated Rifamycin binds osseous tissues and accumulates in bones of the subject in amounts greater than amounts of a non-phosphonated equivalent of the Rifamycin. Preferably, the phosphonated group is coupled to the Rifamycin through a cleavable linker.

The invention further provides a method for prolonging the presence of a Rifamycin in bones of a subject, such as a mammal, wherein a phosphonated Rifamycin having a high affinity to osseous tissues is administered to a subejct. The phosphonated group is coupled to the Rifamycin through a cleavable linker. The phosphonated Rifamycin binds osseous tissues and accumulates in bones of the subject, and the linker is cleaved gradually within the bones thereby releasing the Rifamycin and prolonging the presence of the Rifamycin in the bones.

Although the invention is preferably directed to the prophylaxis and/or treatment of bone-related infections, the invention encompasses therapeutic and prophylactic methods against other diseases caused by or related to bacterial infection, including but not limited to otitis, conjunctivitis, pneumonia, bacteremia, sinusitis, pleural emphysema and endocarditis, low grade infections in the vicinity of calcifications of atherosclerotic vessels, and meningitis. In such methods, an effective therapeutic or prophylactic amount of a compound and/or pharmaceutical composition as defined hereinbefore, is administered to a subject (preferably a human) in an amount sufficient to provide a therapeutic effect and thereby prevent or treat the infection of the subject. Exact amounts can be routinely determined by one skilled in the art and will vary depending on several factors, such as the particular bacterial strain involved and the particular antibacterial compound used.

The pharmaceutical compositions and compounds of the present invention may be formulated, for example, for oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration.

Formulations for parenteral administration can be in the form of aqueous or non-aqueous isotonic sterile injection solutions, suspensions or fat emulsions. The parenteral form used for injection must be fluid to the extent that easy syringability exists. These solutions or suspensions can be prepared from sterile concentrated liquids, powders or granules.

Excipients used in parenteral preparations may also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Parenteral formulations using hydrophobic carriers include, for example, fat emulsions and formulations containing lipids, lipospheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of pharmaceutical compositions and compounds of the present invention can be a ready-to-use solution of the pharmaceutical compositions and compounds in a suitable carrier in sterile, hermetically sealed ampoules or in sterile pre-loaded syringes. The suitable carrier optionally comprises any of the above-mentioned excipients.

Alternatively, the unit dosage of the pharmaceutical compositions and compounds of the present invention can be in a concentrated liquid, powder or granular form for ex tempore reconstitution in the appropriate pharmaceutically acceptable carrier, such as sterile water, at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, physiological saline, phosphate buffered saline, 5% dextrose in water or Ringer's™ solution.

In intramuscular preparations, a sterile formulation of the pharmaceutical compositions of the present invention can be dissolved and administered in a pharmaceutical diluent such as Water-for-Injection (WFI), physiological saline or 5% dextrose in water. A suitable insoluble form of the pharmaceutical compositions may be prepared and administered as a suspension in an aqueous base or a pharmaceutically acceptable oil base, e.g. an ester of a long chain fatty acid such as ethyl oleate.

For oral use, the oral pharmaceutical composition may be made in the form of a unit dosage containing a therapeutically-effective amount of the pharmaceutical compositions. Solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid.

For topical use, the pharmaceutical compositions of present invention can also be prepared in suitable forms to be applied to the skin, or mucus membranes of the nose and throat, and can take the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation. Such topical formulations further can include chemical compounds such as dimethylsulfoxide (DMSO) to facilitate surface penetration of the active ingredient. Alternative means for systemic administration include transmucosal and transdermal administration using penetrants such as bile salts or fusidic acids or other detergents.

The terms "dose", "unit dose", "unit dosage", or "effective dose" refer to physically discrete units that contain a predetermined quantity of active ingredient calculated to produce a desired therapeutic effect. These terms are synonymous with pharmaceutically effective amounts, therapeutically effective amounts, prophylactically effective amounts and amounts sufficient to achieve the stated goals of the methods disclosed herein.

The pharmaceutically effective amount of the compounds of the present invention and the amounts sufficient to achieve the stated goals of the methods disclosed herein vary depending upon the physical characteristics of the subject, the severity of the subject's symptoms, the location of the bacteria, the identity of the bacteria, the formulation and the means used to administer the drug, and the method being practiced. The specific dose for a given subject is usually set by the judgment of the attending physician. However, a pharmaceutically effective and/or sufficient amount of a compound of the present invention is typically between about 0.5 mg/kg body weight to 100 mg/kg body weight, preferably from 1 to 50 mg/kg, more preferably from 5 to 30 mg/kg, regardless of the formulation. In equally preferred embodiments, a pharmaceutically effective amount used for a single dose is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 mg/kg body weight, or a range of these values, regardless of the formulation. In some situations, a dose less than 0.5 mg/kg body weight or greater than 100 mg/kg body weight may be effective.

Suitable frequencies of administration may vary based on whether administration is for the purposes of treatment, prophylaxis or prevention. Administration frequencies of doses for the treatment of a subject having a bacterial infection, or for prophylaxis or prevention of a bacterial infection, include 4, 3, 2 or once daily, every other day, every third day, every fourth day, every fifth day, every sixth day, once weekly, every eight days, every nine days, every ten days, bi-weekly, monthly and bi-monthly. In certain methods and embodiments of the present invention a single dose or infrequent dose (e.g., 2, 3, 4, 5 or six doses) can be sufficient to achieve the stated goals of the methods claimed herein. In other embodiments, the course of treatment may require the administration of many doses over many days, such as administration of a dose 4, 3, 2 or once daily over 1, 2, 3, 4, 5, 6, 7, 8, 9, 10, 11, 12, 13, 14, 15 or more days.

Depending on the means of administration, the dosage may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120 or more minutes, or a period of hours, such as about 0.5, 1, 1.5, 2, 2.5, 3, 3.5, 4, 4.5, 5 or more hours.

While the treatment can be administered in a systemic manner through the means described above, it may also be administered in a localized manner. For example, the treatment may be administered directly to a bone, such as through an injection into a bone. The treatment may also be administered in other localized manners, such as application to a wound through a topical composition or directly into a subcutaneous or other form of wound.

The active compounds, pharmaceutical compositions and pharmaceutically acceptable prodrugs, salts, metabolites and solvates may be also administered to an individual as part of a bone substitute or bone-repair compound such as bone cements or fillers (e.g. Skelite™, Millenium Biologics, Kingston, ON, Canada) and calcium or hydroxyapatite beads.

A wide range of second therapeutic agents, such as other antibiotics, can be used in combination with the compounds, pharmaceutical compositions and methods of the present invention. Antibiotics used as second therapeutic agents may act by interfering with cell wall synthesis, plasma membrane integrity, nucleic acid synthesis, ribosomal function, folate synthesis, etc. Second therapeutic agents may be included in a pharmaceutical composition comprising a phosphonated Rifamycin compound of the present invention, or may be administered concurrently with a pharmaceutical composition comprising a phosphonated Rifamycin compound of the present invention.

A non-limiting list of second therapeutic agents with which the compounds and compositions of the present invention might be combined or co-administered includes: sulfonamides, beta-lactams, tetracyclines, chloramphenicol, aminoglycosides, macrolides, glycopeptides, streptogramins, quinolones, fluoroquinolones, oxazolidinones and lipopeptides. In particular, tetracycline, tetracycline derived antibacterial agents, glycylcycline, glycylcycline derived antibacterial agents, minocycline, minocycline derived antibacterial agents, oxazolidinone antibacterial agents, aminoglycoside antibacterial agents, quinolone antibacterial agents, vancomycin, vancomycin derived antibacterial agents, teicoplanin, teicoplanin derived antibacterial agents, eremomycin, eremomycin derived antibacterial agents, chloroeremomycin, chloroeremomycin derived antibacterial agents, oritavancin, an oritavancin derived antibacterial agent, daptomycin, and daptomycin derived antibacterial agents are preferred.

The second therapeutic agent may be administered before, concurrently with, or after a pharmaceutical formulation of the present invention is administered to a subject.

The compounds and compositions of the invention are conceived to have a broad spectrum of activity, including antibiotic resistant strains, against both Gram-positive (e.g. *Staphylococcus aureus, Staphylococcus epidermis*, coagulase-negative Staphylococci, *Streptococcus pyogenes, Streptococcus viridians*, Group B Streptococci, *Enterococcus faecalis*) and Gram-negative bacteria (e.g. *E. coli, Chlamydia pneumoniae, Enterobacter* sp., *H. influenza, K. pneumoniae, Legionella pneumoniae, P. aeruginosa*)., G) In-Dwelling Devices and Products Coated with a Phosphonated Rifamycin The invention further encompasses in-dwelling devices coated with the compounds and pharmaceutical compositions of the invention. As used herein, the term "in-dwelling device" refers to surgical implants, orthopedic devices, prosthetic devices and catheters, i.e., devices that are introduced to the body of an individual and remain in position for an extended time. Such devices include, but are not limited to, pins, screws and plates, artificial joints and implants, heart valves, pacemakers, vascular grafts, vascular catheters, cerebrospinal fluid shunts, urinary catheters, continuous ambulatory peritoneal dialysis (CAPD) catheters.

According to one embodiment, the in-dwelling device is bathed in or sprayed with a concentration of about 1 mg/ml to about 10 mg/ml of a compound and/or pharmaceutical composition of the invention, before its insertion in the body.

According to another embodiment, the in-dwelling device is made of, or pre-coated with, an osseous-like type of material (e.g. calcium phosphate, Ca-ion and hydroxyapatite (Yoshinari et al., Biomaterials (2001), 22(7): 709-715)). Such material is likely to advantageously improve binding of the compounds and pharmaceutical compositions of the invention to the in-dwelling device, either during the coating of the device with the compounds or pharmaceutical compositions of the invention and/or after their local or systemic administration. The in-dwelling devices may also be coated with an osseous material pre-loaded with or containing bound bone-targeting compound(s) according to the invention. For the above-mentioned embodiments, hydroxyapatite would be preferred as the osseous material. More details on coating methods, uses and advantages of hydroxyapatite-coated prostheses are found in the review by Dumbleton and Manly (The Journal of Bone & Joint Surgery (2004) 86A:2526-40) which is incorporated herein by reference.

H) Methods of Preparation

The inventive compounds, and their salts, solvates, crystal forms, active metabolites, and prodrugs, may be prepared by employing the techniques available in the art using starting materials that are readily available. Certain novel and exemplary methods of preparing the inventive compounds are described in the Exemplification section below. Such methods are within the scope of this invention.

EXAMPLES

The Examples set forth herein provide exemplary syntheses of representative compounds of the invention. Also provided are exemplary methods for assaying the compounds of the invention for their bone-binding activity, assays for determining the minimum inhibitory concentration (MIC) of the compounds of the invention against microorganisms, and methods for testing in vivo activity and cytotoxicity.

Example 1

Synthesis of Phosphonated Rifamycins

A) General Experimental Procedures
A 1) Preparation of Bisphosphonate Building Blocks

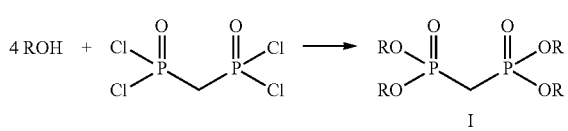

As described in Synth. Commun. (2002), 32; 211-218, tetraesters of methylenebisphosphonic acid (I) can be prepared from the parent tetrachloride and an alcohol.

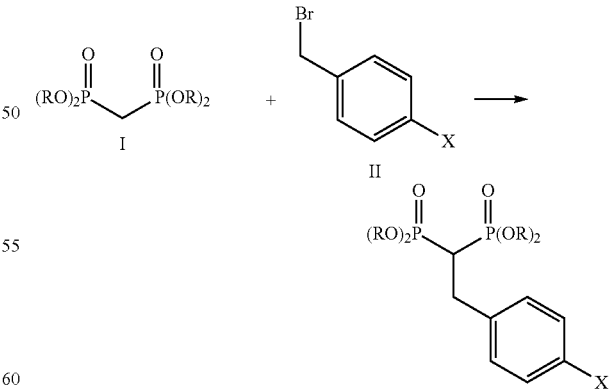

IIIa: X = NO$_2$
IIIb: X = NH$_2$
IIIc: X = NR'PG
IIId: X = NHR'
IIIe: X = CO$_2$R''
IIIf: X = CO$_2$H

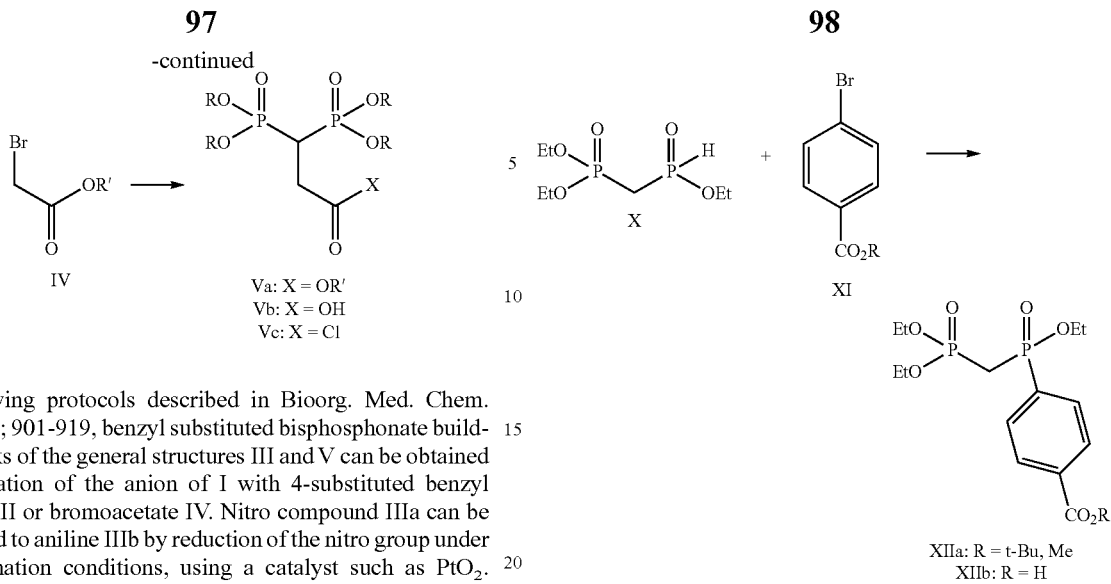

Following protocols described in Bioorg. Med. Chem. (1999), 7; 901-919, benzyl substituted bisphosphonate building blocks of the general structures III and V can be obtained by alkylation of the anion of I with 4-substituted benzyl bromide II or bromoacetate IV. Nitro compound IIIa can be converted to aniline IIIb by reduction of the nitro group under hydrogenation conditions, using a catalyst such as $PtO_2$. Compounds of general formula IIIc with a protected amino group can be deprotected to give secondary amines of general formula IIId. Esters like IIIe and Va can be converted to the corresponding acids IIIf or Vb via ester cleavage. For example, ester IIIe where R"=t-Bu can be treated with TFA to afford the corresponding acid IIIf. Under similar conditions, ester Va where X=Ot-Bu can be converted to acid Vb.

Diethyl (ethoxyphosphinyl)methylphosphonate X can be prepared using the procedure described in Synth. Comm. (2002), 32; 2951-2957 and U.S. Pat. No. 5,952,478 (1999). It can be coupled with a 4-substituted bromobenzene ($X^1$) to access acid XIIb, following cleavage of the ester intermediate XIIa.

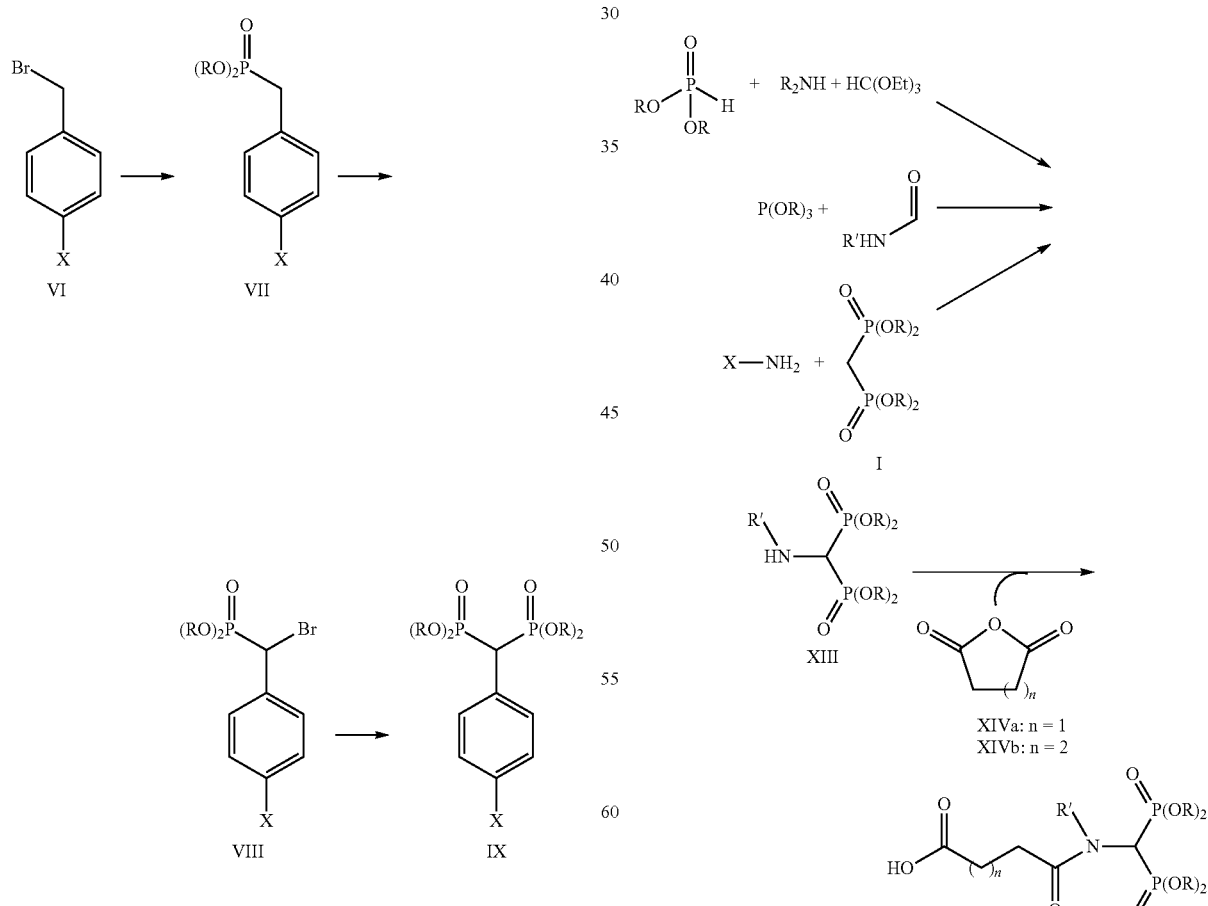

Aryl substituted methylene bisphosphonates of general formula IX can be obtained from the parent benzylic halides VI in a sequence of two Arbuzov reactions separated by a benzylic halogenation.

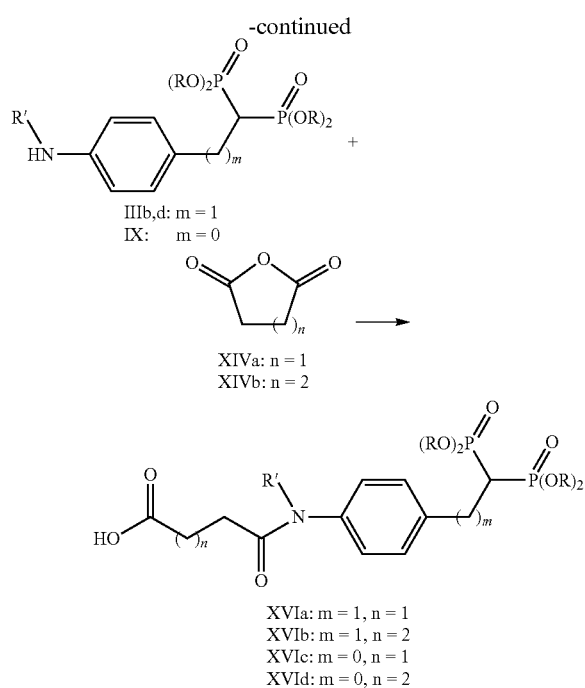

XIVa: n = 1
XIVb: n = 2

XVIa: m = 1, n = 1
XVIb: m = 1, n = 2
XVIc: m = 0, n = 1
XVId: m = 0, n = 2

1-Aminomethylenebisphosphonates of general formula XIII can be prepared from dibenzylamine or diallylamine, dialkyl phosphite and triethyl orthoformate following a protocol described in Synth. Commun. (1996), 26; 2037-2043, or from a trialkyl phosphite and an appropriately substituted formamide (such as allyl formamide) as in Phosphorus, Sulfur and Silicon (2003), 178, 38-46. Alternatively, the methylenebisphosphonate tetraester I can be treated with a strong non-nucleophilic base followed by an electrophilic source of the $NH_2$ group, such as O-diphenylphosphinyl hydroxylamine (as described in J. Org. Chem. (1998), 63, 1221-1225), to furnish XIII. Acylation of XIII with succinic anhydride XIVa or glutaric anhydride XIVb can provide acids XVa and XVb respectively (J. Drug Targeting (1997), 5; 129-138). In a similar fashion, treatment of the previously described IIIb, IIId or IX with XIV(a-b) results in the succinamic and glutaramic acids XVI(a-d).

Olefin XVII can be prepared from I following a protocol described in J. Org. Chem. (1986), 51; 3488-3490. It can be converted to the parent Bisphosphonobutyric acid XVIII as described in J. Org. Chem. (2001), 66; 3704-3708. Alternatively, the acid XVIII can be prepared by deprotection of ester XIX, obtained through the conjugate addition of I on an acrylate ester as described in J. Gen. Chem. USSR (1970), 40, 462-463, or by the treatment of XVII with an acetate ester in the presence of a strong base.

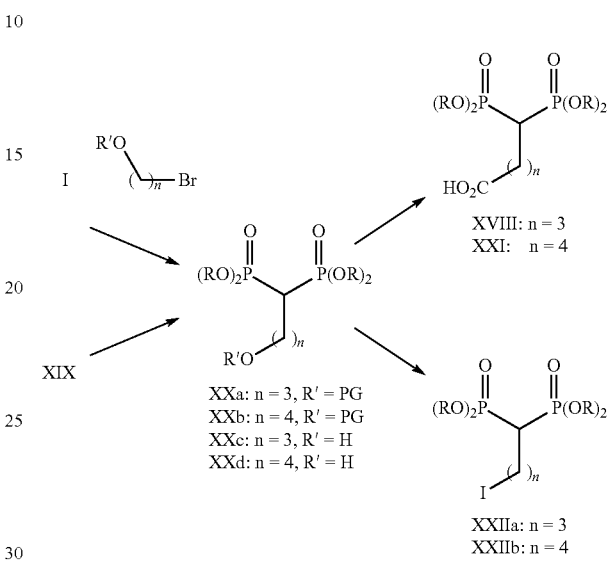

XXa: n = 3, R' = PG
XXb: n = 4, R' = PG
XXc: n = 3, R' = H
XXd: n = 4, R' = H

XVIII: n = 3
XXI: n = 4

XXIIa: n = 3
XXIIb: n = 4

As described in Phosphorus, Sulfur and Silicon, (1998), 132; 219-229, alcohols of general structure XX(c-d) and iodides of general structure XXII(a-b) can be prepared by alkylation of the anion of I by protected ω-hydroxy bromides of various chain length. Alternatively, alcohol XXc can be obtained by reduction of acid XVIII or ester XIX with a suitably selected source of hydride. After deprotection, alcohols can be converted to the corresponding iodides via treatment with in situ generated triphenylphosphine:iodine complex. These alcohols XX(c-d) may additionally be converted to acids of general structure XVIII and XX by conventional methods of oxidation, such as treatment with pyridinium dichromate.

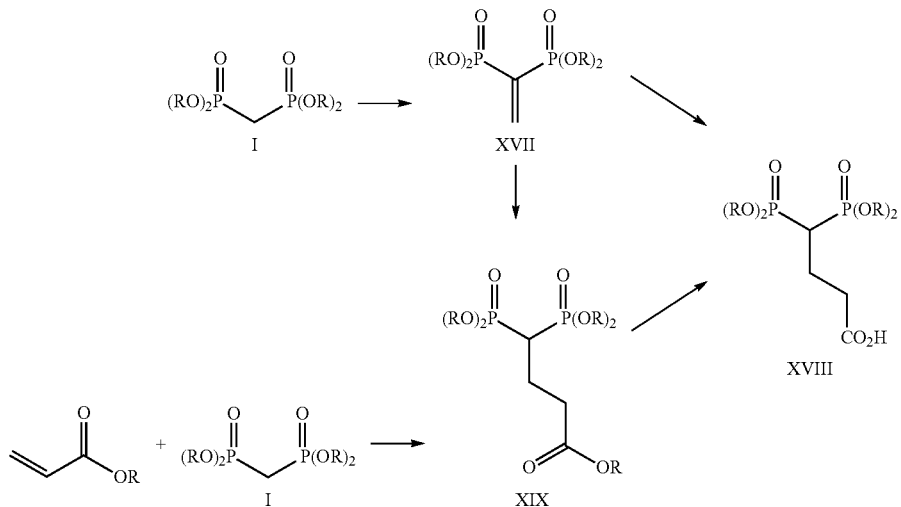

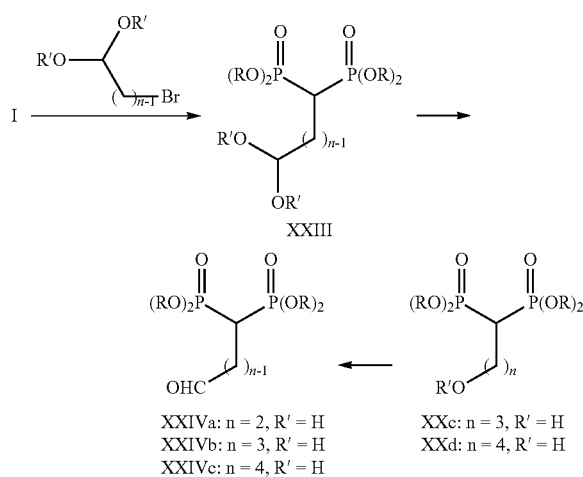

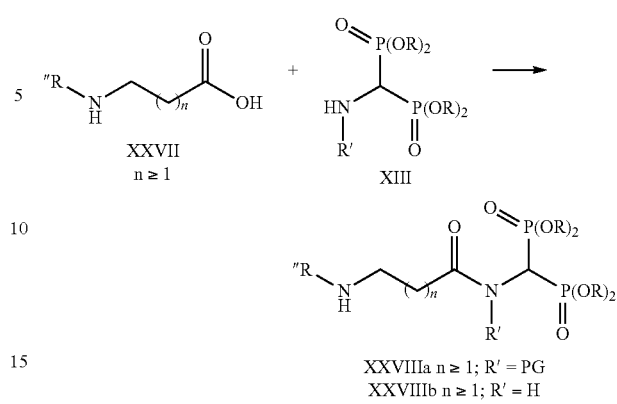

Aldehydes XXIV(a-c) can be prepared by alkylation of the anion of I with a ω-haloalkanal protected as an acetal, followed by acid catalyzed deprotection. Alternatively, they can be obtained by the oxidation of alcohols XX(c-d).

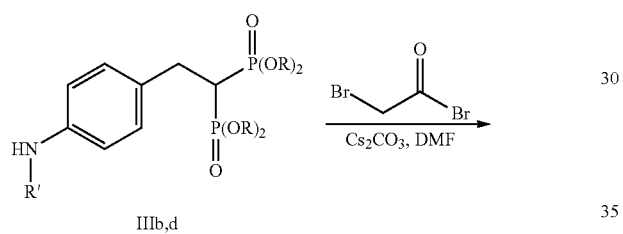

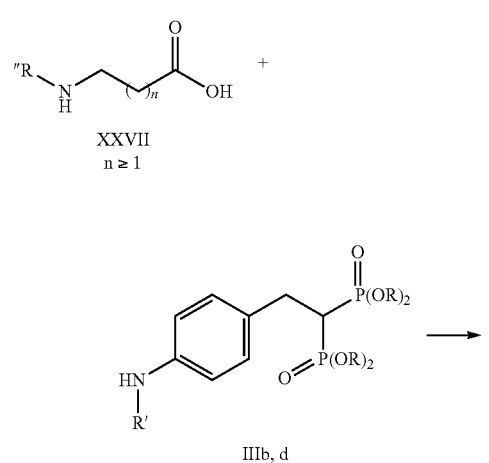

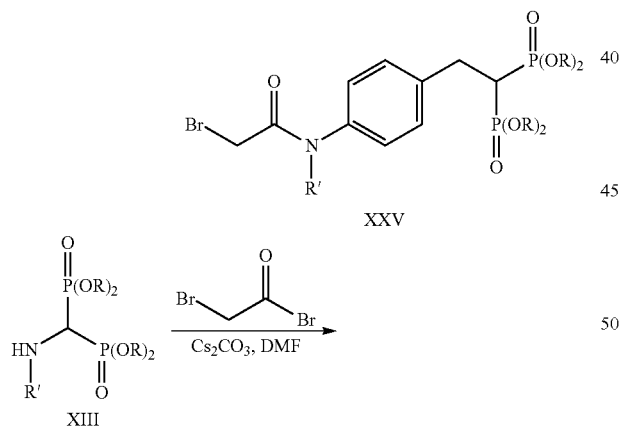

Bromoacetamides XXV and XXVI from the parent amines IIIb, IIId and XIII can be prepared according to a modification of the procedure described in J. Drug Targeting (1995), 3, 273-282.

Bisphosphonated amines XXVIII(a-b) and XXIX(a-b) are easily produced by the acylation of amines XIII and IIIb,d respectively with protected amino acids XXVII under standard amide coupling conditions (Tertiary amine and a standard amide coupling agent such as DCC, EDCI, HBTU, HATU, PyBOP, BOP-Cl).

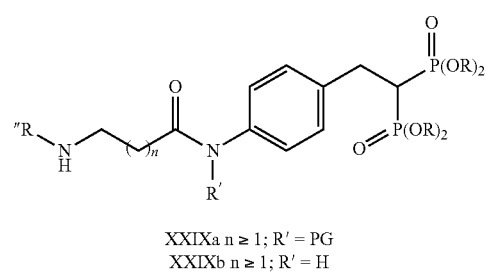

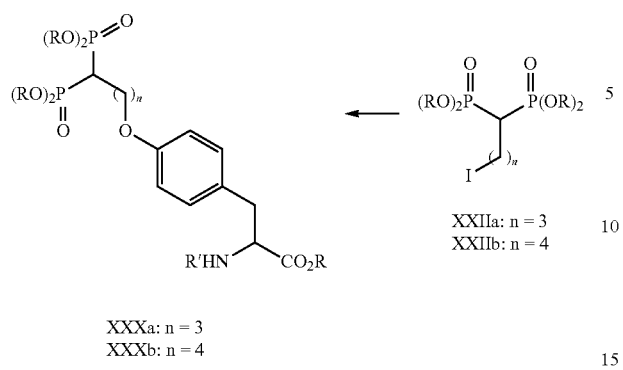
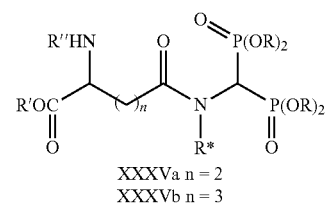

The bisphosphonated tyrosine derivatives such as XXX(a-b) can be prepared via treatment of tyrosine derivatives protected at the amino and the carboxy groups with alcohols XX(c-d) in the presence of a coupling mixture such as an azodicarboxylate diester and a phosphine or with the parent iodides XXII(a-b) with tyrosine derivatives protected at the amino and the carboxy groups in the presence of a base.

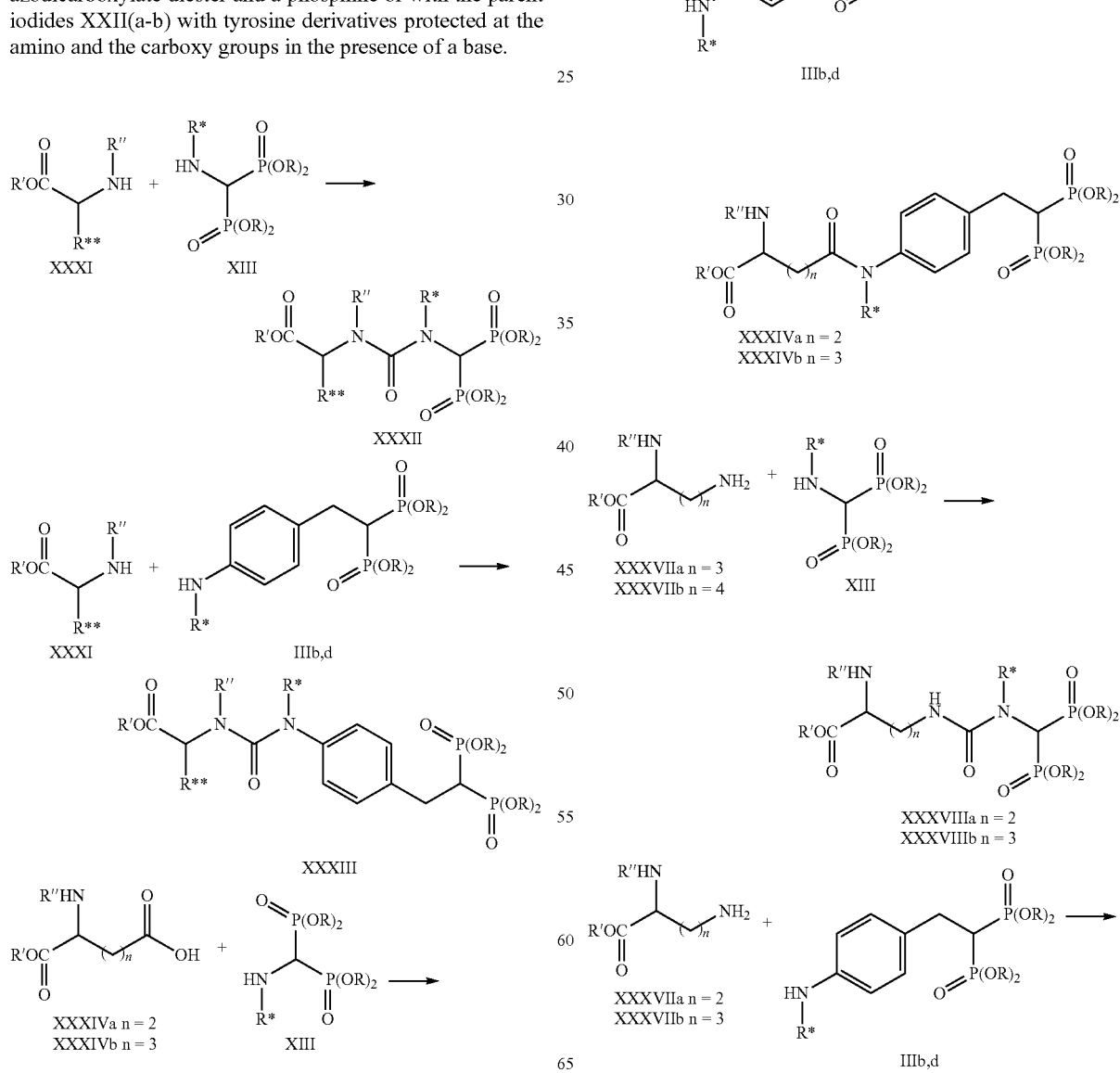

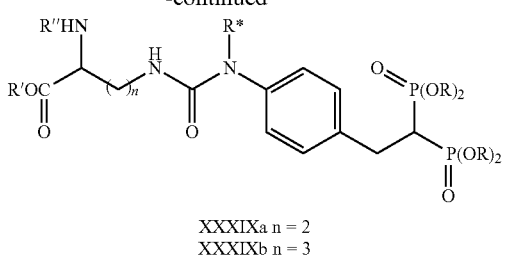

XXXIXa n = 2
XXXIXb n = 3

Bisphosphonates possessing an amino group can be tethered to amino acids to generate compounds possessing several chemically useful functional groups. Thus, bisphosphonated amino acids XXXII, XXXIII, XXXVIII(a-b) and XXXIX(a-b) can be obtained by the reaction of the parent amino acid suitably protected at the other functional groups with amines XIII, IIIb and IIId previously treated with phosgene or a phosgene equivalent such as triphosgene, carbonyl diimidazole, N,N-disuccinimidyl carbonate and nitrophenyl chloroformate. Bisphosphonated amino acids such as XXXV (a-b) and XXXVI(a-b) can be prepared from the same amines XIII, IIIb and IIId by treatment with suitably protected aspartic and glutamic acid derivatives in the presence of a coupling reagent. Similar bisphosphonated amino acids can be prepared from amines XXVIII(a-b) and XXIX(a-b).

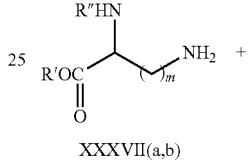

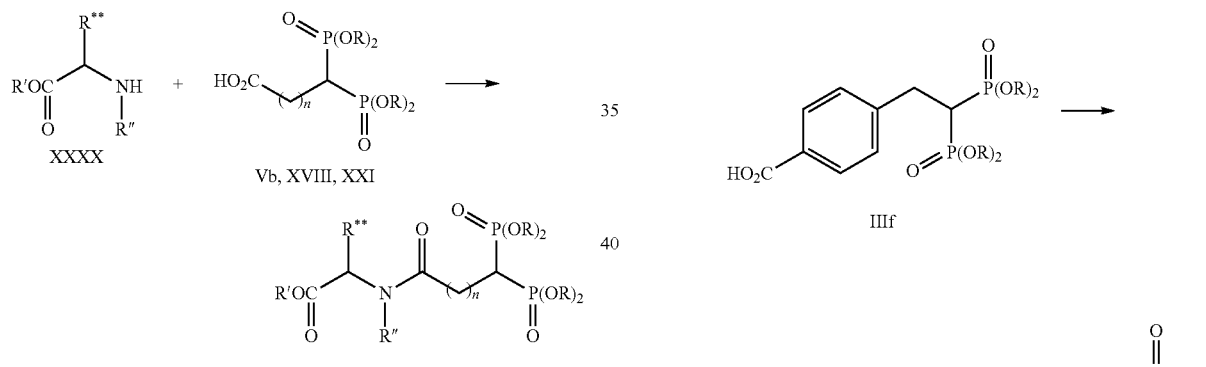

XXXXIa n = 1
XXXXIb n = 2
XXXXIc n = 3

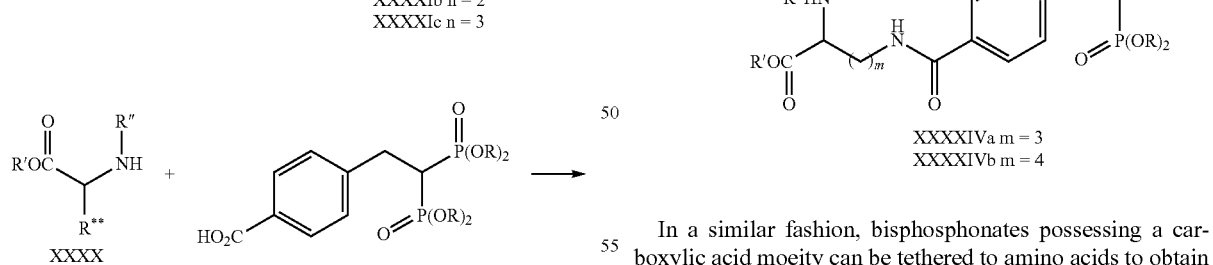

XXXXII

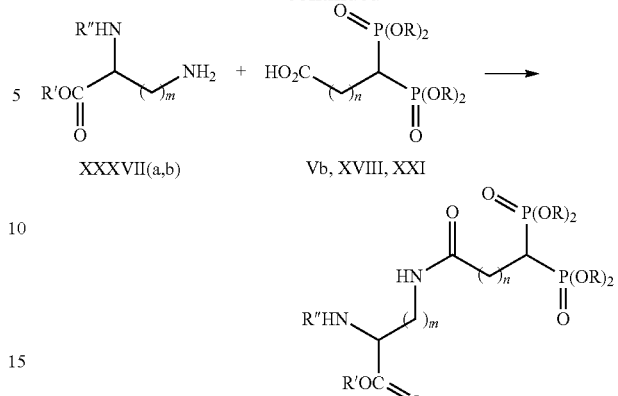

XXXXIIIa m = 3, n=1
XXXXIIIb m = 4, n=1
XXXXIIIc m = 3, n=2
XXXXIIId m = 4, n=2
XXXXIIIe m = 3, n=3
XXXXIIIf m = 4, n=3

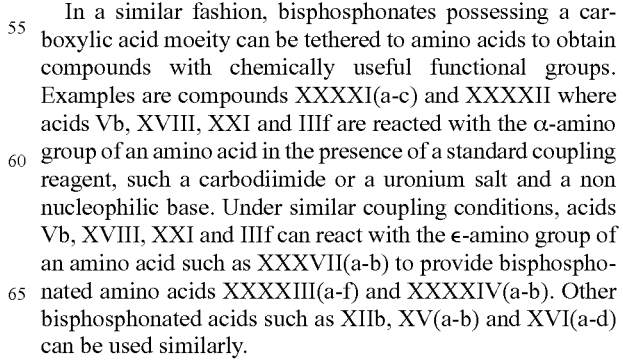

XXXXIVa m = 3
XXXXIVb m = 4

In a similar fashion, bisphosphonates possessing a carboxylic acid moeity can be tethered to amino acids to obtain compounds with chemically useful functional groups. Examples are compounds XXXXI(a-c) and XXXXII where acids Vb, XVIII, XXI and IIIf are reacted with the α-amino group of an amino acid in the presence of a standard coupling reagent, such a carbodiimide or a uronium salt and a non nucleophilic base. Under similar coupling conditions, acids Vb, XVIII, XXI and IIIf can react with the ε-amino group of an amino acid such as XXXVII(a-b) to provide bisphosphonated amino acids XXXXIII(a-f) and XXXXIV(a-b). Other bisphosphonated acids such as XIIb, XV(a-b) and XVI(a-d) can be used similarly.

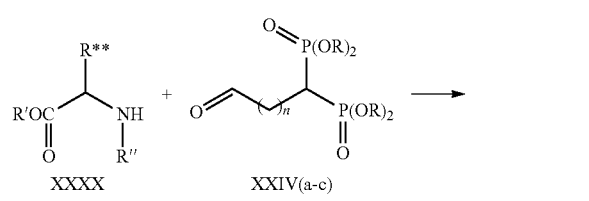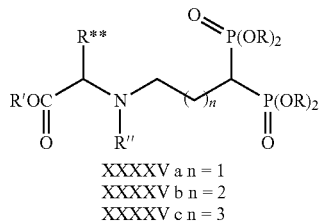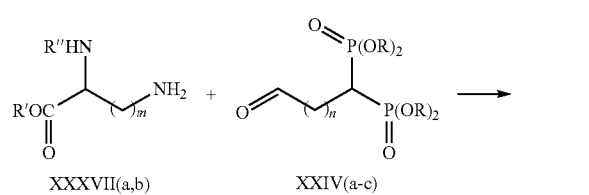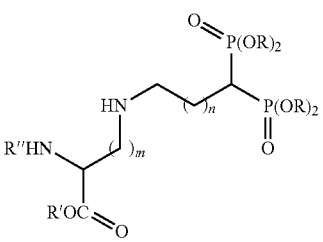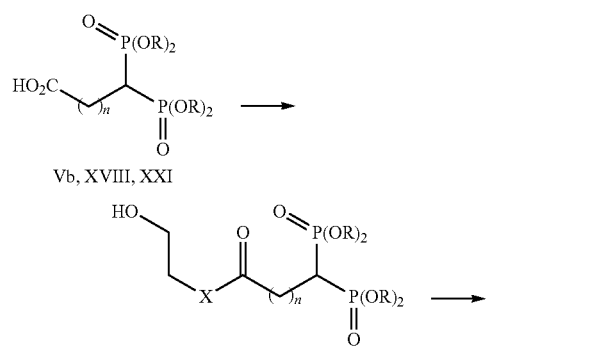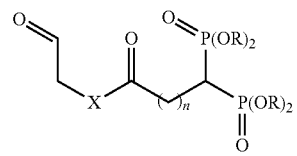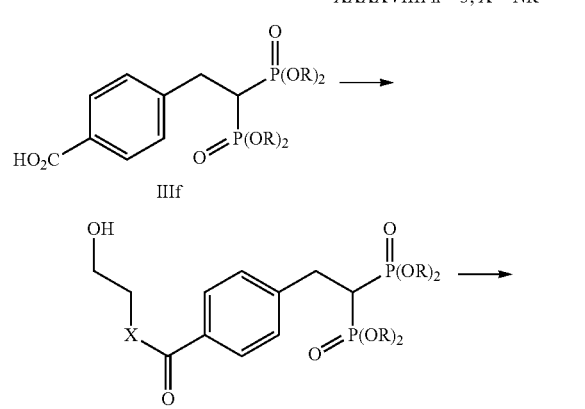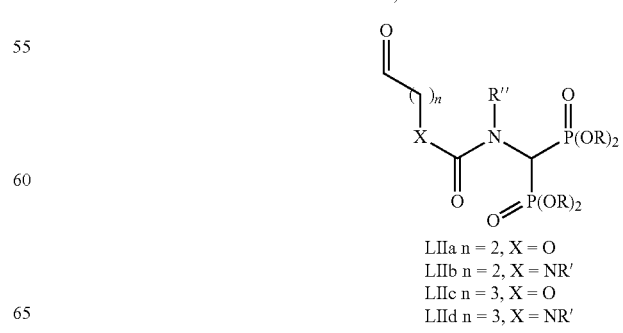

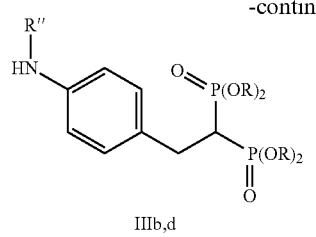

IIIb,d

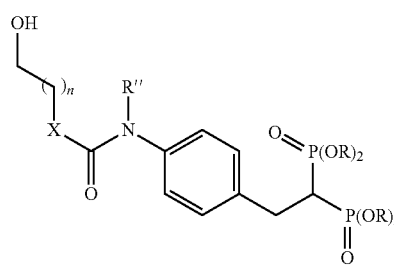

LIIIa n = 2, X = O
LIIIb n = 2, X = NR'
LIIIc n = 3, X = O
LIIId n = 3, X = NR'

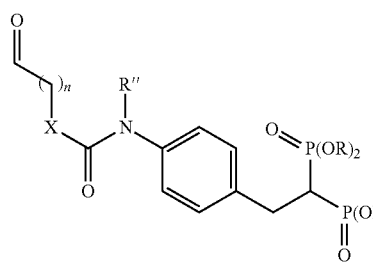

LIVa n = 2, X = O
LIVb n = 2, X = NR'
LIVc n = 3, X = O
LIVd n = 3, X = NR'

In the same manner, bisphosphonated aldehydes, such as XXIV(a-c), can be used to reductively alkylate, in the presence of a hydride reagent such as a borane or a borohydride, either the free α-amino groups of amino acids of the general structure XXXX or the free ε-amino groups of amino acids XXXVII(a-b) to give the bisphosphonated amino acids XXXXV(a-c) and XXXXVI(a-f) respectively. Other bisphosphonated aldehydes such as XXXXVIII(a-f), L(a-b), LII(a-d) and LIV(a-d) can also be used in the same fashion. XXXX-VIII(a-f) and L(a-b) can be prepared by the reaction of acids Vb, XVIII, XXI and IIIfb either with bromoethanol in the presence of a base, or a suitably monoprotected ethylene glycol or an ethanolamine derivative under standard coupling conditions (such as in the presence of a carbodiimide or a uronium salt and a base) to give alcohols XXXXVII(a-f) and IL(a-b) which are subsequently oxidized to the aldehydes by treatment with a halosulfonium ion and a base or a periodinane. LII(a-d) and LIV(a-d) can be obtained by the similar oxidation of alcohols LI(a-d) and LIII(a-d) themselves the product of the sequential treatment of bisphosphonated amines XIII and IIIb,d with phosgene or a phosgene equivalent (such as carbonyl diimidazole and triphosgene) in the presence of a non-nucleophilic base and then monoprotected 1,3-propanediol and 1,4-butanediol derivatives or 3-aminopropan-1-ol and 4-aminobutan-1-ol.

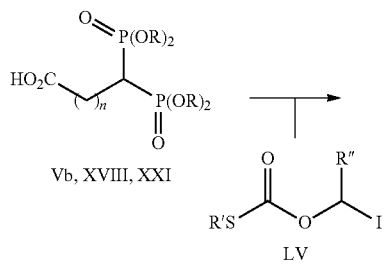

Vb, XVIII, XXI

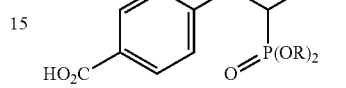

LV

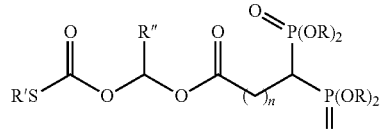

IIIf

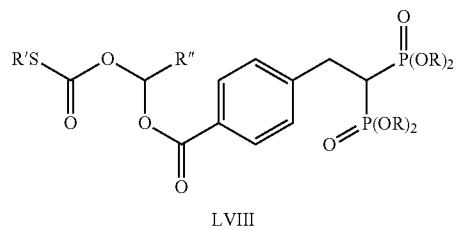

LVIa n = 1
LVIb n = 2
LVIc n = 3

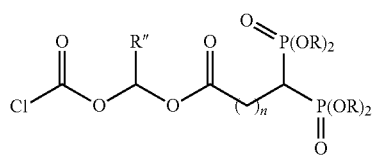

LVIII

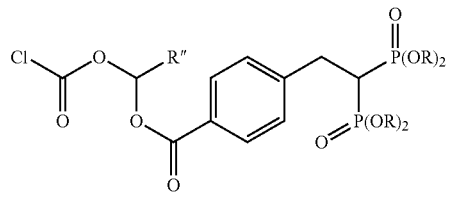

LVIIa n = 1
LVIIb n = 2
LVIIc n = 3

LIX

Bisphosphonates (1-acyloxyalkyl) chloroformates such as LVII(a-c) and LIX can be prepared by the treatment of the parent S-alkyl carbonothioates LVI(a-c) and LVIII with sulfuryl chloride (as described in Folkmann et al, Synthesis (1990); 12: 1159-1166). These are in turn prepared by the treatment of acids Vb, XVIII, XXI and IIIf with a base and then O-1-iodoalkyl S-alkyl carbonothioate LV.

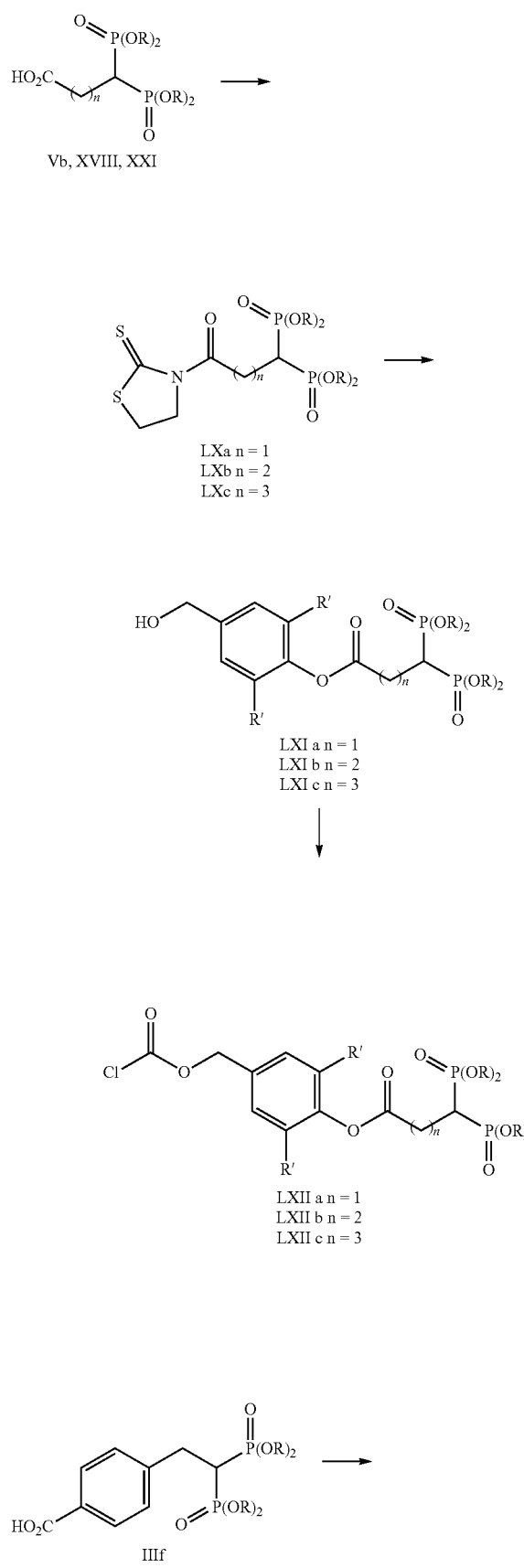

The treatment of acids Vb, XVIII, XXI with a carbodiimide or a uronium salt and 2-mercaptothiazoline furnishes the 3-acyl thiazolidine-2-thiones LX(a-c). These react with p-hydroxybenzyl alcohol derivatives selectively at the phenolic hydroxy group to provide phenyl esters LXI(a-c) as described in Greenwald et al, J. Med. Chem. (1999); 42: 3657-3667. These can be converted to the parent chloroformates LXII(a-c) by treatment with phosgene or triphosgene. A similar preparation of chloroformate LXV can be made from acid IIIf via 3-acyl thiazolidine-2-thione LXIII and phenyl ester LXIV.

Other bisphosphonated acids such as XIIb, XV(a-b) and XVI(a-d) can be used similarly to generate chloroformates similar to LVII(a-c), LIX, LXII(a-c) and LXV.

The bisphosphonate building blocks described in this section are in the form of their phosphonic esters, R being Me, Et, i-Pr or Bn; or as the free bisphosphonic acid.

A 2) Synthesis of Rifamycin-Bisphosphonate Conjugates

The methods for preparing Rifamycin antibiotics have been described: Rifampicin (U.S. Pat. No. 3,342,810), Rifapentin (U.S. Pat. No. 4,002,752), Rifandin (U.S. Pat. No. 4,353,826), Rifabutin (U.S. Pat. No. 4,219,478), Rifalazil (U.S. Pat. No. 4,983,602) and Rifaximin (U.S. Pat. No. 4,341,785).

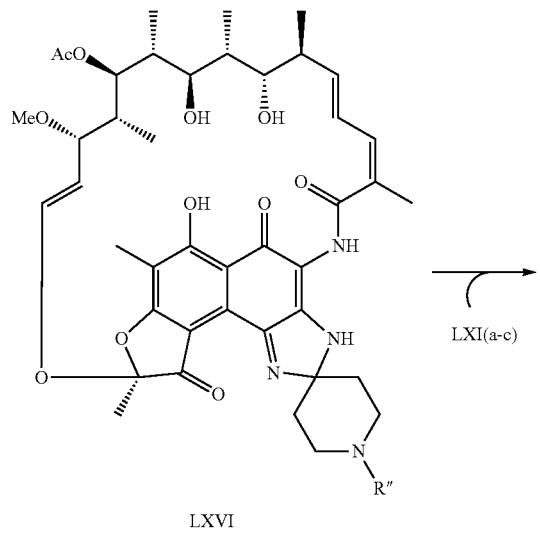

LXVI

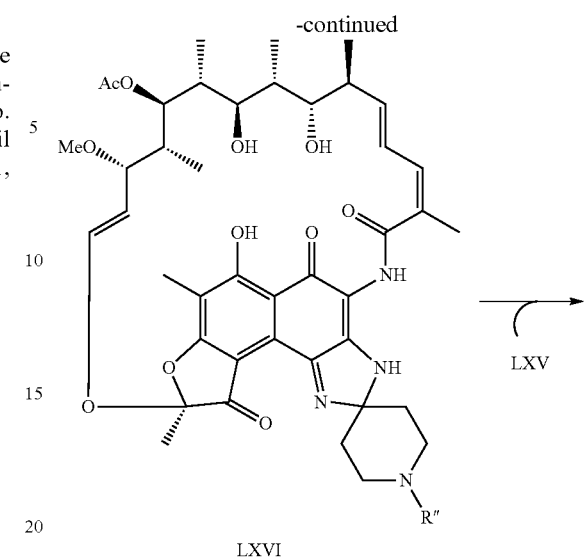

LXVI

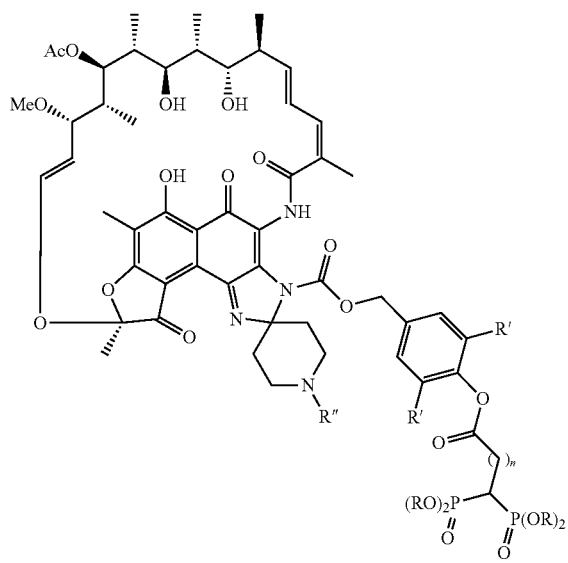

LXVIIa n = 1
LXVIIb n = 2
LXVIIc n = 3

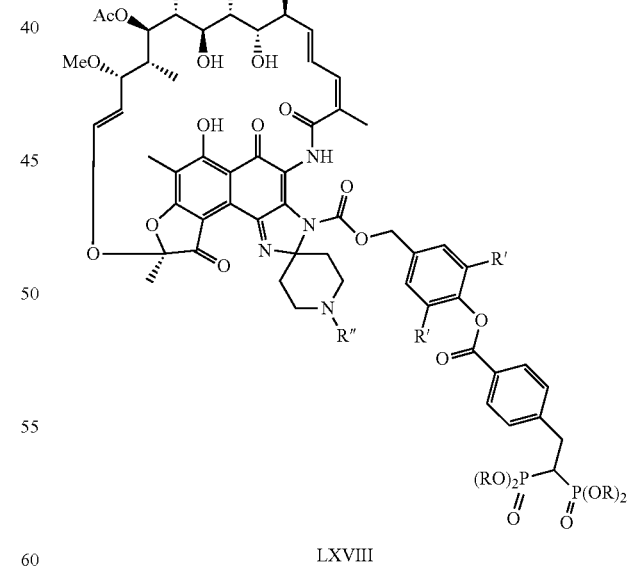

LXVIII

Spiropiperidylrifamycin S compounds LXVI can be treated with chloroformates LXI(a-c) and LXV in the presence of a strong hindered base such as $N^1,N^1,N^8,N^8$-tetramethylnaphthalene-1,8-diamine to provide bisphosphonated rifamycin derivatives LXVII(a-c) and LXVIII.

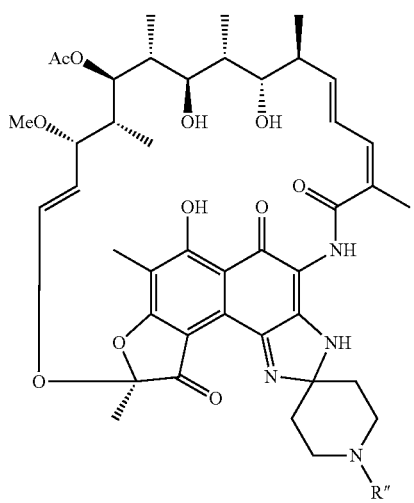

LXVI

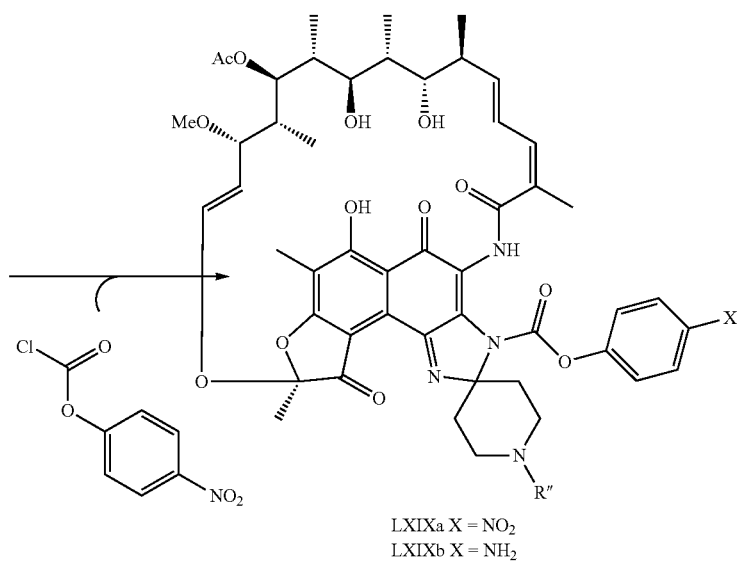

LXIXa X = NO₂
LXIXb X = NH₂

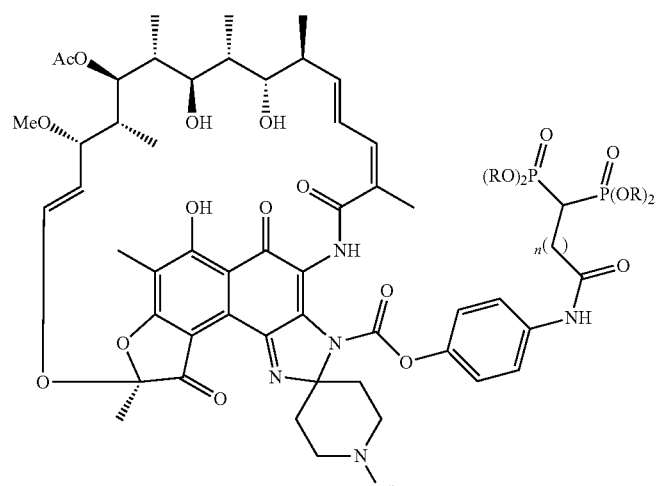

LXXa n = 1
LXXb n = 2
LXXc n = 3

Similarly, LXVI can be treated with 4-nitrophenyl chloroformate in the presence of a hindered base such as 1,8-diazabicyclo[5.4.0]undec-7-ene to furnish the 4-nitrophenyl carbamate LXIXa which can be reduced to the parent 4-aminophenyl carbamate LXIXb by treatment with a mild reducing agent such as stannous chloride. Reaction with chloroformates LVII(a-c) in the presence of a non-nucleophilic base provides bisphosphonated rifamycins LXX(a-c).

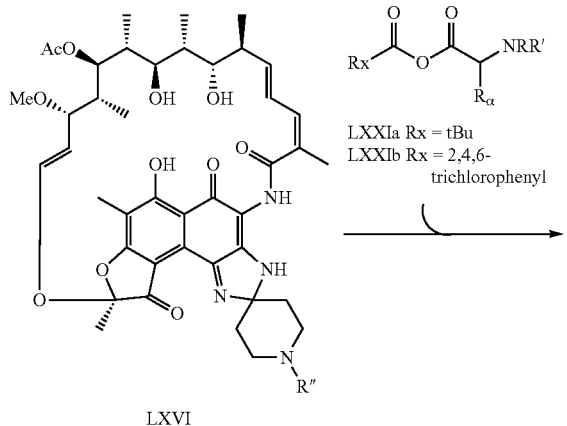

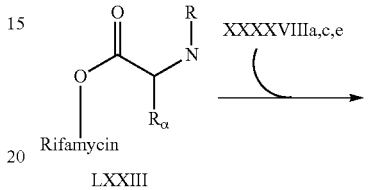

The reaction of spiropiperidylrifamycin S LXVI with the mixed anhydrides prepared from $N^\alpha$-protected amino acids selectively produces the ester products LXXII, in a similar manner to that described for other anhydrides in J. Mol. Struct. (2001), 563-564, 61-78. Deprotection furnishes a free amino group in compounds LXXIII which is used as a handle for bisphosphonate attachment. Of particular interest are compounds LXXIIIa and LXXIIIb, in which a primary and a secondary amino group are respectively available.

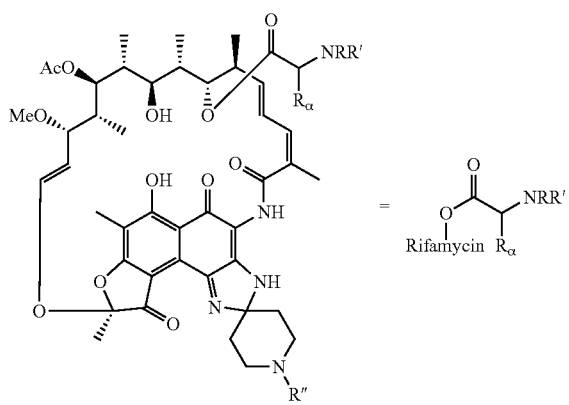

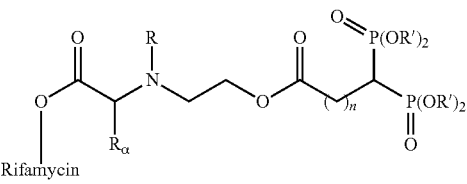

Thus reaction of LXXIII with aldehydes XXXXVIIIa, XXXXVIIIc and XXXXVIIIe in the presence of a source of hydride such as a borane or a borohydride, in particular a mild reagent such as sodium triacetoxyborohydride, furnishes bisphosphonated rifamycins LXXIV(a-c).

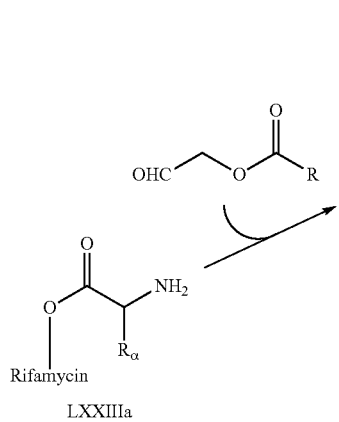
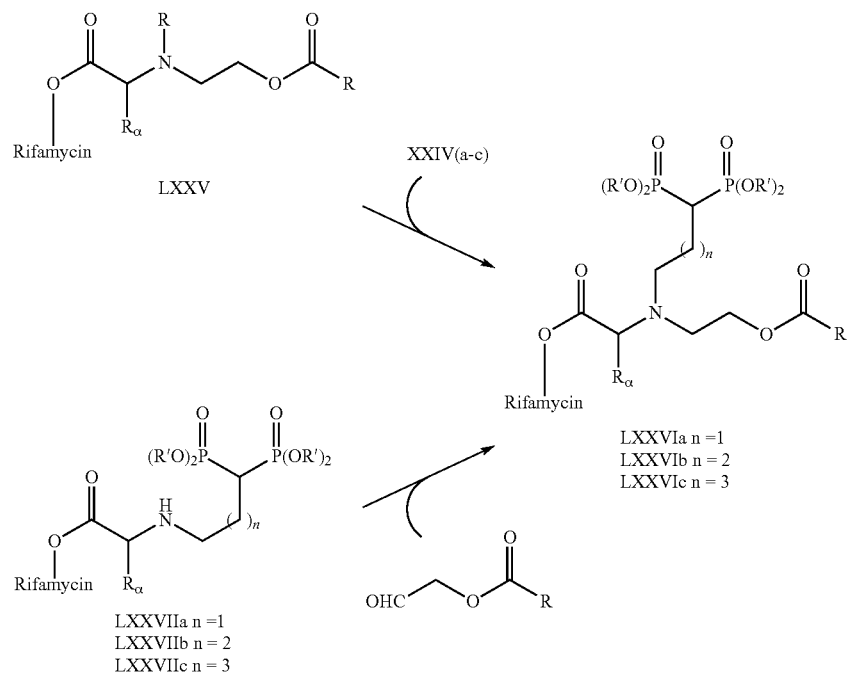

Amino acylated rifamycins LXXIIIa presenting a free amino group can be treated sequentially with 2-acyloxyacetaldehydes and then bisphosphonated aldehydes XXIV(a-c) both steps being carried under reductive conditions involving a source of hydride such as sodium triacetoxyborohydride or a borane, to furnish bisphosphonated rifamycins LXXVI(a-c). The order of the reductive alkylation steps may be inverted and use aldehydes XXIV(a-c) before the 2-acyloxyacetaldehydes, via intermediates LXXVII(a-b) instead. Other bisphosphonated aldehydes, such as L(a-b), LII(a-d) and LIV(a-d) can be used similarly to XXIV(a-c) to provide similar bisphosphonated rifamycins.

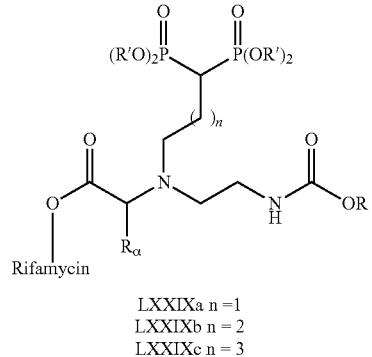

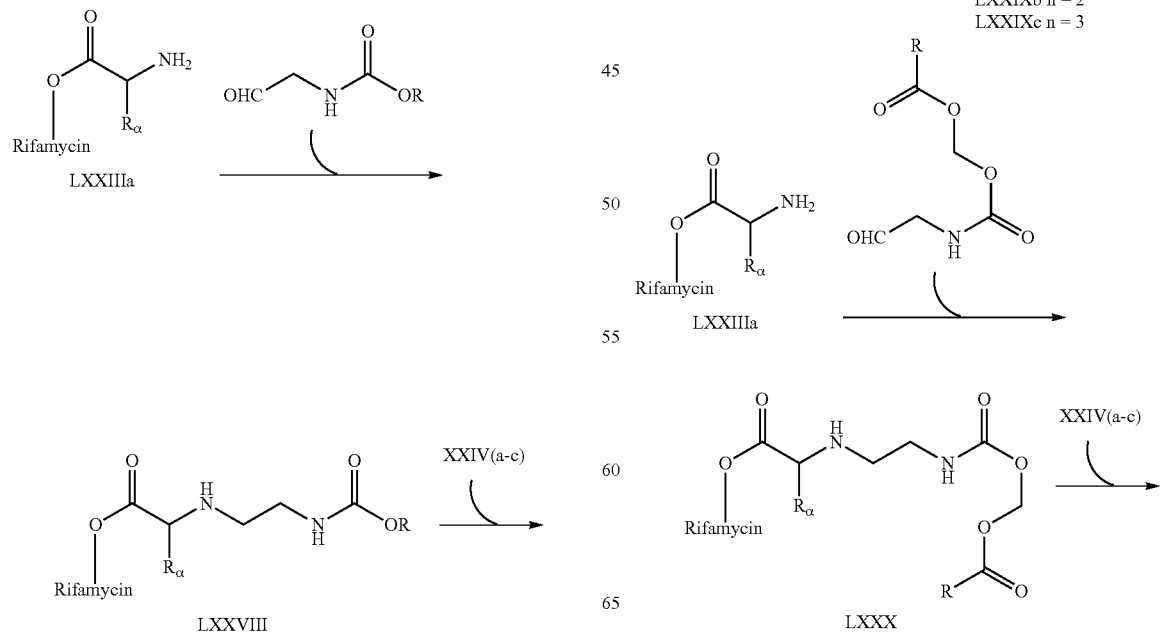

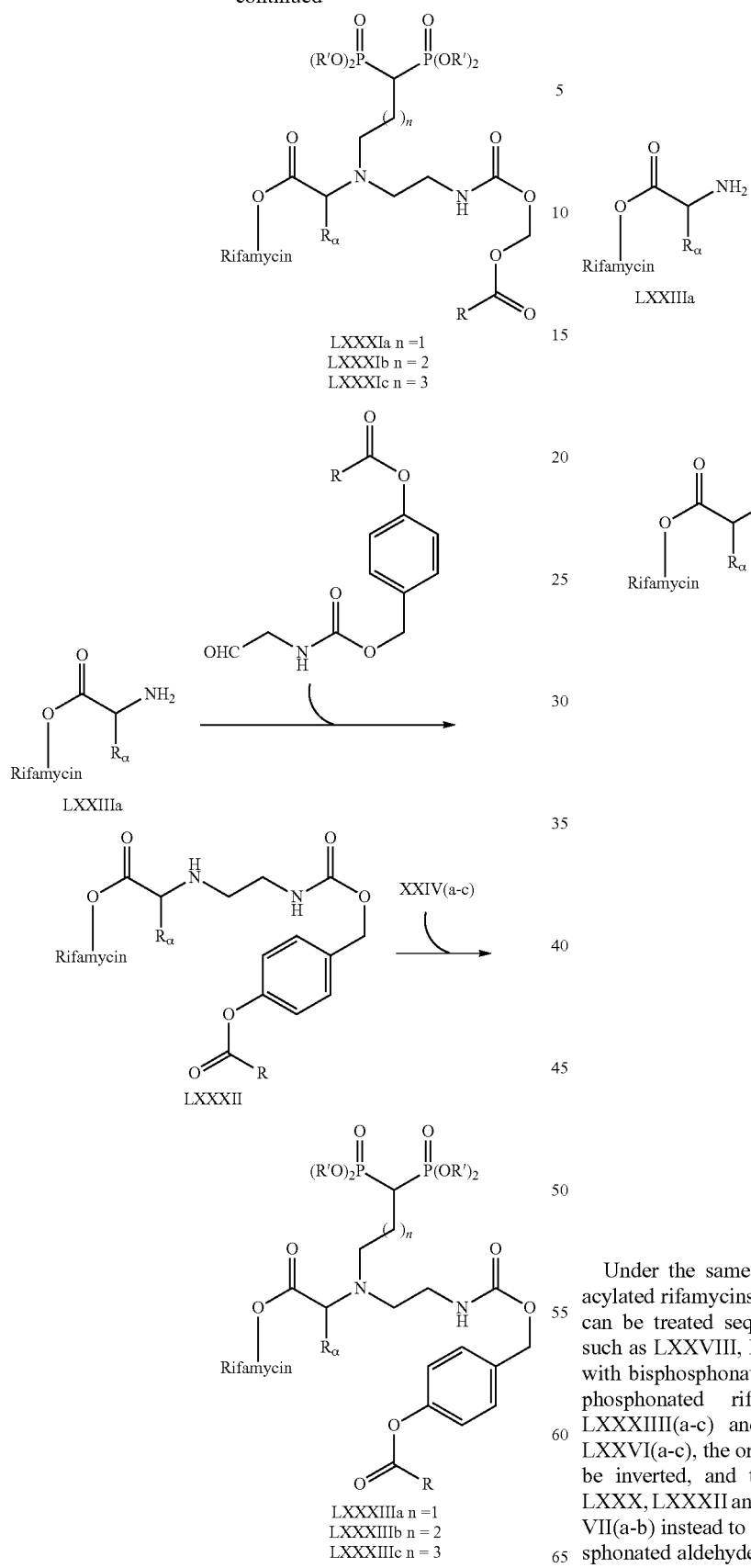
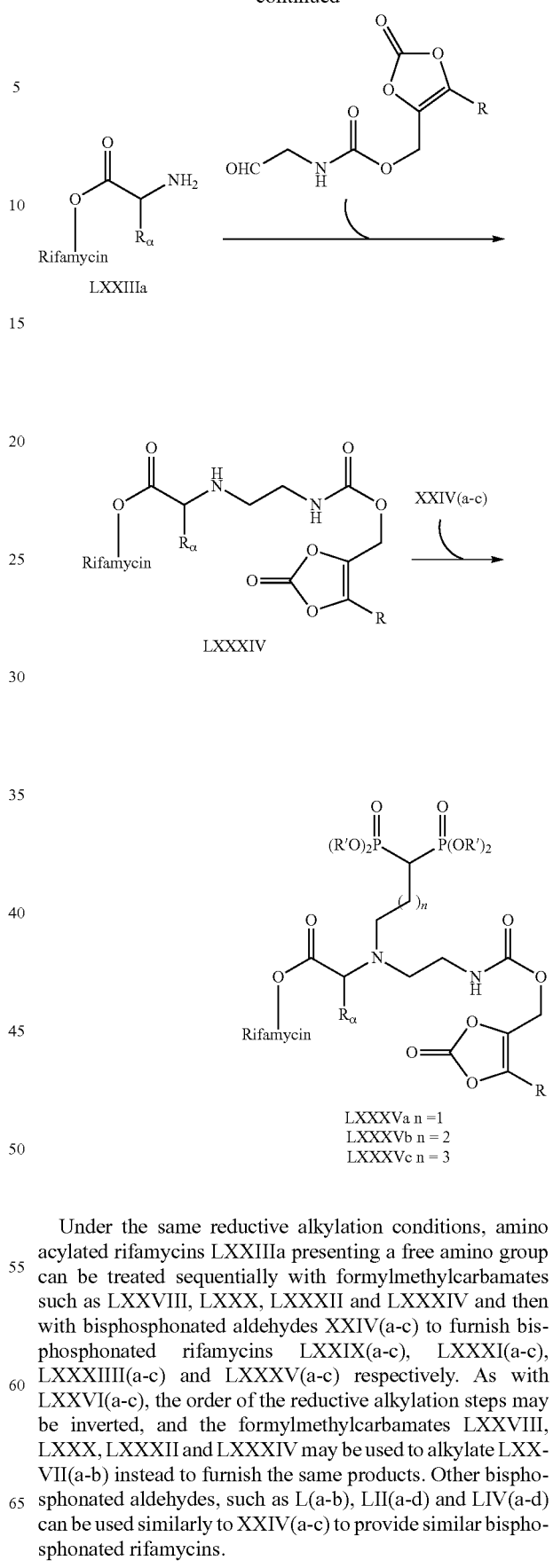

Under the same reductive alkylation conditions, amino acylated rifamycins LXXIIIa presenting a free amino group can be treated sequentially with formylmethylcarbamates such as LXXVIII, LXXX, LXXXII and LXXXIV and then with bisphosphonated aldehydes XXIV(a-c) to furnish bisphosphonated rifamycins LXXIX(a-c), LXXXI(a-c), LXXXIIII(a-c) and LXXXV(a-c) respectively. As with LXXVI(a-c), the order of the reductive alkylation steps may be inverted, and the formylmethylcarbamates LXXVIII, LXXX, LXXXII and LXXXIV may be used to alkylate LXXVII(a-b) instead to furnish the same products. Other bisphosphonated aldehydes, such as L(a-b), LII(a-d) and LIV(a-d) can be used similarly to XXIV(a-c) to provide similar bisphosphonated rifamycins.

XXXXV(a-c) →

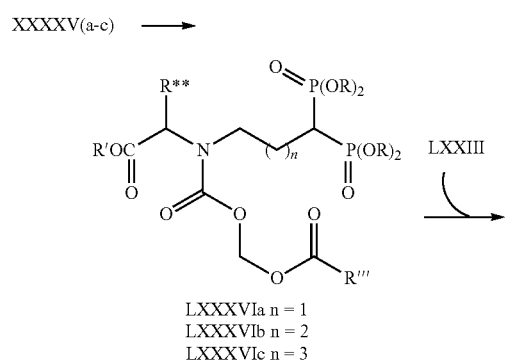

LXXXVIa n = 1
LXXXVIb n = 2
LXXXVIc n = 3

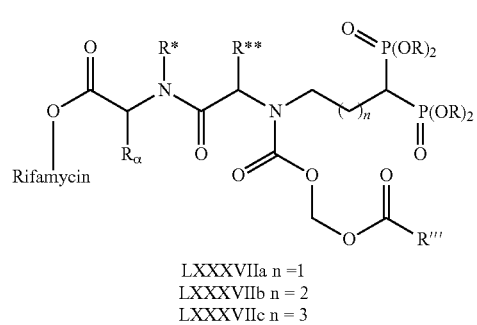

LXXXVIIa n = 1
LXXXVIIb n = 2
LXXXVIIc n = 3

XXXXV(a-c) →

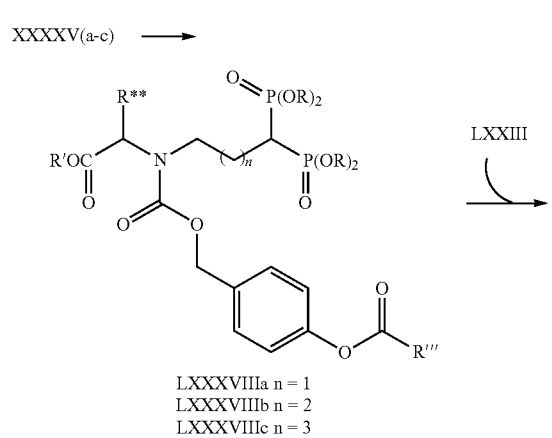

LXXXVIIIa n = 1
LXXXVIIIb n = 2
LXXXVIIIc n = 3

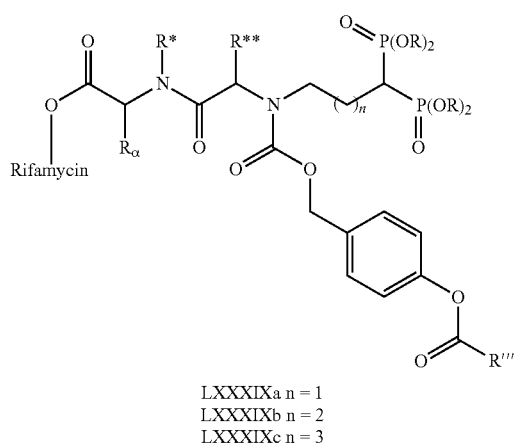

LXXXIXa n = 1
LXXXIXb n = 2
LXXXIXc n = 3

XXXXV(a-c) →

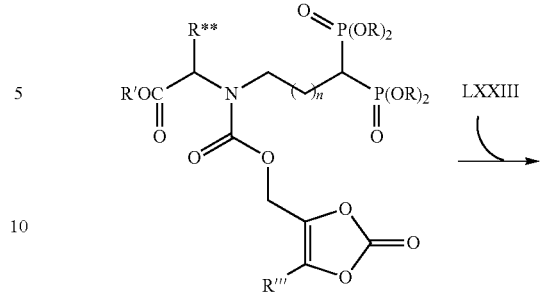

XCa n = 1
XCb n = 2
XCc n = 3

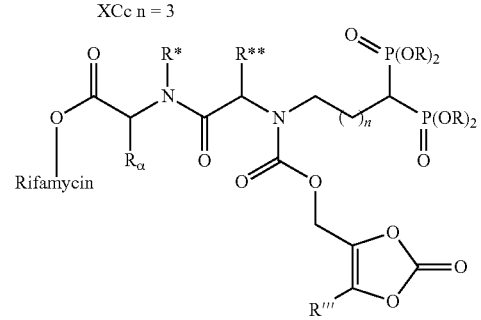

XCIa n = 1
XCIb n = 2
XCIc n = 3

XXXXV(a-c) →

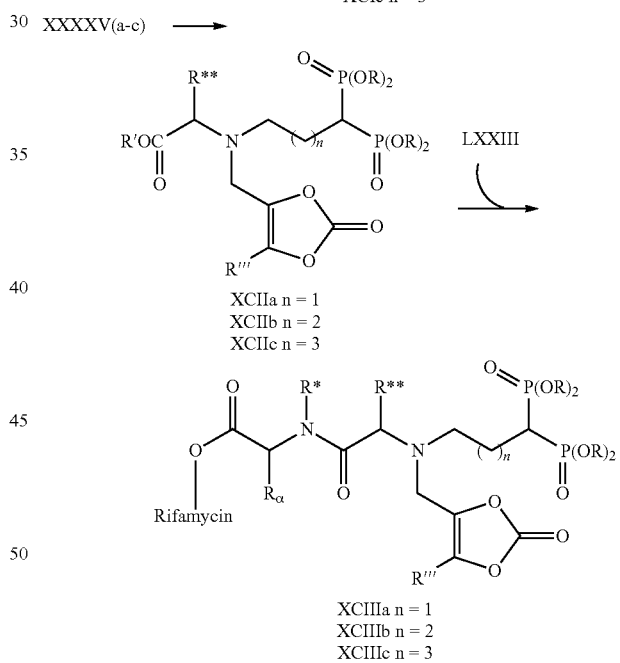

XCIIa n = 1
XCIIb n = 2
XCIIc n = 3

XCIIIa n = 1
XCIIIb n = 2
XCIIIc n = 3

Bisphosphonated aminoacids XXXXV(a-c) can be N-deprotected and treated with acyloxymethyl chloroformate, 4-acyloxyphenylmethyl chloroformate, (2-oxo-1,3-dioxol-4-yl)methyl chloroformates or 4-(chloromethyl)-1,3-dioxol-2-ones in the presence of a non nucleophilic base to provide bisphosphonated amino acids LXXXVI(a-c), LXXXVIII(a-c), XC(a-c) and XCII(a-c) respectively. LXXXVI(a-c) can also be produced by treatment of XXXXV (a-c) with chloromethyl chloroformate and reaction of the product chloromethoxy carbamate with a carboxylate salt. These can be used, after deprotection of the carboxy group, to acylate rifamycin derivatives LXXIII, under standard coupling conditions such as in the presence of a carbodiimide or a uronium salt and a base, to give bisphosphonated rifamycins LXXXVII(a-c), LXXXIX(a-c), XCI(a-c) and XCIII(a-c) respectively.
XXXV(a-b) →
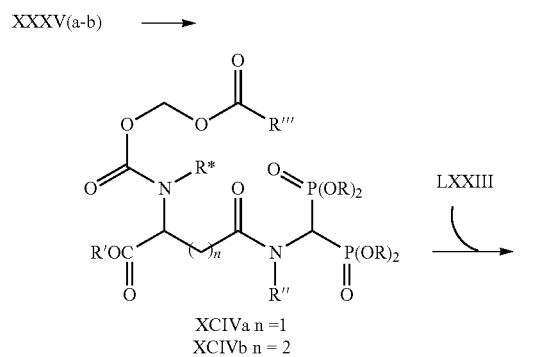
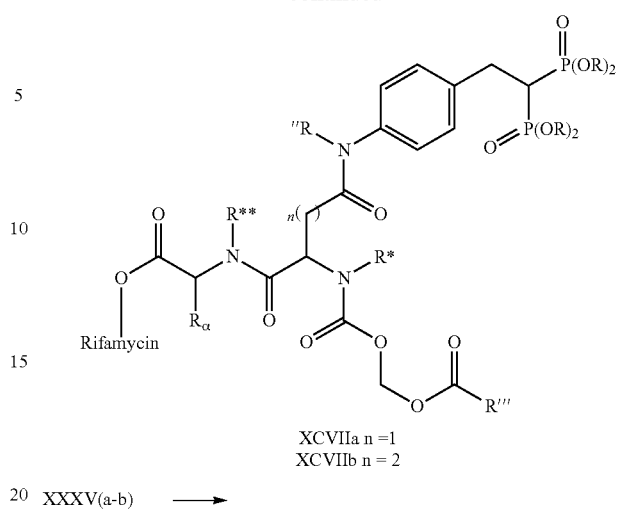
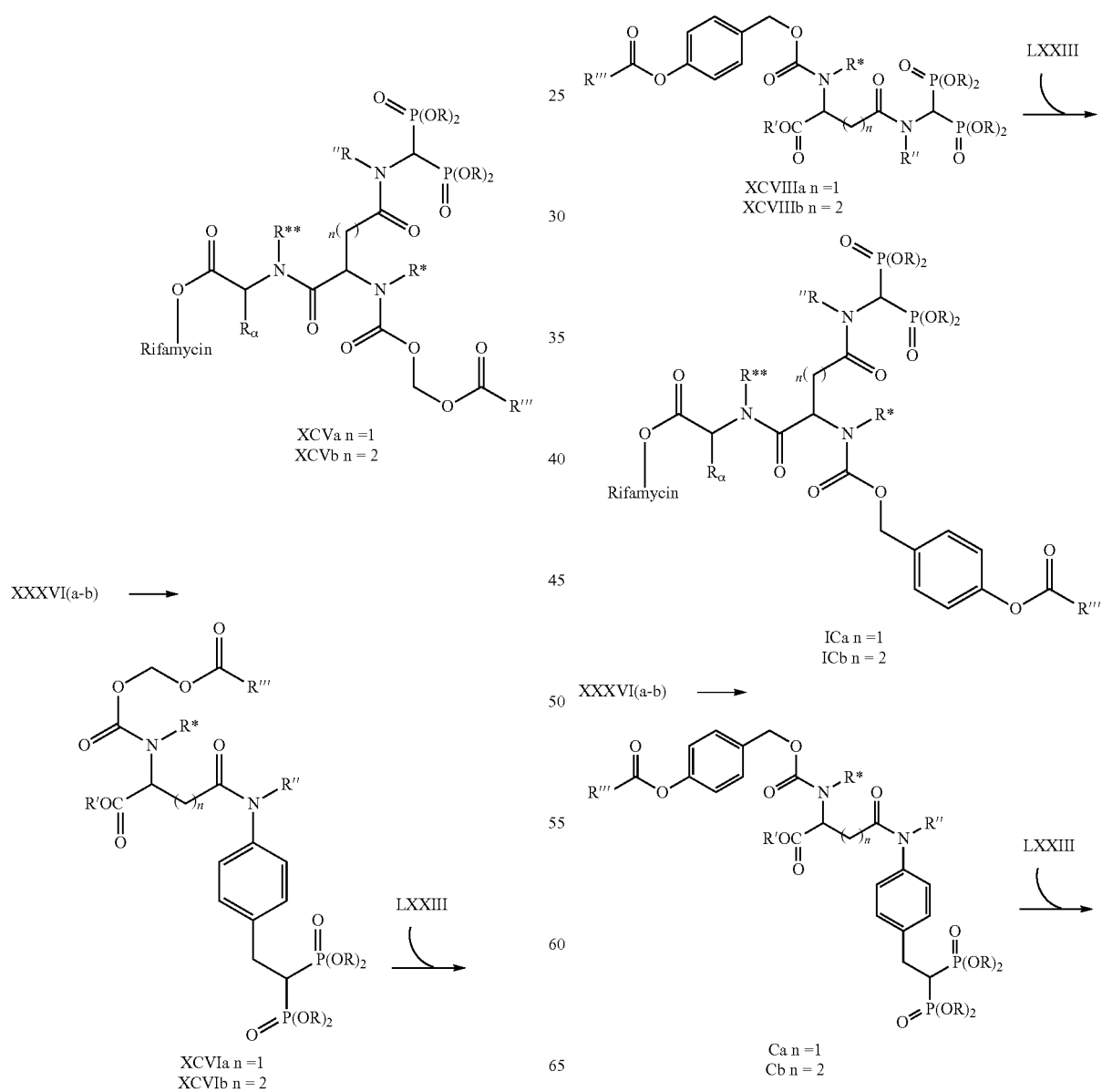

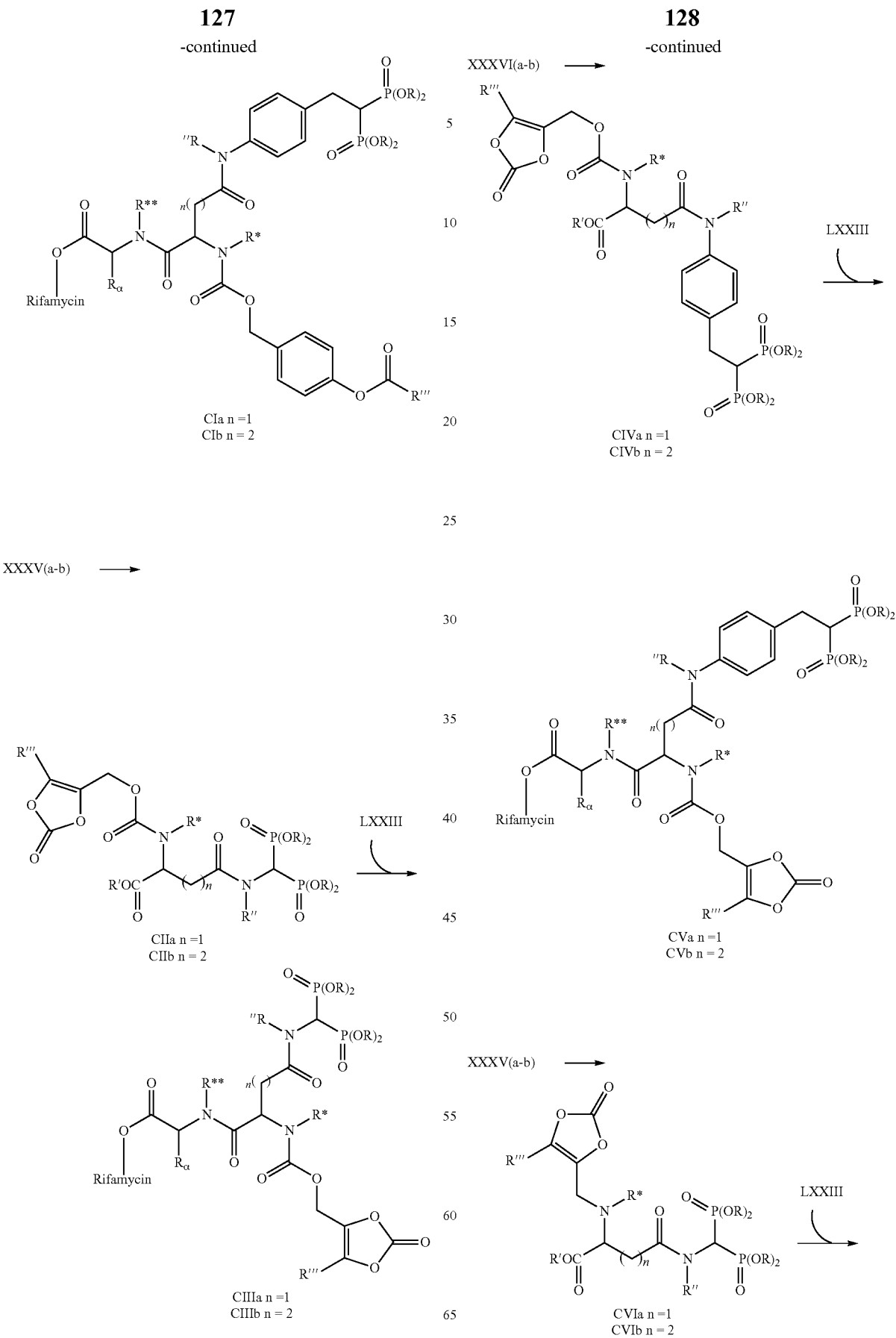

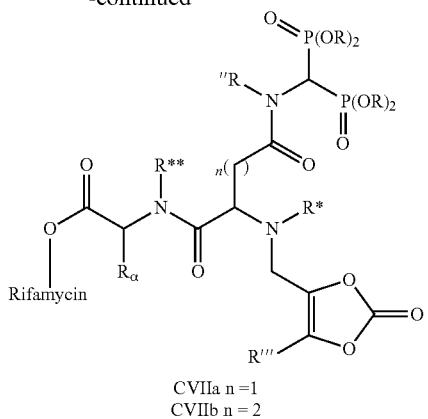

CVIIa n = 1
CVIIb n = 2

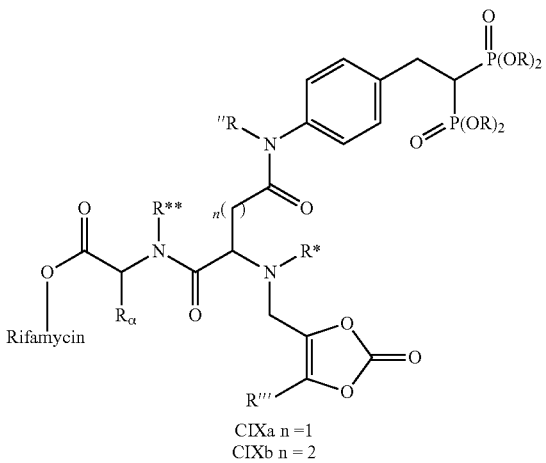

CIXa n = 1
CIXb n = 2

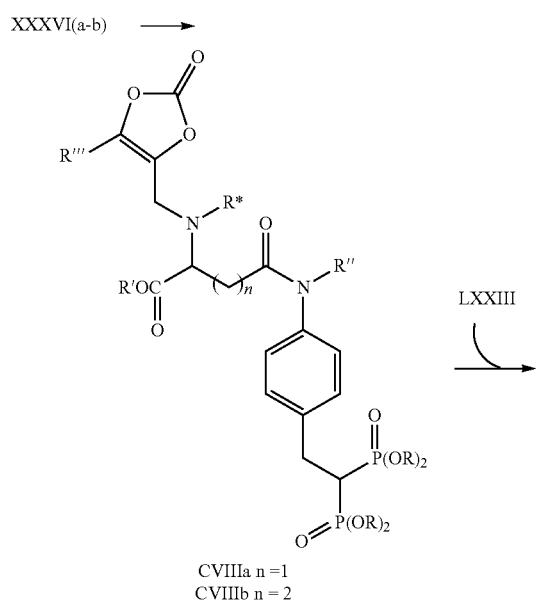

CVIIIa n = 1
CVIIIb n = 2

Similarly, bisphosphonated aminoacids XXXV(a-b) and XXXVI(a-b) can be N"-deprotected and treated with acyloxymethyl chloroformate (or chloromethyl chloroformate and then a carboxylate salt), 4-acyloxyphenylmethyl chloroformate, (2-oxo-1,3-dioxol-4-yl)methyl chloroformates or 4-(chloromethyl)-1,3-dioxol-2-ones in the presence of a non nucleophilic base to provide bisphosphonated amino acids XCIV(a-b), XCVI(a-b), XCVIII(a-b), C(a-b), CII(a-b), CIV (a-b), CVI(a-b) and CVIII(a-b) respectively. These can be used, after deprotection of the carboxy group, to acylate rifamycin derivatives LXXIII, under standard coupling conditions such as in the presence of a carbodiimide or a uronium salt and a base, to give bisphosphonated rifamycins XCV(a-b), XCVII(a-b), IC(a-b), CI(a-b), CIII(a-b), CV(a-b), CVII(a-b) and CIX(a-b) respectively. Similar bisphosphonated rifamycins can be prepared by acylation of LXXIII with bisphosphonated amino acids XXX(a-b), XXXXI(a-c), XXXXII, XXXXIII(a-f) and XXXXIV(a-b).

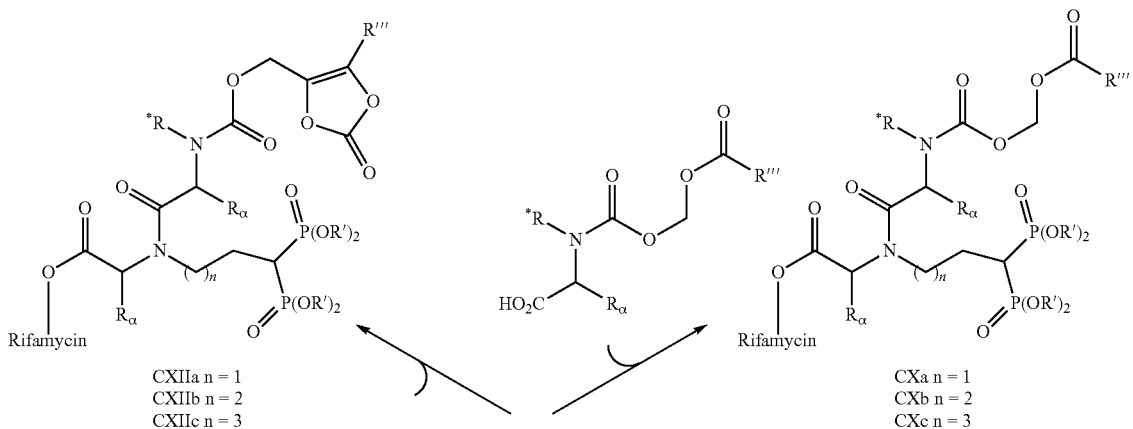

CXIIa n = 1
CXIIb n = 2
CXIIc n = 3

CXa n = 1
CXb n = 2
CXc n = 3

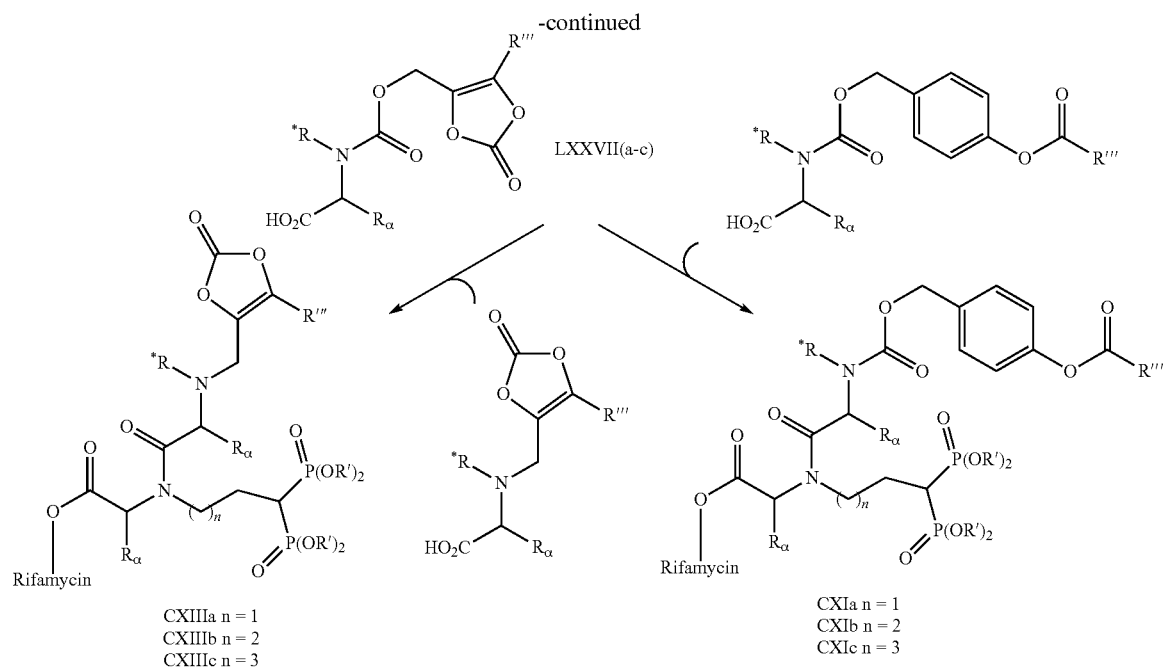

Similar bisphosphonated dipeptidyl rifamycins CX(a-c), CXI(a-c), CXII(a-c) and CXIII(a-c) can be prepared by the acylation of LXXVII(a-c) with adequately substituted amino acids in the presence of a carbodiimide or a uronium salt and a base.

Aminoacylated rifamycin LXXIII can be treated with bromoacetamides XXV and XXVI in the presence of a base to furnish bisphosphonated rifamycins CXIV and CXV respectively. Sequential treatment of amines XIII and IIIb,d with phosgene or a phosgene equivalent (such as triphosgene,

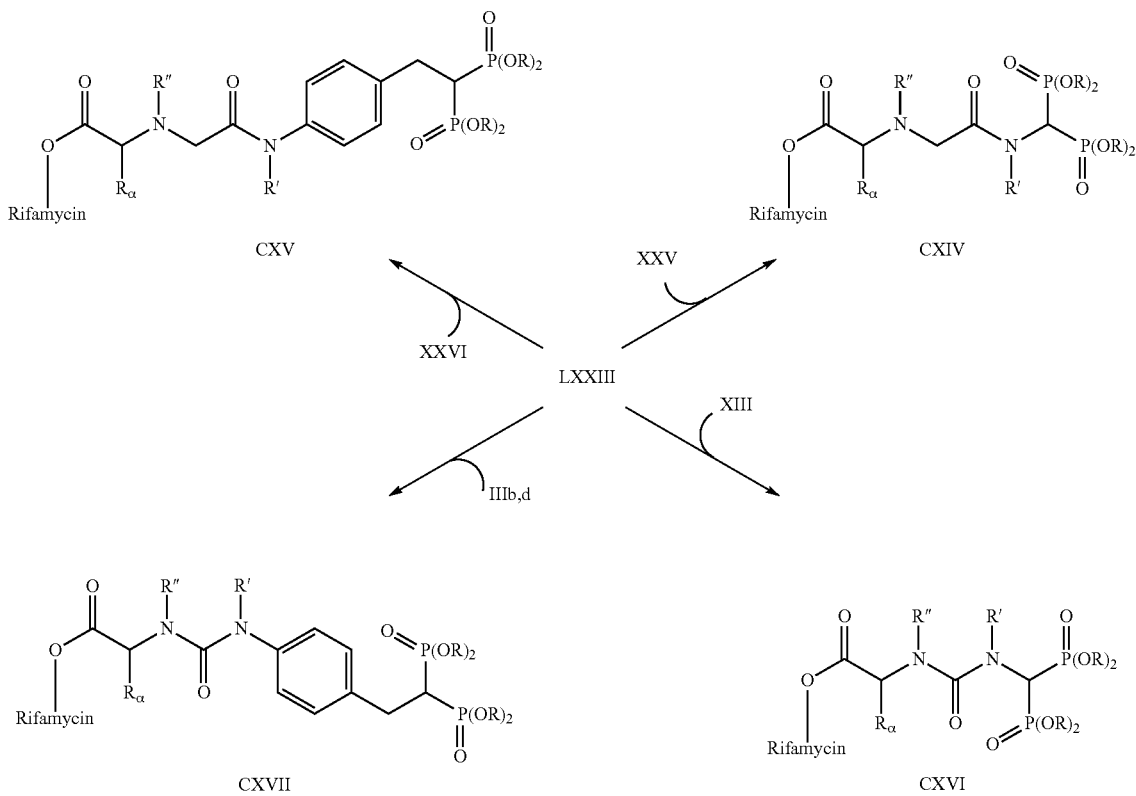

4-nitrophenylchloroformate, carbonyl diimidazole) in the presence of a base, followed by the addition of LXXIII in the presence of additional base yields bisphosphonated rifamycins CXVI and CXVII respectively.

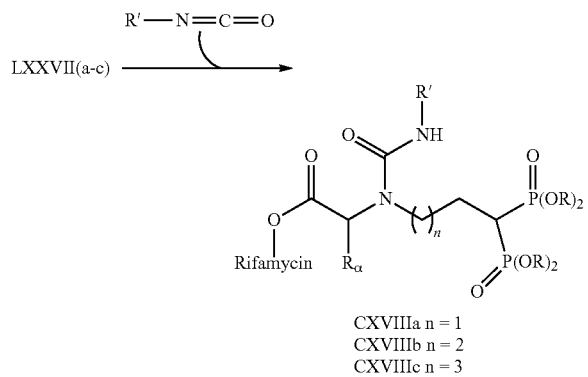

CXVIIIa n = 1
CXVIIIb n = 2
CXVIIIc n = 3

Bisphosphonated aminoacylated rifamycins LXXVII(a-c) can be converted to the parent ureas CXVIII(a-c) by treatment with an isocyanate or the combination of an amine, phosgene (or a phosgene equivalent) and a base.

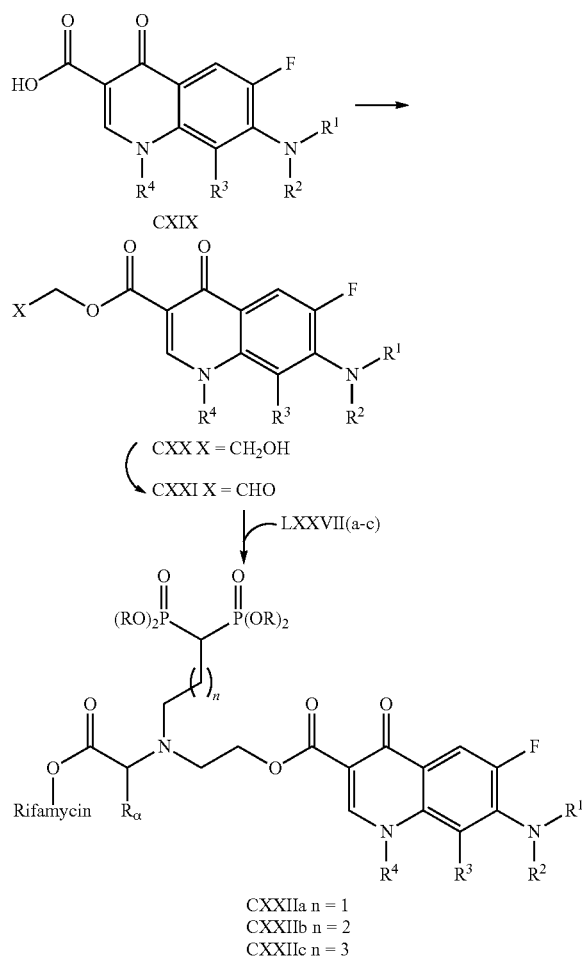

CXXIIa n = 1
CXXIIb n = 2
CXXIIc n = 3

Treatment of a fluoroquinolone CXIX with 2-bromoethanol in the presence of a base, or with a protected form of ethylene glycol in the presence of a coupling reagent such as a carbodiimide or a uronium salt and a base and subsequent deprotection provides fluoroquinolone ester CXX. This later can be oxidized to the parent aldehyde CXXI with a mild oxidant such as chromium trioxide or a periodinane. This aldehyde can then be used to reductively alkylate bisphosphonated rifamycins LXXVII(a-c) in the presence of a mild source of hydride, such as a borane or a borohydride, in particular sodium triacetoxyborohydride, to provide bisphosphonated rifamycin-fluoroquinolone conjugates CXXII(a-c).

The bisphosphonate building blocks described in this section are in the form of their phosphonic esters, R being Me, Et, i-Pr, allyl or Bn; or as the free bisphosphonic acids and/or free bisphosphonate salts. The bisphosphonic esters may be converted to the free acids and acid salts by conventional methods, such as the treatment with trimethylsilyl bromide or Iodide in the presence or the absence of a base, hydrogenation when the bisphosphonate esters are benzyl bisphosphonates, by treatment with a palladium catalyst and a nucleophile when the bisphosphonate esters are allyl bisphosphonates.

The other protecting groups used can be put on and removed using the coventional methods described in the literature, for instance as reviewed in "*Protective Groups in Organic Synthesis*", Greene, T. W. and Wuts, P. M. G., Wiley-Interscience, New York, 1999.

B) Detailed Experimental Procedures

Scheme 1. Synthesis of tetraethyl 5-carboxypentylene-1,1-bisphosphonate

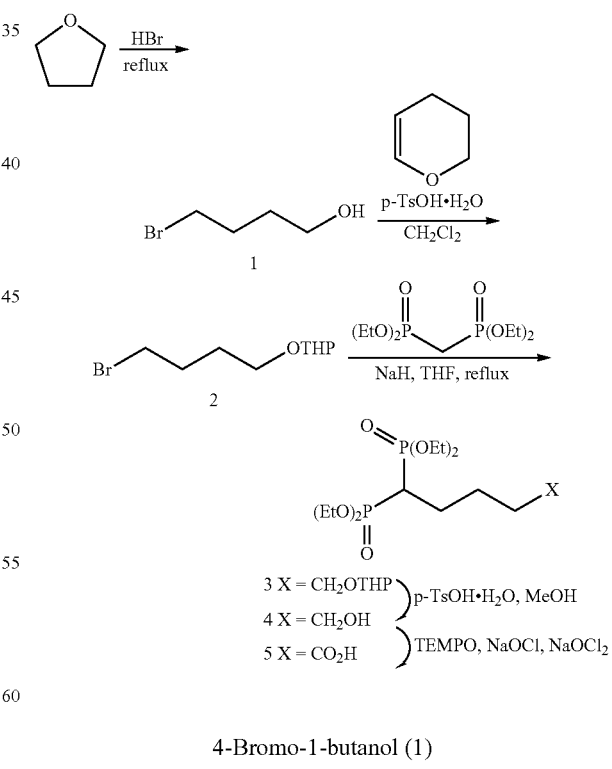

4-Bromo-1-butanol (1)

To 67.5 mL (832.2 mmol) of refluxing tetrahydrofuran was added 31 mL (274 mmol) of 48% hydrobromic acid dropwise and the yellow solution was allowed to reflux for another 2 h. After cooled to room temperature, the reaction was carefully neutralized with saturated sodium bicarbonate aqueous solution. The resultant mixture was extracted with diethyl ether (3×) and dried over anhydrous sodium sulfate. Removal of the solvent afforded the product 1 as a yellow oil (10.7 g, 26%). $^1$H NMR (400 MHz, CDCl$_3$): δ 1.69-1.76 (m, 2H), 2.01-1.94 (m, 2H), 3.46 (t, J=6.6 Hz, 2H), 3.70 (t, J=6.4 Hz, 2H).

2-(4-Bromobutoxy)-tetrahydro-2H-pyran (2)

3,4-Dihydro-2H-pyran (8.5 mL, 90.96 mmol) was added dropwise to the dichloromethane (20 mL) solution of 1 (10.7 g, 69.93 mmol) and p-toluenesulfonic acid monohydrate (26.5 mg, 0.1372 mmol). The mixture was stirred at room temperature over night. After removing the solvent, the residue was purified by flash chromatography on silica gel with 5:1 hexanes/ethyl acetate as the eluent to yield product 2 as a colorless oil (15.3 g, 92%). $^1$H NMR (400 MHz, CDCl$_3$): δ 1.48-1.62 (m, 4H), 1.68-1.85 (m, 4H), 1.94-2.02 (m, 2H), 3.40-3.53 (m, 4H), 3.74-3.88 (m, 2H), 4.57-4.59 (m, 1H).

Tetraethyl 5-(2-tetrahydro-2H-pyranyloxy)pentylene-1,1-bisphosphonate (3)

To the suspension of sodium hydride (60%, 840.5 mg, 21.01 mmol) in 40 mL of THF was carefully added tetraethyl methylenebisphosphonate (6.16 g, 20.95 mmol) and the resultant pale yellow clear solution was stirred at room temperature for 45 min. Then the bromide 2 (4.97 g, 20.96 mmol) was introduced plus 5 mL of THF rinse. The reaction was brought to reflux overnight and allowed to cool to room temperature before being quenched with saturated ammonium chloride aqueous solution. Another small amount of water was required to dissolve the solid. The mixture was extracted with ethyl acetate (3×), dried over anhydrous sodium sulfate and concentrated in vacuo. Flash chromatography on silica gel with 20:1 (v/v) dichloromethane/methanol as the eluent afforded 7.3 g of impure product 3 as a slightly yellow oil. The material was used directly in the next step without further purification. Selected $^1$H NMR signals (400 MHz, CDCl$_3$): δ 2.28 (tt, J=6.1, 24.3 Hz, 1H), 3.37-3.51 (m, 2H), 3.71-3.89 (m, 2H), 4.56-4.58 (m, 1H).

Tetraethyl 5-hydroxypentylene-1,1-bisphosphonate (4)

The crude compound 3 was dissolved in 20 mL of methanol and 74.6 mg (0.3863 mmol) of p-toluenesulfonic acid monohydrate was added. After overnight stirring at room temperature, the mixture was concentrated and subjected to flash chromatography with gradient elution from 15:1 ethyl acetate/methanol to 8:1 then 6:1 to afford 4 as a colorless oil (3.1 g, 41% over two steps). $^1$H NMR (400 MHz, CDCl$_3$): δ 1.24-1.36 (m, 12H), 1.55-1.72 (m, 4H), 1.89-2.03 (m, 2H), 2.16 (bs, 1H), 2.29 (tt, J=6.1, 24.3 Hz, 1H), 3.66 (bs, 2H), 4.11-4.22 (m, 8H).

Tetraethyl 5-carboxypentylene-1,1-bisphosphonate (5)

To a mixture of alcohol 4 (475 mg, 1.318 mmol), TEMPO (15 mg, 0.095 mmol), MeCN (6 mL) and sodium phosphate buffer (6 mL, 0.67 M, pH=6.7) heated to 35° C. were added dropwise a sodium chlorite solution (300 mg in 2 mL of water) and dilute bleach (0.75 mL of solution of 1 mL of commercial bleach in 19 mL of water) simultaneously from separate syringes. The mixture turned from yellow to red. After 5 h, reaction was complete by TLC and $^1$H NMR and was cooled to room temperature. 30 mL of water was added and the pH was adjusted to about 9 with the addition of 3 mL of 1N NaOH. The reaction was quenched by pouring into a cold Na$_2$SO$_3$ solution (500 mg in 10 mL of water) and maintained below 20° C. After 30 min stirring at the same temperature, 30 mL of diethyl ether was used to extract the mixture and the organic phase was discarded. The pH of the aqueous phase was readjusted to between 3-4 by adding 5 mL of 1N HCl and the mixture was extracted with dichloromethane (3×). The combined extracts were dried over sodium sulfate and concentrated to afford the acid 5 quantitatively, which could be used in the following steps without further purification. $^1$HNMR (400 MHz, CDCl$_3$): δ 1.34 (t, J=7.0, 12H), 1.86-2.06 (m, 4H), 2.33 (tt, J=24.2, 5.9, 1H), 2.36 (t, J=7.3, 2H), 4.14-4.22 (8H).

Scheme 2. Synthesis of tetraallyl 1-carboxypropylene-3,3-bisphosphonate

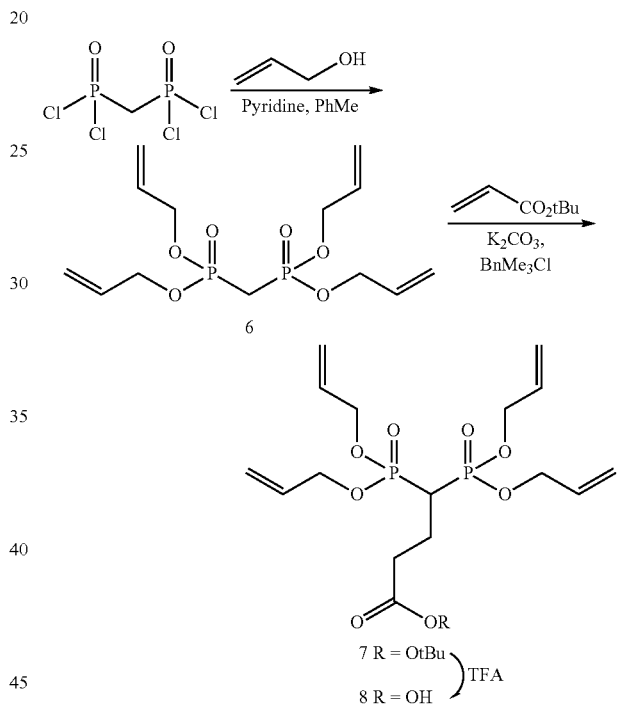

Tetraallyl methylene-1,1-bisphosphonate (6)

To a suspension of tetrachloromethylene bisphosphonate (6.33 g, 25.3 mmol) in toluene (25 mL) at 0° C. was added a mixture of allyl alcohol (6.91 mL, 101 mmol) and pyridine (8.20 mL, 101 mmol) with a dropping funnel over 25 min. After the addition, the reaction mixture was warmed to room temperature and stirred for 20 h. The precipitate was removed by filtration and the solids were washed with toluene. The filtrate was concentrated and purified by flash chromatography on silica gel using 50% acetone/hexanes as eluent. Tetraallyl methylenebisphosphonate 6 was obtained as a clear yellowish oil (5.87 g, 69%). $^1$H NMR (400 MHz, CDCl$_3$) δ 1.33 (t, J=21.1 Hz, 2H), 4.60-4.63 (m, 8H), 5.23-5.27 (m, 4H), 5.35-5.40 (m, 4H), 5.90-6.00 (m, 4H).

Tetraallyl 1-t-butoxy-1-oxo-butylene-4,4-bisphosphonate (7)

To a solution of tetraallyl bisphosphonate 6 (5.50 g, 16.4 mmol) in benzene (26 mL) was added potassium carbonate (2.26 g, 16.4 mmol) and benzyltriethylammonium chloride (373 mg, 1.64 mmol). The mixture was stirred at reflux and t-butyl acrylate (3.56 mL, 24.5 mmol) was added. After refluxing for 18 h, the mixture was cooled to room temperature and filtered over celite. The solids were washed with several portions of benzene and the filtrate was concentrated and purified by silica gel chromatography on a Biotage™ flash chromatography system using 0-10% methanol in ethyl acetate. Bisphosphonate 7 was obtained as a clear yellowish oil (1.94 g, 25%). $^1$H NMR (400 MHz, CDCl$_3$) δ 1.43 (s, 9H), 2.15-2.29 (m, 2H), 2.54-2.69 (m, 3H), 4.59-4.64 (m, 8H), 5.22-5.26 (m, 4H), 5.34-5.40 (m, 4H), 5.90-6.00 (m, 4H).

Tetraallyl 1-carboxypropylene-3,3-bisphosphonate (8)

Bisphosphonate 7 (2.10 g, 4.52 mmol) was stirred in TFA (5 mL) for 15 min and concentrated in vacuo. Purification by silica gel chromatography on a Biotage™ flash chromatography system using 0-10% methanol in CH$_2$Cl$_2$ provided acid 8 as a colorless gum (1.88 g, quant.). $^1$H NMR (400 MHz, CDCl$_3$) δ 2.20-2.34 (m, 2H), 2.67-2.82 (m, 3H), 4.60-4.64 (m, 8H), 5.23-5.26 (m, 4H), 5.35-5.39 (m, 4H), 5.89-5.99 (m, 4H).

Scheme 3. Synthesis of chloroformates 13 and 14

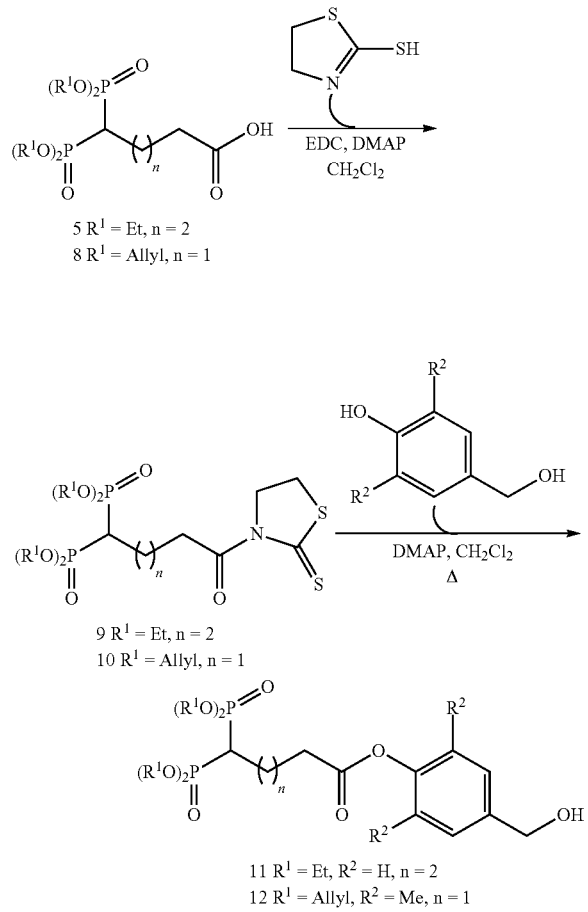

Tetraethyl 1-(thiazolidin-2-thione-3-yl)-1-oxo-pentylene-5,5-bisphosphonate (9)

To a solution of acid 5 (920 mg, 2.46 mmol), 2-mercaptothiazoline (322 mg, 2.70 mmol) and DMAP (30 mg, 0.246 mmol) in CH$_2$Cl$_2$ (12 mL), cooled in an ice-bath was added EDC (707 mg, 3.69 mmol). The mixture was stirred for 10 min after which the ice-bath was removed and stirring was continued for 18 h at room temperature. The reaction mixture was diluted with CH$_2$Cl$_2$, washed with an aqueous solution of CuSO$_4$ (5% wt) and saturated NaCl solution. The organic layer was dried over MgSO$_4$, filtered and concentrated to dryness, providing compound 9 as a yellow oil (1.32 g, quant.) which was used without purification. $^1$H NMR (400 MHz, CDCl$_3$) δ 1.34 (2×t, J=7.1 Hz, 12H), 1.92-2.02 (m, 4H), 2.29 (tt, J=24.1, 5.7 Hz, 1H), 3.25-3.31 (m, 4H), 4.14-4.22 (m, 8H), 4.57 (t, J=7.6 Hz, 2H).

Tetraallyl 1-(thiazolidin-2-thione-3-yl)-1-oxo-butylene-4,4-bisphosphonate (10)

To a solution of acid 8 (500 mg, 1.22 mmol), 2-mercaptothiazoline (161 mg, 1.35 mmol) and DMAP (15 mg, 0.122 mmol) in CH$_2$Cl$_2$ (6 mL), cooled in an ice-bath was added EDC (351 mg, 1.83 mmol). The mixture was stirred for 10 min after which the ice-bath was removed and stirring was continued for 18 h at room temperature. The reaction mixture was diluted with CH$_2$Cl$_2$, washed with an aqueous solution of CuSO$_4$ (5% wt) and saturated NaCl solution. The organic layer was dried over MgSO$_4$, filtered and concentrated to dryness, providing compound 10 as a yellow gum (617 mg, 99%) which was used without purification. $^1$H NMR (400 MHz, CDCl$_3$) δ 2.27-2.41 (m, 2H), 2.68 (tt, J=24.1, 6.6 Hz, 1H), 3.28 (t, J=7.5 Hz, 2H), 3.60 (t, J=7.4 Hz, 2H), 4.57 (t, J=7.6 Hz, 2H), 4.60-4.64 (m, 8H), 5.23-5.26 (m, 4H), 5.35-5.40 (m, 4H), 5.91-6.00 (m, 4H).

Tetraethyl 1-(4-hydroxymethylphenoxy)-1-oxo-pentylene-5,5-bisphosphonate (11)

To a mixture of compound 9 (1.17 g, 2.46 mmol) and 4-hydroxybenzyl alcohol (305 mg, 2.46 mmol) in CH$_2$Cl$_2$ (12 mL) was added DMAP (30 mg, 0.25 mmol) and the mixture was stirred at reflux for 18 h, after which it was concentrated. Purification by silica gel chromatography on a Biotage™ flash chromatography system using 0-10% methanol in ethyl acetate provided alcohol 11 as a colorless oil (1.00 g, 85%). $^1$H NMR (400 MHz, CDCl$_3$) δ 1.34 (t, J=7.0 Hz, 12H), 2.00-2.09 (m, 4H), 2.25-2.40 (m, 1H), 2.55-2.61 (m, 2H), 4.15-4.23 (m, 8H), 4.69 (s, 2H), 7.07 (d, J=8.5 Hz, 2H), 7.38 (d, J=8.2 Hz, 2H).

Tetraallyl 1-(2,6-dimethyl-4-hydroxymethylphenoxy)-1-oxo-butylene-4,4-bisphosphonate (12)

To a mixture of compound 10 (1.18 g, 2.32 mmol) and 4-(hydroxymethyl)-2,6-dimethylphenol (353 mg, 2.32 mmol) in CH$_2$Cl$_2$ (12 mL) was added DMAP (28 mg, 0.23 mmol) and the mixture was stirred at reflux for 24 h, after which it was concentrated. Purification by silica gel chromatography on a Biotage™ flash chromatography system using 0-1% methanol in ethyl acetate provided alcohol 12 as a light yellow oil (229 mg, 18%). $^1$H NMR (400 MHz, C$_6$D$_6$) δ 2.09 (s, 6H), 2.56-2.73 (m, 2H), 2.86 (tt, J=23.8, 6.5 Hz, 1H), 3.09 (t, J=7.6 Hz, 2H), 4.29 (bs, 2H), 4.53-4.67 (m, 8H), 4.95-4.99 (m, 4H), 5.18-5.26 (m, 4H), 5.74-5.85 (m, 4H), 6.84 (s, 2H).

Scheme 4. Rifabutin bisphosphonate conjugate 18 and 19
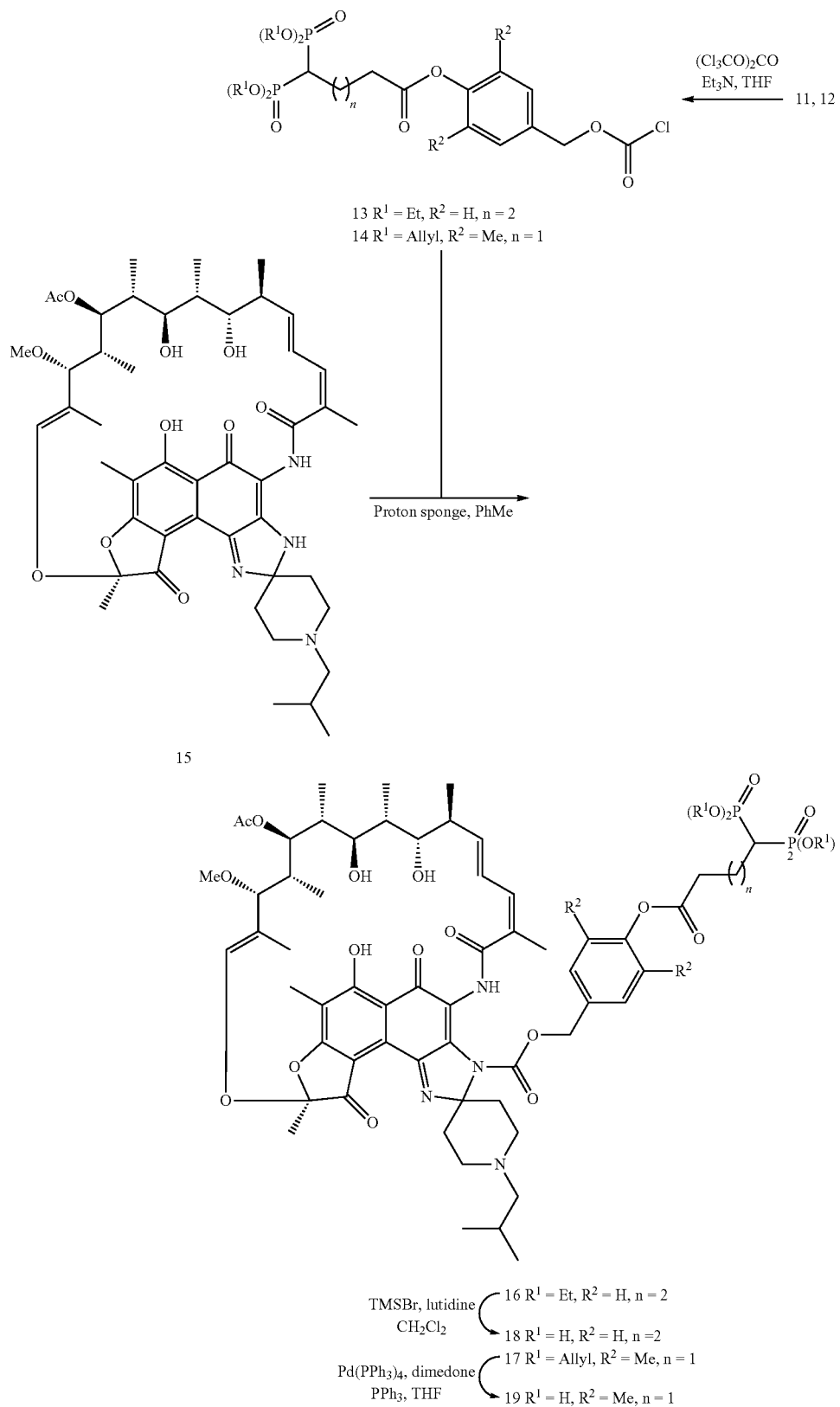

Rifabutin Bisphosphonate Conjugate 16

To a solution of triphosgene (103 mg, 0.35 mmol) in dry THF (3 mL) at −20° C. was added a mixture of alcohol 11 (500 mg, 1.04 mmol) and triethylamine (145 μL, 1.04 mmol) in dry THF (3 mL). The mixture was stirred at −20° C. and followed by $^1$H NMR in CDCl$_3$ (small aliquots were collected, concentrated and analyzed by $^1$H NMR). After 1 h at this temperature, NMR showed mostly chloroformate 13 (83%), with tetraethyl 1-(4-(chloromethyl)phenoxy)-1-oxo-pentylene-5,5-bisphosphonate side-product (12%) and starting alcohol (4%). A solution of Rifabutin 15 (294 mg, 0.35 mmol) and proton sponge (82 mg, 0.38 mmol) in dry THF (5 mL) was added to the chloroformate solution and the stirring was pursued at 3° C. for 3d. The reaction mixture was concentrated and purified by C18 silica gel chromatography on a Biotage™ flash chromatography system using a gradient of 10-100% MeCN in Et$_3$N/CO$_2$ buffer (0.2% aqueous solution of Et$_3$N adjusted to pH 7 by bubbling CO$_2$). Combined fractions were concentrated under vacuum to remove MeCN and the resulting aqueous solution was extracted with CH$_2$Cl$_2$ (5×). The combined organic layers were dried over MgSO$_4$, filtered and concentrated to provide compound 16 as an orange solid (212 mg, 45%). ESI-MS: (M+H) calculated for $C_{67}H_{94}N_4O_{21}P_2$ 1353, found 1353.4.

Rifabutin Bisphosphonate Conjugate 17

To a solution of triphosgene (91 mg, 0.31 mmol) in dry THF (3 mL) at −20° C. was added a mixture of alcohol 12 (500 mg, 0.92 mmol) and triethylamine (128 μL, 0.92 mmol) in dry THF (3 mL). The mixture was stirred at −20° C. and followed by $^1$H NMR in C$_6$D$_6$ (small aliquots were collected, concentrated and analyzed by $^1$H NMR). After 1 h at this temperature, NMR showed mostly chloroformate 14 (66%), with tetraallyl 1-(2,6-dimethyl-4-(chloromethyl)phenoxy)-1-oxo-butylene-4,4-bisphosphonate side product (12%) and starting alcohol (22%). A solution of Rifabutin 15 (260 mg, 0.31 mmol) and proton sponge (72 mg, 0.34 mmol) in dry THF (5 mL) was added to the chloroformate solution and the stirring was pursued at 3° C. for 24 h. The reaction mixture was concentrated and purified by C18 silica gel chromatography on a Biotage™ flash chromatography system using a gradient of 10-100% MeCN in Et$_3$N/CO$_2$ buffer (0.2% aqueous solution of Et$_3$N adjusted to pH 7 by bubbling CO$_2$). Combined fractions were concentrated under vacuum to remove MeCN and the resulting aqueous solution was treated with saturated NaCl solution and extracted with CH$_2$Cl$_2$ (3×). The combined organic layers were dried over MgSO$_4$, filtered and concentrated to provide compound 17 as an orange solid (140 mg, 32%). ESI-MS: (M+H) calculated for $C_{72}H_{96}N_4O_{21}P_2$ 1415, found 1415.2.

Rifabutin Bisphosphonate Conjugate 18

To a solution of compound 16 (212 mg, 0.157 mmol) in CH$_2$Cl$_2$ (7 mL) cooled down to −78° C. was added 2,6-lutidine (727 μL, 6.27 mmol) followed by TMS-Br (413 μL, 3.13 mmol). The reaction mixture was stirred for 30 min at −78° C., then 24 h at room temperature. It was then concentrated to dryness under high vacuum, redissolved in DMF (7 mL) then treated with pyridine (1.02 mL, 12.6 mmol) and HF-pyridine (157 μL, 6.28 mmol). After stirring for 1 h at room temperature the mixture was concentrated to dryness under high vacuum. The crude product was purified by C18 silica gel chromatography on a Biotage™ flash chromatography system using a gradient of 10-100% MeCN in Et$_3$N/CO$_2$ buffer (0.2% aqueous solution of Et$_3$N adjusted to pH 7 by bubbling CO$_2$). Pure fractions were combined, concentrated and lyophilized to provide the bis-triethylammonium salt of compound 18 as a fluffy orange solid (166 mg, 73%). LCMS: 95.4% (254 nm), 96.5% (220 nm), 95.6% (320 nm). ESI-MS: (M+H) calculated for $C_{59}H_{78}N_4O_{21}P_2$ 1241, found 1241.2.

Rifabutin Bisphosphonate Conjugate 19

To a solution of compound 17 (140 mg, 0.099 mmol) in THF (3 mL) was added dimedone (55 mg, 0.40 mmol), triphenylphosphine (10 mg, 0.040 mmol) and tetrakis(triphenylphosphine) palladium (6 mg, 0.0049 mmol). After stirring for 18 h, the reaction mixture was concentrated to dryness then purified by C18 silica gel chromatography on a Biotage™ flash chromatography system using a gradient of 10-100% MeCN in H$_2$O, both containing 0.05% NH$_4$OH. Pure fractions were combined, concentrated and lyophilized to provide the diammonium salt of compound 19 as a fluffy orange solid (94 mg, 73%). LCMS: 95.9% (254 nm), 97.7% (220 nm), 96.7% (320 nm). ESI-MS: (M+H) calculated for $C_{60}H_{80}N_4O_{21}P_2$ 1255, found 1255.2.

Scheme 5. Preparation of
1-(carbonochloridoyloxy)ethyl
4,4-bis(diethylphosphono)butanoate (24)

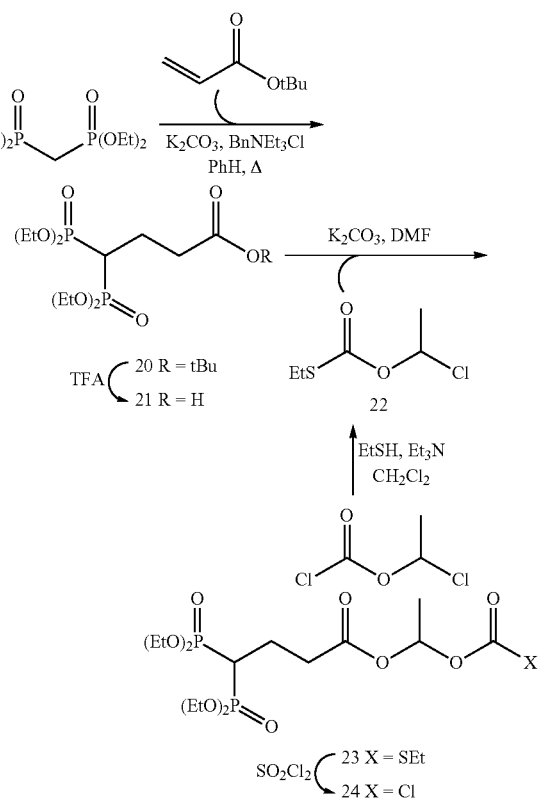

Tetraethyl 1-t-butoxy-1-oxo-butylene-4,4-bisphosphonate (20)

To a solution of tetraethylmethylene bisphosphonate (10.0 g, 34.7 mmol) in benzene (56 mL) were added t-butyl acrylate (5.54 mL, 38.2 mmol), K$_2$CO$_3$ (4.79 g, 34.7 mmol) and benzyl triethylammonium chloride (0.79 g, 3.5 mmol). The mixture was stirred under reflux for 18 hours. After which it was filtered and the filtrate was concentrated. Purification by flash chromatography on silica gel using a gradient of 0-10% methanol/ethyl acetate provided compound 20 as a colorless oil (3.8 g, 26%). $^1$H-NMR (400 MHz, CDCl$_3$) δ 1.34 (t, J=7.0 Hz, 12H), 1.43 (s, 9H), 2.11-2.25 (m, 2H), 2.48 (tt, J=23.9, 6.5 Hz, 1H), 2.56 (t, J=7.4 Hz, 2H), 4.13-4.22 (m, 8H).

Tetraethyl 1-carboxypropylene-3,3-bisphosphonate (21)

t-Butyl ester 20 (4.3 g, 10.3 mmol) was stirred in TFA (8.6 mL) for 15 min., then concentrated to dryness. Purification on reverse-phase Biotage 40M O18 column, using a gradient of 10-60% methanol/H$_2$O provided compound 21 (3.7 g, 99%) as a colorless oil which solidified over time. $^1$H-NMR (400 MHz, CDCl$_3$) δ 1.34 (t, J=7.0 Hz, 12H), 2.18-2.28 (m, 2H), 2.60 (tt, J=23.9, 6.5 Hz, 1H), 2.69 (t, J=7.3 Hz, 2H), 4.14-4.23 (m, 8H).

S-Ethyl O-1-chloroethyl carbonothioate (22)

A solution of ethanethiol (2.39 mL, 32.39 mmol) and triethylamine (4.50 mL, 32.39 mmol) in 20 mL of diethyl ether was added over 30 min to a stirred solution of chloroethyl chloroformate (4.63 g, 32.39 mmol) in 40 mL of diethyl ether cooled to 0-5° C. The mixture was stirred for another 30 min at the same temperature and then for 16 h at room temperature. It was filtered through celite, rinsing the solids with diethyl ether (50 mL), and the combined filtrate was concentrated in vacuo to give the product 22 (3.53 g, 64.8%) as a liquid. NMR (400 MHz, CDCl$_3$) δ 1.36 (t, J=7.3 Hz, 3H), 1.78 (d, J=6.1 Hz, 3H), 2.90 (m, 2H), 6.60 (q, J=6.1 Hz, 1H).

S-Ethyl O-1-(4,4-bis(diethylphosphono)butanoyloxy)ethyl carbonothioate (23)

To a solution of 21 (500 mg, 1.38 mmol) and 22 (234 mg, 1.38 mmol) in 10 mL of anhydrous DMF was added K$_2$CO$_3$ (191 mg, 1.38 mmol) followed by KI (230 mg, 1.38 mmol) and the resulting mixture was stirred at room temperature for 24 h. Water was added and the mixture was extracted with EtOAc (2×60 mL). The combined organic phase was washed with saturated NaCl (1×50 mL), dried over Na$_2$SO$_4$, filtered and concentrated in vacuo. The residue was purified by flash chromatography on silica gel using 15% methanol in ethyl acetate to give the product 23 (290 mg, 42%). $^1$H NMR (400 MHz, CDCl$_3$) δ 1.34 (m, 15H), 1.48 (d, J=6.1 Hz, 3H), 2.21 (m, 2H), 2.48 (tt, J=23.9, 6.5 Hz, 1H), 2.56 (t, J=7.4 Hz, 2H), 2.85 (m, 2H), 4.18 (m, 8H), 6.96 (q, J=6.1 Hz, 1H).

1-(Carbonochloridoyloxy)ethyl 4,4-bis(diethylphosphono)butanoate (24)

Sulfuryl chloride (78 μL, 0.96 mmol) was added drop-wise to a solution of 23 (237 mg, 0.48 mmol) in 10 mL of CH$_2$Cl$_2$ cooled to 0° C. The solution was stirred for 2 h. The solvent was removed under reduced pressure to afford chloroformate 24 and which was used for the next reaction without further purification.

Scheme 6. Synthesis of Rifabutin Bisphosphonate Conjugate 28

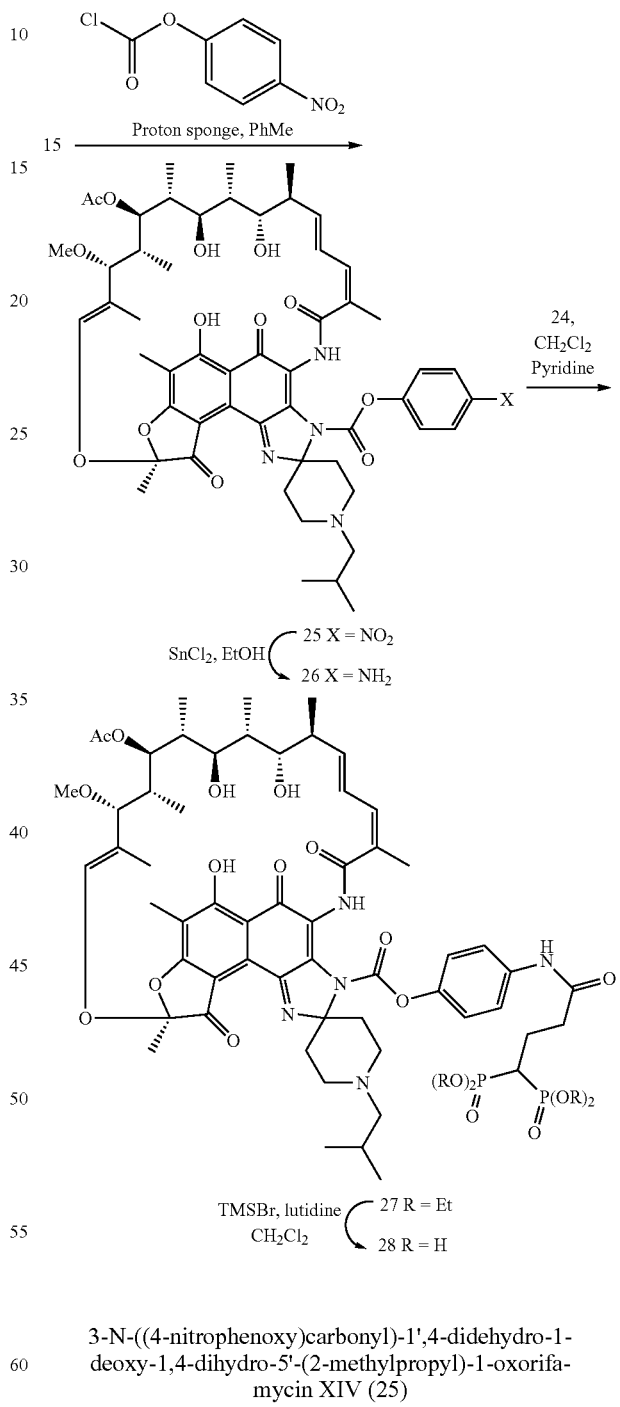

3-N-((4-nitrophenoxy)carbonyl)-1',4-didehydro-1-deoxy-1,4-dihydro-5'-(2-methylpropyl)-1-oxorifamycin XIV (25)

To a solution of rifabutin (15, 1 g, 1.18 mmol) and proton sponge (N,N,N',N'-Tetramethyl-1,8-naphthalenediamine, 278 mg, 1.3 mmol) in 10 mL of THF, cooled in an ice bath, was added, dropwise over 5 min, a solution of 4-nitrophenyl chloroformate (262 mg, 1.3 mmol) in 5 mL of THF. The mixture was stirred in the same bath which was left to come to room temperature on its own. After 20 h, it was concentrated in vacuo and the residue was purified by silica gel chromatography (0-50% ethyl acetate in 2:2:1 Hexanes:CH$_2$Cl$_2$:ethyl acetate) to give 25 (553 mg, 0.55 mmol, 46%) as a dark yellow solid.

3-N-((4-aminophenoxy)carbonyl)-1',4-didehydro-1-deoxy-1,4-dihydro-5'-(2-methylpropyl)-1-oxorifamycin XIV (26)

To a solution of rifabutin 25 (1.35 g, 1.33 mmol) in 25 mL of EtOH, cooled in an ice bath, was added tin (II) chloride (1.30 g, 6.89 mmol) and the mixture was stirred for 20 h, the pH was adjusted to 8 with saturated sodium bicarbonate solution, and the mixture was filtered through Celite. The filter cake was washed with ethanol, and the ethanol was evaporated. The aqueous layer was extracted with CH$_2$Cl$_2$ (3×). The combined organic layers were washed with saturated NaCl solution once, dried over Na$_2$SO$_4$, filtered and concentrated. The crude product was purified by flash chromatography on silica gel using a gradient of 70-100% ethyl acetate in hexanes as eluant to provide 26 (0.493 g, 37%). $^1$H NMR (400 MHz, CDCl$_3$) 8-0.24 (d, J=7.1 Hz, 3H), 0.60 (d, J=6.65 Hz, 3H), 0.92 (m, 9H), 1.02 (d, J=7.1 Hz, 3H), 1.42 (m, 1H), 1.62 (m, 2H), 1.70-1.90 (m, 7H), 2.06 (s, 3H), 2.10-2.60 (m, 6H), 2.35 (s, 3H), 2.60-2.80 (m, 4H), 2.90-3.25 (m, 5H), 3.02 (s, 3H), 3.40 (bs, 2H), 3.43 (bs, 2H), 3.79 (bs, 1H), 5.02 (d, J=10.95 Hz, 1H), 5.20 (m, 1H), 6.05 (m, 1H), 6.23 (m, 1H), 6.63-6.94 (m, 4H).

Rifabutin Bisphosphonate Conjugate 27

To a solution of 26 (0.472 g, 0.48 mmol) and pyridine (46.7 μl, 0.57 mmol) in 15 mL of CH$_2$Cl$_2$, cooled in an ice bath, was added, dropwise over 5 min, a solution of 24 (237 mg, 0.48 mmol) in 10 mL of CH$_2$Cl$_2$. The mixture was stirred in the same bath which was left to come to room temperature on its own. After 16 h, it was concentrated in vacuo and the residue was purified by silica gel chromatography (2-10% methanol in CH$_2$Cl$_2$) to give 27 (172 mg, 27%).

Rifabutin Bisphosphonate Conjugate 28

To a solution of 27 (172 mg, 0.13 mmol) and 2,6-lutidine (754 μL, 6.50 mmol) in 10 mL of CH$_2$Cl$_2$ cooled to −78° C. was added dropwise TMS-Br (429 μL, 3.25 mmol) under argon. The cold bath was removed, the mixture was stirred for 24 hours at room temperature and the solvent was removed under vacuum until dryness. The residue was dissolved in 3 mL of anhydrous DMF, pyridine (735 μL, 9.10 mmol) followed by HF-Pyridine (118 μL, 4.55 mmol) were added. After stirring 1 h at room temperature, the solvent was evaporated in vacuo. The crude residue was purified by reverse phase flash chromatography (linear gradient of 0% to 100% 0.05% NH4OH in acetonitrile/0.05% NH4OH in water). Combined pure fractions were concentrated and lyophilized to yield 28 (48 mg, 30%). LCMS purity: 97.98% (254 nm), 96.98% (220 nm), 92.42% (320 nm); mass calculated for C$_{57}$H$_{75}$N$_5$O$_{20}$P$_2$ 1211, found 1212 (M+H). $^1$H NMR (400 MHz, D$_2$O) δ −0.24 (m, 3H), 0.60 (m, 3H), 0.84 (m, 6H), 1.02 (d, J=7.1 Hz, 6H), 1.25-1.57 (m, 3H), 1.62-2.38 (m, 25H), 2.70 (m, 3H), 3.02-3.12 (m, 5H), 3.22 (bd, 2H), 3.36-3.77 (m, 6H), 3.79-4.16 (m, 4H), 5.02 (m, 1H), 5.88-5.97 (m, 1H), 6.05 (m, 1H), 6.38 (m, 1H), 6.97-7.60 (m, 5H).

Scheme 7. Preparation of Glycine and Sarcosine Esters of Rifabutin (31 and 32)

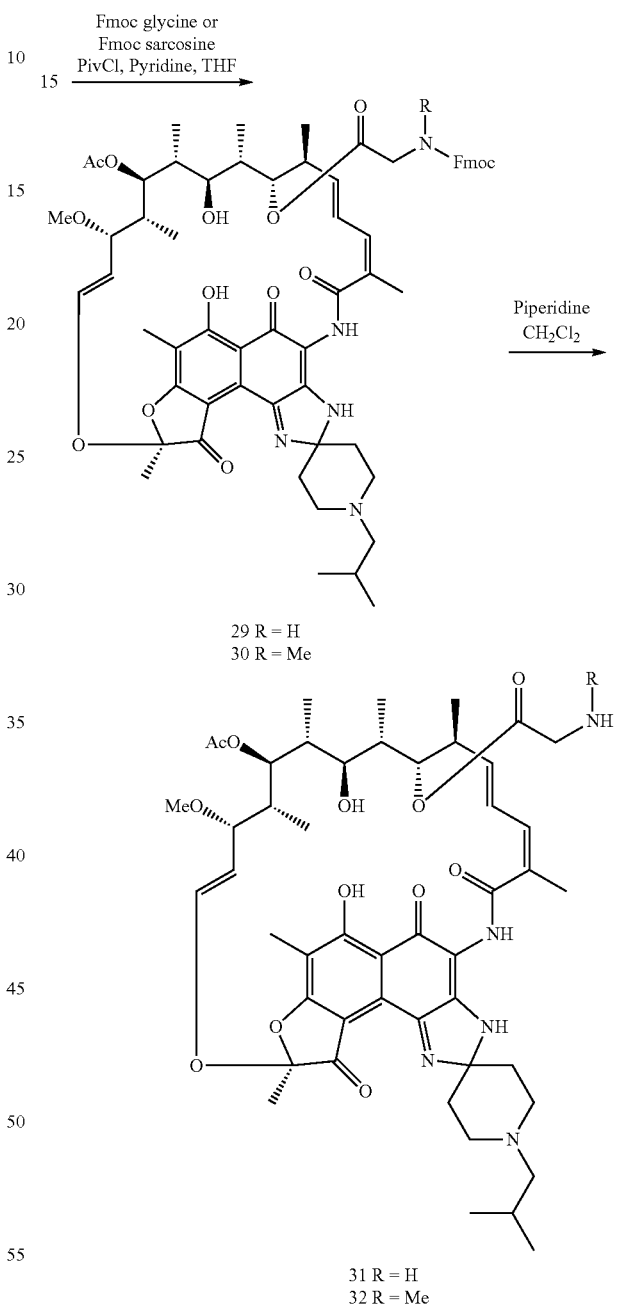

21-O-(N-((9H-fluoren-9-yl)methyloxycarbonyl)-glycinoyl)-1',4-didehydro-1-deoxy-1,4-dihydro-5'-(2-methylpropyl)-1-oxorifamycin XIV (29)

Pivaloyl chloride (145 μL, 1.18 mmol) was added dropwise to a solution of N-Fmoc-glycine (351 mg, 1.18 mmol) and pyridine (95 μL, 1.18 mmol) in THF (3 mL) and the resulting solution was stirred for 1 h before being added to a stirred solution of rifabutin (100 mg, 0.118 mmol) and pyridine (38 µL, 0.47 mmol) in THF (2 mL). The resulting was stirred for 3 days under Ar before being diluted in Et$_2$O (10 mL) and H$_2$O (10 mL). After separation, the aqueous layer was extracted two times with Et$_2$O (2×10 mL). The combined organic layers were washed with a saturated solution of NaCl (10 mL), dried over MgSO$_4$ and concentrated in vacuo. The crude product was purified by reverse phase chromatography eluting with aqueous buffer (Et$_3$N/CO$_2$, pH=7)/CH$_3$CN (10% to 100% linear gradient) and afford 114 mg (0.102 mmol, 86%) of 29 as dark purple solid. $^1$H NMR (400 MHz, CDCl$_3$) δ 8.34 (br s, 1H), 7.94 (br s, 1H), 7.79-7.71 (m, 4H), 7.42 (t, J=3.0 Hz, 2H), 7.34 (t, J=3.0 Hz, 2H), 6.43 (dd, J=16 Hz, 1H), 6.14 (d, J=11 Hz, 1H), 6.08 (d, J=11.2 Hz, 1H), 5.95-5.91 (m, 2H), 5.19 (d, J=11.2 Hz, 1H), 5.05 (dd, J=9.3, 1.2 Hz, 1H), 4.97 (d, J=10.6 Hz, 2H), 4.51-2.19 (m, 3H), 3.83 (d, J=4.6 Hz, 2H), 3.55 (s, 1H), 3.14 (br d, J=1.2 Hz, 1H), 3.10 (s, 3H), 3.08-2.84 (m, 4H), 2.73-2.52 (m, 4H), 2.30 (d, J=6.0 Hz, 2H), 2.21 (s, 3H), 2.31 (m, 1H), 2.05 (s, 6H), 2.02 (m, 2H), 1.86-1.79 (m, 4H), 1.80 (s, 3H), 1.27 (m, 3H), 1.08 (d, J=6.9 Hz, 3H), 0.95 (d, J=6.6 Hz, 9H), 0.53 (d, J=6.9 Hz, 3H), −0.75 (d, J=7.0 Hz, 3H).

21-O-(N-((9H-fluoren-9-yl)methyloxycarbonyl)-N-methyl-glycinoyl)-1',4-didehydro-1-deoxy-1,4-dihydro-5'-(2-methylpropyl)-1-oxorifamycin XIV (30)

To a solution of Fmoc-sarcosine (5.0 g, 16.1 mmol) in THF (30 mL) was added pyridine (1.30 mL, 16.1 mmol) and pivaloyl chloride (1.98 mL, 16.1 mmol) and the mixture was stirred for 1 h at room temperature. A solution of Rifabutin 15 (1.36 g, 1.61 mmol) and pyridine (520 µL, 6.42 mmol) in THF (20 mL) was added to the mixed anhydride solution and the mixture was stirred for 18 h at room temperature. It was then concentrated to half the initial volume, diluted with Et$_2$O and washed with H$_2$O, saturated NaHCO$_3$ solution, H$_2$O and saturated NaCl solution. The organic layer was dried over MgSO$_4$, filtered and concentrated to dryness. Crude product was purified by C18 silica gel chromatography on a Biotage™ flash chromatography system using a gradient of 10-100% MeCN in Et$_3$N/CO$_2$ buffer (0.2% aqueous solution of Et$_3$N adjusted to pH 7 by bubbling CO$_2$). The pure fractions were combined, concentrated under vacuum to remove MeCN and the resulting aqueous solution was extracted with CH$_2$Cl$_2$ (3×). The combined organic layers were dried over MgSO$_4$, filtered and concentrated to provide compound 30 as a dark purple solid (1.23 g, 67%). ESI-MS: (M+H) calculated for C$_{64}$H$_{77}$N$_5$O$_{14}$ 1140, found 1140.3.

21-O-glycinoyl-1',4-didehydro-1-deoxy-1,4-dihydro-5'-(2-methylpropyl)-1-oxorifamycin XIV (31)

Piperidine (100 µL, 1.02 mmol) was added to a stirred solution of N-Fmoc-rifabutin derivative 29 (114 mg, 0.102 mmol) in CH$_2$Cl$_2$ (5 mL). After 24 h of stirring at room temperature, the mixture was concentrated in vacuo. The crude product was purified by reverse phase chromatography eluting with aqueous buffer (Et$_3$N/CO$_2$, pH=7)/CH$_3$CN (10% to 100% linear gradient) to afford 77 mg (0.085 mmol, 84%) of 31 as dark purple solid. $^1$H NMR (400 MHz, CDCl$_3$) δ 8.32 (br s, 1H), 7.94 (s, 1H), 6.41 (t, J=11.1 Hz, 1H), 6.12-6.05 (m, 2H), 5.90 (dd, J=15.8, 7.4 Hz, 1H), 5.12 (d, J=10.3 Hz, 1H), 5.04 (dd, J=15.8, 1.5 Hz, 1H), 3.59 (br s, 1H), 3.48 (m, 1H), 3.20 (d, J=9.5 Hz, 2H), 3.05 (s, 3H), 3.04-2.91 (m, 3H), 2.86 (dd, J=10.1, 3.0 Hz, 1H), 2.72-2.63 (m, 2H), 2.58-2.47 (m, 2H), 2.31 (d, J=7.0 Hz, 2H), 2.27 (s, 3H), 2.19-2.09 (m, 2H), 2.06-1.97 (m, 8H), 1.93-1.84 (m, 2H), 1.84-1.78 (m, 2H), 1.77 (s, 3H), 1.24 (m, 1H), 1.28 (d, J=7.1 Hz, 3H), 0.92 (m, 9H), 0.97 (d, J=6.9 Hz, 3H), 0.40 (d, J=7.1 Hz, 3H).

21-O-(N-methylglycinoyl)-1',4-didehydro-1-deoxy-1,4-dihydro-5'-(2-methylpropyl)-1-oxorifamycin XIV (32)

N-Fmoc-rifabutin derivative 30 (1.23 g, 1.08 mmol) was treated with a 20% v/v solution of piperidine in DMF (15 mL). After stirring for 10 min, the reaction mixture was concentrated to dryness. Crude product was purified by C18 silica gel chromatography on a Biotage™ flash chromatography system using a gradient of 10-100% MeCN in Et$_3$N/CO$_2$ buffer (0.2% aqueous solution of Et$_3$N adjusted to pH 7 by bubbling CO$_2$). The fractions containing product were combined, concentrated under vacuum to remove MeCN and the resulting aqueous solution was extracted with CH$_2$Cl$_2$ (4×). The combined organic layers were dried over MgSO$_4$, filtered and concentrated. A second purification by silica gel chromatography on a Biotage™ flash chromatography system using 0-10% methanol in CH$_2$Cl$_2$ provided compound 32 as a dark purple solid (774 mg, 78%). $^1$H NMR (400 MHz, CDCl$_3$) δ −0.17 (d, J=7.1 Hz, 3H), 0.50 (d, J=6.8 Hz, 3H), 0.91-0.94 (m, 9H), 1.05 (d, J=6.9 Hz, 3H), 1.23-1.27 (m, 1H), 1.77-1.86 (m, 7H), 1.92-2.04 (m, 10H), 2.15-2.21 (m, 1H), 2.25-2.29 (m, 5H), 2.32 (s, 3H), 2.50-2.68 (m, 3H), 2.86-2.89 (m, 1H), 2.93-3.03 (m, 2H), 3.04 (s, 3H), 3.14 (s, 3H), 3.45-3.48 (m, 1H), 4.97 (d, J=10.5 Hz, 1H), 5.04 (dd, J=12.4, 4.4 Hz, 1H), 5.15 (dd, J=10.5, 1.3 Hz, 1H), 5.92 (dd, J=15.8, 7.6 Hz, 1H), 6.06 (dd, J=12.4, 1.5 Hz, 1H), 6.11 (dd, J=11.2, 0.9 Hz, 1H), 6.40 (dd, J=15.8, 11.2 Hz, 1H), 8.14 (s, 1H), 8.32 (bs, 1H). LCMS: 97.5% (254 nm), 96.9% (220 nm), 98.3% (320 nm). ESI-MS: (M+H) calculated for C$_{49}$H$_{67}$N$_5$O$_{12}$ 918, found 918.4.

Scheme 8. Preparation of Rifabutin Bisphosphonate Conjugate 36

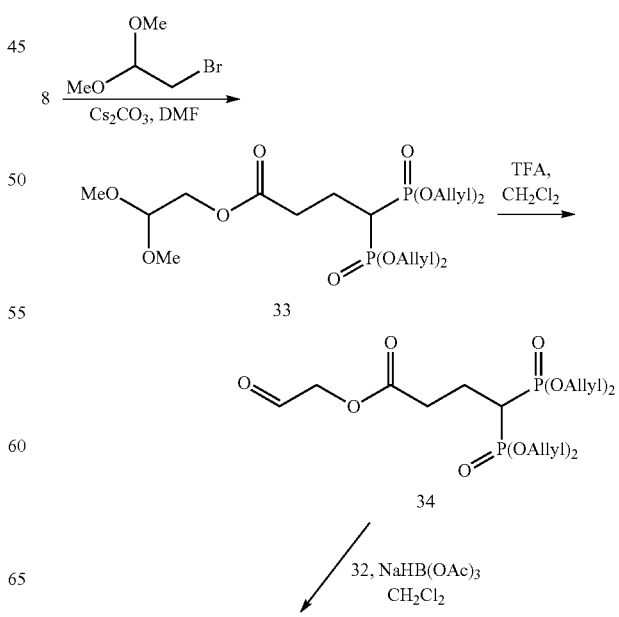

-continued

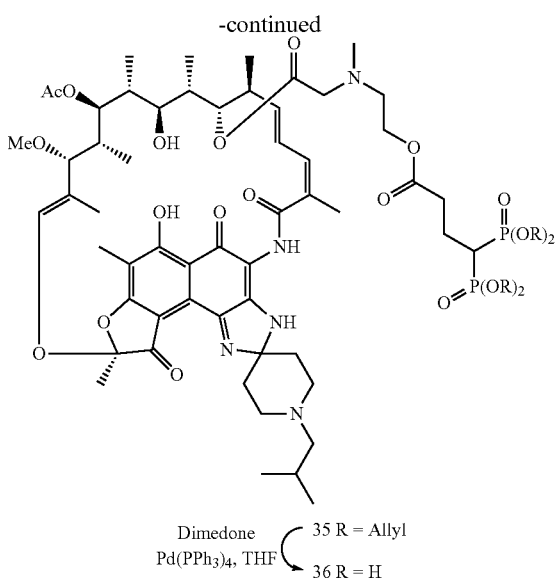

Dimedone
Pd(PPh3)4, THF
⎰ 35 R = Allyl
⎱ 36 R = H

Tetraallyl 1-(2,2-dimethoxyethoxy)-1-oxo-butylene-4,4-bisphosphonate (33)

A mixture of 8 (300 mg, 0.746 mmol), bromoacetaldehyde dimethyl acetal (175 µL, 1.49 mmol) and $Cs_2CO_3$ (243 mg, 0.746 mmol) in 5 mL of anhydrous DMF was stirred at 70° C. for 24 h. After removal of the volatiles in vacuo, the residue was dissolved in $CH_2Cl_2$ (80 mL) and washed successively with aqueous $NaHCO_3$ (1×50 mL), saturated NaCl (1×50 mL), dried over $Na_2SO_4$, filtered and concentrated in vacuo. Purification by flash chromatography on silica gel using a gradient of 0-4% methanol/$CH_2Cl_2$ provided compound 33 (76 mg, 20%). $^1$H NMR (400 MHz, $CDCl_3$) δ 2.29 (m, 2H), 2.58 (tt, J=24.0, 6.5 Hz, 1H), 2.76 (t, J=7.3, 2H), 3.38 (s, 6H), 4.08 (d, J=5.3 Hz, 2H), 4.56 (t, J=5.3 Hz, 1H), 4.60-4.63 (m, 8H), 5.23-5.27 (m, 4H), 5.35-5.40 (m, 4H), 5.90-6.00 (m, 4H).

Tetraallyl 1-(2-oxoethoxy)-1-oxo-butylene-4,4-bis-phosphonate (34)

Compound 33 (72 mg, 0.145 mmol) was dissolved in 4 mL of $CH_2Cl_2$ and 2 mL of TFA (containing 6% $H_2O$) was added. The mixture was stirred for 30 min at room temperature and was then concentrated in vacuo to give the product 34 that was used immediately in the next step. $^1$H NMR (400 MHz, $CDCl_3$) δ 2.29 (m, 2H), 2.64-2.88 (m, 1H), 2.80 (t, J=7.3, 2H), 4.58-4.63 (m, 8H), 4.66 (s, 2H), 5.23-5.27 (m, 4H), 5.35-5.40 (m, 4H), 5.90-6.00 (m, 4H), 9.40 (s, 1H)

Rifabutin Bisphosphonate Conjugate 35

To a solution of compounds 32 (133 mg, 0.145 mmol) and 34 (278 mg, 1.3 mmol) in 8 mL of $CH_2Cl_2$, cooled in an ice bath, was added sodium triacetoxyborohydride (41.14 mg, 0.217 mmol) in portions. The mixture was stirred in the same bath which was left to come to room temperature on its own. After 20 h, it was diluted with $CH_2Cl_2$ (80 mL) and washed successively with aqueous $NaHCO_3$ (2×40 mL), saturated NaCl (1×50 mL), dried over $Na_2SO_4$, filtered and concentrated in vacuo. The residue was purified by silica gel chromatography using a gradient of 0-5% methanol/$CH_2Cl_2$ to give 35 (154 mg, 78%). $^1$H NMR (400 MHz, $CDCl_3$) δ −0.24 (d, J=7.1 Hz, 3H), 0.50 (d, J=6.65 Hz, 3H), 0.92 (m, 9H), 1.02 (d, J=7.1 Hz, 3H), 1.14 (m, 1H), 1.70-1.80 (m, 11H), 1.96 (m, 1H), 2.02 (s, 3H), 2.06 (s, 3H), 2.10-2.35 (m, 8H), 2.38 (s, 3H), 2.42-2.90 (m, 8H), 2.90-3.0 (m, 2H), 3.02 (s, 3H), 3.06 (d, J=12.1 Hz, 1H), 3.20 (s, 2H), 3.40 (d, J=7.43 Hz, 1H), 4.16 (m, 2H), 4.58-4.64 (m, 8H), 4.92 (d, J=10.56 Hz, 1H), 5.10 (dd, J=6.26, 12.52 Hz, 1H), 5.15 (d, J=10.56 Hz, 1H), 5.23-5.27 (m, 4H), 5.35-5.40 (m, 4H), 5.90-6.00 (m, 4H), 6.13 (t, J=7.82 Hz, 2H), 6.38 (dd, J=10.95, 15.65 Hz, 1H), 7.94 (s, 1H), 8.38 (s, 1H).

Rifabutin Bisphosphonate Conjugate 36

To a stirred solution of 35 (154 mg, 0.114 mmol) and dimedone (63.91 mg, 0.456 mmol) in 12 mL of THF was added tetrakis(triphenylphosphine)palladium (6.58 mg, 5.69×10$^{-6}$ mmol). After 3.5 h of stirring at room temperature, the mixture was concentrated in vacuo. The crude product was purified by reverse phase chromatography eluting with 5% to 100% linear gradient $CH_3CN$/aqueous buffer ($NH_4OAc+AcOH+H_2O$, pH=5). Combined pure fractions were concentrated and lyophilized to yield 36 (24 mg, 18%). LCMS purity: 94.5% (254 nm), 93.2% (220 nm), 94.3% (320 nm); mass calculated for $C_{55}H_{79}N_5O_{20}P_2$ 1191, found 1192 (M+H). $^1$H NMR (400 MHz, $D_2O$) δ −0.24 (d, J=7.1 Hz, 3H), 0.52 (d, J=6.65 Hz, 3H), 0.96-1.10 (m, 13H), 1.62 (m, 2H), 1.83 (s, 3H), 1.93 (s, 3H), 1.92-2.29 (m, 14H), 2.64 (m, 1H), 2.71-2.86 (m, 3H), 2.93 (s, 3H), 3.00 (s, 3H), 3.06 (d, J=12.1 Hz, 1H), 3.25 (d, J=7.43, 2H), 3.50 (m, 3H), 3.60-4.02 (m, 6H), 4.42 (m, 2H), 4.94 (d, J=10.56 Hz, 1H), 5.10 (dd, J=6.26, 12.52 Hz, 1H), 5.15 (d, J=10.56 Hz, 1H), 6.16 (m, 2H), 6.44 (d, J=10.95 Hz, 1H), 6.60 (dd, J=10.95, 15.65 Hz, 1H). $^{31}$P NMR (400 MHz, $D_2O$) δ 20.5 (2P)

Scheme 9. Preparation of Rifabutin Bisphosphonate Conjugate 42

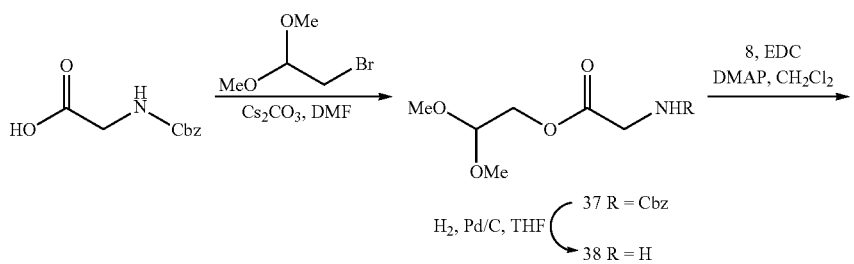

37 R = Cbz
38 R = H
$H_2$, Pd/C, THF

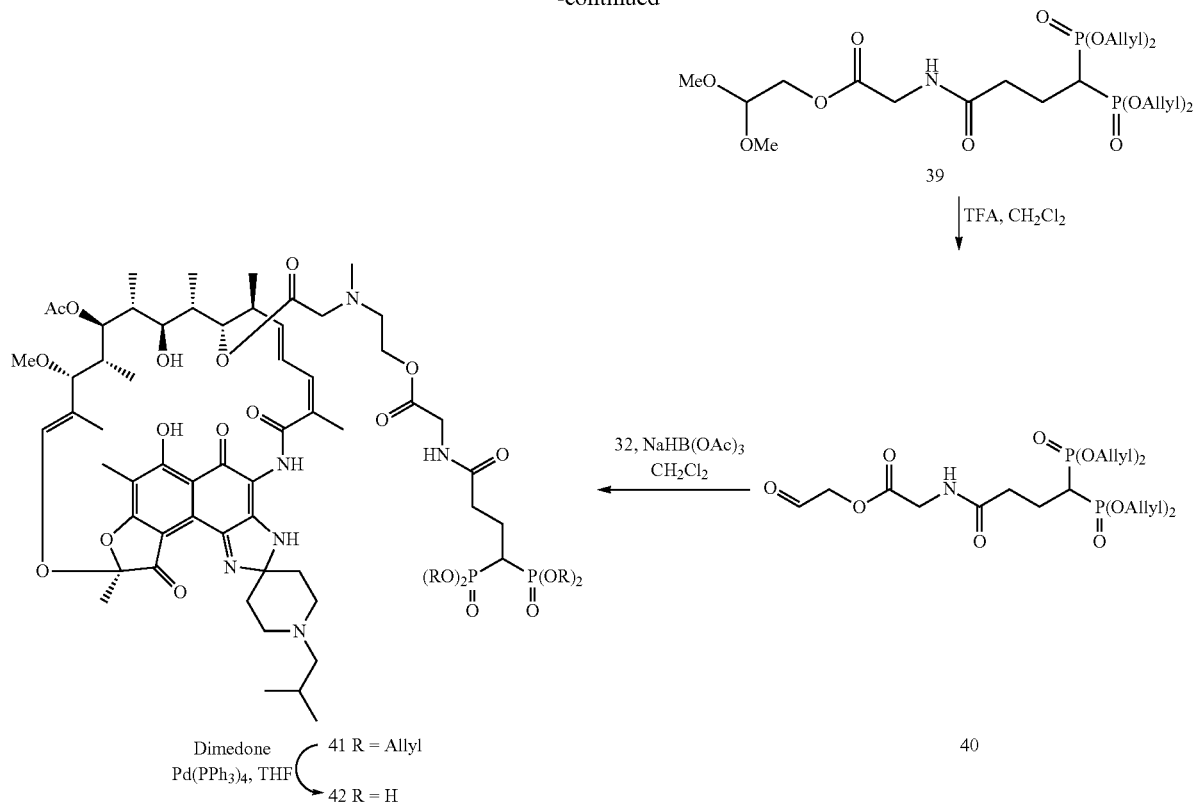

2,2-dimethoxyethyl N-benzyloxycarbonylglycine (37)

A mixture of N-α-CBZ-glycine (2.0 g, 9.57 mmol), bromoacetaldehyde dimethyl acetal (2.25 mL, 19.13 mmol) and Cs$_2$CO$_3$ (2.78 g, 3.12 mmol) in 20 mL of anhydrous DMF was stirred at 100° C. for 24 h. After cooling to room temperature, water was added and the mixture was extracted with ethyl acetate (3×80 mL), dried over Na$_2$SO$_4$, filtered and concentrated in vacuo. The residue was purified by flash chromatography on silica gel using 45-50% ethyl acetate/hexanes to give the product 37 (1.74 g, 61%). $^1$H NMR (400 MHz, CDCl$_3$) δ 3.38 (s, 6H), 3.98 (d, J=5.7 Hz, 2H), 4.12 (d, J=5.3 Hz, 2H), 4.54 (t, J=5.3 Hz, 1H), 5.10 (s, 2H), 5.50 (bs, 1H), 7.32 (m, 5H).

2,2-dimethoxyethyl glycine (38)

To a solution of compound 37 (425 mg, 1.43 mmol) dissolved in 20 mL of anhydrous THF in a Parr apparatus for hydrogenation, was added 160 mg of 10% Pd/C, the system was charged with 60 psi of H$_2$, and the bottle was shaken for 2 h. The catalyst was filtered over Celite, washed with 20 mL of ethyl acetate and the combined filtrate was concentrated in vacuo to give 38 (180 mg, 77%). $^1$H NMR (400 MHz, CDCl$_3$) δ 3.36 (s, 6H), 3.42 (s, 2H), 4.08 (d, J=5.3 Hz, 2H), 4.54 (t, J=5.3 Hz, 1H).

2,2-dimethoxyethyl N-(4,4-bis(diallylphosphoryl)butyryl)glycine (39)

To a solution of compounds 8 (350 mg, 0.87 mmol), 38 (141.9 mg, 1.04 mmol) and 4-DMAP (127.6 mg, 1.04 mmol) in 15 mL of CH$_2$Cl$_2$, cooled in an ice bath, was added EDC (200 mg, 1.04 mmol). The resulting solution was stirred 18 h at room temperature. The reaction mixture was diluted with CH$_2$Cl$_2$ (70 mL), washed successively with aqueous NaHCO$_3$ (1×50 mL), saturated NaCl (1×50 mL), dried over Na$_2$SO$_4$, filtered and concentrated in vacuo. The residue was purified by silica gel chromatography using a gradient of 0-4% methanol/CH$_2$Cl$_2$ to give 39 (135 mg, 28%). $^1$H NMR (400 MHz, CDCl$_3$) δ 2.29 (m, 2H), 2.58 (t, J=7.3 Hz, 2H), 2.86 (tt, J=24.0, 6.5 Hz, 2H), 3.38 (s, 6H), 4.04 (d, J=5.7 Hz, 2H), 4.12 (d, J=5.3 Hz, 2H), 4.56 (t, J=5.3 Hz, 1H), 4.60-4.63 (m, 8H), 5.23-5.27 (m, 4H), 5.35-5.40 (m, 4H), 5.90-6.00 (m, 4H), 6.96 (bt, 1H).

2-oxoethyl N-(4,4-bis(diallylphosphoryl)butyryl)glycine (40)

Compound 39 (120 mg, 0.217 mmol) was dissolved in 5 mL of CH$_2$Cl$_2$ and 2.5 mL of TFA (containing 6% H$_2$O) was added. The mixture was stirred for 30 min at room temperature and was then concentrated in vacuo to give the product 40 that was used as such in the next step. $^1$H NMR (400 MHz, CDCl$_3$) δ 2.29 (m, 2H), 2.64 (m, 2H), 2.86 (m, 1H), 4.04 (bs, 2H), 4.16 (d, J=5.3 Hz, 2H), 4.60 (m, 8H), 4.74 (s, 2H), 5.23-5.27 (m, 4H), 5.35-5.40 (m, 4H), 5.90-6.00 (m, 4H), 9.58 (s, 1H).

Rifabutin Bisphosphonate Conjugate 41

To a solution of compounds 32 (199 mg, 0.217 mmol) and 40 (0.217 mmol) in 10 mL of CH$_2$Cl$_2$, cooled in an ice bath, was added sodium triacetoxyborohydride (69 mg, 0.325 mmol) in portions. The mixture was stirred in the same bath which was left to come to room temperature on its own. After 20 h, it was diluted with CH$_2$Cl$_2$ (80 mL) and washed successively with aqueous NaHCO$_3$ (2×40 mL), saturated NaCl (1×50 mL), dried over Na$_2$SO$_4$, filtered and concentrated in vacuo. The residue was purified by silica gel chromatography using a gradient of 0-5% methanol/ethyl acetate to give 41 (196 mg, 64%). $^1$H NMR (400 MHz, CDCl$_3$) δ −0.18 (d, J=7.1 Hz, 3H), 0.52 (d, J=6.65 Hz, 3H), 0.92 (m, 9H), 1.02 (d, J=7.1 Hz, 3H), 1.14 (m, 1H), 1.70-1.80 (m, 9H), 1.96 (m, 1H), 2.02-2.06 (m, 8H), 2.10-2.36 (m, 6H), 2.38 (s, 3H), 2.42-2.80 (m, 5H), 2.80-3.06 (m, 9H), 3.20 (s, 2H), 3.40 (d, J=7.43 Hz, 1H), 4.04 (d, J=5.7 Hz, 2H), 4.20 (m, 2H), 4.58-4.64 (m, 8H), 4.92 (d, J=10.56 Hz, 1H), 5.10 (dd, J=6.26, 12.52 Hz, 1H), 5.15 (d, J=10.56 Hz, 1H), 5.23-5.27 (m, 4H), 5.35-5.40 (m, 4H), 5.90-6.00 (m, 4H), 6.13 (t, J=7.82 Hz, 2H), 6.42 (dd, J=10.95, 15.65 Hz, 1H), 6.92 (bt, 1H), 7.94 (s, 1H), 8.38 (s, 1H).

Rifabutin Bisphosphonate Conjugate 42

To a stirred solution of 41 (194 mg, 0.137 mmol) and dimedone (77.25 mg, 0.551 mmol) in 15 mL of THF was added tetrakis(triphenylphosphine)palladium (7.96 mg, 6.89×10$^{-6}$ mmol). After 4 h of stirring at room temperature, the mixture was concentrated in vacuo. The crude product was purified by reverse phase chromatography eluting with a linear gradient of 5% to 100% CH$_3$CN in aqueous buffer (NH$_4$OAc+AcOH+H$_2$O, pH=5). Combined pure fractions were concentrated and lyophilized to yield 42 (14 mg, 8%). LCMS purity: 96.96% (254 nm), 97.04% (220 nm), 97.08% (320 nm); mass calculated for C$_{57}$H$_{82}$N$_5$O$_{20}$P$_2$ 1248, found 1249 (M+H). $^1$H NMR (400 MHz, D$_2$O) δ −0.22 (d, J=7.1 Hz, 3H), 0.56 (d, J=6.65 Hz, 3H), 0.96-1.10 (m, 13H), 1.62 (m, 2H), 1.83 (s, 3H), 1.93 (s, 6H), 2.0-2.29 (m, 14H), 2.58-2.92 (m, 4H), 2.83 (s, 3H), 3.0 (s, 3H), 3.02 (d, J=12.1 Hz, 1H), 3.25 (d, J=7.43 Hz, 2H), 3.50 (m, 3H), 3.64-4.09 (m, 6H), 4.42 (s, 2H), 4.44 (m, 2H), 4.94 (d, J=10.56 Hz, 1H), 5.10 (dd, J=6.26, 12.52 Hz, 1H), 5.15 (d, J=10.56 Hz, 1H), 6.16 (m, 2H), 6.44 (d, J=10.95 Hz, 1H), 6.60 (dd, J=10.95, 15.65 Hz, 1H). $^{31}$P NMR (400 MHz, D$_2$O) δ 20.5 (2P)

Scheme 10. Preparation of Rifabutin Bisphosphonate Conjugates 48(a-b)

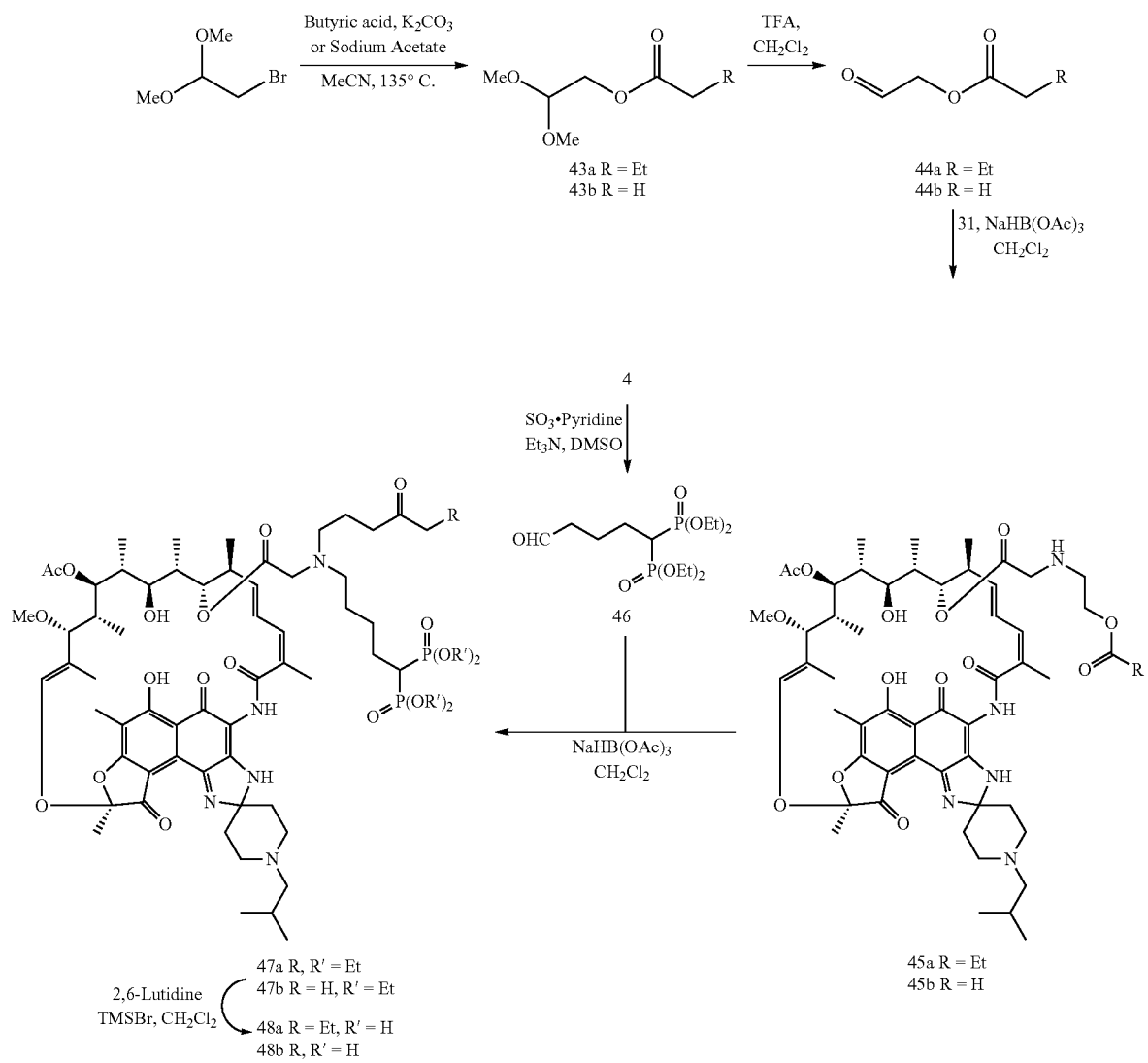

2,2-dimethoxyethyl butyrate (43a)

A mixture of butyric acid (1.0 g, 11.35 mmol), bromoacetaldehyde dimethyl acetal (2.25 mL, 19.13 mmol), tetrabutylammonium bromide (1.83 g, 5.67 mmol) and $K_2CO_3$ (1.56 g, 11.35 mmol) in 10 mL of anhydrous $CH_3CN$ was stirred at 134° C. for 16 h in a sealed tube. It was cooled to room temperature, water was added and the mixture was extracted with $Et_2O$ (3×120 mL). The combined organic phases were washed with saturated NaCl (2×60 mL), dried over $Na_2SO_4$, filtered and concentrated in vacuo. The residue was purified by flash chromatography on silica gel using 20-30% ethyl acetate/hexanes to give the product 43a (1.56 g, 78%). $^1$H NMR (400 MHz, $CDCl_3$) δ 0.90 (t, J=7.43 Hz, 3H), 1.60 (sextet, J=7.43, 7.04 Hz, 2H), 2.24 (t, J=7.04 Hz, 2H), 3.36 (s, 6H), 4.08 (d, J=5.3 Hz, 2H), 4.54 (t, J=5.3 Hz, 1H).

2,2-dimethoxyethyl acetate (43b)

A mixture of sodium acetate (1.0 g, 12.19 mmol), bromoacetaldehyde dimethyl acetal (1.43 mL, 12.19 mmol), and tetrabutylammoniumbromide (1.96 g, 6.09 mmol) in 8 mL of anhydrous $CH_3CN$ was stirred at 134° C. for 16 h in a sealed tube. It was cooled to room temperature, water was added and the mixture extracted with $Et_2O$ (3×100 mL). The combined organic phases were washed with saturated NaCl (1×75 mL), dried over $Na_2SO_4$, filtered and concentrated in vacuo. The residue was purified by flash chromatography on silica gel using 40-60% ethyl acetate/hexanes to give the product 43b (product is volatile, some of the product is lost during the evaporation of solvents). $^1$H NMR (400 MHz, $CDCl_3$) δ 2.03 (s, 3H), 3.36 (s, 6H), 4.08 (d, J=5.3 Hz, 2H), 4.54 (t, J=5.3 Hz, 1H).

2-oxoethyl butyrate (44a)

Compound 43a (176 mg, 1.0 mmol) was dissolved in 8 mL of $CH_2Cl_2$ and 4 mL of TFA (containing 5% $H_2O$) was added. The mixture was stirred for 30 min at room temperature. The solution was then concentrated in vacuo to give the product 44a that was used immediately for the next step. $^1$H NMR (400 MHz, $CDCl_3$) δ 0.92 (m, 3H), 1.64 (m, 2H), 2.24 (t, J=7.04 Hz, 2H), 4.72 (s, 2H), 9.60 (s, 1H).

2-oxoethyl acetate (44b)

Compound 43b (344 mg, 1.45 mmol) was dissolved in 8 mL of $CH_2Cl_2$ and 4 mL of TFA (containing 5% $H_2O$) was added The mixture was stirred for 30 min at room temperature. The solution was then concentrated in vacuo to give the product 44b that was used immediately in the next step (product is volatile, with some loss during the evaporation of solvents). $^1$H NMR (400 MHz, $CDCl_3$) δ 2.10 (s, 3H), 4.72 (s, 2H), 9.58 (s, 1H).

21-O-(N-(2-butyroxyethyl)-glycinoyl)-1',4-didehydro-1-deoxy-1,4-dihydro-5'-(2-methylpropyl)-1-oxorifamycin XIV (45a)

To a solution of compounds 31 (903 mg, 1.0 mmol) and 44a (1.0 mmol) in 15 mL of $CH_2Cl_2$, cooled in an ice bath, was added sodium triacetoxyborohydride (318 mg, 1.5 mmol) in portions. The mixture was stirred in the same bath which was left to come to room temperature on its own. After 20 h, it was diluted with $CH_2Cl_2$ (80 mL) and washed successively with aqueous $NaHCO_3$ (2×60 mL), saturated NaCl (1×60 mL), dried over $Na_2SO_4$, filtered and concentrated in vacuo. The residue was purified by silica gel chromatography using a gradient of 0-5% methanol/ethyl acetate to give 45a (640 mg, 63%). $^1$H NMR (400 MHz, $CDCl_3$) δ −0.18 (d, J=7.1 Hz, 3H), 0.52 (d, J=6.65 Hz, 3H), 0.90-1.0 (m, 12H), 1.10 (d, J=6.26 Hz, 3H), 1.60-1.98 (m, 14H), 1.83 (s, 3H), 1.98 (s, 3H), 2.03 (s, 3H), 2.10-2.35 (m, 3H), 2.29 (s, 3H), 2.37 (t, J=7.04 Hz, 2H), 2.43-3.0 (m, 8H), 3.0 (s, 3H), 3.05 (d, J=12.1 Hz, 1H), 3.25 (d, J=7.43 Hz, 1H), 3.42 (m, 1H), 4.16 (m, 2H), 4.96 (d, J=10.56 Hz, 1H), 5.10 (dd, J=6.26, 10.56 Hz, 1H), 5.15 (d, J=10.56 Hz, 1H), 5.92 (dd, J=7.82, 12.52 Hz, 1H), 6.16 (d, J=12.52 Hz, 1H), 6.20 (d, J=7.82 Hz, 1H), 6.42 (dd, J=10.95, 15.65 Hz, 1H).

21-O-(N-(2-acetoxyethyl)-glycinoyl)-1',4-didehydro-1-deoxy-1,4-dihydro-5'-(2-methylpropyl)-1-oxorifamycin XIV (45b)

To a solution of compounds 31 (1.05 g, 1.16 mmol) and 44b (1.16 mmol) in 20 mL of $CH_2Cl_2$, cooled in an ice bath, was added sodium triacetoxyborohydride (370 mg, 1.74 mmol) in portions. The mixture was stirred in the same bath which was left to come to room temperature on its own. After 20 h, it was diluted with $CH_2Cl_2$ (80 mL) and washed successively with aqueous $NaHCO_3$ (1×80 mL), saturated NaCl (1×60 mL), dried over $Na_2SO_4$, filtered and concentrated in vacuo. The residue was purified by silica gel chromatography using a gradient of 0-5% methanol/ethyl acetate to give 45b (420 mg, 36%). $^1$H NMR (400 MHz, $CDCl_3$) δ −0.18 (d, J=7.1 Hz, 3H), 0.52 (d, J=6.65 Hz, 3H), 0.90-1.0 (m, 9H), 1.10 (d, J=6.26 Hz, 3H), 1.25 (m, 1H), 1.70-1.98 (m, 10H), 1.98 (s, 3H), 2.03 (s, 3H), 2.10 (s, 3H), 2.10-2.35 (m, 5H), 2.29 (s, 3H), 2.37 (t, J=7.04 Hz, 2H), 2.43-3.0 (m, 8H), 3.0 (s, 3H), 3.05 (m, 1H), 3.25 (d, J=7.43 Hz, 1H), 3.42 (m, 1H), 4.16 (m, 2H), 4.96 (d, J=10.56 Hz, 1H), 5.10 (dd, J=6.26, 12.52 Hz, 1H), 5.15 (d, J=10.56 Hz, 1H), 5.92 (dd, J=7.82, 12.52 Hz, 1H), 6.16 (d, J=12.52 Hz, 1H), 6.20 (d, J=7.82 Hz, 1H), 6.42 (dd, J=10.95, 15.65 Hz, 1H).

Tetraethyl 5-oxopentylene-1,1-bisphosphonate (46)

To a stirred solution of oxalyl chloride (280 μL, 3.20 mmol) in 10 mL of $CH_2Cl_2$, cooled to −78° C. under Ar was added DMSO (455 μL, 6.41 mmol), and the solution was stirred at −78° C. for 30 min. A solution of alcohol 4 (770 mg, 2.14 mmol) in 10 mL of $CH_2Cl_2$ was added. The mixture was stirred at −78° C. for 30 min, triethylamine (1.78 mL, 12.83 mmol) was added, before removing the cooling bath was removed and allowing the reaction to warm to room temperature over 30 min. Water was added and the mixture was extracted with $CH_2Cl_2$ (3×70 mL). The combined organic layers were washed with saturated NaCl (1×70 mL), dried over $Na_2SO_4$, filtered and concentrated in vacuo to give 46 in a quantitative yield and which was used for the next reaction without further purification. $^1$H NMR (400 MHz, $CDCl_3$): δ 1.24-1.36 (m, 12H), 1.78-1.92 (m, 4H), 2.18 (tt, J=6.1, 24.3 Hz, 1H), 2.47 (t, J=6.1 Hz, 2H), 4.11-4.22 (m, 8H).

Rifabutin Bisphosphonate Conjugate 47a

To a solution of compounds 45a (630 mg, 0.62 mmol) and 46 (266 mg, 0.74 mmol) in 20 mL of $CH_2Cl_2$, cooled in an ice bath, was added sodium triacetoxyborohydride (197 mg, 0.93 mmol) in portions. The mixture was stirred in the same bath which was left to come to room temperature on its own. After 24 h, it was diluted with $CH_2Cl_2$ (100 mL) and washed successively with aqueous $NaHCO_3$ (1×60 mL), saturated NaCl (1×60 mL), dried over $Na_2SO_4$, filtered and concentrated in vacuo. The residue was purified by silica gel chromatography using a gradient of 0-8% methanol/ethyl acetate to give 47a (500 mg, 60%). $^1$H NMR (400 MHz, $CDCl_3$) δ −0.18 (d, J=7.1 Hz, 3H), 0.44 (d, J=6.65 Hz, 3H), 0.98 (m, 12H), 1.10 (d, J=6.26 Hz, 3H), 1.20-1.70 (m, 16H), 1.80 (s, 3H), 2.03 (s, 3H), 2.08 (s, 3H), 1.86-2.20 (m, 14H), 2.29 (s, 3H), 2.40-2.90

(m, 10H), 3.0 (s, 3H), 3.05 (m, 2H), 3.25 (s, 2H), 3.40 (m, 1H), 4.06 (t, J=7.04 Hz, 2H), 4.16 (m, 8H), 4.96 (d, J=10.56 Hz, 1H), 5.10 (dd, J=6.26, 12.52 Hz, 1H), 5.15 (d, J=10.56 Hz, 1H), 5.92 (dd, J=7.82, 12.52 Hz, 1H), 6.16 (t, J=7.82 Hz, 2H), 6.40 (dd, J=10.95, 15.65 Hz, 1H) 7.85 (s, 1H), 8.37 (s, 1H).

Rifabutin Bisphosphonate Conjugate 47b

To a solution of compounds 45b (420 mg, 0.424 mmol) and 46 (182 mg, 0.509 mmol) in 20 mL of $CH_2Cl_2$, cooled in an ice bath, was added sodium triacetoxyborohydride (370 mg, 1.74 mmol) in portions. The mixture was stirred in the same bath which was left to come to room temperature on its own. After 20 h, it was diluted with $CH_2Cl_2$ (80 mL) and washed successively with aqueous $NaHCO_3$ (1×60 mL), saturated NaCl (1×60 mL), dried over $Na_2SO_4$, filtered and concentrated in vacuo. The residue was purified by silica gel chromatography using a gradient of 0-8% methanol/ethyl acetate to give 47b (440 mg, 78%). $^1$H NMR (400 MHz, $CDCl_3$) δ −0.18 (d, J=7.1 Hz, 3H), 0.44 (d, J=6.65 Hz, 3H), 0.96 (m, 9H), 1.04 (d, J=6.26 Hz, 3H), 1.10 (m, 1H), 1.34 (m, 15H), 1.47 (m, 2H), 1.80 (s, 3H), 1.98 (s, 3H), 2.03 (s, 3H), 1.86-2.20 (m, 16H), 2.29 (s, 3H), 2.60-2.75 (m, 5H), 2.80-3.0 (m, 5H), 3.0 (s, 3H), 3.05 (d, 1H), 3.25 (s, 2H), 3.40 (d, 1H), 4.06 (t, J=7.04 Hz, 2H), 4.16 (m, 8H), 4.96 (d, J=10.56 Hz, 1H), 5.10 (dd, J=6.26, 12.52 Hz, 1H), 5.15 (d, J=10.56 Hz, 1H), 5.92 (dd, J=7.82, 12.52 Hz, 1H), 6.16 (t, J=7.82 Hz, 2H), 6.40 (dd, J=10.95, 15.65 Hz, 1H), 7.88 (s, 1H), 8.37 (s, 1H).

Rifabutin Bisphosphonate Conjugate 48a

To a solution of 47a (500 mg, 0.368 mmol) and 2,6-lutidine (2.13 mL, 18.4 mmol) in 10 mL of $CH_2Cl_2$ cooled to −78° C. was added dropwise TMS-Br (1.21 mL, 9.20 mmol) under Ar. The cold bath was removed, the mixture was stirred for 24 hours at room temperature and the volatiles were removed under vacuum until dryness. The residue was dissolved in 5 mL of anhydrous DMF, pyridine (2.08 mL, 25.75 mmol) and subsequently HF-pyridine (322 μL, 12.87 mmol) were added. After stirring 1 h at room temperature, the volatiles were removed in vacuo. The crude product was purified by reverse phase chromatography eluting with a linear gradient of 0% to 100% $CH_3CN$ in aqueous buffer ($NH_4OAc+AcOH+H_2O$, pH=5). Combined pure fractions were concentrated and lyophilized to yield 48a (280 mg, 61%). LCMS purity: 100% (254 nm), 100% (220 nm), 100% (320 nm); mass calculated for $C_{59}H_{87}N_5O_{20}P_2$ 1247, found 1248 (M+H). $^1$H NMR (400 MHz, $D_2O$) δ −0.22 (d, J=7.1 Hz, 3H), 0.56 (d, J=6.65 Hz, 3H), 0.92 (t, J=7.43 Hz, 3H), 0.98 (m, 7H), 1.10 (d, J=6.26 Hz, 6H), 1.57-1.68 (m, 8H), 1.83 (s, 3H), 1.93 (s, 3H), 2.03 (s, 3H), 2.14 (s, 3H), 1.86-2.10 (m, 8H), 2.29 (m, 1H), 2.39 (t, J=7.04 Hz, 2H), 2.63-2.71 (m, 3H), 3.0 (s, 3H), 3.05 (d, J=12.1 Hz, 1H), 3.25 (m, 4H), 3.48 (m, 3H), 3.80-4.02 (m, 6H), 4.33 (bs, 2H), 4.96 (d, J=10.56 Hz, 1H), 5.10 (dd, J=6.26, 12.52 Hz, 1H), 5.15 (d, J=10.56 Hz, 1H), 6.16 (d, J=12.52 Hz, 1H), 6.20 (d, J=7.82 Hz, 1H), 6.44 (d, J=10.95 Hz, 1H), 6.60 (dd, J=10.95, 15.65 Hz, 1H). $^{31}$P NMR (400 MHz, $D_2O$) δ 21 (2P)

Rifabutin Bisphosphonate Conjugate 48b

To a solution of 47b (440 mg, 0.33 mmol) and 2,6-lutidine (1.92 mL, 16.52 mmol) in 15 mL of $CH_2Cl_2$ cooled to −78° C. was added dropwise TMS-Br (1.09 mL, 8.26 mmol) under Ar. The cold bath was removed, the mixture was stirred for 24 hours at room temperature and the volatiles were removed under vacuum until dryness. The residue was dissolved in 5 mL of anhydrous DMF, pyridine (1.87 mL, 23.14 mmol) followed by HF-pyridine (290 μL, 11.57 mmol) were added. After stirring 1 h at room temperature, the mixture was concentrated in vacuo. The crude product was purified by reverse phase chromatography eluting with a linear gradient of 0% to 100% $CH_3CN$ in aqueous buffer ($NH_4OAc+AcOH+H_2O$, pH=5). Combined pure fractions were concentrated and lyophilized to yield 48b (380 mg, 94%). LCMS purity: 100% (254 nm), 100% (220 nm), 100% (320 nm); mass calculated for $C_{57}H_{83}N_5O_{20}P_2$ 1219, found 1220 (M+H). δ −0.22 (d, J=7.1 Hz, 3H), 0.56 (d, J=6.65 Hz, 3H), 0.98 (m, 7H), 1.10 (d, J=6.26 Hz, 6H), 1.57-1.68 (m, 6H), 1.83 (s, 3H), 1.95 (s, 3H), 2.03 (s, 3H), 2.13 (s, 3H), 2.14 (s, 3H), 1.86-2.10 (m, 14H), 2.29 (m, 1H), 2.63-2.71 (m, 3H), 3.0 (s, 3H), 3.05 (d, J=12.1 Hz, 1H), 3.25 (m, 4H), 3.48 (m, 3H), 3.80-4.02 (m, 6H), 4.33 (bs, 2H), 4.96 (d, J=10.56 Hz, 1H), 5.10 (dd, J=6.26, 12.52 Hz, 1H), 5.15 (d, J=10.56 Hz, 1H), 6.16 (d, J=12.52 Hz, 1H), 6.20 (d, J=7.82 Hz, 1H), 6.44 (d, J=10.95 Hz, 1H), 6.62 (dd, J=10.95, 15.65 Hz, 1H). $^{31}$P NMR (400 MHz, $D_2O$) δ 21 (2P)

Scheme 11. Preparation of Rifabutin Bisphosphonate Conjugate 52

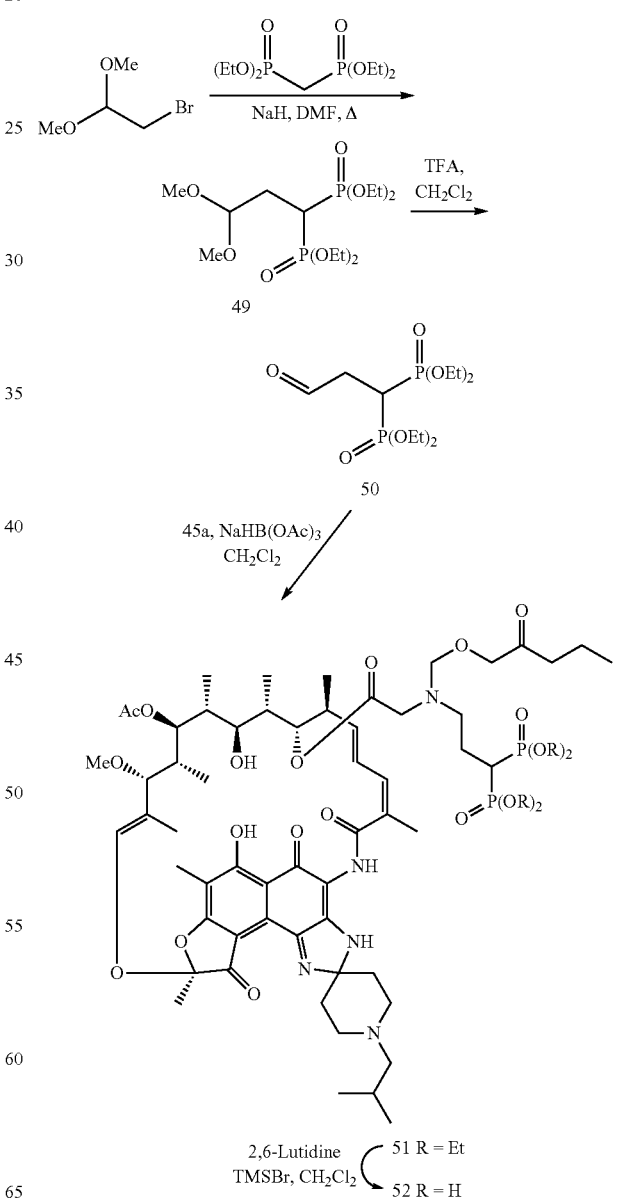

Tetraethyl 3,3-Dimethoxypropylene-1,1-bisphosphonate (49)

To a suspension of sodium hydride (60%, 400 mg, 10 mmol) in 10 mL of DMF was added tetraethyl methylenebisphosphonate (2.88 g, 10 mmol) and the resultant clear pale yellow solution was stirred at room temperature for 1 h. Then bromacetaldehyde dimethyl acetal (1.17 g, 10 mmol) in 5 mL of DMF was introduced. The reaction was stirred at 100° C. for 6 h, allowed to cool to room temperature and quenched with saturated ammonium chloride aqueous solution. The mixture was extracted with $CH_2Cl_2$ (3×70 mL), dried over anhydrous sodium sulfate and concentrated in vacuo. Flash chromatography on silica gel with 20:1 (v/v) dichloromethane/methanol as the eluent afforded product 49 as a mixture ($^1$H NMR shows 10-20% of product and tetraethyl methylenebisphosphonate). The material was used directly in the next step without further purification. $^1$H NMR (400 MHz, $CDCl_3$): δ 1.24-1.36 (m, 12H), 1.80-1.94 (m, 2H), 2.18 (tt, J=6.1, 24.3 Hz, 1H), 3.28 (s, 6H), 4.11-4.22 (m, 8H), 4.62 (t, J=5.3 Hz, 1H).

Tetraethyl 3-oxopropylene-1,1-bisphosphonate (50)

Compound 49 (74 mg, 0.196 mmol) was dissolved in 5 mL of $CH_2Cl_2$ and 2.5 mL of TFA (containing 5% $H_2O$) was added and the mixture was stirred for 30 min at room temperature. The solution was then evaporated in vacuo to give the product 50 that was used immediately for the next step. $^1$H NMR (400 MHz, $CDCl_3$): δ 1.24-1.36 (m, 12H), 2.28 (tt, J=6.1, 24.3 Hz, 1H), 3.0 (dt, J=6.1, 24.3 Hz, 2H), 4.11-4.22 (m, 8H), 9.75 (s, 1H).

Rifabutin Bisphosphonate Conjugate 51

To a solution of compounds 45a (200 mg, 0.196 mmol) and 50 (0.196 mmol) in 12 mL of $CH_2Cl_2$, cooled in an ice bath, was added, sodium triacetoxyborohydride (62.56 mg, 0.29 mmol) in portions. The mixture was stirred in the same bath which was left to come to room temperature on its own. After 16 h, it was diluted with $CH_2Cl_2$ (80 mL) and washed successively with aqueous $NaHCO_3$ (2×40 mL), saturated NaCl (1×40 mL), dried over $Na_2SO_4$, filtered and concentrated in vacuo. The residue was purified by silica gel chromatography using a gradient of 0-5% methanol/ethyl acetate to give 51 (174 mg, 66%). $^1$H NMR (400 MHz, $CDCl_3$) δ −0.18 (d, J=7.1 Hz, 3H), 0.44 (d, J=6.65 Hz, 3H), 0.90-1.0 (m, 12H), 1.10 (d, J=6.26 Hz, 3H), 1.32 (m, 12H), 1.60-1.88 (m, 12H), 1.98 (s, 3H), 2.03 (s, 3H), 1.90-2.10 (m, 3H), 2.10-2.62 (m, 12H), 2.63-3.0 (m, 8H), 3.0 (s, 3H), 3.05 (d, J=12.1 Hz, 1H), 3.25 (d, J=7.43 Hz, 2H), 3.42 (m, 1H), 4.06 (m, 2H), 4.20 (m, 8H), 4.96 (d, J=10.56 Hz, 1H), 5.10 (m, 2H), 5.92 (dd, J=7.82, 12.52 Hz, 1H), 6.16 (m, 2H), 6.40 (dd, J=10.95, 15.65 Hz, 1H), 7.85 (s, 1H), 8.38 (s, 1H).

Rifabutin Bisphosphonate Conjugate 52

To a solution of 51 (174 mg, 0.13 mmol) and 2,6-lutidine (0.758 mL, 6.58 mmol) in 10 mL of $CH_2Cl_2$ cooled to −78° C. was added dropwise TMS-Br (0.43 mL, 3.26 mmol) under Ar. The cold bath was removed, the mixture was stirred for 24 hours at room temperature and the volatiles were removed under vacuum until dryness. The residue was dissolved in 4 mL of anhydrous DMF, pyridine (0.739 mL, 9.15 mmol) followed by HF-pyridine (119 μL, 4.57 mmol) were added. After stirring 1 h at room temperature, the solvent was evaporated in vacuo. The crude product was purified by reverse phase chromatography eluting with a linear gradient of 0% to 100% of $CH_3CN$ in aqueous buffer ($NH_4OAc+AcOH+H_2O$, pH=5). Combined pure fractions were concentrated and lyophilized to yield 52 (103 mg, 64%). LCMS purity: 94.73% (254 nm), 93.77% (220 nm), 94.96% (320 nm); mass calculated for $C_{57}H_{83}N_5O_{20}P_2$ 1219, found 1220 (M+H). $^1$H NMR (400 MHz, $D_2O$) δ −0.22 (d, J=7.1 Hz, 3H), 0.56 (d, J=6.65 Hz, 3H), 0.92 (t, J=7.43 Hz, 3H), 0.98 (m, 7H), 1.10 (d, J=6.26 Hz, 6H), 1.57-1.68 (m, 4H), 1.83 (s, 3H), 1.93 (s, 3H), 2.03 (s, 3H), 2.14 (s, 3H), 1.86-2.16 (m, 14H), 2.29 (m, 1H), 2.39 (t, J=7.04 Hz, 2H), 2.63-2.71 (m, 3H), 3.0 (s, 3H), 3.05 (d, J=12.1 Hz, 1H), 3.25 (d, J=7.43 Hz, 2H), 3.40-3.52 (m, 6H), 3.80-4.02 (m, 4H), 4.33 (bs, 2H), 4.96 (d, J=10.56 Hz, 1H), 5.10 (dd, J=6.26, 12.52 Hz, 1H), 5.15 (d, J=10.56 Hz, 1H), 6.16 (m, 2H), 6.44 (d, J=10.95 Hz, 1H), 6.60 (dd, J=10.95, 15.65 Hz, 1H). $^{31}$P NMR (400 MHz, $D_2O$) δ 19 (2P)

Scheme 12. Preparation of Rifabutin Bisphosphonate Conjugate 59

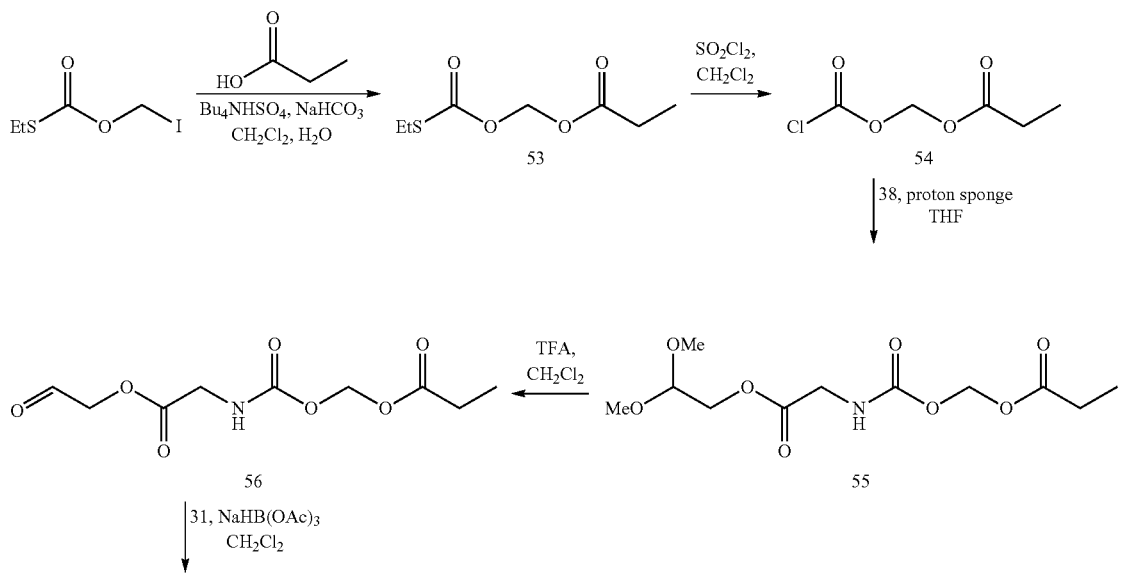

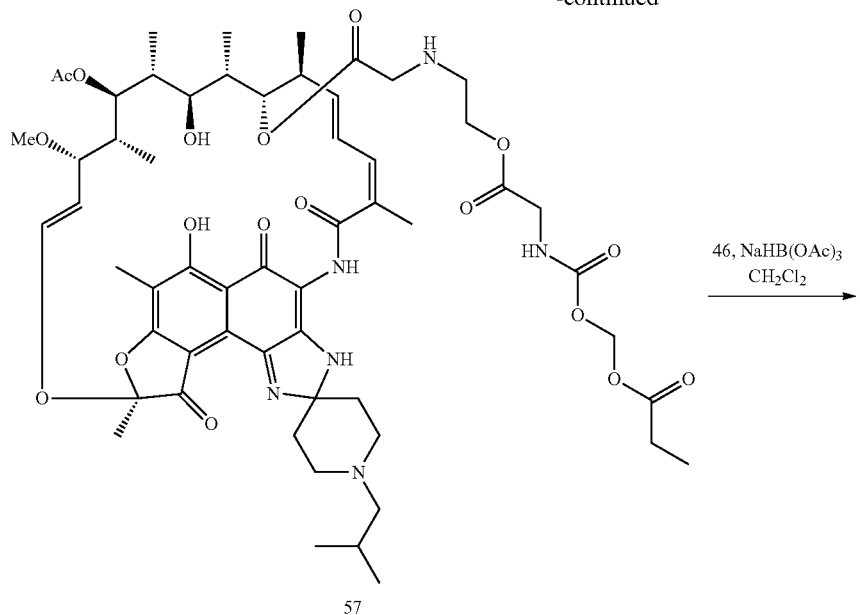

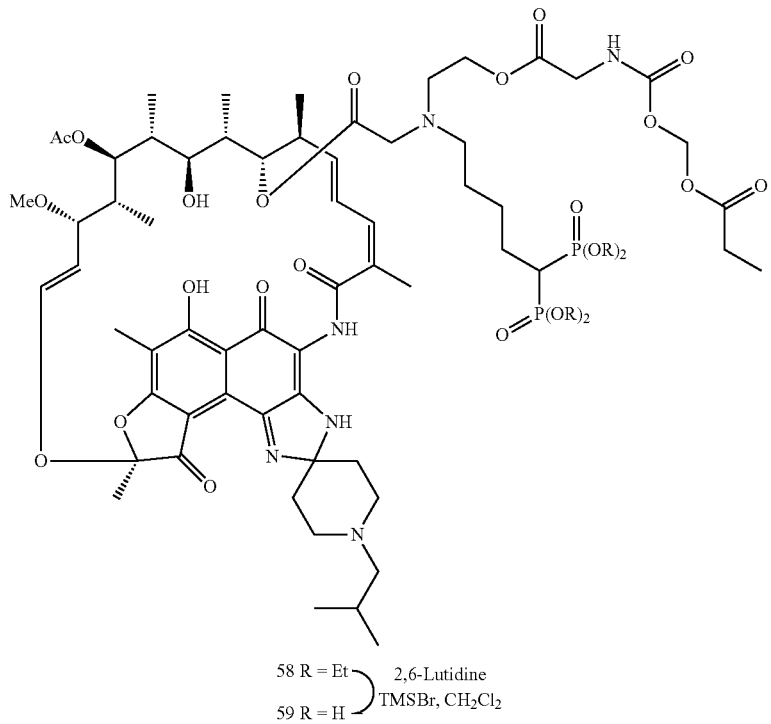

Compounds 53 and 54 were prepared as described in *Synthesis*, 1990, 1159-1166.

S-Ethyl O-(propionyloxy)methyl carbonothioate (53)

Sodium bicarbonate (1.52 g, 18.1 mmol) followed by tetrabutylammonium hydrogen sulfate (3.07 g, 9.03 mmol) was added to a stirring suspension of proprionic acid (674 μL, 9.03 mmol) in $CH_2Cl_2$ (20 mL) and $H_2O$ (20 mL) at room temperature. After 1.5 hr O-iodomethyl S-ethyl carbonothiolate (2.00 g, 8.13 mmol) dissolved in $CH_2Cl_2$ (1 mL) was added drop-wise over 10 min and stirring was continued for a further 3 hr. The reaction mixture was diluted with $CH_2Cl_2$ (40 mL) and washed with $H_2O$ and saturated aqueous NaCl then dried over $Na_2SO_4$, concentrated and resuspended in $Et_2O$. The mixture was stirred overnight at room temperature followed by filtration and concentration which resulted in the pale yellow liquid 53 (1.56 g, 100%). $^1$H NMR (400 MHz, $CDCl_3$) δ 1.16 (t, J=7.5, 3H), 1.33 (t, J=7.4, 3H), 2.40 (q, J=7.4, 2H), 2.90 (q, J=7.4, 2H), 5.81 (s, 2H).

(Carbonochloridoyl)methyl propionate (54)

Thionyl chloride (101 μL, 1.25 mmol) was added drop-wise to a solution of 53 (160 mg, 0.832 mmol) in $CH_2Cl_2$ (0.5 mL) at 0° C. then the solution was stirred for a further 1.5 hr.

The solvent was removed under reduced pressure resulting in the volatile chloroformate 54 (138 mg, 100%). $^1$H NMR (400 MHz, CDCl$_3$) δ 1.18 (t, J=7.4, 3H), 2.45 (q, J=7.4, 2H), 5.83 (s, 2H).

(Propionyloxy)methyl ((2,2-dimethoxyethoxy)carbonyl)methylcarbamate (55)

To a solution of 38 (375 mg, 2.30 mmol) and proton sponge (N,N,N',N'-Tetramethyl-1,8-naphthalenediamine, 493 mg, 2.30 mmol) in 20 mL of THF, cooled in an ice bath, was added, dropwise over 5 min, a solution of (carbonochloridoyl)methyl propionate (54, 338 mg, 2.30 mmol) in 10 mL of THF. The mixture was stirred in the same bath which was left to come to room temperature on its own. After 16 h, it was concentrated in vacuo, water was added and the mixture was extracted with CH$_2$Cl$_2$ (2×75 mL), dried over Na$_2$SO$_4$ and concentrated in vacuo. The residue was purified by silica gel chromatography (50-60% ethyl acetate in Hexanes) to give 55 (g, 46%). $^1$H NMR (400 MHz, CDCl$_3$) δ 1.11 (t, J=7.43 Hz, 3H), 2.36 (q, J=7.43 Hz, 2H), 3.36 (s, 6H), 4.0 (d, J=5.86 Hz, 2H), 4.14 (d, J=5.47 Hz, 2H), 4.54 (t, J=5.47 Hz, 1H), 5.56 (bt, 1H), 5.71 (s, 2H).

(Propionyloxy)methyl ((formyl methoxy)carbonyl)methylcarbamate (56)

Compound 55 (268 mg, 0.91 mmol) was dissolved in 10 mL of CH$_2$Cl$_2$ and 5 mL of TFA (containing 5% H$_2$O) was added. The mixture was stirred for 30 min at room temperature. The solution was then concentrated to dryness in vacuo to give the product 56 that was used immediately for the next step. $^1$H NMR (400 MHz, CDCl$_3$) δ 1.15 (t, J=7.43 Hz, 3H), 2.40 (q, J=7.43 Hz, 2H), 4.16 (d, J=5.47 Hz, 2H), 4.78 (s, 2H), 5.75 (s, 2H), 6.30 (bs, 1H), 9.60 (s, 1H).

Rifabutin Derivative 57

To a solution of compounds 31 (750 mg, 0.83 mmol) and 56 (0.83 mmol) in 20 mL of CH$_2$Cl$_2$, cooled in an ice bath, was added sodium triacetoxyborohydride (264 mg, 1.24 mmol) in portions. The mixture was stirred in the same bath which was left to come to room temperature on its own. After 24 h, it was diluted with CH$_2$Cl$_2$ (150 mL), washed successively with aqueous NaHCO$_3$ (2×60 mL), saturated NaCl (1×60 mL), dried over Na$_2$SO$_4$, filtered and concentrated in vacuo. The residue was purified by silica gel chromatography using a gradient of 0-5% methanol/ethyl acetate to give 57 (572 mg, 61%). $^1$H NMR (400 MHz, CDCl$_3$) δ −0.18 (d, J=7.1 Hz, 3H), 0.52 (d, J=6.65 Hz, 3H), 0.98 (m, 9H), 1.06 (d, J=6.26 Hz, 3H), 1.18 (m, 3H), 1.25 (m, 3H), 1.75-2.20 (m, 18H), 2.20-2.39 (m, 7H), 2.43-2.80 (m, 3H), 2.80-3.55 (m, 10H), 4.05-4.34 (m, 4H), 4.83-5.10 (m, 3H), 5.67-5.98 (m, 4H), 6.14 (m, 2H), 6.38 (m, 1H), 8.0 (s, 1H), 8.35 (s, 1H).

Rifabutin Bisphosphonate Conjugate 58

To a solution of compounds 57 (572 mg, 0.504 mmol) and 46 (216 mg, 0.605 mmol) in 20 mL of CH$_2$Cl$_2$, cooled in an ice bath, was added sodium triacetoxyborohydride (160 mg, 0.756 mmol) in portions. The mixture was stirred in the same bath which was left to come to room temperature on its own. After 40 h, it was diluted with CH$_2$Cl$_2$ (150 mL) and washed successively with aqueous NaHCO$_3$ (2×60 mL), saturated NaCl (1×50 mL), dried over Na$_2$SO$_4$, filtered and concentrated in vacuo. The residue was purified by silica gel chromatography using a gradient of 0-8% methanol/CH$_2$Cl$_2$ to give 58 (216 mg, 29%). $^1$H NMR (400 MHz, CDCl$_3$) δ −0.18 (d, J=7.1 Hz, 3H), 0.44 (d, J=6.65 Hz, 3H), 0.98 (m, 7H), 1.02 (d, J=6.26 Hz, 3H), 1.15 (t, J=7.43 Hz, 3H), 1.36 (m, 14H), 1.54 (m, 1H), 1.80 (s, 3H), 2.03 (s, 3H), 2.08 (s, 3H), 1.86-2.04 (m, 14H), 2.29 (s, 3H), 2.36 (q, J=7.43 Hz, 2H), 2.14-2.70 (m, 8H), 2.83 (bt, 3H), 2.96 (m, 2H), 3.04 (s, 3H), 3.22 (s, 2H), 3.40 (m, 1H), 3.98 (m, 2H), 4.20 (m, 12H), 4.96 (d, J=10.56 Hz, 1H), 5.10 (dd, J=6.26, 12.52 Hz, 1H), 5.15 (d, J=10.56 Hz, 1H), 5.76 (s, 2H), 5.92 (dd, J=7.82, 12.52 Hz, 1H), 6.16 (t, J=7.82 Hz, 2H), 6.40 (dd, J=10.95, 15.65 Hz, 1H) 7.83 (s, 1H), 8.37 (s, 1H).

Rifabutin Bisphosphonate Conjugate 59

To a solution of 58 (216 mg, 0.146 mmol) and 2,6-lutidine (0.85 mL, 7.31 mmol) in 10 mL of CH$_2$Cl$_2$ cooled to −78° C. was added dropwise TMS-Br (0.483 mL, 3.65 mmol) under Ar. The cold bath was removed, the mixture was stirred for 24 hours at room temperature and the solvent was removed under vacuum until dryness. The residue was dissolved in 5 mL of anhydrous DMF, pyridine (828 µL, 10.24 mmol) followed by HF-pyridine (128 µL, 5.12 mmol) were added. After stirring 1 h at room temperature, the solvent was evaporated in vacuo. The crude product was purified by reverse phase chromatography eluting with a linear gradient of 0% to 100% CH$_3$CN in aqueous buffer (NH$_4$OAc+AcOH+H$_2$O, pH=4.7). Combined pure fractions were concentrated and lyophilized to yield 59 (72 mg, 36%). LCMS purity: 98.9% (254 nm), 99.0% (220 nm), 99.0% (320 nm); mass calculated for C$_{62}$H$_{90}$N$_6$O$_{24}$P$_2$ 1364, found 1365 (M+H). $^1$H NMR (400 MHz, D$_2$O) δ −0.22 (d, J=7.1 Hz, 3H), 0.56 (d, J=6.65 Hz, 3H), 0.92-1.16 (m, 15H), 1.57-1.80 (m, 6H), 1.83 (s, 3H), 1.80-2.04 (m, 15H), 1.93 (s, 3H), 2.03 (s, 3H), 2.17 (s, 3H), 2.29 (m, 1H), 2.45 (q, J=7.43 Hz, 2H), 2.63-2.83 (m, 3H), 3.0 (s, 3H), 3.05 (d, J=12.1 Hz, 1H), 3.25 (m, 4H), 3.48 (m, 3H), 3.75-4.02 (m, 8H), 4.43 (m, 2H), 4.98 (d, J=10.56 Hz, 1H), 5.10 (dd, J=6.26, 12.52 Hz, 1H), 5.15 (d, J=10.56 Hz, 1H), 5.76 (s, 2H), 6.16 (m, 2H), 6.44 (d, J=10.95 Hz, 1H), 6.60 (m, 1H). $^{31}$P NMR (400 MHz, D$_2$O) δ 21 (2P)

Scheme 13. Preparation of Rifabutin Bisphosphonate Conjugate 66

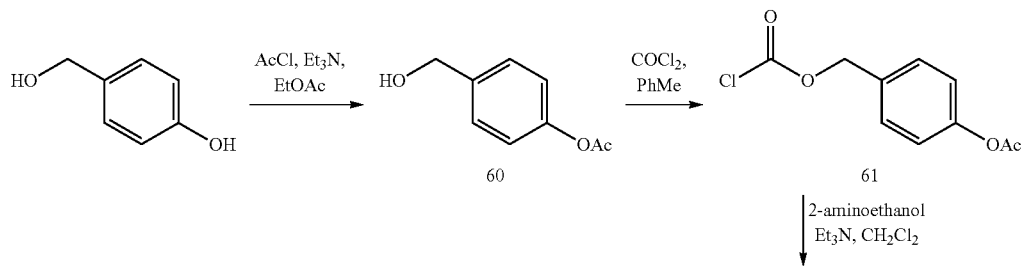

165
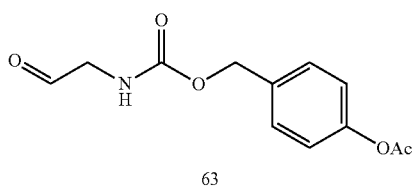
63
166
-continued
CrO$_3$, pyridine
CH$_2$Cl$_2$
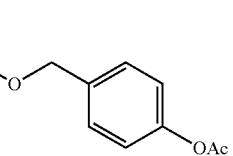
62
↓ 31, NaHB(OAc)$_3$
CH$_2$Cl$_2$
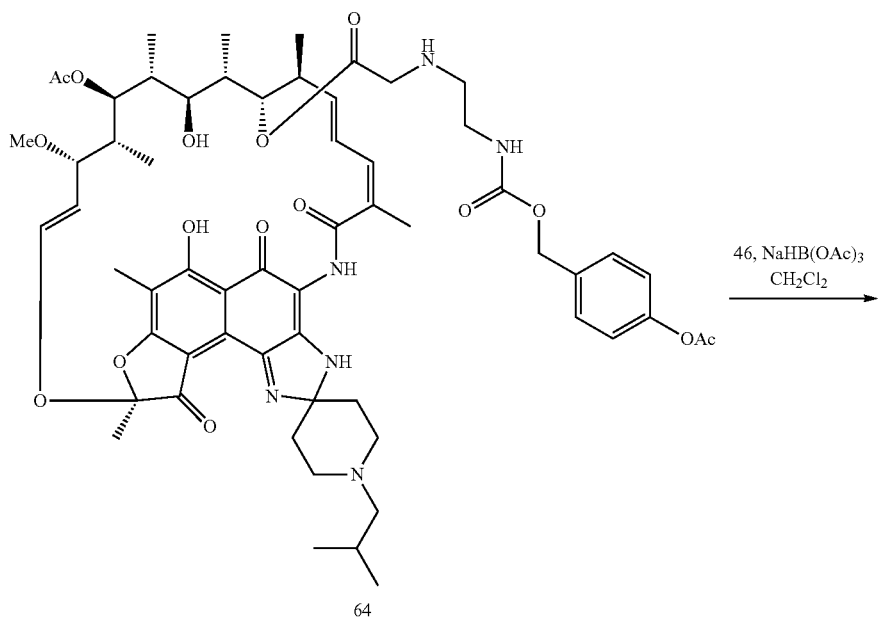
64
46, NaHB(OAc)$_3$
CH$_2$Cl$_2$ →
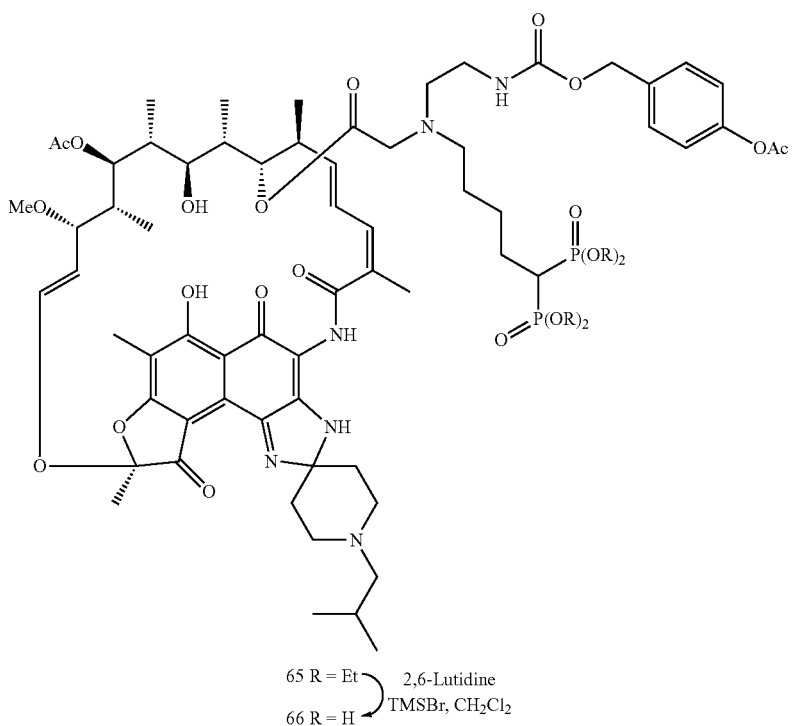
65 R = Et
66 R = H
2,6-Lutidine
TMSBr, CH$_2$Cl$_2$

4-(Hydroxymethyl)phenyl acetate (60)

To a solution of 4-hydroxybenzyl alcohol (7.5 g, 60 mmol) and 8.4 mL of triethylamine (8.4 mL, 60 mmol) in 100 mL of ethyl acetate, cooled in an ice bath, was added, via canula over 15 min, a solution of acetyl chloride (4.7 mL, 66 mmol) in 50 mL of ethyl acetate. The mixture was stirred in the same bath, which was left to come to room temperature on its own. After 18 h, the precipitate was removed by filtration. It was rinsed with 50 mL of ethyl acetate in small portions. The combined filtrates were concentrated in vacuo and purified by flash chromatography on silica gel, using 3:2 hexanes:ethyl acetate as the eluent, to afford 60 (2.853 g, 17 mmol, 29%) as an oil. $^1$H NMR (400 MHz, CDCl$_3$) δ 2.31 (s, 3H), 4.69 (d, J=5.8 Hz, 2H), 7.08 (d, J=8.6 Hz, 2H), 7.38 (d, J=8.4 Hz, 2H).

4-((Carbonochloridoyl)methyl)phenyl acetate (61)

To a solution of phosgene in toluene (20% w/w, 2.2 mL, 4.2 mmol), cooled in an ice bath, was added dropwise a solution of 60 (321 mg, 1.9 mmol) in 2 mL of toluene. The mixture was stirred in the same bath, which was left to come to room temperature on its own. After 18 h, the mixture was concentrated in vacuo to give 61, which was used in the next step without further purification. $^1$H NMR (400 MHz, CDCl$_3$) δ 2.30 (s, 3H), 5.28 (s, 2H), 7.13 (d, J=8.6 Hz, 2H), 7.42 (d, J=8.7 Hz, 2H).

4-Acetoxybenzyl 2-hydroxyethylcarbamate (62)

Crude 61 (from 321 mg of 60, max 1.9 mmol) was taken up in 8 mL of CH$_2$Cl$_2$ and the solution was added to a mixture of ethanolamine (140 μL, 2.3 mmol) and triethylamine (540 μL, 3.9 mmol) in 7 mL of CH$_2$Cl$_2$ cooled in an ice bath. The mixture was stirred in the same bath, which was left unmaintained. After 4 h, it was diluted with 100 mL of ethyl acetate and washed with 50 mL of each of 1% HCl in 2/3 saturated brine, 2/3 saturated brine and saturated aqueous NaHCO$_3$ (twice). The organics were dried over Na$_2$SO$_4$ and concentrated in vacuo to furnish 62 (364 mg, 1.44 mmol, 76% over two steps) as a gum. $^1$H NMR (400 MHz, CDCl$_3$) δ 2.30 (s, 3H), 3.35 (broad q, J=5.2 Hz, 2H), 3.72 (broad q, J=5.2 Hz, 2H), 5.09 (s, 2H), 5.15 (broad s, 1H), 7.07 (d, J=8.5 Hz, 2H), 7.37 (d, J=8.4 Hz, 2H).

4-Acetoxybenzyl formylmethylcarbamate (63)

A solution of pyridine (1.15 mL) in 20 mL of CH$_2$Cl$_2$ was cooled in an ice bath and chromium trioxide (711 mg) was added in one portion. The mixture was stirred at the same temperature for 5 min and at room temperature for 1 h. A solution of 62 (300 mg, 1.18 mmol) in 10 mL of CH$_2$Cl$_2$ was added in one portion and the mixture was stirred for 45 min at room temperature. The solution was decanted, diluted with 100 mL of CH$_2$Cl$_2$ and washed with aqueous NaHCO$_3$ (2×75 mL), saturated NaCl (1×75 mL), dried over Na$_2$SO$_4$, filtered and concentrated in vacuo to give the crude aldehyde which was used without further purification. $^1$H NMR (400 MHz, CDCl$_3$) δ 2.20 (s, 3H), 4.03 (s, 2H), 5.0 (s, 2H), 5.42 (broad s, 1H), 6.97 (d, J=8.5 Hz, 2H), 7.27 (d, J=8.4 Hz, 2H), 9.56 (s, 1H).

Rifabutin Derivative 64

To a solution of compounds 31 (500 mg, 0.55 mmol) and 63 (160 mg, 0.63 mmol) in 20 mL of CH$_2$Cl$_2$, cooled in an ice bath, was added sodium triacetoxyborohydride (205 mg, 0.97 mmol) in portions. The mixture was stirred in the same bath which was left to come to room temperature on its own. After 20 h, it was diluted with CH$_2$Cl$_2$ (120 mL) and washed successively with aqueous NaHCO$_3$ (2×50 mL), saturated NaCl (1×50 mL), dried over Na$_2$SO$_4$, filtered and concentrated in vacuo. The residue was purified by silica gel chromatography using a gradient of 0-2% methanol/ethyl acetate to give 64 (328 mg, 52%). $^1$H NMR (400 MHz, CDCl$_3$) δ −0.18 (d, J=7.1 Hz, 3H), 0.52 (d, J=6.65 Hz, 3H), 0.98 (m, 9H), 1.06 (d, J=6.26 Hz, 3H), 1.20 (m, 1H), 1.80 (s, 3H), 2.02 (s, 3H), 2.05 (s, 3H), 1.76-2.05 (m, 8H), 2.25 (m, 10H), 2.50-2.68 (m, 6H), 2.83-3.20 (m, 6H), 3.0 (s, 3H), 3.50 (bs, 1H), 3.78 (m, 1H), 4.96 (t, J=10.56 Hz, 1H), 5.06 (dd, J=6.26, 10.56 Hz, 1H), 5.10 (s, 2H), 5.70 (bs, 1H), 5.90 (m, 1H), 6.05 (m, 2H), 6.40 (m, 1H), 7.04 (d, J=8.5 Hz, 2H), 7.40 (d, J=8.4 Hz, 2H). 7.80 (s, 1H), 8.37 (s, 1H).

Rifabutin Bisphosphonate Conjugate 65

To a solution of compounds 64 (328 mg, 0.288 mmol) and 46 (124 mg, 0.345 mmol) in 15 mL of CH$_2$Cl$_2$, cooled in an ice bath, was added sodium triacetoxyborohydride (91.63 mg, 0.432 mmol) in portions. The mixture was stirred in the same bath which was left to come to room temperature on its own. After 18 h, it was diluted with CH$_2$Cl$_2$ (100 mL) and washed successively with aqueous NaHCO$_3$ (2×50 mL), saturated NaCl (1×50 mL), dried over Na$_2$SO$_4$, filtered and concentrated in vacuo. The residue was purified by silica gel chromatography using a gradient of 0-8% methanol/ethyl acetate to give 65 (218 mg, 42%). $^1$H NMR (400 MHz, CDCl$_3$) δ −0.18 (d, J=7.1 Hz, 3H), 0.44 (d, J=6.65 Hz, 3H), 0.98 (m, 9H), 1.06 (d, J=6.26 Hz, 3H), 1.20 (m, 1H), 1.30-1.44 (m, 13H), 1.57 (m, 2H), 1.77 (s, 3H), 1.98 (s, 3H), 2.02 (s, 3H), 1.76-2.05 (m, 14H), 2.22 (s, 3H), 2.29 (s, 3H), 2.20-2.30 (m, 4H), 2.42-2.65 (m, 6H), 2.83-3.20 (m, 5H), 2.96 (s, 3H), 3.42 (s, 1H), 4.16 (m, 8H), 4.96 (d, J=10.56 Hz, 1H), 5.10 (m, 4H), 5.57 (bs, 1H), 5.86 (dd, J=7.82, 12.52 Hz, 1H), 6.16 (m, 2H), 6.40 (dd, J=10.95, 15.65 Hz, 1H), 7.04 (d, J=8.5 Hz, 2H), 7.40 (d, J=8.4 Hz, 2H). 8.0 (s, 1H), 8.37 (s, 1H).

Rifabutin Bisphosphonate Conjugate 66

To a solution of 65 (218 mg, 0.147 mmol) and 2,6-lutidine (0.855 mL, 7.36 mmol) in 10 mL of CH$_2$Cl$_2$ cooled to −78° C. was added dropwise TMS-Br (0.486 mL, 3.68 mmol) under Ar. The cold bath was removed, the mixture was stirred for 24 hours at room temperature and the volatiles were removed under vacuum until dryness. The residue was dissolved in 5 mL of anhydrous DMF, pyridine (834 μL, 10.31 mmol) followed by HF-pyridine (129 μL, 5.15 mmol) were added. After stirring 1 h at room temperature, the solvent was evaporated in vacuo. The crude product was purified by reverse phase chromatography eluting with a linear gradient of 0% to 100% CH$_3$CN in aqueous buffer (NH$_4$OAc+AcOH+H$_2$O, pH=4.7). Combined pure fractions were concentrated and lyophilized to yield 66 (124 mg, 61%). LCMS purity: 97.5% (254 nm), 97.5% (220 nm), 97.9% (320 nm); mass calculated for C$_{65}$H$_{90}$N$_6$O$_{22}$P$_2$ 1368, found 1369 (M+H). $^1$H NMR (400 MHz, D$_2$O) δ −0.32 (d, J=7.1 Hz, 3H), 0.57 (d, J=6.65 Hz, 3H), 0.92-1.16 (m, 12H), 1.57-2.07 (m, 25H), 1.83 (s, 3H), 1.95 (s, 3H), 2.03 (s, 3H), 2.05 (s, 3H), 2.29 (m, 1H), 2.34 (s, 3H), 2.63 (m, 1H), 2.84 (s, 3H), 3.05 (d, J=12.1 Hz, 1H), 3.05-3.37 (m, 8H), 3.52 (broad d, 1H), 3.65-4.02 (m, 5H), 5.10 (t, J=10.56 Hz, 2H), 5.17 (d, J=12.52 Hz, 2H), 5.98 (d, J=12.52 Hz, 1H), 6.16 (dd, J=6.26, 10.56 Hz, 1H), 6.41 (d, J=10.95 Hz, 1H), 6.58 (m, 1H), 7.17 (d, J=8.5 Hz, 2H), 7.44 (d, J=8.4 Hz, 2H). $^{31}$P NMR (400 MHz, D$_2$O) δ 21 (2P)

Scheme 14. Preparation of Rifabutin Bisphosphonate Conjugate 71

(318 mg, 2 mmol, quant.) as an oil. $^1$H NMR (400 MHz, CDCl$_3$) δ 0.93 (t, J=7.4 Hz, 3H), 1.37 (sextet, J=7.4 Hz, 2H), 1.59 (pentet, J=7.2 Hz, 2H), 2.25 (broad s, 1H), 3.34 (broad q, J=5.2 Hz, 2H), 3.72 (broad q, J=4.8 Hz, 2H), 4.06 (t, J=6.6 Hz, 2H), 5.05 (broad s, 1H).

Butyl formylmethylcarbamate (68)

A solution of pyridine (1.8 mL) in 28 mL of CH$_2$Cl$_2$ was cooled in an ice bath and chromium trioxide (1.12 g) was added in one portion. The mixture was stirred at the same temperature for 20 min and at room temperature for 1 h. A

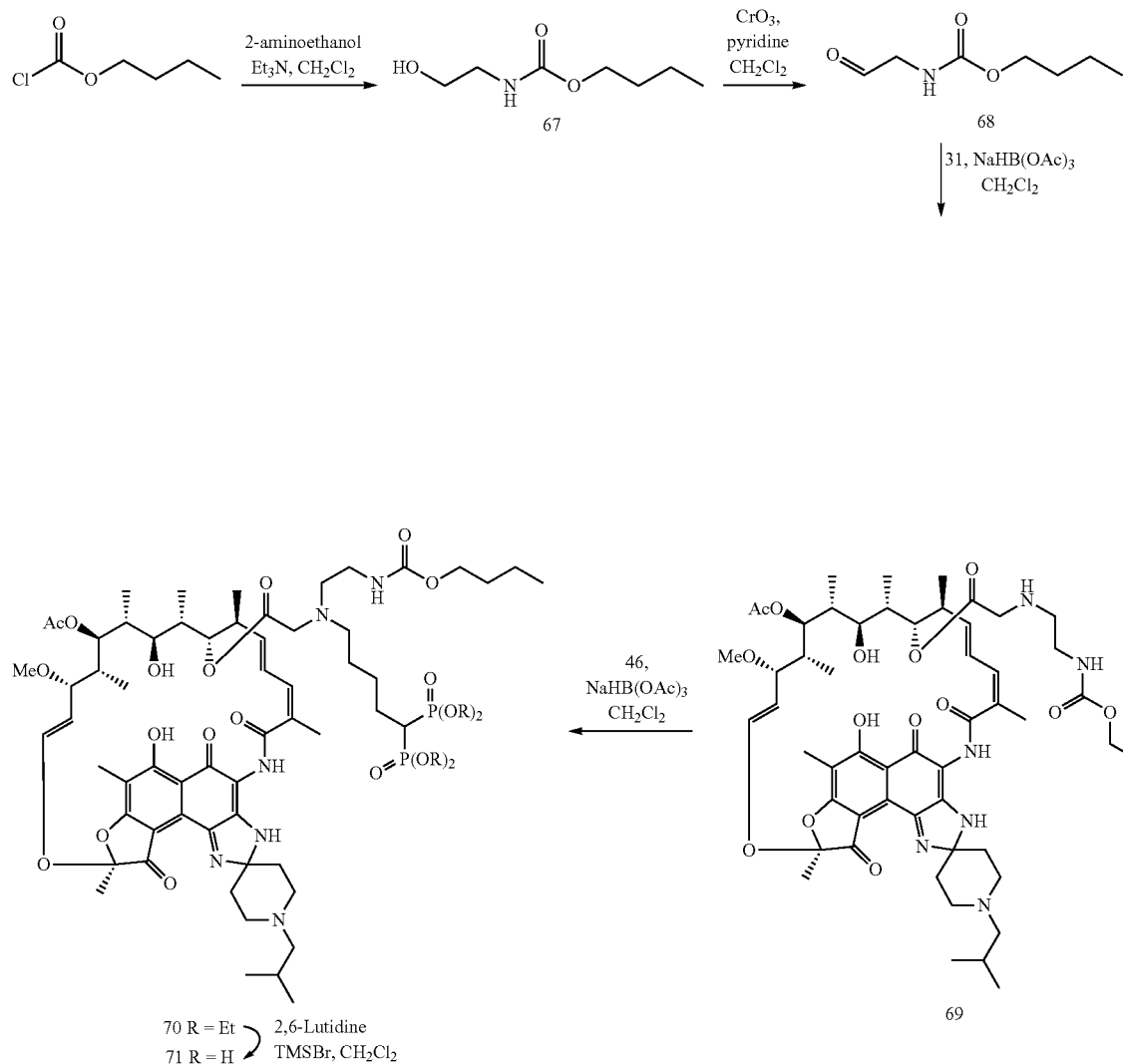

Butyl 2-hydroxyethylcarbamate (67)

A solution of butyl chloroformate (250 μL, 2 mmol) in 7 mL of CH$_2$Cl$_2$ was added to a mixture of ethanolamine (140 μL, 2.3 mmol) and triethylamine (540 μL, 3.9 mmol) in 7 mL of CH$_2$Cl$_2$ cooled in an ice bath. The mixture was stirred in the same bath, which was left unmaintained. After 5 h, it was diluted with 100 mL of ethyl acetate and washed with 50 mL of each of 1% HCl in 2/3 saturated brine, 2/3 saturated brine and saturated aqueous NaHCO$_3$ (twice). The organics were dried over Na$_2$SO$_4$ and concentrated in vacuo to furnish 62 solution of 67 (300 mg) in 2 mL of CH$_2$Cl$_2$ was added in one portion and the mixture was stirred for 1 h at room temperature. It was filtered through a pad of silica gel (5 g) and rinsed through with 50 mL of ethyl acetate. The filtrate was concentrated in vacuo to give the crude aldehyde which was used without further purification. $^1$H NMR (400 MHz, CDCl$_3$) δ 0.93 (t, J=7.4 Hz, 3H), 1.38 (sextet, J=7.4 Hz, 2H), 1.61 (pentet, J=7.1 Hz, 2H), 4.09 (t, J=6.7 Hz, 2H), 4.14 (d, J=5.0 Hz, 2H), 5.30 (broad s, 1H), 9.66 (s, 1H).

Rifabutin derivative 69

To a solution of compounds 31 (470 mg, 0.52 mmol) and 68 (82.75 mg, 0.52 mmol) in 15 mL of $CH_2Cl_2$, cooled in an ice bath, was added sodium triacetoxyborohydride (165 mg, 0.78 mmol) in portions. The mixture was stirred in the same bath which was left to come to room temperature on its own. After 20 h, it was diluted with $CH_2Cl_2$ (100 mL) and washed successively with aqueous $NaHCO_3$ (2×40 mL), saturated NaCl (1×40 mL), dried over $Na_2SO_4$, filtered and concentrated in vacuo. The residue was purified by silica gel chromatography using a gradient of 0-6% methanol/ethyl acetate to give 69 (185 mg, 34%). δ −0.18 (d, J=7.1 Hz, 3H), 0.52 (d, J=6.65 Hz, 3H), 0.96 (m, 12H), 1.05 (d, J=6.26 Hz, 3H), 1.22-1.45 (m, 5H), 1.60-1.98 (m, 10H), 1.83 (s, 3H), 1.98 (s, 3H), 2.03 (s, 3H), 2.10-2.25 (m, 2H), 2.29 (s, 3H), 2.53-2.70 (m, 4H), 2.82-3.25 (m, 6H), 3.03 (s, 3H), 3.17 (d, J=12.1 Hz, 1H), 3.52 (m, 1H), 4.16 (m, 3H), 4.96 (d, J=10.56 Hz, 1H), 5.07 (dd, J=6.26, 10.56 Hz, 1H), 5.12 (d, J=10.56 Hz, 1H), 5.57 (bs, 1H), 5.92 (dd, J=7.82, 12.52 Hz, 1H), 6.16 (d, J=12.52 Hz, 1H), 6.20 (d, J=7.82 Hz, 1H), 6.42 (dd, J=10.95, 15.65 Hz, 1H), 8.20 (s, 1H), 8.27 (s, 1H).

Rifabutin bisphosphonate conjugate 70

To a solution of compounds 69 (185 mg, 0.176 mmol) and 46 (76 mg, 0.212 mmol) in 15 mL of $CH_2Cl_2$, cooled in an ice bath, was added sodium triacetoxyborohydride (56.17 mg, 0.265 mmol) in portions. The mixture was stirred in the same bath which was left to come to room temperature on its own. After 18 h, it was diluted with $CH_2Cl_2$ (80 mL) and washed successively with aqueous $NaHCO_3$ (2×50 mL), saturated NaCl (1×50 mL), dried over $Na_2SO_4$, filtered and concentrated in vacuo. The residue was purified by silica gel chromatography using a gradient of 0-8% methanol/ethyl acetate to give 70 (154 mg, 62%). $^1$H NMR (400 MHz, $CDCl_3$) δ −0.18 (d, J=7.1 Hz, 3H), 0.44 (d, J=6.65 Hz, 3H), 0.98 (m, 12H), 1.06 (d, J=6.26 Hz, 3H), 1.20 (m, 1H), 1.30-1.44 (m, 15H), 1.57 (m, 4H), 1.80 (s, 3H), 2.03 (s, 3H), 2.08 (s, 3H), 1.76-2.08 (m, 16H), 2.29 (s, 3H), 2.10-2.30 (m, 2H), 2.42-2.65 (m, 5H), 2.83-3.20 (m, 6H), 3.42 (bd, 1H), 3.06 (s, 3H), 4.06 (m, 2H), 4.16 (m, 8H), 4.96 (d, J=10.56 Hz, 1H), 5.10 (dd, J=6.26, 12.52 Hz, 1H), 5.15 (d, J=10.56 Hz, 1H), 5.40 (bs, 1H), 5.92 (dd, J=7.82, 12.52 Hz, 1H), 6.16 (d, J=12.52 Hz, 1H), 6.20 (d, J=7.82 Hz, 1H), 6.40 (dd, J=10.95, 15.65 Hz, 1H), 8.0 (s, 1H), 8.37 (s, 1H).

Rifabutin Bisphosphonate Conjugate 71

To a solution of 70 (154 mg, 0.11 mmol) and 2,6-lutidine (0.644 mL, 5.54 mmol) in 10 mL of $CH_2Cl_2$ cooled to −78° C. was added dropwise TMS-Br (0.366 mL, 2.77 mmol) under Ar. The cold bath was removed, the mixture was stirred for 24 hours at room temperature and the volatiles were removed under vacuum until dryness. The residue was dissolved in 4 mL of anhydrous DMF, pyridine (628 µL, 7.76 mmol) followed by HF-pyridine (97 µL, 3.88 mmol) were added. After stirring 1 h at room temperature, the solvent was evaporated in vacuo. The crude product was purified by reverse phase chromatography eluting with linear gradient of 0% to 100% $CH_3CN$ in aqueous buffer ($NH_4OAc+AcOH+H_2O$, pH=4.7). Combined pure fractions were concentrated and lyophilized to yield 71 (92 mg, 65%). LCMS purity: 89.4% (254 nm), 90.6% (220 nm), 90.5% (320 nm); mass calculated for $C_{60}H_{90}N_6O_{20}P_2$ 1276, found 1277 (M+H). $^1$H NMR (400 MHz, $D_2O$) δ −0.27 (d, J=7.1 Hz, 3H), 0.57 (d, J=6.65 Hz, 3H), 0.92-1.16 (m, 14H), 1.20 (m, 1H), 1.40 (m, 3H), 1.60-2.10 (m, 22H), 1.83 (s, 3H), 1.95 (s, 3H), 2.03 (s, 3H), 2.05 (s, 3H), 2.10 (s, 3H), 2.29 (m, 1H), 2.63 (m, 1H), 3.03 (s, 3H), 3.05-3.37 (m, 8H), 3.52 (broad d, 1H), 3.65-4.02 (m, 8H), 5.04 (d, J=10.56 Hz, 1H), 5.10 (dd, J=6.26, 12.52 Hz, 1H), 5.17 (d, J=12.52 Hz, 1H), 6.08 (d, J=12.52 Hz, 1H), 6.16 (dd, J=6.26, 10.56 Hz, 1H), 6.41 (d, J=10.95 Hz, 1H), 6.58 (m, 1H). $^{31}$P NMR (400 MHz, $D_2O$) δ 21 (2P)

Scheme 15. Preparation of Rifabutin Bisphosphonate Conjugates 79(a-b)

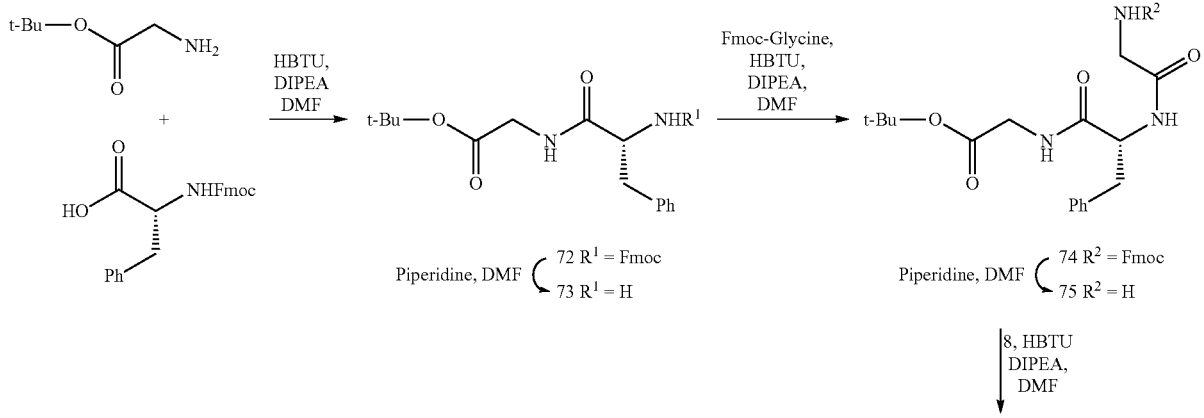

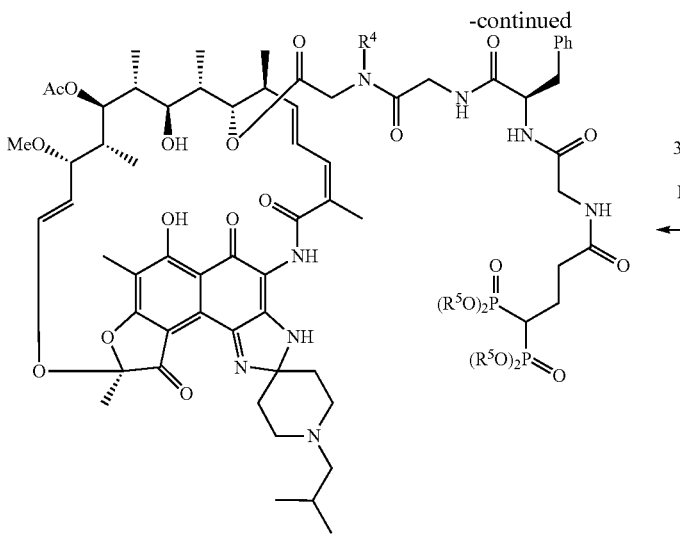
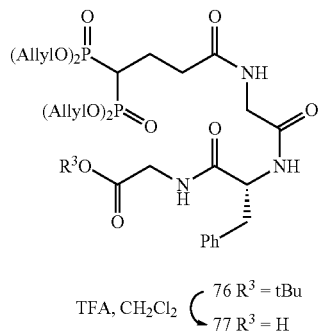

tButyl N-(N-(9-fluorenylmethyloxycarbonyl)-L-phenylalanyl)glycine (72)

To a solution of Fmoc-phenylalanine (1.0 g, 2.58 mmol) in DMF (13 mL) at 0° C. was added DIEA (899 µL, 5.16 mmol) and HBTU (979 mg, 2.58 mmol). After stirring for 10 min at 0° C., glycine t-butyl ester (353 µL, 2.58 mmol) was added and stirring was pursued for 1 h at 0° C. The reaction mixture was diluted with ethyl acetate, washed with H$_2$O, 1N HCl solution, saturated NaHCO$_3$ solution and saturated NaCl solution. The organic layer was dried over MgSO$_4$, filtered and concentrated to dryness. The crude product was purified by silica gel chromatography on a Biotage™ flash chromatography system using 50% ethyl acetate in hexanes. Dipeptide 72 was obtained as a white solid (1.05 g, 81%). $^1$H NMR (400 MHz, CDCl$_3$) δ 1.45 (s, 9H), 3.08-3.13 (m, 2H), 3.78-3.95 (m, 2H), 4.18 (t, J=6.9 Hz, 1H), 4.31-4.37 (m, 2H), 4.40-4.47 (m, 1H), 5.27 (bs, 1H), 6.21 (bs, 1H), 7.17-7.22 (m, 2H), 7.24-7.32 (m, 5H), 7.40 (t, J=7.5 Hz, 2H), 7.53 (t, J=7.9 Hz, 2H), 7.76 (d, J=7.5 Hz, 2H).

tButyl N-(L-phenylalanyl)glycine (73)

Fmoc-protected dipeptide 72 (500 mg, 1.00 mmol) was treated with a 5% v/v solution of piperidine in DMF (5 mL). After stirring for 1 h, the reaction mixture was concentrated to dryness. The crude material was used for the next step without purification.

tButyl N-(N-(N-(9-fluorenylmethyloxycarbonyl)-glycyl)L-phenylalanyl)glycine (74)

To a solution of Fmoc-glycine (297 mg, 1.00 mmol) in DMF (5 mL) at 0° C. was added DIEA (348 µL, 2.00 mmol) and HBTU (379 mg, 1.00 mmol). After stirring for 10 min at 0° C., the resulting activated ester solution was added to crude dipeptide 73 (1.00 mmol) and the reaction mixture was stirred for 2 h at 0° C. It was diluted with ethyl acetate, washed with H$_2$O, 1N HCl solution, saturated NaHCO$_3$ solution and saturated NaCl solution. The organic layer was dried over MgSO$_4$, filtered and concentrated to dryness. The crude product was purified by silica gel chromatography on a Biotage™ flash chromatography system using a gradient of 0-75% ethyl acetate in CH$_2$Cl$_2$. Tripeptide 74 was obtained as a white solid (546 mg, 98%). $^1$H NMR (400 MHz, CDCl$_3$) δ 1.44 (s, 9H), 3.10 (d, J=6.8 Hz, 2H), 3.74-3.95 (m, 4H), 4.21 (t, J=7.0 Hz, 1H), 4.40 (d, J=7.2 Hz, 2H), 4.70 (q, J=7.5 Hz, 1H), 5.36 (bs, 1H), 6.31 (bs, 1H), 6.53 (d, J=7.4 Hz, 1H), 7.17-7.22 (m, 3H), 7.24-7.28 (m, 2H), 7.30-7.34 (m, 2H), 7.41 (t, J=7.4 Hz, 2H), 7.59 (d, J=7.3 Hz, 2H), 7.77 (d, J=7.3 Hz, 2H).

tButyl N-(N-(glycyl)-L-phenylalanyl)glycine (75)

Fmoc-protected tripeptide 74 (546 mg, 0.98 mmol) was treated with a 5% v/v solution of piperidine in DMF (5 mL). After stirring for 45 min, the reaction mixture was concentrated to dryness. The crude material was used for the next step without purification.

tButyl N-(N-(N-(4,4-bis(diallylphosphoryl)butyryl)glycyl)L-phenylalanyl)glycine (76)

To a solution of bisphosphonate 8 (400 mg, 0.98 mmol) in DMF (5 mL) at 0° C. was added DIEA (341 µL, 1.96 mmol) and HBTU (372 mg, 0.98 mmol). After stirring for 10 min at 0° C., the resulting activated ester solution was added to crude tripeptide 75 (0.98 mmol) and stirring was pursued for 2.5 h at 0° C. The reaction mixture was diluted with ethyl acetate, washed with H$_2$O, 1N HCl solution, saturated NaHCO$_3$ solution and saturated NaCl solution. The organic layer was dried over MgSO$_4$, filtered and concentrated to dryness. The crude product was purified by silica gel chromatography on a Biotage™ flash chromatography system using a gradient of 0-10% methanol in ethyl acetate. Compound 76 was obtained as a colorless gum (652 mg, 92%). $^1$H NMR (400 MHz, CDCl$_3$) δ 1.44 (s, 9H), 2.22-2.37 (m, 2H), 2.57 (t, J=6.4 Hz, 2H), 2.62 (tt, J=23.9, 7.0 Hz, 1H), 3.03-3.09 (m, 1H), 3.14-3.20 (m, 1H), 3.77-3.93 (m, 4H), 4.58-4.63 (m, 8H), 4.66-

4.71 (m, 1H), 5.21-5.26 (m, 4H), 5.33-5.41 (m, 4H), 5.89-5.99 (m, 4H), 6.58-6.66 (m, 2H), 7.09 (d, J=8.2, 1H), 7.19-7.23 (m, 3H), 7.27-7.30 (m, 2H).

N-(N-(N-(4,4-bis(diallylphosphoryl)butyryl)glycyl) L-phenylalanyl)glycine (77)

Compound 76 (293 mg, 0.405 mmol) was treated with a 50% v/v solution of TFA in CH$_2$Cl$_2$ (2 mL). After stirring for 2.5 h, the reaction mixture was concentrated to dryness and coevaporated several times with Et$_2$O/hexanes. After drying under vacuum, acid 77 was obtained as a colorless gum (279 mg, quant.) and was used without purification. $^1$H NMR (400 MHz, CDCl$_3$) δ 2.22-2.36 (m, 2H), 2.58-2.80 (m, 3H), 2.97-3.03 (m, 1H), 3.11-3.17 (m, 1H), 3.95-3.97 (m, 2H), 4.00-4.03 (m, 2H), 4.55-4.62 (m, 8H), 5.09-5.14 (m, 1H), 5.23-5.30 (m, 4H), 5.33-5.41 (m, 4H), 5.86-5.98 (m, 4H), 6.99-7.06 (m, 3H), 7.16-7.25 (m, 3H), 7.43-7.46 (m, 1H), 7.71-7.75 (m, 1H).

Rifabutin Bisphosphonate Conjugate 78a

To a solution of compound 77 (268 mg, 0.40 mmol) in DMF (4 mL) at 0° C. was added DIEA (139 μL, 0.80 mmol) and HBTU (152 mg, 0.40 mmol). After stirring for 10 min at 0° C., sarcosyl-rifabutin 32 (367 mg, 0.40 mmol) was added and stirring was pursued for 1 h at 0° C. The reaction mixture was diluted with ethyl acetate, washed with H$_2$O, 0.5N HCl solution, saturated NaHCO$_3$ solution and saturated NaCl solution. The organic layer was dried over MgSO$_4$, filtered and concentrated to dryness. The crude product was purified by silica gel chromatography on a Biotage™ flash chromatography system using 0-10% methanol in CH$_2$Cl$_2$. Bisphosphonate conjugate 78a was obtained as a dark purple solid (506 mg, 81%). ESI-MS: (M+H) calculated for C$_{78}$H$_{106}$N$_8$O$_{22}$P$_2$ 1569, found 1570.4.

Rifabutin Bisphosphonate Conjugate 78b

To a solution of compound 77 (321 mg, 0.46 mmol) in DMF (4 mL) at 0° C. was added DIEA (160 μL, 0.92 mmol) and HBTU (174 mg, 0.46 mmol). After stirring for 10 min at 0° C., glycyl-Rifabutin 31 (415 mg, 0.46 mmol) was added and stirring was pursued for 1 h at 0° C. The reaction mixture was diluted with ethyl acetate, washed with H$_2$O, 0.5N HCl solution, saturated NaHCO$_3$ solution and saturated NaCl solution. The organic layer was dried over MgSO$_4$, filtered and concentrated to dryness. The crude product was purified by silica gel chromatography on a Biotage™ flash chromatography system using 0-10% methanol in CH$_2$Cl$_2$. Bisphosphonate conjugate 78b was obtained as a dark purple solid (593 mg, 83%). ESI-MS: (M+H) calculated for C$_7$H$_{104}$N$_8$O$_{22}$P$_2$ 1555, found 1555.4.

Rifabutin Bisphosphonate Conjugate 79a

To a solution of bisphosphonate conjugate 78a (249 mg, 0.16 mmol) in DMF (2.8 mL) was added morpholine (2.8 mL, 31.7 mmol) and tetrakistriphenylphosphine palladium (9 mg, 0.008 mmol). The mixture was stirred at room temperature for 4 h and concentrated to dryness then purified by C18 silica gel chromatography on a Biotage™ flash chromatography system using a gradient of 10-100% MeCN in H$_2$O, both containing 0.05% NH$_4$OH. Pure fractions were combined, concentrated and lyophilized to provide the diammonium salt of compound 79a as a fluffy purple solid (165 mg, 73%). LCMS: 100% (254 nm), 100% (220 nm), 100% (320 nm). ESI-MS: (M+H) calculated for C$_{66}$H$_{90}$N$_8$O$_{22}$P$_2$ 1409, found 1409.4.

Rifabutin Bisphosphonate Conjugate 79b

To a solution of bisphosphonate conjugate 78b (200 mg, 0.13 mmol) in DMF (2.2 mL) was added morpholine (2.2 mL, 25.7 mmol) and tetrakistriphenylphosphine palladium (7.5 mg, 0.0065 mmol). The mixture was stirred at room temperature for 4 h and concentrated to dryness then purified by C18 silica gel chromatography on a Biotage™ flash chromatography system using a gradient of 10-100% MeCN in H$_2$O, both containing 0.05% NH$_4$OH. Pure fractions were combined, concentrated and lyophilized to provide the diammonium salt of compound 79b as a fluffy purple solid (141 mg, 75%). LCMS: 99.0% (254 nm), 99.1% (220 nm), 99.2% (320 nm). ESI-MS: (M+H) calculated for C$_{65}$H$_{88}$N$_8$O$_{22}$P$_2$ 1395, found 1395.4.

Scheme 16. Preparation of Rifabutin Bisphosphonate Conjugates 89

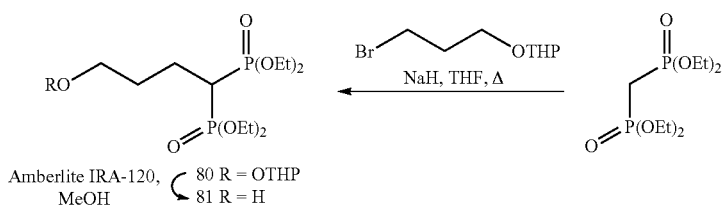

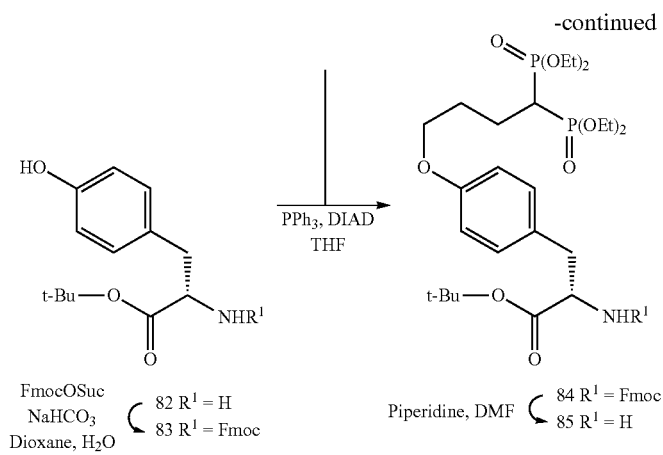
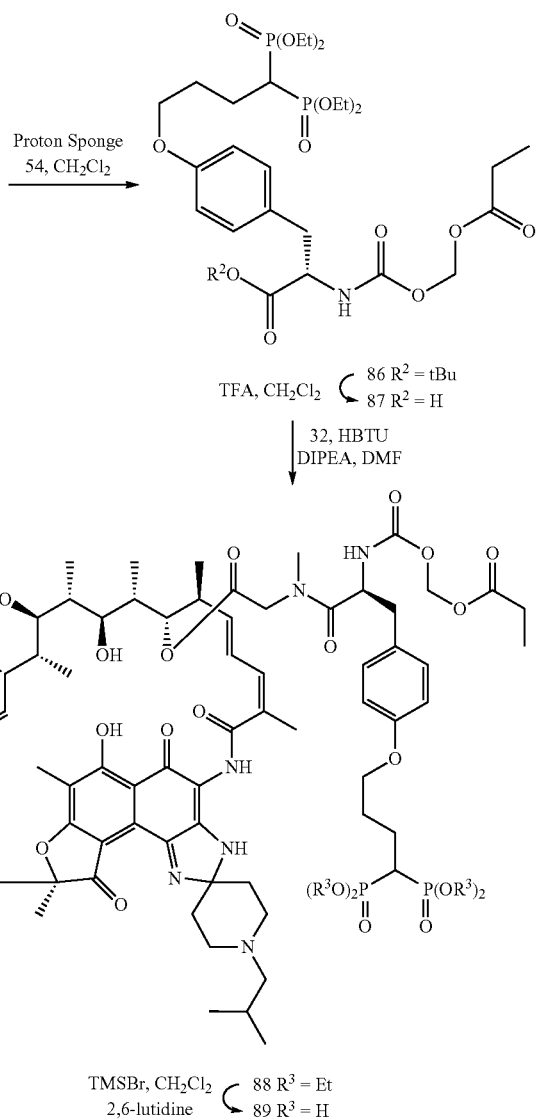

Tetraethyl 4-(2-Tetrahydro-2H-pyranyloxy)butylene-1,1-bisphosphonate (80)

To a suspension of NaH (60% suspension in mineral oil, 900 mg, 22.0 mmol) in dry THF (20 mL) was added dropwise tetraethyl methylenebisphosphonate (6.46 g, 22.4 mmol). The resulting clear solution was stirred 15 min at room temperature, after which 2-(3-bromopropoxy)tetrahydro-2H-pyran (5.05 g, 22.6 mmol) was added dropwise. The reaction mixture was heated to reflux for 6 h, diluted with $CH_2Cl_2$ (75 mL) and washed with brine (2×50 mL), dried ($MgSO_4$) and evaporated. It was used as such in the following step.

Tetraethyl 4-hydroxybutylene-1,1-bisphosphonate (81)

To a stirred solution of the crude product 80 (max. 22.4 mmol) in methanol (40 mL) was added Amberlite IR-120 (0.6 g). The reaction mixture was heated to 50° C. for 4 h, filtered and evaporated. The crude product was purified by flash chromatography on silica gel with gradient elution from 5-10% methanol/ethyl acetate to give pure 81 (2.67 g, 34% from tetraethyl methylenebisphosphonate). $^1$H NMR (400 MHz, $CDCl_3$) δ 1.30-1.36 (m, 12H), 1.75-1.85 (m, 2H), 1.97-2.13 (m, 2H), 2.30-2.64 (m, 2H), 3.66 (t, J=5.8, 2H), 4.12-4.23 (m, 8H).

tButyl N-(9-fluorenylmethoxycarbonyl)-L-tyrosine (83)

To a stirring suspension of L-tyrosine O-t-butyl ester (1.00 g, 4.21 mmol) and $NaHCO_3$ (354 mg, 4.21 mmol) in 1,4-dioxane/water (1:1, 20 mL) was added 9-fluorenylmethyl-N-succinimidyl carbonate (1.42 g, 4.21 mmol) and the resulting mixture was stirred for 18 hr at room temperature. The solvent was reduced to 10 mL followed by the addition of 50 mL of cold 1N HCl. The product was extracted with ethyl acetate (3×). The organic extracts were washed with $H_2O$ and saturated aqueous NaCl then dried over $Na_2SO_4$. The solution was then concentrated after filtration to give the colourless solid 83 (1.94 g, 100%) which was used without purification: $^1$H NMR (400 MHz, $CDCl_3$) δ 1.43 (s, 9H), 2.97-3.06 (m, 2H), 4.21 (bt, J=7.1, 1H), 4.33 (dd, J=7.1, 10.5, 1H), 4.41-4.53 (m, 2H), 5.01 (bs, 1H), 5.30, (d, J=8.2, 1H), 6.73 (d, J=8.5, 2H), 7.00 (d, J=8.5, 2H), 7.31 (t, J=7.5, 2H), 7.40 (t, J=7.5, 2H), 7.57 (dd, J=3.3, 7.3, 2H), 7.76 (d, J=7.5, 2H).

tButyl N-(9-fluorenylmethoxycarbonyl)-O-(4,4-bis(diethylphosphoryl)butyl)-L-tyrosine (84)

A solution of 83 (664 mg, 1.44 mmol) and PPh$_3$ (454 mg, 1.73 mmol) in THF (20 mL) was cooled in an ice-bath followed by the addition of diisopropyl azodicarboxylate (336 mg, 1.74 mmol). After a further 10 min a solution of 81 (500 mg, 1.44 mmol) in THF (5 mL) was added and the resulting solution was stirred while warming to room temperature overnight. The solvent was removed at reduced pressure and the crude material was purified by silica gel chromatography (0 to 10% methanol in ethyl acetate over 10 column volumes then 10 to 20% over 5 column volumes) using a Biotage Horizon™ apparatus resulting in the colourless liquid 84 (491 mg, 43%): $^1$H NMR (400 MHz, CDCl$_3$) δ 1.33 (t, J=7.1, 6H), 1.34 (t, J=7.1, 6H), 1.43 (s, 9H), 2.04-2.18 (m, 4H), 2.37 (tt, J=6.3, 24.2, 1H), 2.98-3.07 (m, 2H), 3.92 (t, J=5.8, 2H), 4.14-4.22 (m, 8H), 4.33 (dd, J=7.1, 10.4, 1H), 4.43 (dd, J=7.2, 10.5, 1H), 4.50 (dd, J=6.0, 8.4, 1H), 5.24, (d, J=8.1, 1H), 6.78 (d, J=8.5, 2H), 7.04 (d, J=8.4, 2H), 7.28-7.33 (m, 2H), 7.40 (t, J=7.6, 2H), 7.77 (d, J=7.6, 2H): $^{31}$P (162 MHz, CDCl$_3$) δ 24.74 (s, 2P).

tButyl O-(4,4-bis(diethylphosphoryl)butyl)-L-tyrosine (85)

A solution of 84 (490 mg, 0.622 mmol) in piperidine/DMF (1:1, 4 mL) was stirred at room temperature for 45 min. After diluting with water and adjusting the pH to ~3 by the addition of 1N HCl the aqueous layer was washed with diethyl ether (2×) then the pH was readjusted to ~10 by the addition of 1N NaOH. The product was extracted with ethyl acetate (3×) washed with saturated aqueous NaCl and dried over Na$_2$SO$_4$. The crude material was purified by silica gel chromatography (0 to 10% methanol in CH$_2$Cl$_2$ over 10 column volumes then 10 to 20% over 5 column volumes) using a Biotage Horizon™ apparatus resulting in the colourless liquid 85 (271 mg, 77%): $^1$H NMR (400 MHz, CDCl$_3$) δ 1.33 (t, J=7.1, 6H), 1.34 (t, J=7.1, 6H), 1.43 (s, 9H), 2.04-2.17 (m, 4H), 2.37 (tt, J=5.8, 24.1, 1H), 2.77 (dd, J=7.6, 13.7, 1H), 2.97 (dd, J=5.5, 13.7, 1H), 3.55 (dd, J=5.5, 7.6, 1H), 3.94 (t, J=5.8, 2H), 4.14-4.23 (m, 8H), 6.78 (d, J=8.6, 2H), 7.10 (d, J=8.6, 2H): $^{31}$P (162 MHz, CDCl$_3$) δ 24.76 (s, 2P).

tButyl N-propionyloxymethoxycarbonyl-O-(4,4-bis(diethylphosphoryl)butyl)-L-tyrosine (86)

A solution of 54 (138 mg, 0.832 mmol) in CH$_2$Cl$_2$ (1 mL) was added to a a stirring solution of 85 (340 mg, 0.601 mmol) and proton sponge (180 mg, 0.842 mmol) in CH$_2$Cl$_2$ at room temperature. After 18 hr the solution was diluted with CH$_2$Cl$_2$ then washed with cold 1N HCl, saturated aqueous NaCl and dried over Na$_2$SO$_4$. The crude material was purified by silica gel chromatography (0 to 10% methanol in CH$_2$Cl$_2$ over 10 column volumes then 10 to 15% over 5 column volumes) using a Biotage Horizon™ apparatus resulting in the pale pink liquid 86 (271 mg, 77%): $^1$H NMR (400 MHz, CDCl$_3$) δ 1.15 (t, J=7.5, 3H), 1.33 (t, J=7.1, 6H), 1.34 (t, J=7.1, 6H), 1.42 (s, 9H), 2.00-2.17 (m, 4H), 2.36 (tt, J=6.0, 24.2, 1H), 2.38 (q, J=7.5, 2H), 3.03 (dd, J=1.6, 5.8, 2H), 3.93 (t, J=5.8, 2H), 4.14-4.22 (m, 8H), 4.47 (dt, J=5.7, 8.1, 1H), 5.30 (d, J=8.1, 1H), 5.72 (s, 2H), 6.78 (d, J=8.6, 2H), 7.03 (d, J=8.6, 2H): $^{31}$P (162 MHz, CDCl$_3$) δ 24.74 (s, 2P).

N-propionyloxymethoxycarbonyl-O-(4,4-bis(diethylphosphoryl)butyl)-L-tyrosine (87)

A solution of 86 (375 mg, 0.593 mmol) in TFA/CH$_2$Cl$_2$ (1:1, 3 mL) was stirred at room temperature for 1.5 hr. The solvent was removed at reduced pressure followed by one co-evaporation with toluene to give the crude product 87 that was used without purification: $^1$H NMR (400 MHz, CDCl$_3$) δ 1.15 (t, J=7.5, 3H), 1.34 (t, J=7.1, 6H), 1.35 (t, J=7.1, 6H), 1.98-2.18 (m, 4H), 2.39 (q, J=7.5, 2H), 2.56 (tt, J=6.1, 24.9, 1H), 3.06-3.17 (m, 2H), 3.95 (t, J=5.6, 2H), 4.14-4.24 (m, 8H), 4.65 (dt, J=5.7, 7.9, 1H), 5.29 (d, J=8.2, 1H), 5.73 (s, 2H), 6.81 (d, J=8.5, 2H), 7.06 (d, J=8.5, 2H): $^{31}$P (162 MHz, CDCl$_3$) δ 24.03 (s, 2P).

Rifabutin Bisphosphonate Conjugate 88

A solution of 87 (340 mg, 0.532 mmol), 32 (488 mg, 0.532 mmol), and DIEA (185 µL, 1.06 mmol) in DMF (5 mL) was cooled in an ice-bath after which HBTU was added and the resulting solution was stirred while slowly warming to room temperature overnight. The reaction mixture was diluted with ethyl acetate then washed with 1N HCl, H$_2$O and saturated aqueous NaCl then dried over Na$_2$SO$_4$. The crude product was purified by silica gel chromatography (0 to 10% methanol in CH$_2$Cl$_2$ over 10 column volumes) using a Biotage Horizon™ apparatus resulting in the dark purple solid 88 (698 mg, 85%-two steps): ESI-MS: (MH$^+$) calculated for C$_{75}$H$_{108}$N$_6$O$_{24}$P$_2$, 1539.7; found 1539.4.

Rifabutin Bisphosphonate Conjugate 89

A solution of protected conjugate 88 (659 mg, 0.451 mmol) and 2,6-lutidine (2.62 mL, 22.6 mmol) in CH$_2$Cl$_2$ (5 mL) was cooled to −78° C. and trimethylsilylbromide (2.38 mL, 18.1 mmol) was added drop-wise. After 1 hr the solution was brought to room temperature and stirred for a further 24 hr then concentrated to dryness under high vacuum. The residue was resuspended in DMF (5 mL) followed by the addition of pyridine (730 µL, 9.03 mmol) and 70% HF in pyridine (193 µL, 6.77 mmol). After 2 hr the solution was again evaporated to dryness. The crude product was purified by 2 consecutive C18 reverse phase chromatographies using a Biotage Horizon™ apparatus. First a 10-70% gradient of MeCN in 0.05% aqueous NH$_4$OH (10 column volumes) then a gradient of 10-70% MeCN in 50 mM NH$_4$OAc, pH 4.5 for the second column (10 column volumes). Lyophilization of the combined pure fractions provided conjugate 89 as the di-ammonium salt (130 mg, 20%): LCMS: 100% (254 nm), 100% (220 nm), 100% (320 nm): ESI-MS: (MH$^+$) calculated for C$_{67}$H$_{92}$N$_6$O$_{24}$P$_2$, 1427.6; found 1427.2.

Scheme 17. Preparation of Rifabutin Bisphosphonate Conjugates 95

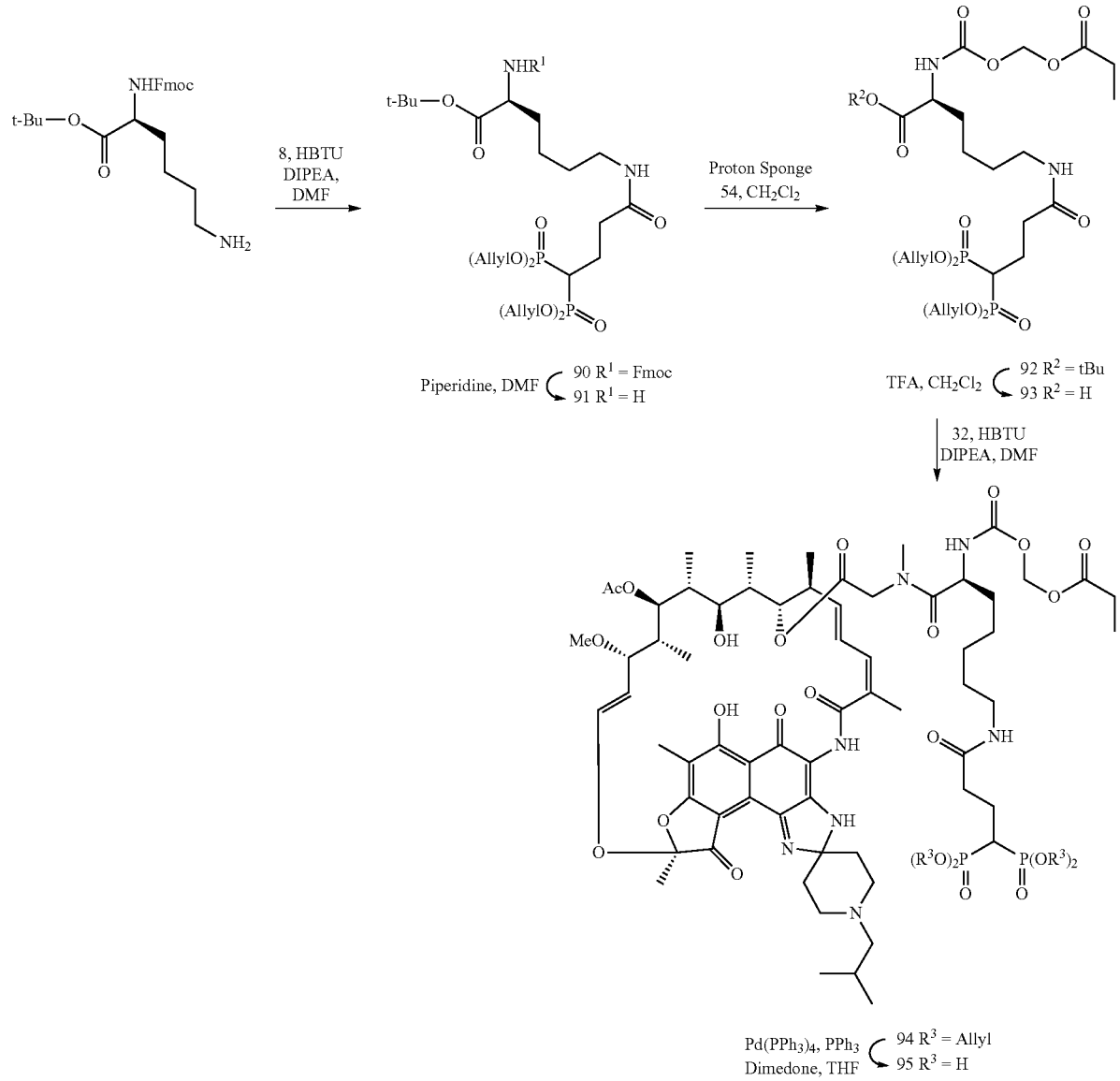

tButyl N$^\alpha$-(9-fluorenylmethoxycarbonyl)-N$^\epsilon$-(4,4-bis(diallylphosphoryl)butyryl)-L-lysine (90)

A solution of N-(9-fluorenylmethoxycarbonyl)-L-lysine O-t-butyl ester (405 mg, 0.954 mmol), 8 (390 mg, 0.954 mmol), and DIEA (332 μL, 1.91 mmol) in DMF (5 mL) was cooled in an ice-bath and stirred for 1 hr after which HBTU was added and the resulting solution was stirred while slowly warming to room temperature overnight. The reaction mixture was diluted with ethyl acetate then washed with H$_2$O and saturated aqueous NaCl then dried over Na$_2$SO$_4$. The crude product was purified by silica gel chromatography (0 to 10% methanol in CH$_2$Cl$_2$ over 14 column volumes) using a Biotage Horizon™ apparatus resulting in the pale pink solid 90 (505 mg, 65%): $^1$H NMR (400 MHz, CDCl$_3$) δ 1.31-1.70 (m, 6H), 1.47 (s, 9H), 2.21-2.35 (m, 2H), 2.51 (t, J=7.4, 2H), 2.55 (tt, J=7.0, 24.0, 1H), 3.19-3.25 (m, 2H), 4.15-4.28 (m, 2H), 4.37 (dd, J=2.5, 7.6, 1H), 4.57-4.61 (m, 8H), 5.23 (d, J=10.3, 4H), 5.36 (dt, J=1.5, 16.9, 4H), 5.45 (d, J=8.2, 1H), 5.87-5.98 (m, 4H), 6.10-13 (m, 1H), 7.31 (t, J=7.4, 2H), 7.40 (t, J=7.6, 2H), 7.61 (bd, J=7.4, 2H), 7.76 (d, J=7.6, 2H): $^{31}$P (162 MHz, CDCl$_3$) δ 24.64 (s, 2P).

tButyl N$^\epsilon$-(4,4-bis(diallylphosphoryl)butyryl)-L-lysine (91)

A solution of 90 (502 mg, 0.616 mmol) in piperidine/DMF (0.05:1, 5 mL) was stirred at room temperature for 18 hr. After diluting with ethyl acetate (40 mL) the organic layer was washed with water and brine then dried over Na$_2$SO$_4$ and concentrated in vacuo. The crude material was purified by silica gel chromatography (methanol in ethyl acetate, 5% over 5 column volumes then 5 to 30% over 10 column volumes) using a Biotage Horizon™ apparatus resulting in the colourless liquid 91 (249 mg, 68%): $^1$H NMR (400 MHz, CDCl$_3$) δ 1.39-1.74 (m, 6H), 1.45 (s, 9H), 2.21-2.35 (m, 2H), 2.51 (t, J=7.4, 2H), 2.55 (tt, J=6.9, 23.9, 1H), 3.19-3.25 (m, 2H), 3.29 (dd, J=5.2, 7.6, 1H), 4.58-4.63 (m, 8H), 5.25 (dq, J=1.3, 10.3, 4H), 5.38 (dq, J=1.4, 17.1, 4H), 5.90-6.00 (m, 4H), 6.14 (bd, J=4.9, 1H): $^{31}$P (162 MHz, CDCl$_3$) δ 24.67 (s, 2P).

tButyl N$^α$-propionyloxymethoxycarbonyl-N$^ε$-(4,4-bis(diallylphosphoryl)butyryl)-L-lysine (92)

A solution of 54 (77 mg, 0.46 mmol) in CH$_2$Cl$_2$ (1 mL) was added to a stirring solution of 91 (242 mg, 0.408 mmol) and proton sponge (103 mg, 0.482 mmol) in CH$_2$Cl$_2$ (2 mL) at room temperature. After 18 hr the solution was concentrated and the residue was resuspened in ethyl acetate (30 mL) then washed with cold 10% KHSO$_4$, water and saturated aqueous NaCl then dried over Na$_2$SO$_4$. The crude material was purified by silica gel chromatography (ethyl acetate; 3 column volumes then a gradient of methanol in ethyl acetate, 0 to 10% over 10 column volumes then 10 to 30% over 5 column volumes) using a Biotage Horizon™ apparatus resulting in the pale yellow liquid 92 (168 mg, 57%): $^1$H NMR (400 MHz, CDCl$_3$) δ 1.15 (t, J=7.5, 3H), 1.30-1.71 (m, 5H), 1.46 (s, 9H), 1.76-1.84 (m, 1H), 2.21-2.33 (m, 2H), 2.39 (q, J=7.5, 2H), 2.52 (t, J=7.2, 2H), 2.56 (tt, J=6.9, 23.8, 1H), 3.15-3.27 (m, 2H), 4.21 (dt, J=4.9, 8.0, 1H), 4.58-4.63 (m, 8H), 5.24 (dt, J=1.2, 10.4, 4H), 5.34-5.41 (m, 4H), 5.64 (d, J=8.2, 1H), 5.73 (AB q, J=5.8, 2H), 5.90-6.00 (m, 4H), 6.15 (bt, J=5.4, 1H): $^{31}$P (162 MHz, CDCl$_3$) δ 24.67 (AB q, J=7.9, 2P).

N$^α$-Propionyloxymethoxycarbonyl-N$^ε$-(4,4-bis(diallylphosphoryl)butyryl)-L-lysine (93)

A solution of 92 (165 mg, 0.228 mmol) in TFA/CH$_2$Cl$_2$ (1:1, 2 mL) was stirred at room temperature for 1 hr. The solvent was removed at reduced pressure followed by one co-evaporation with toluene to give the crude product 93 as a yellow liquid which was used without purification: $^1$H NMR (400 MHz, CDCl$_3$) δ 1.15 (t, J=7.5, 3H), 1.22-1.30 (m, 1H), 1.40-1.64 (m, 3H), 1.83-1.89 (m, 2H), 2.21-2.34 (m, 2H), 2.39 (q, J=7.5, 2H), 2.55 (t, J=7.1, 2H), 2.57 (tt, J=7.0, 23.9, 1H), 3.23-3.38 (m, 2H), 4.41 (dt, J=5.4, 6.9, 1H), 4.59-4.65 (m, 8H), 5.28 (bt, J=10.4, 4H), 5.36-5.42 (m, 4H), 5.73 (s, 2H), 5.88-5.99 (m, 4H), 6.58 (bt, J=4.9, 1H): $^{31}$P (162 MHz, CDCl$_3$) δ 24.24 (AB q, J=4.9, 2P).

Rifabutin Bisphosphonate Conjugate 94

A solution of 93 (165 mg, 0.228 mmol), 32 (209 mg, 0.228 mmol), and DIEA (38 μL, 456 mmol) in DMF (5 mL) was cooled in an ice-bath after which HBTU was added and the resulting solution was stirred while slowly warming to room temperature overnight. The reaction mixture was diluted with ethyl acetate, washed with H$_2$O and brine then dried over Na$_2$SO$_4$. The crude product was purified by silica gel chromatography (methanol in CH$_2$Cl$_2$; 0 to 10% over 10 column volumes then 10 to 20% over 5 column volumes) using a Biotage Horizon™ apparatus resulting in the dark purple solid 94 (698 mg, 69% for two steps): ESI-MS: (MH$^+$) calculated for C$_{76}$H$_{109}$N$_7$O$_{24}$P$_2$, 1567.7; found 1567.4.

Rifabutin Bisphosphonate Conjugate 95

A solution of protected conjugate 94 (230 mg, 0.147 mmol), dimedone (86 mg, 0.59 mmol) and PPh$_3$ (12 mg, 0.044 mmol) in THF (6 mL) was degassed followed by the addition of Pd(PPh$_3$)$_4$ (9 mg, 0.007 mmol). The solution was stirred for 18 h then concentrated to dryness under high vacuum. The crude product was purified by C18 reverse phase chromatography (MeCN in 0.05% aqueous NH$_4$OH 10% over 3 column volumes then a gradient of 10 to 70% over 12 column volumes) using a Biotage Horizon™ apparatus. Lyophilization of the combined pure fractions provided conjugate 95 as the di-ammonium salt (211 mg, 48%): LCMS: 99.6% (254 nm), 100% (220 nm), 100% (320 nm): ESI-MS: (MH$^+$) calculated for C$_{64}$H$_{93}$N$_7$O$_{24}$P$_2$, 1406.6; found 1402.2.

Scheme 18. Preparation of Rifabutin Bisphosphonate Conjugate 102

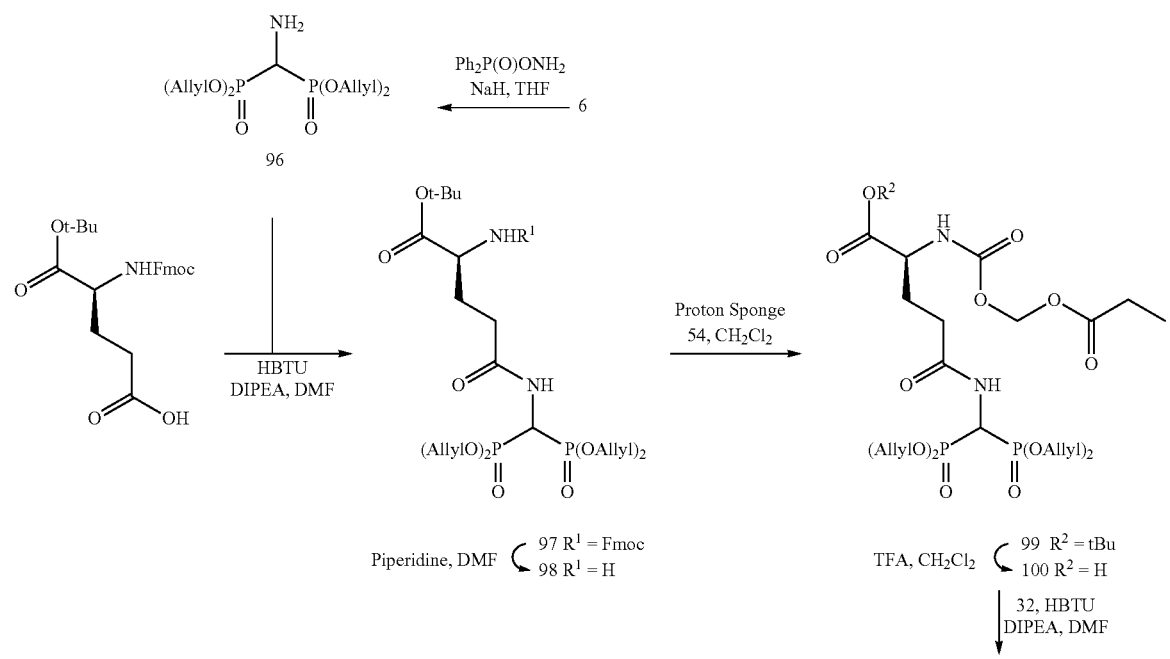

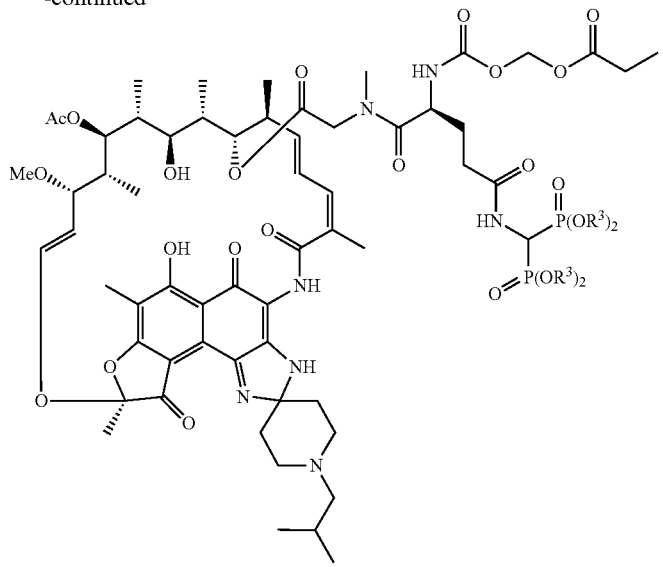

Pd(PPh3)4, PPh3, dimedone, THF
101 R³ = Allyl
102 R³ = H

Tetrallyl 1-aminomethylenebisphosphonate (96)

To a solution of bisphosphonate 6 (2.0 g, 5.95 mmol) in DMF (6 mL) was added NaH (60% dispersion in mineral oil, 254 mg, 6.35 mmol) portionwise. The solution was stirred for 45 min at room temperature and added to a solution of O-(diphenylphosphinyl)hydroxylamine (1.35 g, 5.77 mmol) in THF (40 mL), cooled in a dry ice/acetone bath. The resulting mixture was stirred for 10 min at the same temperature then 18 h at room temperature. $CH_2Cl_2$ (40 mL) was added, the solids were removed by filtration and washed with several portions of $CH_2Cl_2$. The combined filtrates were concentrated in vacuo and purified by flash chromatography on silica gel using a gradient of 0-5% methanol/ethyl acetate to provide aminobisphosphonate 96 as a clear yellow oil (1.24 g, 59%). $^1$H NMR (400 MHz, $CDCl_3$) δ 1.69 (bs, 2H), 3.52 (t, J=20.8 Hz, 1H), 4.64-4.67 (m, 8H), 5.24-5.27 (m, 4H), 5.36-5.42 (m, 4H), 5.92-6.02 (m, 4H).

tButyl N²-(9-fluorenylmethoxycarbonyl)-N⁵-(bis(diallylphosphoryl)methyl)-L-glutamine (97)

To a solution of Fmoc-Glu-Ot-Bu (646 mg, 1.52 mmol) in DMF (5 mL) at 0° C. was added DIEA (529 μL, 3.04 mmol) and HBTU (576 mg, 1.52 mmol). After stirring for 15 min at 0° C., amino bisphosphonate 96 (533 mg, 1.52 mmol) in DMF (2.6 mL) was added and stirring was pursued for 5 h at 0° C. The reaction mixture was diluted with $CH_2Cl_2$, washed with $H_2O$, 0.5 N HCl solution, saturated $NaHCO_3$ solution and saturated NaCl solution. The organic layer was dried over $MgSO_4$, filtered and concentrated to dryness. The crude product was purified by silica gel chromatography on a Biotage™ flash chromatography system using a gradient of 0-5% methanol in $CH_2Cl_2$. Compound 97 was obtained as a light yellow oil (898 mg, 78%). $^1$H NMR (400 MHz, $CDCl_3$) δ 1.46 (s, 9H), 1.82-1.91 (m, 1H), 2.15-2.32 (m, 3H), 4.20-4.27 (m, 2H), 4.38-4.47 (m, 2H), 4.58-4.68 (m, 8H), 5.20-5.26 (m, 5H), 5.34-5.40 (m, 4H), 5.54 (d, J=7.9 Hz, 1H), 5.87-5.98 (m, 4H), 6.59 (bs, 1H), 7.30-7.34 (m, 2H), 7.41 (t, J=7.5 Hz, 2H), 7.61 (d, J=7.5 Hz, 2H), 7.77 (d, J=7.5 Hz, 2H).

tButyl N⁵-(bis(diallylphosphoryl)methyl)-L-glutamine (98)

Fmoc-protected compound 97 (898 mg, 1.18 mmol) was treated with a 5% v/v solution of piperidine in DMF (5.9 mL). After stirring for 4 h, the reaction mixture was concentrated to dryness and purified by silica gel chromatography on a Biotage™ flash chromatography system using a gradient of 0-5% methanol in $CH_2Cl_2$. Compound 98 was obtained as a colorless oil (274 mg, 43%). $^1$H NMR (400 MHz, $CDCl_3$) δ 1.46 (s, 9H), 1.72-1.81 (m, 1H), 2.04-2.31 (m, 3H), 2.36-2.43 (m, 1H), 2.46-2.54 (m, 1H), 3.41 (dd, J=9.5, 4.3 Hz, 1H), 4.59-4.67 (m, 8H), 5.15 (dt, J=22.1, 9.1 Hz, 1H), 5.23-5.26 (m, 4H), 5.35-5.39 (m, 4H), 5.88-5.98 (m, 4H), 7.50 (bs, 1H).

tButyl N²-propionyloxymethoxycarbonyl-N⁵-(bis(diallylphosphoryl)methyl)-L-glutamine (99)

To a solution of compound 98 (274 mg, 0.51 mmol) and proton sponge (131 mg, 0.61 mmol) in $CH_2Cl_2$ (2 mL) was added freshly prepared chloroformate 54 (0.61 mmol) in $CH_2Cl_2$ (3 mL). The mixture was stirred for 18 h at room temperature, after which it was diluted with $CH_2Cl_2$, washed with cold 10% $KHSO_4$ solution, $H_2O$ and saturated NaCl solution. The organic layer was dried over $MgSO_4$, filtered and concentrated to dryness. The crude product was purified by silica gel chromatography on a Biotage™ flash chromatography system using a gradient of 0-5% methanol in CH$_2$Cl$_2$. Compound 99 was obtained as a yellowish gum (285 mg, 84%). $^1$H NMR (400 MHz, CDCl$_3$) δ 1.15 (t, J=7.5 Hz, 3H), 1.46 (s, 9H), 1.88-1.97 (m, 1H), 2.17-2.25 (m, 1H), 2.30-2.34 (m, 2H), 2.39 (q, J=7.6 Hz, 2H), 4.22-4.27 (m, 1H), 4.62 (bs, 8H), 5.13 (dt, J=21.9, 10.1 Hz, 1H), 5.25 (d, J=10.1, 4H), 5.35-5.39 (m, 4H), 5.69-5.76 (m, 3H), 5.88-5.99 (m, 4H), 6.40 (d, J=10.0 Hz, 1H).

N$^2$-propionyloxymethoxycarbonyl-N$^5$-(bis(diallylphosphoryl)methyl)-L-glutamine (100)

Compound 99 (285 mg, 0.43 mmol) was treated with a 50% v/v solution of TFA in CH$_2$Cl$_2$ (4.2 mL). After stirring for 3 h, the reaction mixture was concentrated to dryness and coevaporated several times with benzene. After drying under vacuum, acid 100 was obtained as a yellowish gum which slowly solidified (260 mg, 99%) and was used without purification. $^1$H NMR (400 MHz, DMSO-d$_6$) δ 1.02 (t, J=7.5 Hz, 3H), 1.70-1.80 (m, 1H), 1.92-2.01 (m, 1H), 2.28-2.35 (m, 2H), 2.35 (q, J=7.5 Hz, 2H), 3.93-3.98 (m, 1H), 4.53 (bs, 8H), 5.03 (dt, J=22.9, 9.9 Hz, 1H), 5.19-5.22 (m, 4H), 5.31-5.37 (m, 4H), 5.64 (s, 2H), 5.86-5.96 (m, 4H), 7.89 (d, J=7.9 Hz, 1H), 8.82 (d, J=9.9 Hz, 1H).

Rifabutin bisphosphonate conjugate 101

To a solution of compound 100 (260 mg, 0.43 mmol) in DMF (4 mL) at 0° C. was added DIEA (148 μL, 0.85 mmol) and HBTU (162 mg, 0.43 mmol). After stirring for 10 min at 0° C., sarcosyl-Rifabutin 32 (391 mg, 0.43 mmol) was added and stirring was pursued for 1.5 h at 0° C. The reaction mixture was diluted with CH$_2$Cl$_2$, washed with H$_2$O, 0.5N HCl solution, saturated NaHCO$_3$ solution and saturated NaCl solution. The organic layer was dried over MgSO$_4$, filtered and concentrated to dryness. The crude product was purified by silica gel chromatography on a Biotage™ flash chromatography system using 0-10% methanol in CH$_2$Cl$_2$. Bisphosphonate conjugate 101 was obtained as a dark purple solid (460 mg, 71%). ESI-MS: (M+H) calculated for C$_{72}$H$_{101}$N$_7$O$_{24}$P$_2$ 1510, found 1510.4.

Rifabutin Bisphosphonate Conjugate 102

To a solution of compound 101 (452 mg, 0.30 mmol) in THF (3 mL) was added dimedone (168 mg, 1.20 mmol), triphenylphosphine (31 mg, 0.12 mmol) and tetrakis(triphenylphosphine) palladium (17 mg, 0.015 mmol). After stirring for 6 h, the reaction mixture was concentrated to dryness then purified by C18 silica gel chromatography on a Biotage™ flash chromatography system using a gradient of 10-70% MeCN in H$_2$O, both containing 0.05% NH$_4$OH. Pure fractions were combined, concentrated and lyophilized to provide the diammonium salt of compound 102 as a fluffy purple solid (317 mg, 76%). LCMS: 99.0% (254 nm), 99.2% (220 nm), 99.2% (320 nm). ESI-MS: (M+H) calculated for C$_{60}$H$_{85}$N$_7$O$_{24}$P$_2$ 1350, found 1350.2.

Scheme 19. Preparation of Rifabutin Bisphosphonate Conjugate 110

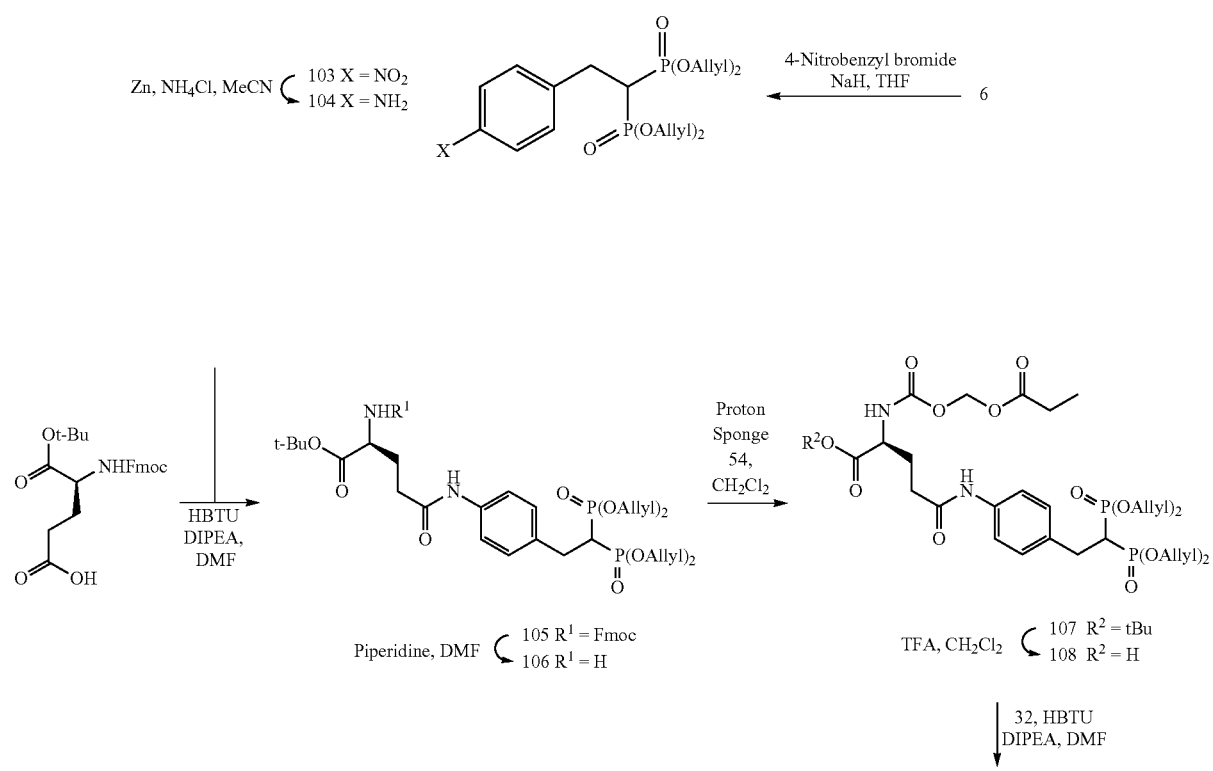

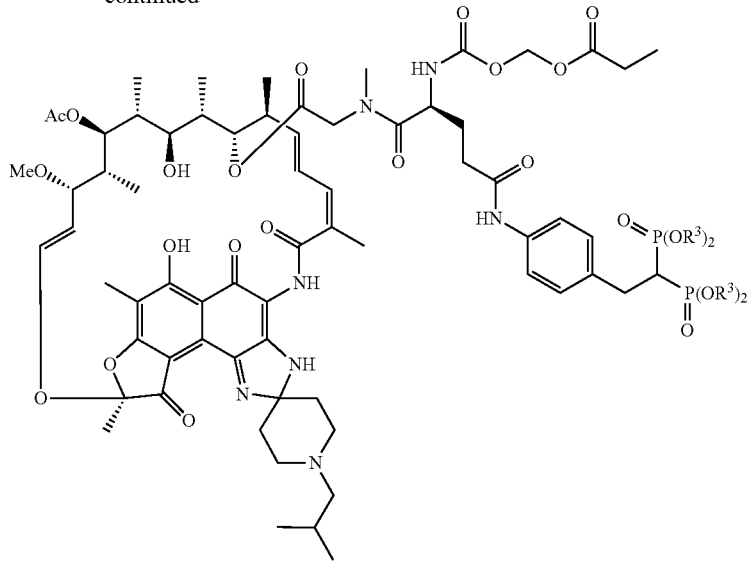

Pd(PPh₃)₄, PPh₃
dimedone, THF

109 R³ = Allyl
110 R³ = H

Tetrallyl 1-(4-nitrobenzyl)methylenebisphosphonate (103)

To a solution of bisphosphonate 6 (8.02 g, 23.9 mmol) in DMF (24 mL) was added NaH (60% dispersion in mineral oil, 954 mg, 23.9 mmol) portionwise and the solution was stirred for 1.5 h at room temperature. A solution of p-nitrobenzyl bromide (7.75 g, 35.9 mmol) in THF (32 mL) was added and the mixture was stirred for 3 h at room temperature. It was then poured into a mixture of saturated aqueous NH₄Cl solution and water and extracted with CH₂Cl₂ (3×). The combined organic layers were washed with saturated brine once, dried over MgSO₄ and concentrated in vacuo. The crude product was purified by flash chromatography on silica gel using a gradient of 0-50% ethyl acetate in CH₂Cl₂ as eluant to provide nitrobenzyl bisphosphonate 103 as a clear yellow oil (4.42 g, 39%), as well as a small amount of the parent tetrallyl 1,1-bis(4-nitrobenzyl)methylenebisphosphonate (874 mg, 6%). $^1$H NMR (400 MHz, CDCl₃) δ 2.73 (tt, J=23.8, 6.5 Hz, 1H), 3.37 (dt, J=16.4, 6.5 Hz, 2H), 4.51-4.61 (m, 8H), 5.21-5.25 (m, 4H), 5.29-5.35 (m, 4H), 5.83-5.93 (m, 4H), 7.44 (d, J=8.8 Hz, 2H), 8.14 (d, J=8.8 Hz, 2H).

Tetrallyl 1-(4-aminobenzyl)methylenebisphosphonate (104): To a solution of nitroarene 103 (460 mg, 0.98 mmol) in methanol (9 mL) was added saturated aqueous NH₄Cl solution (3 mL) and zinc powder (319 mg, 4.88 mmol). 15 drops of aqueous 1N HCl were added and the reaction was stirred at room temperature for 18 h. ethyl acetate and saturated NaHCO₃ aqueous solution were added and the mixture was filtered through celite. The filtrate was transferred into an extraction funnel and the layers were separated. The aqueous layer was extracted with ethyl acetate (2×). The combined organic layers were washed with saturated NaCl solution once, dried over MgSO₄, filtered and concentrated. The crude product was purified by flash chromatography on silica gel using a gradient of 0-5% methanol in CH₂Cl₂ as eluant to provide aminobenzyl bisphosphonate 104 as a clear yellow oil (4.42 g, 39%). $^1$H NMR (400 MHz, CDCl₃) δ 2.69 (tt, J=24.0, 6.1 Hz, 1H), 3.18 (dt, J=16.7, 6.2 Hz, 2H), 4.46-4.60 (m, 8H), 5.19-5.22 (m, 4H), 5.29-5.35 (m, 4H), 5.84-5.94 (m, 4H), 6.60 (d, J=8.6 Hz, 2H), 7.06 (d, J=8.4 Hz, 2H).

tButyl N²-(9-fluorenylmethoxycarbonyl)-N⁵-(4-(2,2-bis(diallylphosphoryl)ethyl)phenyl)-L-glutamine (105)

To a solution of Fmoc-Glu-Ot-Bu (253 mg, 0.59 mmol) in DMF (3 mL) at 0° C. was added DIEA (207 μL, 1.19 mmol) and HBTU (225 mg, 0.59 mmol). After stirring for 10 min at 0° C., aminobenzyl bisphosphonate 104 (262 mg, 0.59 mmol) in DMF (2 mL) was added and stirring was pursued for 2 h at 0° C. The reaction mixture was diluted with CH₂Cl₂, washed with H₂O, 0.5N HCl solution, saturated NaHCO₃ solution and saturated NaCl solution. The organic layer was dried over MgSO₄, filtered and concentrated to dryness. The crude product was purified by silica gel chromatography on a Biotage™ flash chromatography system using 1-10% methanol in CH₂Cl₂. Compound 105 was obtained as a yellow gum (431 mg, 86%). $^1$H NMR (400 MHz, CDCl₃) δ 1.46 (s, 9H), 1.86-1.92 (m, 1H), 2.26-2.38 (m, 3H), 2.70 (tt, J=24.0, 6.3 Hz, 1H), 3.24 (dt, J=16.8, 6.3 Hz, 2H), 4.19-4.29 (m, 2H), 4.40-4.60 (m, 10H), 5.19-5.22 (m, 4H), 5.28-5.34 (m, 4H), 5.58 (d, J=8.0 Hz, 1H), 5.83-5.93 (m, 4H), 7.21 (d, J=8.3, 2H), 7.27-7.34 (m, 2H), 7.38-7.43 (m, 2H), 7.50 (d, J=8.2 Hz, 2H), 7.60 (d, J=7.4 Hz, 2H), 7.77 (d, J=7.5 Hz, 2H), 8.28 (s, 1H).

tButyl N⁵-(4-(2,2-bis(diallylphosphoryl)ethyl)phenyl)-L-glutamine (106)

Fmoc-protected compound 105 (431 mg, 0.51 mmol) was treated with a 5% v/v solution of piperidine in DMF (2.5 mL). After stirring for 2.5 h, the reaction mixture was concentrated to dryness and purified by silica gel chromatography on a Biotage™ flash chromatography system using a gradient of 0-10% methanol in CH₂Cl₂. Compound 106 was obtained as a colorless oil (246 mg, 77%). $^1$H NMR (400 MHz, CDCl₃) δ 1.46 (s, 9H), 1.82-1.91 (m, 1H), 2.16-2.24 (m, 1H), 2.45-2.60 (m, 2H), 2.71 (tt, J=23.9, 6.2 Hz, 1H), 3.24 (dt, J=16.6, 6.2

Hz, 2H), 4.42 (dd, J=8.8, 4.5 Hz, 1H), 4.47-4.61 (m, 8H), 5.19-5.22 (m, 4H), 5.29-5.35 (m, 4H), 5.83-5.94 (m, 4H), 7.21 (d, J=8.3 Hz, 2H), 7.44 (d, J=8.3 Hz, 2H), 8.57 (bs, 1H).

tButyl $N^2$-propionyloxymethoxycarbonyl-$N^5$-(4-(2,2-bis(diallylphosphoryl)ethyl)phenyl)-L-glutamine (107)

To a solution of compound 106 (246 mg, 0.39 mmol) and proton sponge (101 mg, 0.47 mmol) in $CH_2Cl_2$ (2 mL) was added freshly prepared chloroformate 54 (0.47 mmol) in $CH_2Cl_2$ (3 mL). The mixture was stirred for 18 h at room temperature, after which it was diluted with $CH_2Cl_2$, washed with cold 10% $KHSO_4$ solution, $H_2O$ and saturated NaCl solution. The organic layer was dried over $MgSO_4$, filtered and concentrated to dryness. The crude product was purified by silica gel chromatography on a Biotage™ flash chromatography system using a gradient of 0-5% methanol in ethyl acetate. Compound 107 was obtained as a colorless gum which slowly solidifies (192 mg, 65%). $^1$H NMR (400 MHz, $CDCl_3$) δ 1.15 (t, J=7.5 Hz, 3H), 1.46 (s, 9H), 1.92-2.00 (m, 1H), 2.28-2.45 (m, 5H), 2.72 (tt, J=24.0, 6.3 Hz, 1H), 3.25 (dt, J=16.4, 6.4 Hz, 2H), 4.25-4.31 (m, 1H), 4.47-4.61 (m, 8H), 5.19-5.23 (m, 4H), 5.29-5.35 (m, 4H), 5.69-5.73 (m, 2H), 5.80 (d, J=5.8 Hz, 1H), 5.83-5.94 (m, 4H), 7.22 (d, J=8.1 Hz, 2H), 7.48 (d, J=8.1 Hz, 2H), 8.06 (bs, 1H).

$N^2$-propionyloxymethoxycarbonyl-$N^5$-(4-(2,2-bis(diallylphosphoryl)ethyl)phenyl)-L-glutamine (108)

Compound 107 (192 mg, 0.25 mmol) was treated with a 50% v/v solution of TFA in $CH_2Cl_2$ (4 mL). After stirring for 3 h, the reaction mixture was concentrated to dryness and coevaporated several times with $Et_2O$/hexanes. After drying under vacuum, acid 108 was obtained as a colorless gum (181 mg, quant.) and was used without purification. $^1$H NMR (400 MHz, DMSO-$d_6$) δ 1.02 (t, J=7.5 Hz, 3H), 1.77-2.87 (m, 1H), 2.06-2.12 (m, 1H), 2.36 (q, J=7.4 Hz, 2H), 2.37-2.42 (m, 2H), 3.01-3.18 m, 3H), 3.97-4.03 (m, 1H), 4.36-4.53 (m, 8H), 5.26-5.29 (m, 4H), 5.31-5.33 (m, 4H), 5.46 (s, 2H), 5.80-5.91 (m, 4H), 7.19 (d, J=8.7 Hz, 2H), 7.46 (d, J=8.5 Hz, 2H), 7.92 (d, J=7.9 Hz, 1H), 9.86 (bs, 1H).

Rifabutin Bisphosphonate Conjugate 109

To a solution of compound 108 (181 mg, 0.25 mmol) in DMF (2 mL) at 0° C. was added DIEA (87 μL, 0.50 mmol) and HBTU (95 mg, 0.25 mmol). After stirring for 15 min at 0° C., sarcosyl-Rifabutin 32 (230 mg, 0.25 mmol) was added and stirring was pursued for 2 h 45 min at 0° C. The reaction mixture was diluted with $CH_2Cl_2$, washed with $H_2O$, 0.5N HCl solution, saturated $NaHCO_3$ solution and saturated NaCl solution. The organic layer was dried over $MgSO_4$, filtered and concentrated to dryness. The crude product was purified by silica gel chromatography on a Biotage™ flash chromatography system using 0-10% methanol in $CH_2Cl_2$. Bisphosphonate conjugate 109 was obtained as a dark purple solid (338 mg, 85%). ESI-MS: (M+H) calculated for $C_{79}H_{107}N_7O_{24}P_2$ 1600, found 1600.6.

Rifabutin bisphosphonate conjugate 110

To a solution of compound 109 (338 mg, 0.21 mmol) in THF (2 mL) was added dimedone (118 mg, 0.84 mmol), triphenylphosphine (22 mg, 0.084 mmol) and tetrakis(triphenylphosphine) palladium (12 mg, 0.011 mmol). After stirring for 4.5 h, the reaction mixture was concentrated to dryness then purified by C18 silica gel chromatography on a Biotage™ flash chromatography system using a gradient of 10-70% MeCN in $H_2O$, both containing 0.05% $NH_4OH$. Pure fractions were combined, concentrated and lyophilized to provide the diammonium salt of compound 110 as a fluffy purple solid (247 mg, 80%). LCMS: 100% (254 nm), 100% (220 nm), 100% (320 nm). ESI-MS: (M+H) calculated for $C_{67}H_{91}N_7O_{24}P_2$ 1440, found 1440.4.

Scheme 20. Preparation of Rifabutin Bisphosphonate Conjugate 118

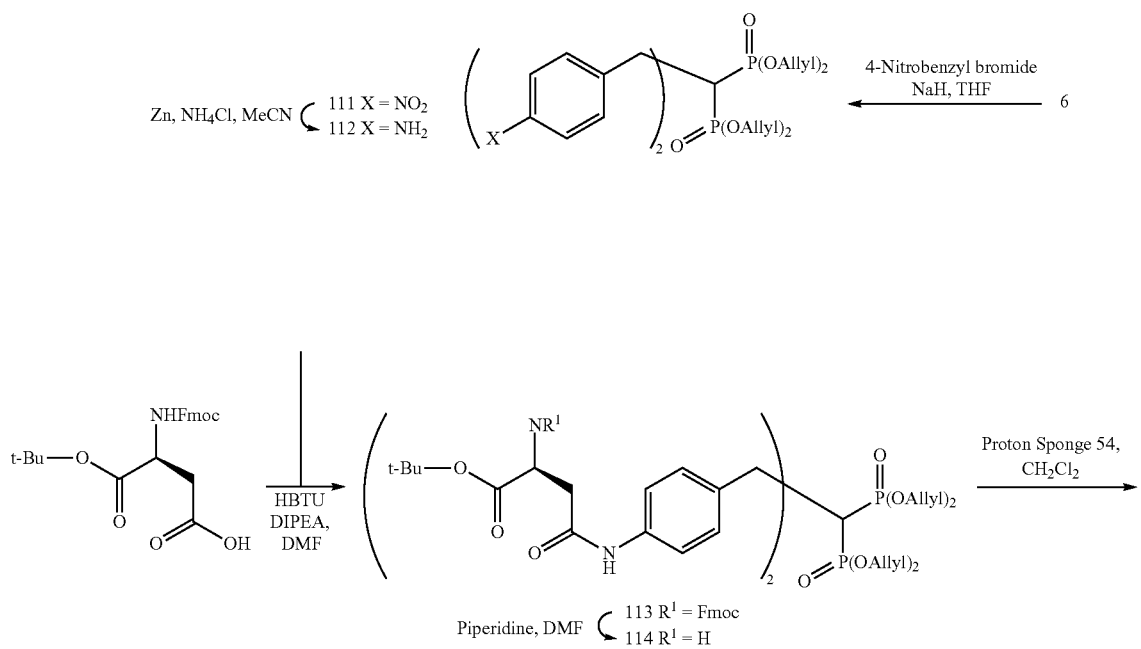

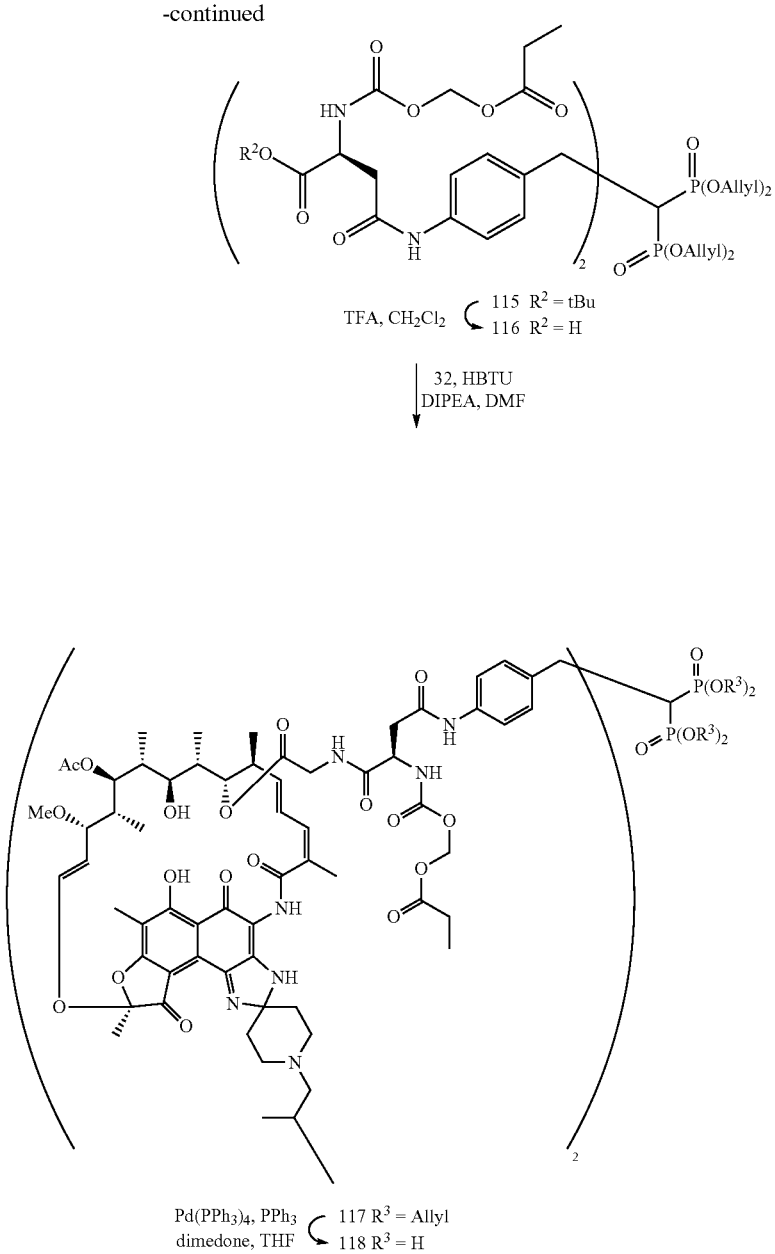

Tetrallyl 1,1-bis(4-nitrobenzyl)methylenebisphosphonate (111)

The bisphosphonate 111 was obtained as a side product from the reaction forming compound 103. It was obtained as a clear yellow oil (874 mg, 6%). $^1$H NMR (400 MHz, CDCl$_3$) δ 3.44 (t, J=16.5 Hz, 4H), 4.40-4.55 (m, 8H), 5.17-5.24 (m, 8H), 5.73-5.82 (m, 4H), 7.57 (d, J=8.8 Hz, 4H), 8.12 (d, J=8.8 Hz, 4H).

Tetrallyl 1,1-bis(4-aminobenzyl)methylenebisphosphonate (112)

To a solution of 111 (440 mg, 0.725 mmol) in methanol (6 mL) was added saturated aqueous NH$_4$Cl solution (6 mL) and zinc powder (474 mg, 7.25 mmol). 40 drops of aqueous 1N HCl were added and the reaction was stirred at room temperature for 1.5 h. The mixture was filtered through glassfiber filterpaper and concentrated. The residue was suspended in water and the product was extracted with ethyl acetate (3×). The combined organic layers were washed with saturated aqueous NaCl, dried over Na$_2$SO$_4$, filtered and concentrated. The crude product was purified by flash silica gel chromatography (40-100% acetone in hexanes) resulting in 112 as a clear yellow oil (266 mg, 67%). $^1$H NMR (400 MHz, CDCl$_3$) δ 3.23-3.44 (m, 4H), 4.37-4.60 (m, 8H), 5.16-5.33 (m, 8H), 5.73-5.93 (m, 4H), 6.94-7.00 (m, 2H), 7.22-7.37 (m, 2H).

Tetrallyl 1,1-bis(4-((S)-3-(9-fluorenylmethoxycarbonyl)amino-4-t-butoxy-4-oxo-butyrylamino)benzyl)methylenebisphosphonate (113)

To a solution of Fmoc-Glu-Ot-Bu (445 mg, 1.05 mmol) in DMF (5 mL) at 0° C. was added DIEA (365 µL, 2.09 mmol) and HBTU (397 mg, 1.05 mmol). After stirring for 5 min at 0° C., aminobenzyl bisphosphonate 112 (260 mg, 0.476 mmol) in DMF (2 mL) was added and stirring was continued while warming to room temperature overnight. The reaction mixture was diluted with ethyl acetate, washed with $H_2O$ and saturated aqueous NaCl then dried over $Na_2SO_4$. The crude product was purified by silica gel chromatography (0 to 20% methanol in ethyl acetate) using a Biotage Horizons™ system. Compound 113 was obtained as a glass-like solid (479 mg, 73%). $^1$H NMR (400 MHz, CDCl$_3$) δ 1.46 (s, 18H), 1.85-1.95 (m, 2H), 2.26-2.38 (m, 6H), 3.31 (t, J=16.3, 4H), 4.20 (t, J=6.8, 2H), 4.24-4.51 (m, 14H), 5.13 (dd, J=10.3, 1.0, 4H), 5.20 (dd, J=17.1, 1.2, 4H), 5.60 (d, J=7.9, 2H), 5.73-5.82 (m, 4H), 7.27-7.44 (m, 12H), 7.42 (d, J=8.3, 4H), 7.60 (bd, J=7.3, 4H), 7.76 (bd, J=7.5, 4H), 8.28 (s, 2H): $^{31}$P (162 MHz, CDCl$_3$) δ 26.00 (s, 2P).

Tetrallyl 1,1-bis(4-((S)-3-amino-4-t-butoxy-4-oxo-butyrylamino)benzyl)methylenebisphosphonate (114)

Fmoc-protected compound 113 (475 mg, 0.518 mmol) was treated with a 5% v/v solution of piperidine in DMF (5.5 mL). After stirring for 1.5 hr, the reaction mixture was diluted with ethyl acetate, and washed with water and saturated aqueous NaCl then dried over $Na_2SO_4$. The crude product was purified by silica gel chromatography (0-20% methanol in $CH_2Cl_2$) on a Biotage Horizons™ system. Compound 114 was obtained as a pale yellow oil (282 mg, 90%). $^1$H NMR (400 MHz, CDCl$_3$) δ 1.46 (s, 18H), 1.80-1.89 (m, 2H), 2.15-2.23 (m, 2H), 2.44-2.59 (m, 4H), 3.32 (t, J=16.2, 4H), 4.33-4.39 (m, 4H), 4.44-4.50 (m, 4H), 5.14 (dd, J=10.5, 1.4, 4H), 5.22 (dd, J=17.1, 1.5, 4H), 5.74-5.83 (m, 4H), 7.39 (AB q, J=8.6, 8H), 8.45 (s, 2H): $^{31}$P (162 MHz, CDCl$_3$) δ 26.05 (s, 2P).

Tetrallyl 1,1-bis(4-((S)-3-(propionyloxymethoxycarbonyl)amino-4-t-butoxy-4-oxo-butyrylamino)benzyl)methylenebisphosphonate (116)

To a solution of compound 114 (282 mg, 0.308 mmol) and proton sponge (66 mg, 0.308 mmol) in $CH_2Cl_2$ (2 mL) was added freshly prepared chloroformate 54 (88 mg, 0.46 mmol) in $CH_2Cl_2$ (2 mL). The mixture was stirred for 20 hr at room temperature. The organic layer was concentrated to dryness and the crude product was purified by silica gel chromatography (0-10% methanol in ethyl acetate) on a Biotage Horizons™ system. Compound 115 was obtained as a pale yellow oil (259 mg, 72%). $^1$H NMR (400 MHz, CDCl$_3$) δ 1.15 (t, J=7.6, 6H), 1.46 (s, 18H), 1.91-2.00 (m, 2H), 2.31-2.45 (m, 6H), 2.39 (q, J=7.6, 4H), 3.33 (t, J=16.5, 4H), 4.26-4.31 (m, 2H), 4.34-4.41 (m, H), 4.44-4.51 (m, 4H), 5.15 (dd, J=1.2, 10.4, 4H), 5.22 (dd, J=1.5, 17.2, 4H), 5.69-5.71 (m, 6H), 5.74-5.84 (m, 4H), 7.38 (d, J=8.5, 4H), 7.45 (d, J=8.5, 4H), 7.99 (s, 2H): $^{31}$P (162 MHz, CDCl$_3$) δ 26.04 (s, 2P).

Tetrallyl 1,1-bis(4-((S)-3-(propionyloxymethoxycarbonyl)amino-3-carboxy-propanoylamino)benzyl)methylenebisphosphonate (116)

Compound 115 (250 mg, 0.212 mmol) was treated with a 50% v/v solution of TFA in $CH_2Cl_2$ (2 mL). After stirring for 1 hr, the reaction mixture was concentrated to dryness and then coevaporated with toluene. After drying under vacuum, acid 116 was obtained as a colorless gum (226 mg, 100%) and was used without purification. $^1$H NMR (400 MHz, DMSO-d$_6$) δ 1.02 (t, J=7.5, 6H), 1.77-1.87 (m, 2H), 2.06-2.12 (m, 2H), 2.31-2.42 (m, 8H), 3.09 (br, J=16.5, 4H), 3.97-4.03 (m, 2H), 4.36-4.49 (m, 8H), 5.12 (dd, J=1.2, 10.4, 4H), 5.22 (dd, J=1.5, 17.2, 4H), 5.64 (s, 4H), 5.75-5.83 (m, 4H), 7.25 (d, J=8.6, 4H), 7.42 (d, J=8.6, 4H), 7.96 (d, J=7.9, 2H), 9.85 (s, 2H): $^{31}$P (162 MHz, CDCl$_3$) δ 26.07 (s, 2P).

Dimeric Rifabutin Bisphosphonate Conjugate 117

To a solution of compound 116 (226 mg, 0.212 mmol) and DIEA (151 µL, 0.869 mmol) in DMF (4 mL) at 0° C. was added HBTU (161 mg, 0.425 mmol). After stirring for 10 min at 0° C., compound 32 (390 mg, 0.425 mmol) was added and the reaction mixture was stirred while warming to room temperature overnight. It was then diluted with ethyl acetate, washed with $H_2O$ and saturated aqueous NaCl. The organic layer was dried over $Na_2SO_4$, filtered and concentrated to dryness. The crude product was purified by silica gel chromatography (0 to 20% methanol in $CH_2Cl_2$) using a Biotage Horizons™ system. Bisphosphonate conjugate 117 was obtained as a dark purple solid (393 mg, 65%). ESI-MS: (MH2$^+$) calculated for $C_{145}H_{192}N_{14}O_{42}P_2$, 1433.5; found 1433.0.

Dimeric rifabutin bisphosphonate conjugate 118

A solution of compound 117 (380 mg, 0.133 mmol), dimedone (74 mg, 0.53 mmol) and triphenylphosphine (3 mg, 0.01 mmol) was degassed for 10 min followed by the addition of Pd(PPh$_3$)$_4$ (15 mg, 0.013 mmol). The resulting mixture was stirred at room temperature for 20 hr. The reaction mixture was concentrated to dryness then purified by two sequential C18 reversed phase chromatographies using a Biotage Horizons™ system: using 10 to 60% MeCN in 0.05% NH$_4$OH in $H_2O$ for the first one, then 20 to 80% MeCN in 30 mM TEA/carbonate (pH 7) for the second one. Pure fractions were combined, concentrated and lyophilized to provide the diammonium salt of compound 118 as a purple solid (120 mg, 80%). LCMS: 97.8% (254 nm), 98.2% (220 nm), 98.0% (320 nm): ESI-MS: (MH$^+$) calculated for $C_{133}H_{176}N_{14}O_{42}P_2$: 2705.8: found 2705.3.

Scheme 21. Preparation of Rifabutin Bisphosphonate Conjugate 128
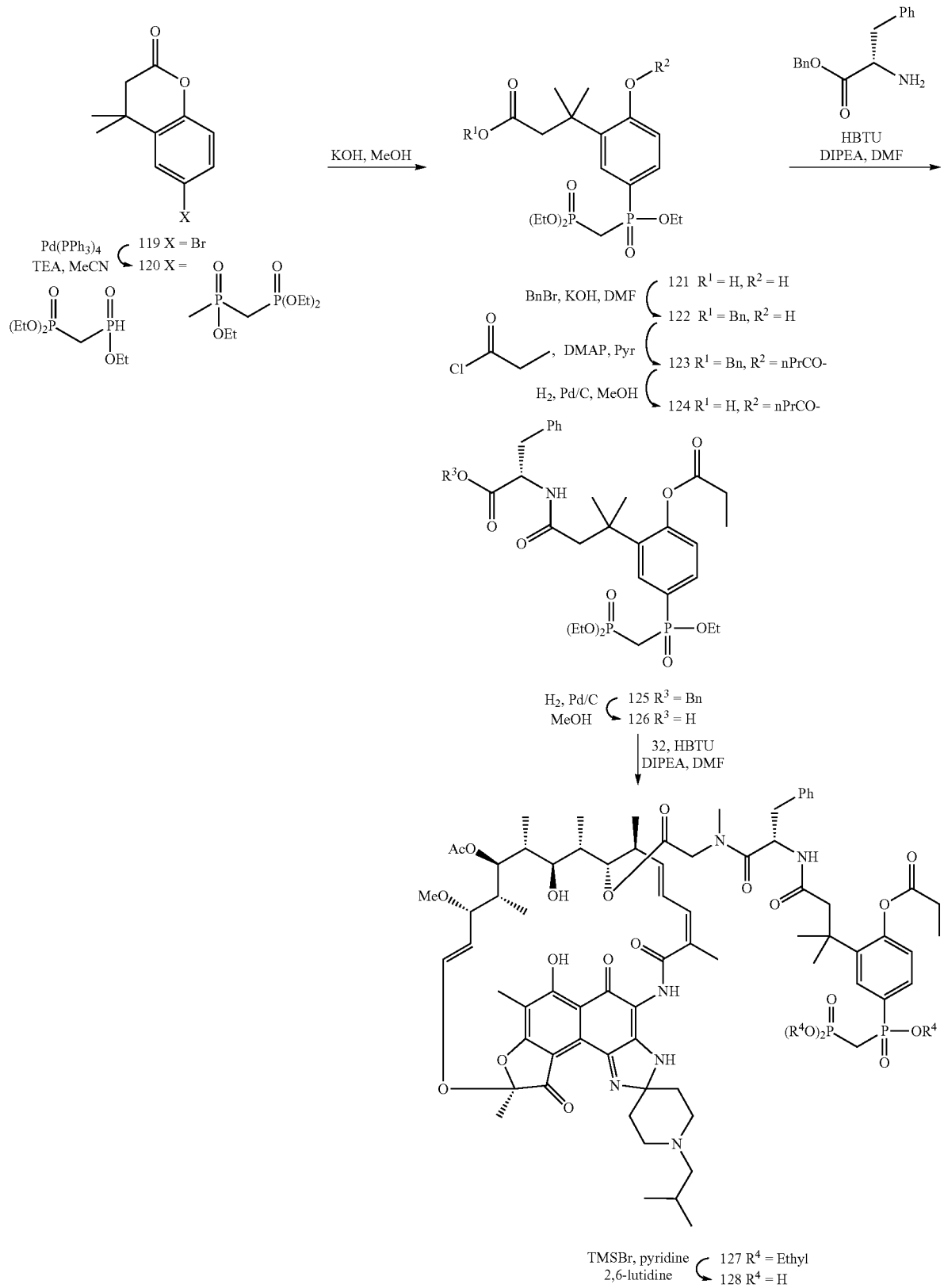

6-(ethoxy(diethylphosphonomethyl)phosphinoyl)-3,4-dihydro-4,4-dimethylchromen-2-one (120)

A mixture of 6-bromo-4,4-dimethylchroman-2-one (3.5 g, 9.7 mmol), diethyl(ethoxyphosphinyl)methylphosphonate (1.7 g, 9.7 mmol), triethylamine (4.1 mL, 29 mmol) and Pd(PPh$_3$)$_4$ (0.56 g, 0.48 mmol) in acetonitrile (20 mL) was heated to 100° C. for 18 hr. The reaction mixture was cooled and diluted with acetonitrile (50 mL) followed by washing with aqueous HCl (10%), water and saturated aqueous NaCl. The organic phase was dried over Na$_2$SO$_4$, filtered and concentrated. The crude product was purified by silica gel chromatography (0-10% methanol in CH$_2$Cl$_2$) on a Biotage™ flash chromatography system, resulting in 120 as pale yellow oil (3.0 g, 73%): $^1$H NMR (400 MHz, CDCl$_3$) δ 1.21 (t, J=7.2, 3H), 1.30-1.37 (m, 6H), 1.40 (s, 6H), 2.61 (dd, J=1.7, 17.2, 20.7, 2H), 2.66 (s, 2H), 3.95-4.08 (m, 2H), 4.11-4.21 (m, 4H), 7.16 (dd, J=3.1, 8.3, 2H), 7.73 (dd, J=3.1, 8.3, 2H): $^{31}$P (162 MHz, CDCl$_3$) δ 20.07 (d, J=7.7, 1 P), 33.74 (d, J=7.7, 1 P).

3-(2-Hydroxy-5-(ethoxy(diethylphosphonomethyl)phosphinoyl)phenyl)-3-methylbutanoic acid (121)

A solution of 120 (0.99 g, 2.4 mmol) and KOH (0.095 g, 2.4 mmol) in methanol was stirred at room temperature for 2 hr. The solvent was removed removed under reduced pressure and the product was resuspended in water, the pH was adjusted to 4 by the addition of HCl, and the product was extracted with CH$_2$Cl$_2$. The organics were dried over Na$_2$SO$_4$, filtered and concentrated, resulting in 121 as a pale yellow oil (1.1 g, 105%) which was used without purification. $^1$H NMR (400 MHz, CDCl$_3$) δ 1.26 (t, J=7.2, 3H), 1.29-1.37 (m, 6H), 1.45 (s, 3H), 1.48 (s, 3H), 2.63 (dd, J=17.7, 20.9, 2H), 2.93 (AB q, J=14.2, 2H), 4.00-4.20 (m, 6H), 6.74 (bs, 1H), 7.56 (ddd, J=1.6, 8.5, 12.2, 2H), 7.63 (d, J=13.3, 1H).

Benzyl 3-(2-hydroxy-5-(ethoxy(diethylphosphonomethyl)phosphinoyl)phenyl)-3-methylbutanoate (122)

An aqueous KOH solution (0.14 g, 2.5 mmol) was added to a stirring solution of 121 (1.1 g, 2.5 mmol) in acetonitrile (5 mL). After 10 min the solvent was evaporated under reduced pressure and the residue was dried under vacuum for 1 hr. The pale yellow solid was resuspended in DMF (10 mL) followed by the addition of benzylbromide (330 μL, 2.8 eq). The resulting solution was stirred at room temperature for 2 hr. The mixture was diluted with EtOAC (80 mL) and washed with H$_2$O and saturated aqueous NaCl, followed by drying over Na$_2$SO$_4$. The crude product was purified by silica gel chromatography (0-10% methanol in CH$_2$Cl$_2$) on a Biotage™ flash chromatography system, resulting in 122 as a pale yellow liquid (0.64 g, 48%): $^1$H NMR (400 MHz, CDCl$_3$) δ 1.23 (t, J=7.1, 3H), 1.26 (t, J=7.1, 3H), 1.30 (t, J=7.1, 3H), 1.45 (s, 3H), 1.49 (s, 3H), 2.60 (dd, J=17.4, 20.9, 2H), 3.00 (AB q, J=14.0, 2H), 3.78-3.88 (m, 2H), 3.99-4.15 (m, 4H), 4.93 (s, 2H), 6.75-6.78 (m, 1H), 7.14 (dd, J=2.0, 7.5, 2H), 7.25-7.31 (m, 3H), 7.58 (ddd, J=1.4, 8.0, 11.9, 1H), 7.64 (d, J=13.4, 1H): $^{31}$P (162 MHz, CDCl$_3$) δ 21.04 (d, J=4.6, 1 P), 36.00 (d, J=4.6, 1 P).

Benzyl 3-(2-propionyloxy-5-(ethoxy(diethylphosphonomethyl)phosphinoyl)phenyl)-3-methylbutanoate (123)

Proprionyl chloride (190 μL, 2.17 mmol) was added dropwise to a stirring solution of crude phenol 122 (880 mg, 1.67 mmol) and DMAP (2 mg, 0.016 mmol) in pyridine (5 mL). The reaction was continued for 3 hr at room temperature followed by the addition of ethyl acetate (100 mL). The organic layer was washed with cold aqueous HCl (0.5 N), H$_2$O and saturated aqueous NaCl then dried over Na$_2$SO$_4$ and concentrated in vacuo. The crude product was purified by silica gel chromatography (0 to 20% methanol in ethyl acetate) using a Biotage Horizons™ system, resulting in 123 as a pale yellow liquid (644 mg, 66%): $^1$H NMR (400 MHz, CDCl$_3$) δ 1.25 (t, J=7.0, 3H), 1.26 (t, J=7.5, 3H), 1.30 (t, J=7.0, 3H), 1.46 (s, 3H), 1.48 (s, 3H), 2.50-2.63 (m, 4H), 2.82 (AB q, J=14.4, 2H), 3.93-4.16 (m, 6H), 4.93 (s, 2H), 7.12-7.18 (m, 3H), 7.26-7.32 (m, 3H), 7.70 (ddd, J=1.8, 8.4, 11.6, 1H), 7.86 (dd, J=1.8, 13.4, 1H): $^{31}$P (162 MHz, CDCl$_3$) δ 20.21 (d, J=9.7, 1 P), 34.03 (d, J=9.7, 1 P).

3-(2-propionyloxy-5-(ethoxy(diethylphosphonomethyl)phosphinoyl)phenyl)-3-methylbutanoic acid (124)

Compound 123 (300 mg, 0.515 mmol) was dissolved in methanol (5 mL) and hydrogenated over Pd/C (30%, 95 mg) under H$_2$ (1 atm) for 3 hr. The catalyst was filtered off and the solvent removed under reduced pressure resulting in the pale-yellow liquid 124 (234 mg, 92%): $^1$H NMR (400 MHz, CDCl$_3$) δ 1.21 (t, J=7.0, 3H), 1.25 (m, 9H), 1.49 (s, 3H), 1.52 (s, 3H), 2.55-2.68 (m, 4H), 2.72 (AB q, J=13.8, 2H), 3.90-4.13 (m, 6H), 7.15 (dd, J=3.5, 8.1, 1H), 7.67 (ddd, J=1.8, 8.3, 11.8, 1H), 7.84 (dd, J=1.8, 13.7, 1H): $^{31}$P (162 MHz, CDCl$_3$) δ 17.53 (d, J=3.7, 1P), 31.82 (d, J=3.7, 1P).

Benzyl N-(3-(2-propionyloxy-5-(ethoxy(diethylphosphonomethyl)phosphinoyl)phenyl)-3-methylbutanoyl)-L-phenylalanine (125)

To a solution of acid 124 (319 mg, 0.648 mmol) in DMF (5 mL) at 0° C. was added DIEA (226 μL, 130 mmol) and HBTU (246 mg, 0.648 mmol). After stirring for 15 min at 0° C., L-Phenylalanine benzyl ester hydrochloride (189 mg, 0.648 mmol) was added and stirring was continued while warming to room temperature overnight. The reaction mixture was diluted with ethyl acetate, washed with H$_2$O and saturated aqueous NaCl then dried over Na$_2$SO$_4$. The crude product was purified by silica gel chromatography (gradient of 0 to 20% methanol in ethyl acetate) using a Biotage Horizons™ system. Compound 125 was obtained as a colourless liquid (150 mg, 32%). $^1$H NMR (400 MHz, CDCl$_3$) δ 1.20 (t, J=7.0, 3H), 1.21 (t, J=7.0, 3H), 1.25-1.32 (m, 18H), 1.44 (s, 3H), 1.45 (s, 3H), 1.47 (s, 3H), 1.48 (s, 3H), 2.47-2.67 (m, 12H), 2.87 (bd, J=6.2, 4H), 3.89-4.18 (m, 12H), 5.03 (AB q, J=12.3, 2H), 5.05 (AB q, J=12.3, 2H), 5.88 (bt, J=8.8, 2H), 6.91-6.95 (m, 4H), 7.01 (ddd, J=3.5, 5.2, 8.7, 2H), 7.17-7.23 (m, 10H), 7.31-7.32 (m, 6H), 7.71 (ddd, J=1.8, 8.1, 11.6, 1H), 7.75 (ddd, J=1.8, 8.1, 11.6, 1H), 7.86 (t, J=14.0, 1H), 7.87 (t, J=14.0, 1H): $^{31}$P (162 MHz, CDCl$_3$) δ 20.31 (d, J=4.9, 1 P), 20.37 (d, J=4.9, 1 P), 33.93 (bd, J=9.5, 2P).

N-(3-(2-Propionyloxy-5-(ethoxy(diethylphosphonomethyl)phosphinoyl)phenyl)-3-methylbutanoyl)-L-phenylalanine (126)

Compound 125 (240 mg, 0.329 mmol) was dissolved in methanol (10 mL) and hydrogenated over Pd/C (60 mg, 30%) under H$_2$ (1 atm) for 3 hr. The catalyst was filtered off and the solvent removed under reduced pressure resulting in the pale-yellow liquid 126 (197 mg, 94%): $^1$H NMR (400 MHz, CDCl$_3$) δ 1.23 (t, J=7.0, 3H), 1.25 (t, J=7.0, 3H), 1.29-1.40 (m, 18H), 1.41 (s, 3H), 1.43 (s, 3H), 1.54 (s, 3H), 1.56 (s, 3H), 2.27 (d, J=12.9, 1H), 2.42 (d, J=12.8, 1H), 2.54-2.90 (m, 12H), 2.96 (d, J=6.2, 1H), 2.99 (d, J=6.3, 1H), 3.89-4.30 (m, 12H), 4.56-4.78 (m, 2H), 5.72 (d, J=8.5, 1H), 5.85 (d, J=8.9, 1H), 7.07 (dd, J=2.1, 3.6, 2H), 7.09 (dd, J=2.1, 3.6, 2H), 7.13-7.24 (m, 10H), 7.58-7.67 (m, 2H), 7.79-7.87 (m, 2H): $^{31}$P (162 MHz, CDCl$_3$) δ 22.28 (d, J=5.3, 1P), 22.37 (d, J=1.9, 1 P), 34.38 (d, J=5.3, 1 P), 34.91 (d, J=1.9, 1 P).

Rifabutin Bisphosphonate Conjugate 127

To a solution of compound 126 (197 mg, 0.308 mmol) and DIEA (107 µL, 0.616 mmol) in DMF (5 mL) at 0° C. was added HBTU (117 mg, 0.308 mmol). After stirring for 10 min at 0° C., compound 32 (283 mg, 0.308 mmol) was added and reaction mixture was stirred while warming to room temperature overnight. The reaction mixture was diluted with ethyl acetate, washed with saturated aqueous NH$_4$Cl, H$_2$O and saturated aqueous NaCl. The organic layer was dried over Na$_2$SO$_4$, filtered and concentrated to dryness. The crude product was purified by silica gel chromatography (0 to 10% methanol in CH$_2$Cl$_2$) using a Biotage Horizons™ system. Bisphosphonate conjugate 127 was obtained as a dark purple solid (250 mg, 53%). ESI-MS: (MH2$^+$) calculated for C$_{79}$H$_{108}$N$_6$O$_{21}$P$_2$, 1539.7; found 1539.6.

Rifabutin Bisphosphonate Conjugate 128

A solution of compound 127 (245 mg, 0.159 mmol) and 2,6-lutidine (739 µL, 6.36 mmol) in CH$_2$Cl$_2$ (5 mL) was cooled to −70° C. then trimethylsilylbromide (630 µL, 4.77 mmol) was added drop-wise. After 1 hr the solution was brought to room temperature and stirred for a further 24 hr then concentrated to dryness under high vacuum. The residue was resuspended in DMF (5 mL) followed by the addition of pyridine (257 µL, 3.18 mmol) and 70% HF in pyridine (80 µL, 3.18 mmol). After 30 min the solution was again evaporated to dryness. The crude product was purified by 2 consecutive C18 reverse phase chromatographies using a Biotage Horizon™ apparatus: A) 10 to 70% MeCN in 0.05% aqueous NH$_4$OH, 10 column volumes; B) 20 to 80% MeCN in 30 mM TEA/carbonate, pH 6.5, 10 column volumes. Lyophilization of the combined pure fractions provided conjugate 128 as the di-TEA salt (92 mg, 39%): LCMS: 100% (254 nm), 100% (220 nm), 100% (320 nm): ESI-MS: (MH$^+$) calculated for C$_{73}$H$_{96}$N$_6$O$_{21}$P$_2$, 1455.6; found 1455.4.

Scheme 22. Preparation of Rifabutin Bisphosphonate Conjugate 138

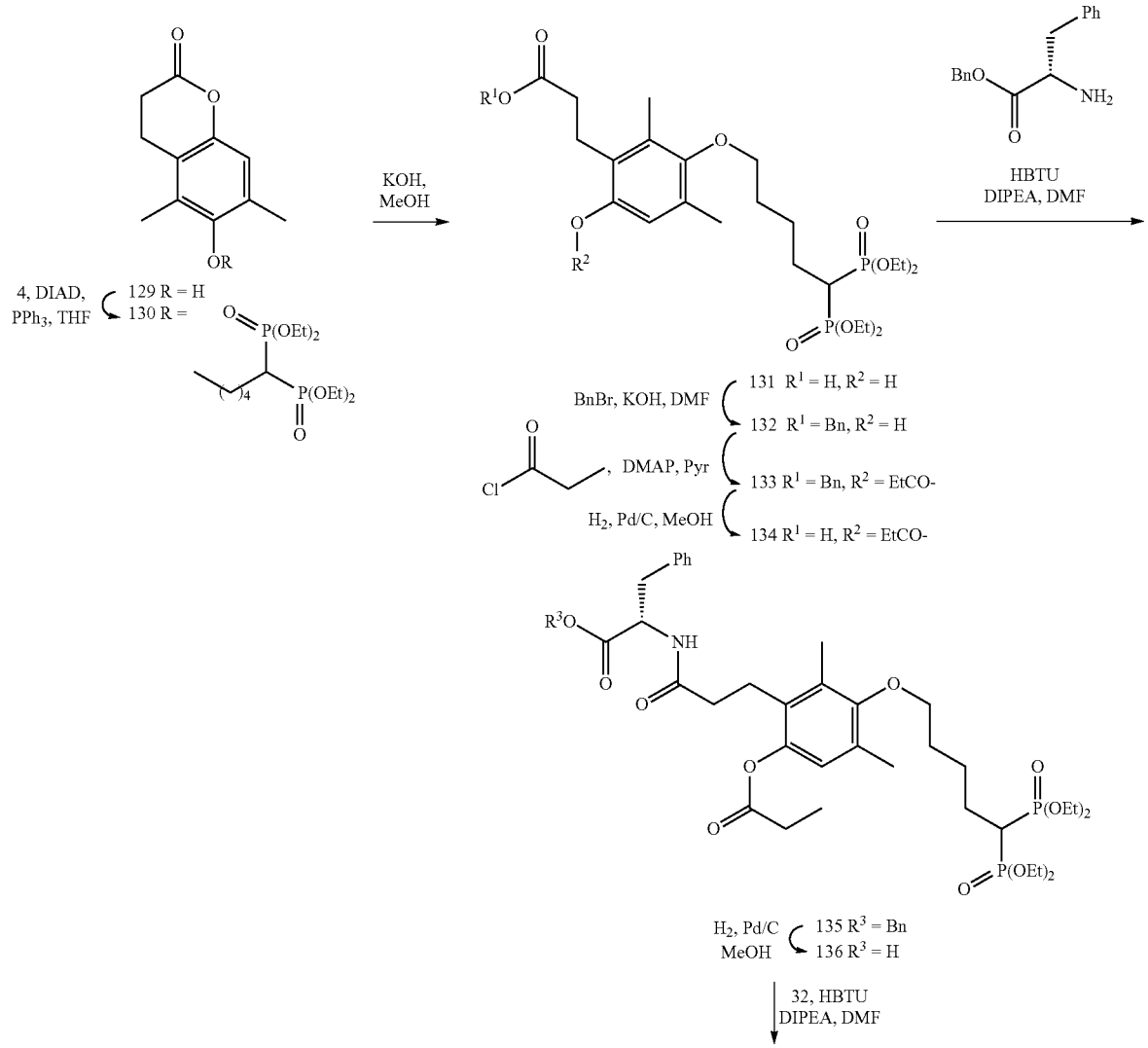

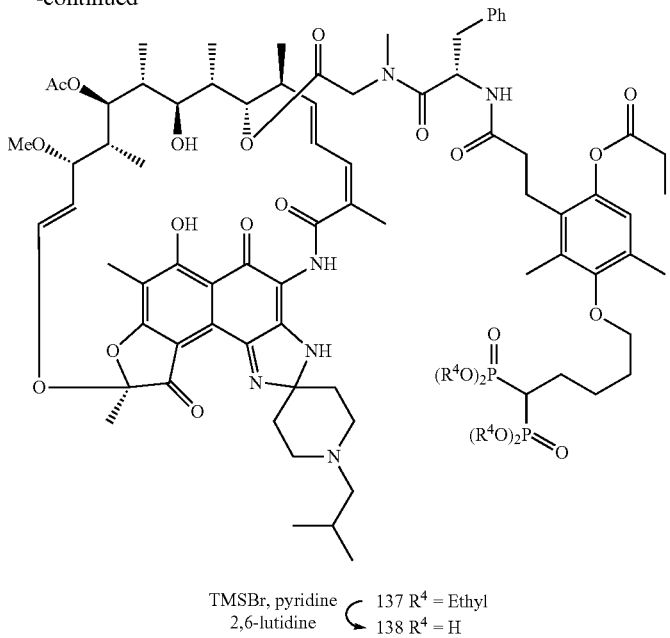

TMSBr, pyridine
2,6-lutidine
137 R⁴ = Ethyl
138 R⁴ = H

3,4-Dihydro-5,7-dimethyl-6-(5,5-bis(diethylphosphoryl)pentyloxy)chromen-2-one (130)

Diisopropyl azodicarboxylate (363 mg, 1.87 mmol) and PPh$_3$ (491 mg, 1.87 mmol) were added to a cooled (ice-bath) solution of 4 (562 mg, 1.56 mmol) in dry THF (15 mL). After 5 min 129 (300 mg, 1.56 mmol) was added and the resulting mixture was stirred for 1.5 hr while cooling in an ice-bath then 16 hr at room temperature. The solvent was removed under reduced pressure and the crude product was purified by silica gel chromatography (0 to 10% MeOH in EtOAc, 10 CV) using a Biotage Horizons™ apparatus resulting in the yellow oil 130 (559 mg, 67%): $^1$H NMR (400 MHz, CDCl$_3$) δ 1.34 (t, J=7.0, 12H), 1.79-1.83 (m, 4H), 1.97-2.07 (m, 2H), 2.19 (s, 3H), 2.24 (s, 3H), 2.31 (tt, J=6.3, 24.1, 1H), 2.74 (dd, J=6.3, 8.2, 2H), 2.89 (bd, J=8.0, 2H), 3.69 (bt, J=5.7, 2H), 4.13-4.23 (m, 8H), 6.72 (s, 1H): $^{31}$P (162 MHz, CDCl$_3$) δ 24.96 (s, 2P).

3-(2-Hydroxy-4,6-dimethyl-5-(5,5-bis(diethylphosphoryl)pentyloxy)phenyl) propanoic acid (131)

A solution of KOH (104 mg, 1.86 mmol) in water (8 mL) was added to a solution of 130 (906 mg, 1.69 mmol) in MeCN. The resulting mixture was stirred at room temperature for 30 min then concentrated under reduced pressure to give the light brown coloured solid potassium salt of 131 (968 mg, 97%), which was used without purification: $^1$H NMR (400 MHz, CDCl$_3$) δ 1.33 (bt, J=7.2, 12H), 1.69-1.81 (m, 4H), 1.91-2.04 (m, 2H), 2.13 (s, 3H), 2.16 (s, 3H), 2.37 (tt, J=5.9, 24.2, 1H), 2.64 (bt, J=6.8, 2H), 2.86 (bt, J=7.1, 2H), 3.58 (bt, J=6.4, 2H), 4.09-4.21 (m, 8H), 6.54 (s, 1H): $^{31}$P (162 MHz, CDCl$_3$) δ 24.98 (s, 2P).

Benzyl 3-(2-hydroxy-4,6-dimethyl-5-(5,5-bis(diethylphosphoryl)pentyloxy)phenyl) propanoate (132)

The potassium salt of 131 (935 mg, 1.69 mmol) was dissolved in dry DMF followed by the drop-wise addition of BnBr (201 μL, 1.69 mmol). The resulting solution was stirred at room temperature for 2 hr followed by dilution with EtOAc (100 mL). The organic layer was washed with H$_2$O and saturated aqueous NaCl then dried over Na$_2$SO$_4$. The crude product was purified by silica gel chromatography (0 to 10% MeOH in CH$_2$Cl$_2$, 10 CV) using a Biotage Horizons™ apparatus resulting in the yellow oil 132 (900 mg, 83%): $^1$H NMR (400 MHz, CDCl$_3$) δ 1.34 (t, J=7.1, 12H), 1.75-1.82 (m, 4H), 1.95-2.07 (m, 2H), 2.17 (s, 3H), 2.19 (s, 3H), 2.31 (tt, J=6.2, 24.2, 1H), 2.69 (t, J=6.2, 2H), 2.90 (t, J=6.1, 2H), 3.64 (bt, J=5.8, 2H), 4.13-4.22 (m, 8H), 5.11 (s, 2H), 6.60 (s, 1H), 7.29-7.38 (m, 5H): $^{31}$P (162 MHz, CDCl$_3$) δ 25.00 (s, 2P).

Benzyl 3-(2-propionyloxy-4,6-dimethyl-5-(5,5-bis(diethylphosphoryl)pentyloxy)phenyl)propanoate (133)

Proprionyl chloride (210 μL, 2.40 mmol) was added dropwise to a solution of 132 (898 mg, 1.40 mmol) and DMAP (cat) in pyridine (7 mL). After stirring for 20 hr at room temperature the solution was quenched by the addition of cold 1N HCl (40 mL) and the product was extracted with EtOAc. The organic layer was washed with H$_2$O and saturated aqueous NaCl then dried over Na$_2$SO$_4$. The crude product was purified by silica gel chromatography (0 to 20% MeOH in CH$_2$Cl$_2$, 15 CV) using a Biotage Horizons™ apparatus resulting in the yellow oil 133 (816 mg, 84%): $^1$H NMR (400 MHz, CDCl$_3$) δ 1.27 (t, J=7.6, 3H), 1.34 (t, J=7.1, 12H), 1.77-1.83 (m, 4H), 1.95-2.05 (m, 2H), 2.21 (s, 6H), 2.32 (tt, J=6.2, 24.2, 1H), 2.44-2.49 (m, 2H), 2.55 (q, J=7.4, 2H), 2.80-2.84 (m, 2H), 3.67-3.70 (m, 2H), 4.14-4.23 (m, 8H), 5.12 (s, 2H), 6.67 (s, 1H), 7.31-7.36 (m, 5H): $^{31}$P (162 MHz, CDCl$_3$) δ 24.98 (s, 2P).

3-(2-propionyloxy-4,6-dimethyl-5-(5,5-bis(diethylphosphoryl)pentyloxy)phenyl)propanoic acid (134)

Compound 133 (815 mg, 1.17 mmol) was dissolved in MeOH (10 mL) and stirred with Pd/C (400 mg, 49%) under H$_2$ (1 atm) for 8 hr. The catalyst was filtered off and the solvent removed under reduced pressure resulting in the crude colourless liquid 134 (650 mg, 92%), which was used without purification: $^1$H NMR (400 MHz, CDCl$_3$) δ 1.27 (t, J=7.5, 3H), 1.33 (t, J=7.2, 6H), 1.34 (t, J=7.2, 6H), 1.73-1.79 (m, 4H), 1.92-2.06 (m, 2H), 2.22 (s, 3H), 2.24 (s, 3H), 2.36 (tt, J=6.2, 24.3, 1H), 2.44-2.48 (m, 2H), 2.59 (q, J=7.7, 2H), 2.80-2.83 (m, 2H), 3.73 (t, J=6.1, 2H), 4.13-4.22 (m, 8H), 6.69 (s, 1H): $^{31}$P (162 MHz, CDCl$_3$) δ 25.03 (s, 2P).

Benzyl N-(3-(2-propionyloxy-4,6-dimethyl-5-(5,5-bis(diethylphosphoryl)pentyloxy)phenyl)propanoyl)-L-phenylalanine (135)

To a solution of acid 134 (221 mg, 0.363 mmol) in DMF (3 mL) at 0° C. was added DIEA (127 μL, 0.726 mmol) and L-phenylalanine t-Butyl ester (94 mg, 0.36 mmol). After stirring for 15 min at 0° C., HBTU (138 mg, 0.363 mmol) was added and stirring was continued for 2 hr at 0° C. then 2 hr at room temperature. The reaction mixture was diluted with EtOAc and washed with cold aqueous $NaHSO_4$ (10%), $H_2O$ and saturated aqueous NaCl then dried over $Na_2SO_4$. The crude product was purified by silica gel chromatography (0 to 20% gradient of MeOH in $CH_2Cl_2$, 10 CV) using a Biotage Horizons™ system. Compound 135 was obtained as a pale yellow coloured liquid (276 mg, 94%). $^1$H NMR (400 MHz, $CDCl_3$) δ 1.24 (t, J=7.5, 3H), 1.34 (t, J=7.1, 12H), 1.40 (s, 9H), 1.76-1.79 (m, 4H), 1.93-2.06 (m, 2H), 2.19-2.30 (m, 2H), 2.21 (s, 3H), 2.22 (s, 3H), 2.31 (tt, J=5.9, 24.2, 1H), 2.57 (q, J=7.5, 2H), 2.76-2.82 (m, 2H), 3.06 (bd, J=6.3, 2H), 3.67 (bd, J=5.9, 2H), 4.13-4.22 (m, 8H), 4.74 (dt, J=5.9, 7.6, 1H), 5.86 (d, J=7.5, 1H), 6.68 (s, 1H), 7.06-7.08 (m, 2H), 7.21-7.25 (m, 3H): $^{31}$P (162 MHz, $CDCl_3$) δ 24.93 (s, 2P).

N-(3-(2-propionyloxy-4,6-dimethyl-5-(5,5-bis(diethylphosphoryl)pentyloxy)phenyl)propanoyl)-L-phenylalanine (136)

Compound 135 (272 mg, 0.335 mmol) was treated with a 50% v/v solution of TFA in $CH_2Cl_2$ (4 mL). After stirring for 3 hr the reaction mixture was concentrated to dryness and coevaporated with toluene. After drying under vacuum, acid 136 was obtained as a colorless liquid (304 mg, 120%) and was used without purification. $^1$H NMR (400 MHz, $CDCl_3$) δ 1.25 (t, J=7.3, 3H), 1.32-1.37 (m, 12H), 1.70-1.81 (m, 4H), 1.93-2.02 (m, 2H), 2.13 (s, 3H), 2.20 (s, 3H), 2.20-2.29 (m, 2H), 2.47 (tt, J=5.8, 24.5, 1H), 2.57 (q, J=7.7, 2H), 2.74-2.81 (m, 1H), 2.87-2.93 (m, 1H), 3.01 (dd, J=6.2, 14.0, 1H), 3.15 (dd, J=5.5, 14.0, 1H), 3.66 (t, J=6.8, 2H), 4.14-4.22 (m, 8H), 4.75-4.80 (m, 1H), 6.12 (d, J=7.6, 1H), 6.67 (s, 1H), 7.06-7.09 (m, 2H), 7.14-7.24 (m, 3H): $^{31}$P (162 MHz, $CDCl_3$) δ 24.35 (s, 1 P), 24.39 (s, 1 P).

Rifabutin Bisphosphonate Conjugate 137

To a solution of compound 136 (253 mg, 0.335 mmol) and DIEA (117 μL, 0.670 mmol) in DMF (5 mL) at 0° C. was added HBTU (128 mg, 0.335 mmol). After stirring for 10 min at 0° C., compound 32 (307 mg, 0.335 mmol) was added and the reaction mixture was stirred while warming to room temperature over 5 hr. It was then diluted with EtOAc, washed with saturated aqueous $NH_4Cl$, $H_2O$ and saturated aqueous NaCl. The organic layer was dried over $Na_2SO_4$, filtered and concentrated to dryness. The crude product was purified by silica gel chromatography (0 to 20% MeOH in $CH_2Cl_2$, 15 CV) using a Biotage Horizons™ system. Bisphosphonate conjugate 137 was obtained as a dark purple solid (485 mg, 88%). ESI-MS: (MH$^+$) calculated for $C_{85}H_{120}N_6O_{23}P_2$, 1655.8; found 1655.4.

Rifabutin Bisphosphonate Conjugate 138

A solution of compound 137 (219 mg, 0.132 mmol) and 2,6-lutidine (645 μL, 5.55 mmol) in $CH_2Cl_2$ (5 mL) was cooled to −70° C. then trimethylsilylbromide (648 μL, 4.23 mmol) was added drop-wise. After 1 hr the solution was brought to room temperature and stirred for a further 24 hr then concentrated to dryness under high vacuum. The crude product was suspended in MeCN/10% $NaHSO_4$ and stirred for 4 hrs followed by C18 reverse phase chromatography (10 to 70% MeCN in 0.05% aqueous $NH_4OH$, 15 CV) using a Biotage Horizon™ apparatus. Lyophilization of the combined pure fractions provided conjugate 138 as the di-$NH_4$ salt (12 mg, 6%): LCMS: 96.3% (254 nm), 98.0% (220 nm), 93.5% (320 nm): ESI-MS: (MH$^+$) calculated for $C_{77}H_{104}N_6O_{23}P_2$, 1543.7; found 1543.4.

Scheme 23. Preparation of Rifabutin Bisphosphonate Conjugate 140

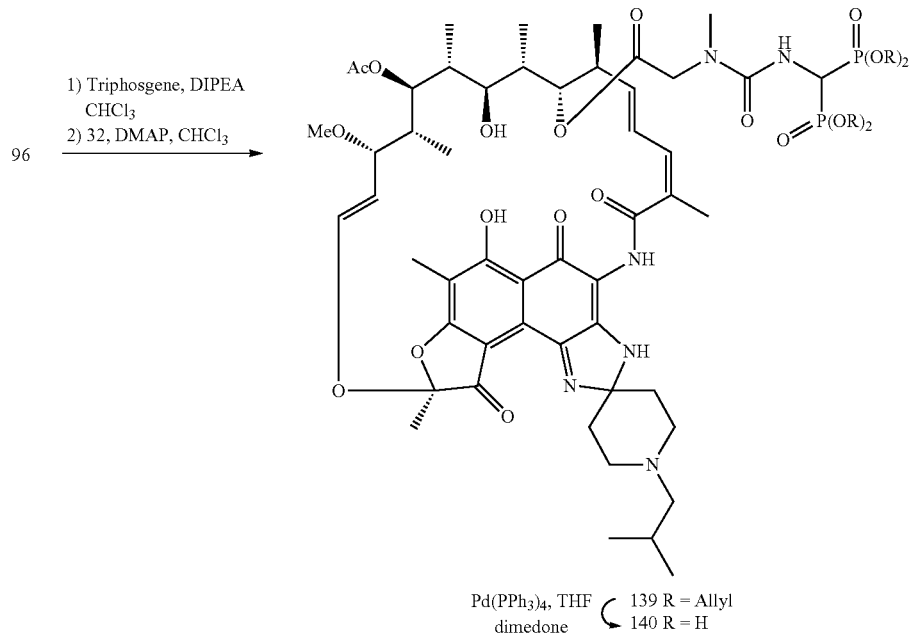

Rifabutin Bisphosphonate Conjugate 139

To a solution of triphosgene (49 mg, 0.1634 mmol) in CHCl$_3$ (3 ml) was added dropwise a solution of aminomethylenebisphosphonate 96 (115 mg, 0.3268 mmol) and diisopropylethylamine (0.12 ml, 0.6536 mmol) in CHCl$_3$ (10 mL). The reaction mixture was stirred at room temperature for 60 minutes and then 32 (300 mg, 0.3268 mmol) was added in one portion. After 2 hours at room temperature, 30 ml of a saturated solution of NH$_4$Cl were added and the mixture was extract 3 times with 30 ml of CH$_2$Cl$_2$. The organic phase was dried over Na$_2$SO$_4$, filtered and concentrated in vacuo. The crude 139 (231 mg, 54% yield) obtained was used directly in the next step.

Rifabutin bisphosphonate conjugate 140

Argon was bubbled through a solution of 139 (230 mg, 0.1775 mmol), triphenylphosphine (19 mg, 0.071 mmol) and dimedone (100 mg, 0.71 mmol) in anhydrous THF (10 ml) for 10 minutes at room temperature. Then tetrakistriphenylphosphine palladium (11 mg, 0.0089 mmol) was added and the reaction mixture was stirred at room temperature overnight before being concentrated to dryness. The residue was dissolved in 0.005% aqueous NH$_4$OH (2 ml, pH 9) and purified by reverse phase C18 silica gel chromatography on a Biotage™ flash chromatography system with a gradient of 20-100% acetonitrile in 0.005% aqueous NH$_4$OH to provide 140 as a deep red solid (92 mg, 45% yield). $^1$H NMR (400 MHz, D$_2$O) δ 0.00 (m, 3H), 0.41-0.42 (m, 3H), 0.78 (m, 1H), 0.90-0.91 (d, J=6.7 Hz, 3H), 0.98 (d, J=7.0 Hz, 3H), 1.08 (d, J=5.9 Hz, 6H), 1.24-1.28 (t, J=7.3 Hz, 1H), 1.54 (m, 1H), 1.72 (m, 1H), 1.82 (s, 3H), 1.93 (m, 1H), 1.99 (s, 3H), 2.02 (s, 3H), 2.17 (s, 3H), 2.27 (m, 1H), 2.46 (m, 1H), 2.76 (m, 1H), 2.96 (s, 3H), 3.00 (s, 3H), 3.16-3.21 (q, J=7.3 Hz, 1H), 3.23-3.25 (m, 1H), 3.71-3.75 (m, 2H), 3.88 (m, 3H), 4.14-4.18 (d, J=18.7 Hz, 1H), 4.21-4.32 (t, J=20.7 Hz, 1H), 4.97-5.00 (d, J=9.9 Hz, 1H), 5.07 (m, 1H), 5.22-5.28 (m, 1H), 5.93-6.04 (m, 1H), 6.13-6.16 (d, J=12.4 Hz, 1H), 6.38-6.40 (d, J=11.0 Hz, 1H), 6.53-6.60 (m, 1H). $^{31}$P (162 MHz, D$_2$O): δ 15.01, 15.11

LC/MS purity: 98.7% (254 nm), 99.8% (220 nm), 99.7% (320 nm). MS (MH$^-$) 1135.2

Scheme 24. Preparation of rifabutin bisphosphonate conjugates 142(a-b)

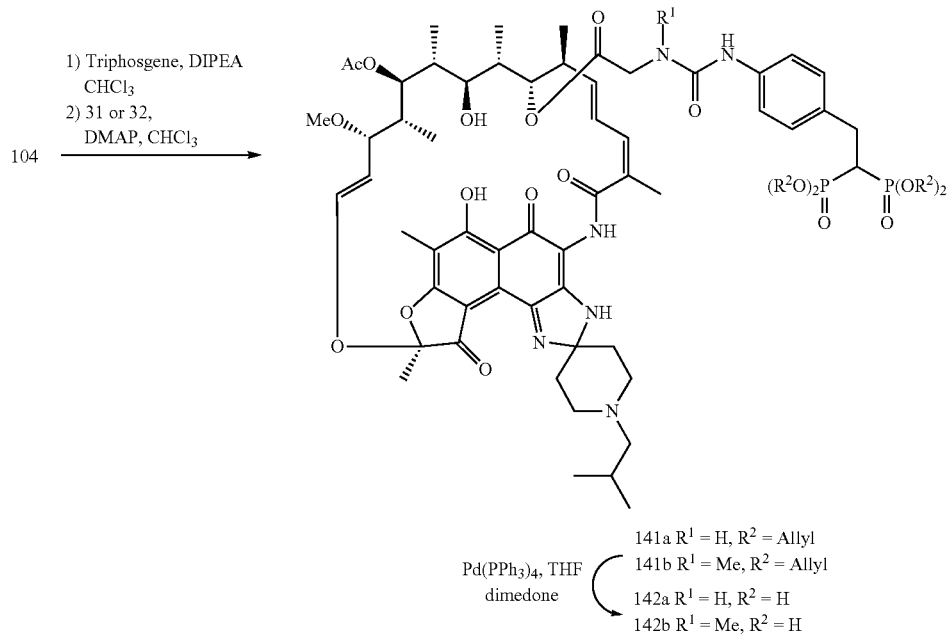

141a R$^1$ = H, R$^2$ = Allyl
141b R$^1$ = Me, R$^2$ = Allyl
142a R$^1$ = H, R$^2$ = H
142b R$^1$ = Me, R$^2$ = H

Rifabutin Bisphosphonate Conjugate 141a

To a solution of triphosgene (70.8 mg, 0.2389 mmol) in 5 mL of anhydrous methylene chloride was added a pre-mixed mixture of compound 104 (209.1 mg, 0.4737 mmol) and DIPEA (0.17 mL, 0.9759 mmol) in 1 mL of methylene chloride plus 1 mL methylene chloride rinse at room temperature. After 30 min, the reaction was completed as indicated by $^1$H and $^{31}$P NMR. $^1$H NMR (400 MHz, CDCl$_3$, NMR signals from DIPEA salt were not reported) δ 2.69 (tt, J=6.2, 24.2, 1H), 3.25 (dt, J=6.6, 16.8, 2H), 4.48-4.62 (m, 8H), 5.21 (m, 4H), 5.31 (m, 4H), 5.82-5.92 (m, 4H), 6.99 (d, J=8.4), 7.21 (d, J=8.2); $^{31}$P NMR (162 MHz, CDCl$_3$) δ 24.32. To the mixture was added another 0.17 mL of DIPEA (0.9759 mmol) followed by compound 31 (428 mg, 0.4734 mmol). After stirring overnight at room temperature, LC/MS indicated the reaction to be complete. The mixture was diluted with methylene chloride, washed with saturated ammonium chloride solution (2×) and dried over sodium sulfate. After concentration, the resultant dark purple material 141a (642.5 mg, 99%) was used directly in the following step without further purification. $^1$H NMR (400 MHz, CDCl$_3$) δ −0.20 (d, J=7.0, 3H), 0.51 (d, J=7.0, 3H), 0.89-0.94 (m, 9H), 1.06 (d, J=7.0, 3H), 1.20-1.28 (m, 2H), 1.29-1.35 (m, 1H), 1.40-1.47 (m, 1H), 1.61 (s, 3H), 1.81 (s, 3H), 1.74-2.08 (m, 6H), 2.03 (s, 3H), 2.10-2.20 (m, 2H), 2.29 (s, 3H), 2.50-2.74 (m, 3H), 2.71 (tt, J=6.2, 24.2, 1H), 2.86-3.04 (m, 3H), 3.07 (s, 3H), 3.10 (d, J=4.8, 1H), 3.23 (dt, J=6.2, 16.9, 2H), 3.51-3.54 (m, 1H), 3.62 (dd, J=2.6, 17.6, 1H), 4.06 (dd, J=7.0, 17.9, 1H), 4.47-4.61 (m, 8H), 4.95 (d, J=10.7, 1H), 5.04 (dd, J=4.0, 12.5, 1H), 5.14 (d, J=11.0, 1H), 5.18-5.23 (m, 4H), 5.28-5.36 (m, 4H), 5.39-5.44 (m, 1H), 5.83-5.98 (m, 4H), 6.06 (t, J=10.6, 2H), 6.29 (dd, J=11.0, 15.8, 1H), 7.17 (d, J=8.4, 2H), 7.37 (d, J=8.4, 2H), 7.42 (s, 1H), 7.85 (s, 1H), 8.41 (br s, 1H); $^{31}$P NMR (162 MHz, CDCl$_3$) δ 24.74.

Rifabutin Bisphosphonate Conjugate 141b

To a solution of triphosgene (73.9 mg, 0.2490 mmol) in 5 mL of anhydrous methylene chloride was added a pre-mixed mixture of compound 104 (220 mg, 0.4984 mmol) and DIPEA (0.18 mL, 1.033 mmol) in 1 mL of methylene chloride plus 1 mL methylene chloride rinse at room temperature. After 30 min, the reaction was completed as indicated by $^1$H and $^{31}$P NMR. To the mixture was added another 0.18 mL of DIPEA (1.033 mmol) followed by compound 32 (458 mg, 0.4989 mmol). After stirring overnight at room temperature, LC/MS indicated the reaction to be complete. The mixture was diluted with methylene chloride, washed with saturated ammonium chloride solution (2×) and dried over sodium sulfate. After concentration, the resultant dark purple material 141b (661.7 mg, 96%) was used directly in the following step without further purification. $^1$H NMR (400 MHz, CDCl$_3$) δ −0.19 (d, J=7.0, 3H), 0.53 (d, J=6.6, 3H), 0.91-0.94 (m, 9H), 1.06 (d, J=7.0, 3H), 1.12-1.48 (m, 4H), 1.79 (s, 3H), 1.74-2.06 (m, 5H), 1.91 (s, 3H), 2.05 (s, 3H), 2.10-2.30 (m, 3H), 2.27 (s, 3H), 2.52-2.66 (m, 3H), 2.71 (tt, J=6.3, 24.2, 1H), 2.90-3.03 (m, 2H), 2.94 (s, 3H), 3.05 (s, 3H), 3.21 (dt, J=6.2, 16.9, 2H), 3.52-3.56 (m, 3H), 4.22 (d, J=17.6, 1H), 4.44-4.60 (m, 8H), 4.90 (d, J=10.7, 1H), 5.04 (dd, J=4.4, 12.5, 1H), 5.14 (d, J=11.0, 1H), 5.16-5.22 (m, 4H), 5.28-5.36 (m, 4H), 5.82-5.94 (m, 4H), 6.04-6.10 (m, 2H), 6.34 (dd, J=11.0, 15.8, 1H), 7.06 (s, 1H), 7.15 (d, J=8.4, 2H), 7.34 (d, J=8.8, 2H), 7.84 (s, 1H), 8.33 (br s, 1H); $^{31}$P NMR (162 MHz, CDCl$_3$) δ 24.78.

Rifabutin bisphosphonate conjugate 142a

Compound 141a (641 mg, 0.4674 mmol) and dimedone (265.9 mg, 1.8968 mmol) were dissolved in 5 mL of anhydrous THF and 32.0 mg (0.02769 mmol) of Pd(PPh$_3$)$_4$ was added at room temperature under argon atmosphere. After overnight stirring, LC/MS indicated the reaction to be incomplete and another 58.8 mg (0.05088 mmol) of Pd(PPh$_3$)$_4$ was added. After 3 h, reaction was completed as indicated by LC/MS and the mixture was concentrated. The material was loaded on a Biotage C18 reverse phase column with DMSO and was eluted with gradient mixture of acetonitrile/0.05% ammonium hydroxide (aq, pH=10) from 10% to 70% over 10 column volumes. The strongly colored fractions were immediately combined and acidified to pH=6.7 with 1N HCl (aq) prior to the removal of acetonitrile by rotavapor. The resultant mixture was extracted with methylene chloride (3×) or until the aqueous phase was only slightly colored. The organic extract was dried over sodium sulfate and concentrated to dryness. The obtained material 142a (420.7 mg, 0.3473 mmol, 74%) turned out to be pure by LC/MS and was suspended in small amount of methylene chloride before 0.12 mL (0.8564 mmol) of triethylamine was added. The resultant homogeneous solution was stirred at room temperature for 30 min before being concentrated to dryness to afford the dark purple solid 142a (427.2 mg, 70%) as a mono-triethylamine salt (determined by $^1$H NMR). $^1$H NMR (400 MHz, D$_2$O) δ 0.90 (d, J=6.6, 3H), 0.41 (d, J=6.6, 3H), 0.79 (br s, 2H), 0.90 (d, J=6.6, 3H), 0.98 (d, J=7.0, 3H), 1.04 (d, J=6.3, 6H), 1.26 (t, J=7.4, 12H), 1.60 (br s, 2H), 1.78 (s, 3H), 1.97 (s, 3H), 2.00 (s, 3H), 2.15 (s, 3H), 2.10-2.28 (m, 3H), 2.47 (br s, 2H), 2.99-3.14 (m, 4H), 3.02 (s, 3H), 3.18 (q, J=7.3, 9H), 3.35 (d, J=7.3, 2H), 3.59 (br s, 4H), 3.80-3.92 (m, 2H), 4.99 (d, J=10.7, 1H), 5.04-5.11 (m, 1H), 5.24-5.31 (m, 1H), 6.02 (dd, J=8.8, 15.0, 1H), 6.19 (d, J=12.8, 1H), 6.36 (d, J=11.0, 1H), 6.74-6.84 (m, 1H), 7.24 (d, J=8.4, 2H), 7.38 (d, J=8.4, 2H); $^{31}$P NMR (162 MHz, D$_2$O) δ 20.36.

Rifabutin Bisphosphonate Conjugate 142b

Compound 141b (660 mg, 0.4764 mmol), PPh$_3$ (48.9 mg, 0.1864) and dimedone (267.8 mg, 1.910 mmol) were dissolved in 5 mL of anhydrous THF and 27.8 mg (0.02406 mmol) of Pd(PPh$_3$)$_4$ was added at room temperature under argon atmosphere. After overnight stirring, reaction was complete as indicated by LC/MS and the mixture was concentrated. After several failed attempts, the product was eventually purified using the combination of two separate reverse phase purifications. First, the material was loaded on a C18 reverse phase column for a Biotage™ flash chromatography system with DMSO and was eluted with a gradient of 10% to 70% acetonitrile in 0.05% ammonium hydroxide (aq, pH=10) over 10 column volumes. The strongly colored fractions were immediately combined and acidified to pH=4 with 1N HCl (aq) prior to the removal of acetonitrile by rotavapor. The resultant mixture was extracted with methylene chloride (3×) or until the aqueous phase was only sightly colored. The organic extracts were dried over sodium sulfate and concentrated to dryness. Then, the obtained material was loaded on another C18 reverse phase column for a Biotage™ flash chromatography system with DMSO/acetonitrile and was eluted with a gradient of 5% to 50% acetonitrile in 30 mM triethylammonium bicarbonate buffer (aq, pH=6.5) over 10 column volumes. The strongly colored fractions were immediately combined and acidified to pH=4.5 with 1N HCl(aq) prior to the removal of acetonitrile by rotavapor. The resultant mixture was extracted with methylene chloride (3×) or until the aqueous phase was only slightly colored. The organic extract was dried over sodium sulfate and concentrated to dryness to afford dark purple solid 142b (249.5 mg, 43%) as a mono-triethylamine salt (determined by $^1$H NMR). $^1$H NMR (400 MHz, CD$_3$OD) δ −0.22 (br s, 3H), 0.53 (br s, 3H), 0.94 (br s, 3H), 1.01 (d, J=6.6, 3H), 1.13 (br s, 6H), 1.32 (t, J=7.0, 12H), 1.76 (s, 3H), 1.99 (s, 3H), 2.10 (s, 3H), 2.14 (s, 3H), 1.78-2.22 (m, 4H), 2.42-2.60 (m, 4H), 2.95 (s, 3H), 3.00 (s, 3H), 2.92-3.04 (m, 2H), 3.13-3.28 (m, 12H), 3.38-3.50 (m, 4H), 3.66 (d, J=17.2, 1H), 3.64-3.78 (m, 2H), 4.00 (d, J=17.2, 1H), 5.04 (d, J=10.3, 1H), 5.16 (d, J=10.3, 1H), 5.86-5.94 (m, 1H), 6.02 (d, J=12.5, 1H), 6.17 (d, J=11.0, 1H), 6.48-6.58 (m, 1H), 7.34 (d, J=8.1, 2H), 7.38 (d, J=8.4, 2H); $^{31}$P NMR (162 MHz, CD$_3$OD) δ 21.70, 21.32.

Scheme 25. Preparation of Rifabutin Bisphosphonate Conjugates 147

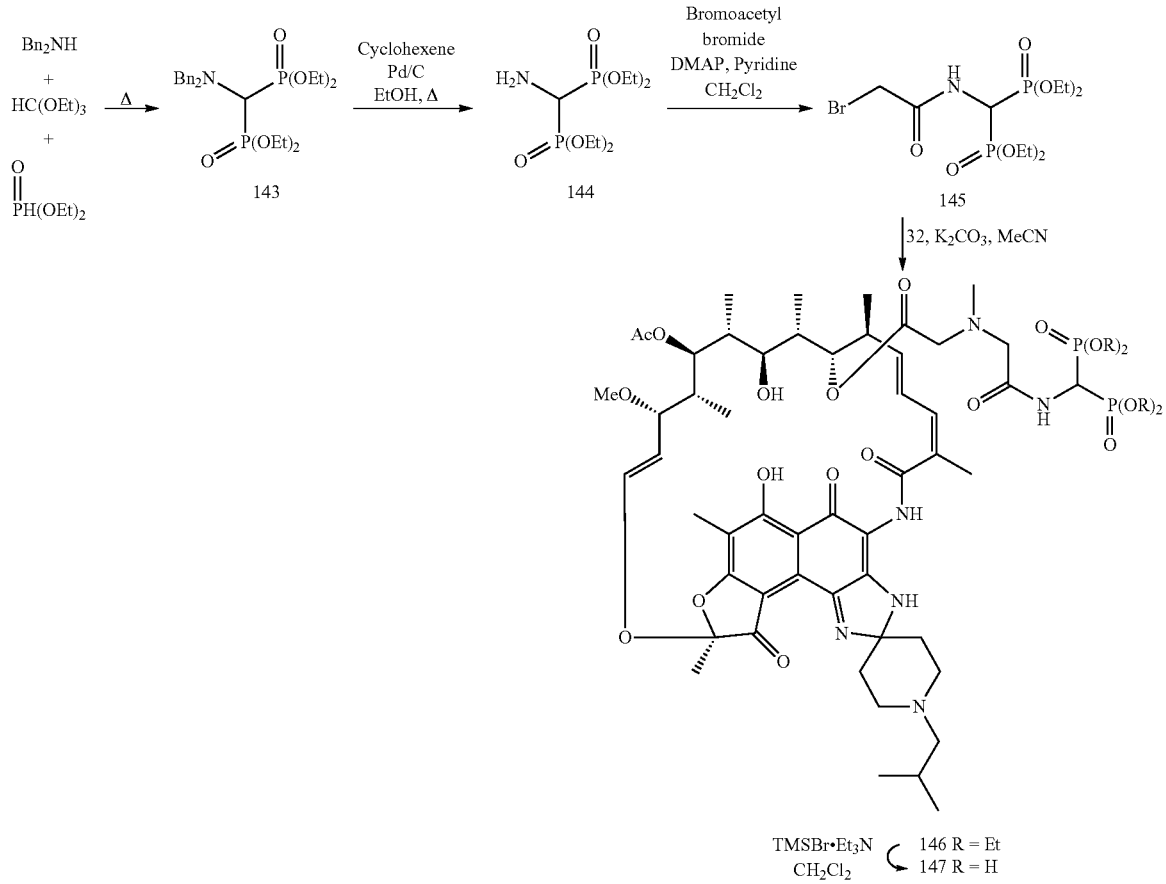

Tetraethyl N,N-dibenzyl-1-aminomethylenebisphosphonate (143)

Compound I was prepared according to a modified protocol derived from Synth. Comm. (1996), 26: 2037-2043. Triethyl orthoformate (8.89 g, 60 mmol), diethyl phosphite (16.57 g, 120 mmol) and dibenzyl amine (11.80 g, 60 mmol) were combined in a 100 mL round bottom flask fitted with a distillation head. The reaction was heated to a temperature of 180-195° C. for 1 h under Ar. When EtOH evolution was complete, the reaction mixture was cooled to room temperature, diluted with $CHCl_3$ (300 mL), washed with aqueous NaOH (2M, 3×60 mL) and brine (2×75 mL), then dried over $MgSO_4$. After evaporation, a crude yield of 25.2 g (87%) was obtained. A 4.95 g portion of the crude oil was purified by chromatography (ethyl acetate:hexane:methanol 14:4:1) to yield pure 143 (2.36 g, 41%). $^1H$ NMR (400 MHz, $CDCl_3$) δ 1.32 (dt, J=2.0, 7.0, 12H), 3.55 (t, J=25.0, 1H), 3.95-4.25 (m, 12H), 7.20-7.45 (m, 10H).

Tetraethyl 1-aminomethylenebisphosphonate (144)

Compound 143 (2.00 g, 4.14 mmol) was dissolved in EtOH (40 mL). To this solution was added palladium on carbon (10%, 1.5 g) and cyclohexene (2.5 mL, 24.7 mmol). The reaction mixture was refluxed under argon for 15 hours, filtered through celite and evaporated to give 144 as a slightly impure pale yellow oil (1.50 g, 119%), which was used directly in the next step without further purification. $^1H$ NMR (400 MHz, $CDCl_3$) δ 1.35 (t, J=7.0, 12H), 3.58 (t, J=20.3, 1H), 3.65-3.90 (br s, 2H), 4.20-4.28 (m, 8H).

Tetraethyl 1-(2-bromoacetamido)methylenebisphosphonate (145)

A solution of bromoacetyl bromide (0.35 mL, 4.0 mmol) in $CH_2Cl_2$ (1 mL) was added dropwise to a stirred, cooled (ice-bath) solution of 144 (1.1 g, 3.6 mmol) and pyridine (0.59 mL, 7.3 mmol) in $CH_2Cl_2$ (10 mL). After stirring at the same temperature for 4 hours, the reaction was quenched by the addition of water. The product was extracted with $CH_2Cl_2$ and the combined organics were washed with 10% aqueous HCl, brine, dried over sodium sulfate and concentrated at reduced pressure. The crude yellow oil was purified by silica gel column chromatography (0% to 3% methanol in $CH_2Cl_2$) resulting in 11 as a colourless solid (0.58 g, 37%). $^1H$ NMR (400 MHz, $CDCl_3$) δ 1.35 (t, J=7.2, 12H), 3.92 (s, 2H), 4.12-4.28 (m, 8H), 4.92 (dt, J=10.2, 21.7, 1H), 6.91 (bd, J=10.0, 1H).

Rifabutin Bisphosphonate Conjugate 146

Compound 145 (24.9 mg, 0.05870 mmol), 32 (54.4 mg, 0.05925 mmol) and $K_2CO_3$ (16.3 mg, 0.1179 mmol) were stirred in 1 mL of anhydrous acetonitrile at room temperature overnight. The mixture was diluted with dichloromethane, washed with water (2×) and dried over $Na_2SO_4$. After concentration, the product was purified by silica gel chromatography on a Biotage™ flash chromatography system, eluting with a gradient of 0 to 3% methanol in dichloromethane over 15 column volumes to afford a dark purple solid 146 (53.6 mg, 72%). $^1$H NMR (400 MHz, $CDCl_3$) δ −0.16 (d, J=7.0, 3H), 0.48 (d, J=7.0, 3H), 0.91-0.94 (m, 9H), 1.04 (d, J=7.0, 3H), 1.12-1.32 (m, 3H), 1.33-1.37 (m, 12H), 1.79 (s, 3H), 1.74-2.00 (m, 5H), 2.01 (s, 3H), 2.05 (s, 3H), 2.12-2.30 (m, 3H), 2.28 (s, 3H), 2.39 (s, 3H), 2.48-2.68 (m, 3H), 2.84-2.90 (m, 1H), 2.92-3.04 (m, 2H), 3.03 (s, 3H), 3.16 (d, J=4.8, 1H), 3.24 (s, 2H), 3.31 (d, J=13.2, 1H), 3.41-3.45 (m, 1H), 4.14-4.28 (m, 8H), 4.94 (d, J=10.3, 1H), 5.02-5.07 (m, 2H), 5.13-5.17 (m, 1H), 5.92 (dd, J=7.7, 15.7, 1H), 6.08-6.13 (m, 2H), 6.43 (dd, J=11.4, 16.1, 1H), 7.68 (d, J=10.3, 1H), 7.91 (s, 1H), 8.42 (br s, 1H); $^{31}$P NMR (162 MHz, $CDCl_3$) δ 17.58.

Rifabutin Bisphosphonate Conjugate 147

Compound 146 (45.7 mg, 0.03623 mmol) and 0.25 mL (1.784 mmol) of triethylamine were dissolved in 1 mL of dichloromethane before 0.12 mL (0.9092 mmol) of TMSBr was carefully added at room temperature. After overnight stirring, the orange-red suspension turned to dark purple. The mixture was concentrated to dryness and the residue was dissolved in 1 mL of acetonitrile prior to the addition of 2.2 mL (0.22 mmol) of 0.1N HCl(aq). The mixture was stirred for 30 min and basified to pH=9.5 with the addition of 0.05 mL (0.36 mmol) of triethylamine. Acetonitrile was removed and the residue was lyophilized. The product was purified by C18 reverse phase chromatography on a Biotage™ flash chromatography system, eluting with a gradient of 5% to 50% MeCN in 30 mM triethylammonium bicarbonate buffer (aq, pH=6.5) over 10 column volumes to afford the dark purple solid 147 (31 mg, 68%) as a mono-triethylammonium salt. $^1$H NMR (400 MHz, $D_2O$) δ 0.00 (d, J=5.9, 3H), 0.44 (d, J=7.0, 3H), 0.82 (br s, 2H), 0.94 (d, J=7.0, 3H), 0.99 (d, J=7.0, 3H), 1.07 (d, J=6.2, 6H), 1.26 (t, J=7.3, 12H), 1.59 (br s, 2H), 1.81 (s, 3H), 1.90-2.04 (m, 4H), 2.00 (s, 3H), 2.17 (s, 3H), 2.20-2.28 (m, 2H), 2.46 (s, 3H), 2.48-2.56 (m, 2H), 3.00 (s, 3H), 3.03 (br s, 1H), 3.19 (q, J=7.3, 9H), 3.38 (d, J=7.0, 1H), 3.43 (d, J=6.6, 2H), 3.44-3.56 (m, 2H), 3.60-3.84 (m, 4H), 4.31 (t, J=19.1, 1H), 4.98 (d, J=11.0, 1H), 5.10-5.14 (m, 1H), 5.22 (dd, J=7.7, 12.5, 1H), 6.09 (dd, J=8.1, 15.4, 1H), 6.18 (dd, J=12.8, 1H), 6.42 (d, J=10.6, 1H), 6.66-6.74 (m, 1H); $^{31}$P NMR (162 MHz, $D_2O$) δ 13.78.

Scheme 26. Preparation of rifabutin bisphosphonate conjugates 150

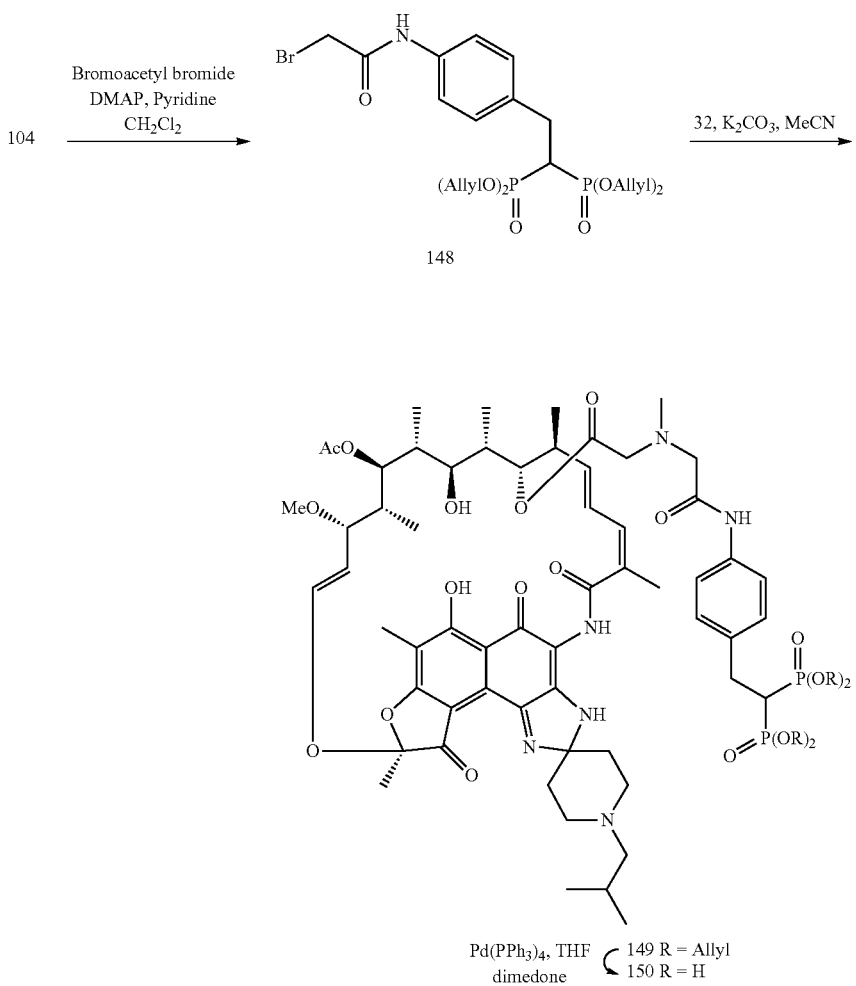

Tetrallyl 1-(4-(2-bromoacetamido)benzyl)methylenebisphosphonate (148)

To a solution of aminomethylenebisphosphonate 104 (1.24 g, 3.53 mmol) in CH$_2$Cl$_2$ (44 mL) at 0° C. was added pyridine (428 µL, 5.29 mmol) followed by bromoacetylbromide (307 µL, 3.53 mmol). The reaction mixture was stirred at 0° C. for 30 min and poured into a saturated aqueous NH$_4$Cl solution. The layers were separated and the aqueous layer was extracted with CH$_2$Cl$_2$ (2×). The combined organic layers were dried over MgSO$_4$, filtered and concentrated. The crude product was purified by flash chromatography on silica gel using ethyl acetate as eluant to provide bromide 148 as a clear colorless oil (1.24 g, 74%). $^1$H NMR (400 MHz, CDCl$_3$) δ 3.91 (s, 2H), 4.61-4.67 (m, 8H), 5.04 (dt, J=21.7, 10.1 Hz, 1H), 5.24-5.28 (m, 4H), 5.35-5.40 (m, 4H), 5.88-5.99 (m, 4H), 7.07 (d, J=10.5 Hz, 1H).

Rifabutin Bisphosphonate Conjugate 149

To a solution of 148 (140 mg, 0.249 mmol) in acetonitrile (5 ml) were added potassium carbonate (70 mg. 0.5 mmol) and 32 (228 mg, 0.249 mmol). The reaction was stirred at room temperature overnight and then concentrated to dryness. The residue was dissolved in CH$_2$Cl$_2$ (50 ml) and washed twice with brine (50 ml), then dried over Na$_2$SO$_4$, filtered and concentrated in vacuo. The crude product 149 (340 mg, 98% yield), a dark purple solid, was used directly in the next step. $^1$H NMR (400 MHz, CDCl$_3$) δ −0.16 (d, J=7.0 Hz, 3H), 0.48-0.50 (d, J=7.0 Hz, 3H), 0.92 (t, J=6.6 Hz, 9H), 1.02-1.04 (d, J=6.6 Hz, 3H), 1.22-1.25 (m, 2H), 1.59 (m, 2H), 1.79-1.85 (m, 5H), 1.96 (s, 2H), 2.02 (s, 3H), 2.17 (m, 1H), 2.27 (s, 5H), 2.38 (s, 2H), 2.47-2.82 (m, 5H), 2.86-2.88 (m, 1H), 2.95-3.04 (m, 5H), 3.13-3.29 (m, 6H), 3.45 (m, 1H), 4.52-4.57 (m, 8H), 4.95 (d, J=9.9 Hz, 1H), 5.08 (dd, J=12.5 and 4.8 Hz, 1H), 5.18-5.32 (m, 8H), 5.83-5.92 (m, 4H), 6.08 (d, J=12.4 Hz, 2H), 6.39-6.43 (m, 1H), 7.22 (d, J=8.4 Hz, 2H), 7.57 (d, J=8.4 Hz, 1H), 7.79 (s, 1H), 8.4 (s, 1H), 9.33 (s, 1H). $^{31}$P (162 MHz, CDCl$_3$): δ 24.66

Rifabutin Bisphosphonate Conjugate 150

Argon was bubbled through a solution of 149 (340 mg, 0.2429 mmol) and dimedone (136 mg, 0.9716 mmol) in anhydrous THF (10 ml) for 10 minutes at room temperature. Then tetrakistriphenylphosphine palladium (14 mg, 0.0121 mmol) was added. The reaction mixture was stirred at room temperature overnight and then concentrated dto dryness. The residue was dissolved in 30 mM triethylammonium bicarbonate buffer (2 ml, pH 6.5) and purified on C18 reverse phase chromatography on a Biotage™ flash chromatography system, eluting with a gradient of 20% to 100% MeCN in 30 mM triethylammonium bicarbonate buffer (aq, pH=6.5). Red colored fractions were acidified to pH 2 then extracted with CH$_2$Cl$_2$. Pure fractions were combined and concentrated to provide 149 as a deep red solid (152 mg, 51% yield). $^1$H NMR (400 MHz, CDCl$_3$) δ −0.09 (d, J=6.2 Hz, 3H), 0.48-0.50 (d, J=6.5 Hz, 3H), 0.83 (bs, 4H), 0.95 (d, J=6.5 Hz, 3H), 1.00 (t, J=7.2 Hz, 6H), 1.17 (t, J=7.1 Hz, 18H), 1.79 (s, 6H), 1.90 (m, 3H), 2.00 (d, J=8.8 Hz, 6H), 2.27 (s, 6H), 2.43 (s, 3H), 2.47-2.60 (m, 6H), 2.83 (d, J=7.0 Hz, 15H), 2.97-3.10 (m, 8H), 3.18-3.28 (m, 12H), 4.96 (d, J=9.9 Hz, 2H), 5.23 (m, 1H), 5.75 (m, 1H), 6.07 (d, J=12.5 Hz, 2H), 6.52 (m, 1H), 7.30-7.42 (m, 4H), 7.68 (bs, 1H) 9.34 (bs, 1H) $^{31}$P (162 MHz, CDCl$_3$): δ 20.18 LC/MS purity: 97.3% (254 nm), 99.8% (220 nm), 98.4% (320 nm). MS (MH⁻)

Scheme 27. Preparation of rifabutin bisphosphonate conjugates 155

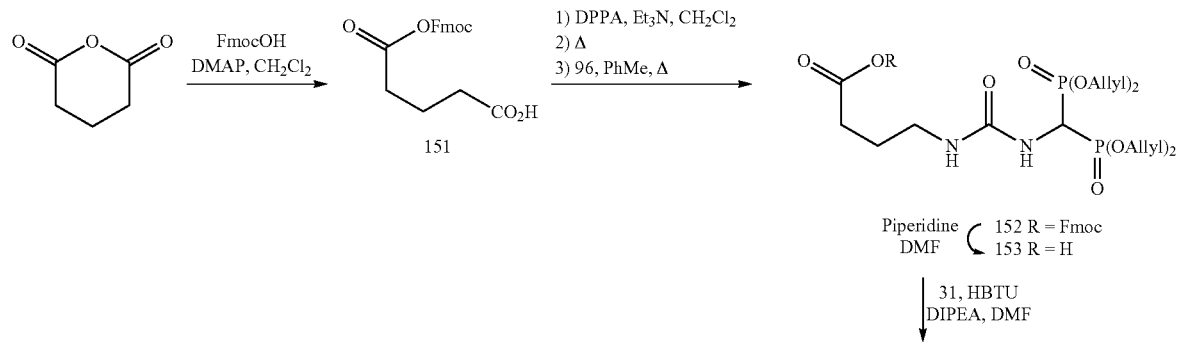

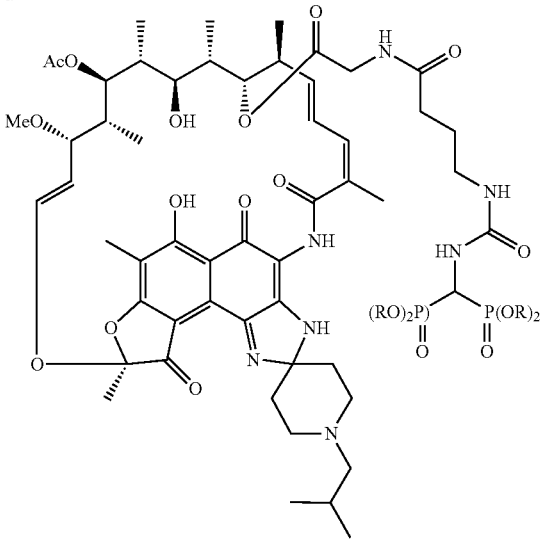

Pd(PPh₃)₄, DMF   154 R = Allyl
morpholine            155 R = H

4-(((9H-Fluoren-9-yl)methoxy)carbonyl)butanoic acid (151)

To a solution of glutaric anhydride (1.0 g, 8.76 mmol) and (9H-fluoren-9-yl)methanol (1.56 g, 7.97 mmol) in $CH_2Cl_2$ (44 mL) was added DMAP (107 mg, 0.88 mmol) and the mixture was stirred for 20 h at room temperature. The reaction mixture was concentrated, diluted with $H_2O$ and saturated $NaHCO_3$ solution and washed with ethyl acetate. The organic layer was extracted with saturated $NaHCO_3$ solution (3×). The combined aqueous layers were acidified to pH=2 with conc. HCl solution, extracted with a 4:1 mixture of $CHCl_3$/i-PrOH (3×'). The organic layers were combined, dried over $MgSO_4$, filtered and concentrated to dryness, yielding acid 151 as a white solid (1.5 g, 61%). $^1H$ NMR (400 MHz, $CDCl_3$) δ 1.95 (quint, J=7.3 Hz, 2H), 2.40 (t, J=7.3 Hz, 2H), 2.47 (t, J=7.3 Hz, 2H), 4.21 (t, J=6.9 Hz, 1H), 4.43 (d, J=7.0 Hz, 2H), 7.32 (dt, J=7.4, 1.1 Hz, 2H), 7.41 (t, J=7.4 Hz, 2H), 7.59 (d, J=7.5 Hz, 2H), 7.78 (d, J=7.5 Hz, 2H).

(9H-Fluoren-9-yl)methyl 4-(3-(bis(diallylphosphoryl)methyl)ureido)butanoate (152)

To a solution of acid 151 (500 mg, 1.61 mmol) in $CH_2Cl_2$ (5.4 mL) was added triethylamine (269 μL, 1.93 mmol) and diphenylphosphorylazide (418 μL, 1.93 mmol). After stirring at room temperature for 18 h, the mixture was concentrated and the residue was heated at 100° C. for 1 h under vacuum on a Kugelrohr apparatus. The resulting isocyanate was dissolved in toluene (5 mL), amino-bisphosphonate 96 (565 mg, 1.61 mmol) was added and the mixture was heated at 70° C. for 2.5 h, then concentrated and purified by silica gel chromatography on a Biotage™ flash chromatography system using 0-10% methanol in ethyl acetate, providing urea 152 as a light yellow oil (778 mg, 73%). $^1H$ NMR (400 MHz, $CDCl_3$) δ 1.77 (quint, J=7.2 Hz, 2H), 2.39 (t, J=7.5 Hz, 2H), 3.14-3.19 (m, 2H), 4.19 (t, J=7.0 Hz, 1H), 4.40 (d, J=7.0 Hz, 2H), 4.55-4.66 (m, 8H), 5.05 (dt, J=22.1, 9.9 Hz, 1H), 5.17-5.24 (m, 4H), 5.31-5.39 (m, 4H), 5.61 (bs, 1H), 5.84-5.97 (m, 4H), 6.18 (bs, 1H), 7.32 (t, J=7.5 Hz, 2H), 7.41 (t, J=7.5 Hz, 2H), 7.58 (d, J=7.5 Hz, 2H), 7.77 (d, J=7.6 Hz, 2H).

4-(3-(Bis(diallylphosphoryl)methyl)ureido)butanoic acid (153)

Ester 152 (778 mg, 1.18 mmol) was treated with a 5% v/v solution of piperidine in DMF (6 mL). After stirring for 50 min, the reaction mixture was diluted with saturated $NaHCO_3$ solution and washed once with $Et_2O$. The aqueous layer was acidified to pH 2 with conc. HCl solution and extracted with a 4:1 mixture of $CHCl_3$/i-PrOH (3×). The organic layers were combined, dried over $MgSO_4$, filtered and concentrated to dryness, yielding acid 153 as yellowish oil (520 mg, 92%) which was used without purification. $^1H$ NMR (400 MHz, $CDCl_3$) δ 1.84 (quint, J=6.4 Hz, 2H), 2.35 (t, J=6.6 Hz, 2H), 3.26-3.29 (m, 2H), 4.52-4.67 (m, 8H), 5.04 (dt, J=22.2, 10.1 Hz, 1H), 5.20-5.27 (m, 4H), 5.30-5.40 (m, 4H), 5.751 (bs, 1H), 5.84-5.98 (m, 4H), 6.90 (d, J=10.3 Hz, 1H).

Rifabutin Bisphosphonate Conjugate 154

To a solution of compound 153 (152 mg, 0.32 mmol) in DMF (2 mL) at 0° C. was added DIEA (110 μL, 0.63 mmol) and HBTU (120 mg, 0.32 mmol). After stirring for 5 min at 0° C., glycyl-rifabutin 31 (286 mg, 0.32 mmol) in DMF (1.5 mL) was added and stirring was pursued for 30 min at 0° C. The reaction mixture was diluted with ethyl acetate, washed with $H_2O$, 0.5N HCl solution, saturated $NaHCO_3$ solution and saturated NaCl solution. The organic layer was dried over $MgSO_4$, filtered and concentrated to dryness. The crude product was purified by silica gel chromatography on a Biotage™ flash chromatography system using 0-10% methanol in $CH_2Cl_2$. Bisphosphonate conjugate 154 was obtained as a dark purple solid (249 mg, 57%). ESI-MS: (M+H) calculated for $C_{66}H_{93}N_7O_{20}P_2$ 1366, found 1366.4.

Rifabutin Bisphosphonate Conjugate 155

To a solution of bisphosphonate conjugate 154 (140 mg, 0.10 mmol) in DMF (1.7 mL) was added morpholine (1.7 mL, 20.0 mmol) and tetrakistriphenylphosphine palladium (6 mg, 0.005 mmol). The mixture was stirred at room temperature for 4 h and concentrated to dryness then purified by C18 silica gel chromatography on a Biotage™ flash chromatography system using a gradient of 10-100% MeCN in H$_2$O, both containing 0.05% NH$_4$OH. Pure fractions were combined, concentrated and lyophilized to provide the diammonium salt of compound 155 as a fluffy purple solid (40 mg, 33%). LCMS: 96.6% (254 nm), 95.7% (220 nm), 97.3% (320 nm). ESI-MS: (M+H) calculated for C$_{54}$H$_{77}$N$_7$O$_{20}$P$_2$ 1206, found 1206.2.

Scheme 28. Preparation of Rifabutin Bisphosphonate Conjugates 164 t-Butyldimethyl(2-aminoethoxy)silane (157)

1.97 mL (32.74 mmol) of 156 and 2.455 g (36.06 mmol) of imidazole were dissolved in 15 mL of CH$_2$Cl$_2$ and 5.18 g (34.37 mmol) of TBSCl was carefully added. After 1 h at room temperature, the mixture was concentrated and loaded on a silica gel flash chromatographic column. Elution with a mixture of 20:1 (v/v) CH$_2$Cl$_2$/methanol containing 0.5% (by volume) triethylamine failed to afford pure product. The eluted mixture was dissolved in water, extracted with diethyl ether (3×) and dried over sodium sulfate. Removal of the solvent yielded 1.73 g (30%) of 157 as a brown oil. $^1$H NMR

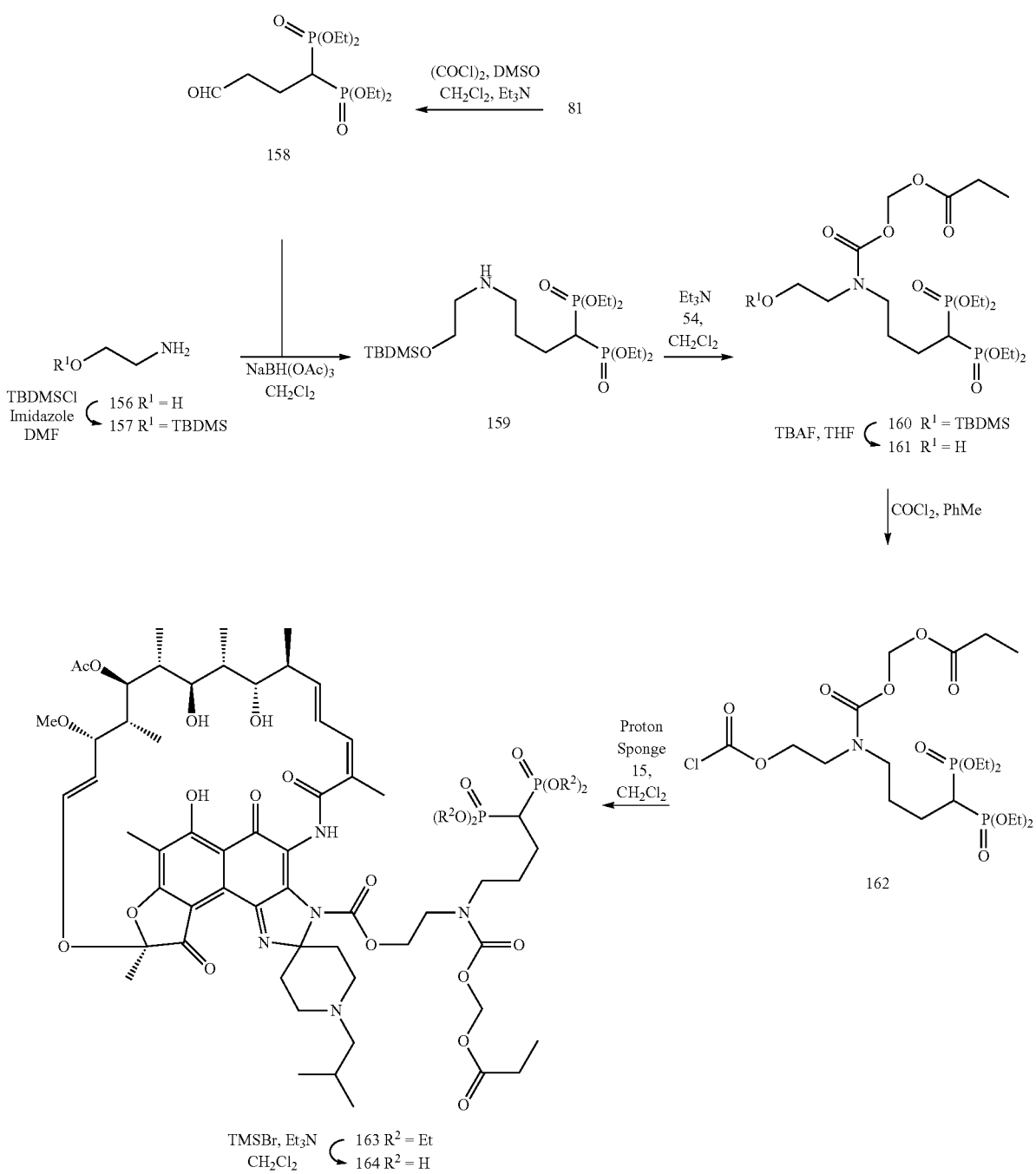

(400 MHz, CDCl$_3$) δ 0.06 (s, 6H), 0.90 (s, 9H), 1.74 (br s, 2H), 2.77 (t, J=5.1, 2H), 3.63 (t, J=5.2, 2H).

Tetraethyl 4-oxobutylene-1,1-bisphosphonate (158)

Oxalyl chloride (0.19 mL, 2.178 mmol) was dissolved in 4 mL of CH$_2$Cl$_2$ and cooled to −78° C. To this solution was carefully added 0.31 mL (4.365 mmol) of DMSO and strong bubbling was observed. After 15 min, a pre-cooled (−78° C.) solution of compound 81 (499 mg, 1.441 mmol) in 2 mL of dichloromethane was cannulated into the first solution. The turbid mixture was stirred for another 30 min before 1.26 mL (7.233 mmol) of DIPEA was added. The reaction turned clear and was kept at low temperature for 30 min. The mixture was then switched to an ice-water bath and it was stirred for another 10 min, before quenching the reaction with saturated ammonium chloride (aq). The mixture was separated, the organic layer was collected, washed sequentially with saturated ammonium chloride (aq, 1×), saturated sodium bicarbonate (1×), brine (1×) and dried over sodium sulfate. Removal of the solvent afforded 158 (485.1 mg, 98%) as a slightly brown oil. $^1$H NMR (400 MHz, CDCl$_3$) δ 1.34 (t, J=6.6, 12H), 2.16-2.30 (m, 2H), 2.42 (tt, J=6.3, 23.8, 1H), 2.87 (t, J=7.0, 2H), 4.14-4.22 (m, 8H), 9.77 (s, 1H).

Tetraethyl 4-(2-t-butyldimethylsilyloxyethylamino) butylene-1,1-bisphosphonate (159)

Compounds 157 (248.2 mg, 1.416 mmol) and 158 (485 mg, 1.409 mmol) were dissolved in 5 mL of dichloromethane in an ice bath. After 5 min, NaBH(OAc)$_3$ (446.8 mg, 2.108 mmol) was added. The mixture was stirred at room temperature overnight before being quenched with saturated sodium bicarbonate. The organic layer was collected and the aqueous layer was extracted with dichloromethane (3×). The combined organics were dried over sodium sulfate, filtered and concentrated. The mixture was subjected to a flash chromatography on silica gel eluting with 20:1 (v/v) dichloromethane/methanol followed by 10:1 and 5:1 to afford 264.3 mg (37%) of product 159 as a colorless oil. $^1$H NMR (400 MHz, CDCl$_3$) δ 0.06 (s, 6H), 0.89 (s, 9H), 1.34 (t, J=7.3, 12H), 1.75-1.87 (m, 4H), 2.32 (tt, J=5.9, 24.2, 1H), 2.66 (t, J=7.4, 2H), 2.73 (t, J=5.1, 2H), 3.73 (t, J=5.5, 2H), 4.16-4.24 (m, 8H).

Tetraethyl 4-(N-(propionyloxymethoxycarbonyl)-2-t-butyldimethylsilyloxyethylamino) butylene-1,1-bisphosphonate (160)

Compound 159 (264 mg, 0.5242 mmol), triethylamine (0.09 mL, 0.6423 mmol) and freshly prepared chloroformate 54 (0.5353 mmol) were stirred in 3 mL of dichloromethane for 1 h at room temperature and the mixture was concentrated. Flash chromatography on silica gel eluting with 30:1 (v/v) ethyl acetate/methanol afforded the pale yellow oil 160 (175.6 mg, 53%) as a 1:1 rotameric mixture. $^1$H NMR (400 MHz, CDCl$_3$) δ 0.03 (s, 6H), 0.88 (s, 9H), 1.15 (t, J=7.3, 3H), 1.32-1.36 (m, 12H), 1.78-1.95 (m, 4H), 2.26 (tt, J=5.5, 24.6, 1H), 2.38 (q, J=7.7, 2H), 2.32 (t, J=6.3, 2H), 2.36 (t, J=5.9, 2H), 3.68 (t, J=5.9, 1H), 3.76 (t, J=5.9, 1H), 4.13-4.22 (m, 8H), 5.75 (s, 1H), 5.76 (s, 1H).

Tetraethyl 4-(N-(propionyloxymethoxycarbonyl)-2-hydroxyethylamino) butylene-1,1-bisphosphonate (161)

Compound 160 (175 mg, 0.2761 mmol) in 2 mL of THF was treated with 0.28 mL (0.28 mmol) 1M TBAF THF solution. After 1 h at room temperature, the mixture was concentrated and flash chromatography on silica gel eluting with 20:1 (v/v) dichloromethane/methanol yielded 101.6 mg (71%) of 161 as pale yellow oil in a 1:1 rotameric mixture. $^1$H NMR (400 MHz, CDCl$_3$) δ 1.15 (t, J=7.3, 3H), 1.34 (t, J=7.3, 12H), 1.82-2.00 (m, 4H), 2.27 (tt, J=4.8, 24.2, 1H), 2.36-2.42 (m, 2H), 2.29-3.47 (m, 4H), 3.72 (t, J=5.5, 1H), 3.80 (t, J=4.8, 1H), 4.14-4.24 (m, 8H), 5.75 (s, 1H), 5.77 (s, 1H).

Tetraethyl 4-(N-(propionyloxymethoxycarbonyl)-2-(chloroformyloxy)ethylamino) butylene-1,1-bisphosphonate (162)

Cool the 20% phosgene toluene solution (0.11 mL, 0.2091 mmol) to 0° C. and the solution of compound 161 (100 mg, 0.1925 mmol) in 0.5 mL of toluene was added in one portion followed by 0.5 mL of toluene rinse. After 1 h, the reaction was ~50% completed and another 0.11 mL (0.2091 mmol) of phosgene solution was added. After 30 min, reaction was complete as indicated by $^1$H NMR and was concentrated. The resultant 1:1 rotameric mixture chloroformate 162 was used directly in the next step without further purification. $^1$H NMR (400 MHz, CDCl$_3$) δ 1.15 (t, J=7.3, 3H), 1.35 (t, J=7.0, 12H), 1.82-1.94 (m, 4H), 2.20-2.44 (m, 3H), 2.29-3.47 (m, 4H), 3.33 (dt, J=6.6, 18.4, 2H), 3.58 (dt, J=5.9, 14.0, 2H), 4.13-4.22 (m, 8H), 4.39 (t, J=5.5, 1H), 4.47 (t, J=5.1, 1H), 5.76 (s, 1H), 5.77 (s, 1H).

Rifabutin Bisphosphonate Conjugate 163

Rifabutin 15 (163 mg, 0.1924 mmol), chloroformate 162 (0.1925 mmol, crude from the previous step) and 83.6 mg (0.3901 mmol) of proton sponge was stirred in 2 mL of THF at room temperature overnight. The mixture was diluted with ethyl acetate, washed with water (2×) and dried over sodium sulfate. Purification was performed by silica gel chromatography on a Biotage™ flash chromatography system, eluting with a gradient of 2% to 10% methanol in ethyl acetate over 10 column volumes followed by the elution with pure methanol. The resultant red solid 163 (147.5 mg, 55%) didn't yield satisfactory $^1$H and $^{31}$P NMR spectra due to rotameric isomers. LC/MS indicated the pure product. MS for C$_{66}$H$_{99}$N$_5$O$_{23}$P$_2$: 1392 (M+H).

Rifabutin Bisphosphonate Conjugate 164

To the mixture of compound 163 (140.1 mg, 0.1006 mmol) and triethylamine (0.70 mL, 4.9956 mmol) in 1 mL of CH$_2$Cl$_2$ was carefully added 0.33 mL (2.500 mmol) of TMSBr at room temperature. After 21 h of stirring, the reaction was concentrated to dryness. The resultant material was redissolved in 2 mL of dichloromethane and 0.16 mL (1.978 mmol) of pyridine and 0.03 mL (1.197 mmol) of HF-Py was added. After 1 h, the mixture was concentrated to dryness. The material was purified on C18 reverse phase silica gel on a Biotage™ flash chromatography system, loading with water and eluting with a gradient of 5% to 50% acetonitrile in 30 mM triethylammonium bicarbonate buffer (aq, pH=6.5) over 10 column volumes. The strongly colored fractions were combined and acetonitrile was removed by rotavapor. The resultant aqueous solution was washed with dichloromethane (2×) and lyophilized to yield the red-orange solid 164 (75.3 mg, 54%). No satisfactory $^1$H NMR was observed for this compound due to the rotameric mixture. $^{31}$P NMR (162 MHz, D$_2$O) δ 20.81, 20.87.

Example 2

Determination of In Vitro Antibacterial Activity and Cytotoxicity

In Vitro Antibacterial Activity

Susceptibility of *S. aureus* strains to the known antibiotics and synthesized compounds was determined by following the guidelines set by NCCLS (M26-A). Compounds were diluted two-fold serially in DMSO and transferred to cation-adjusted Mueller Hinton broth (CAMHB; Becton Dickinson). 50 μL of compounds diluted in CAMHB was mixed with 100 μL of bacteria diluted in CAMHB in 96-well microtiter plates. The final concentration of micro-organisms in the assay was 5×10⁵c.f.u. per mL and the final concentration of DMSO in the assay was 1.25%. Assays were set up in duplicate and incubated at 37° C. for 18 h. The lowest concentration of compound that inhibited visible growth was reported as the minimum inhibitory concentration (MIC).

Susceptibility testing experiments were also carried out in the presence of serum. These experiments were carried out similar to the susceptibility testing with the following modifications. 75 μL of compounds diluted in CAMHB was mixed with 75 μL of bacteria diluted in 100% serum from any given source (commercial pooled mouse serum (MS) and human serum (HS), Equitech-Bio Inc.) or diluted in 8% purified human serum albumin (HSA) (Calbiochem). The final concentration of animal serum in the assay was 50% and the final concentration of purified human serum albumin in the assay was 4%; the concentrations of all other components were identical to those described for susceptibility testing. The data is summarized in Table 1.

TABLE 1

Antibacterial susceptibility of bacteria to selected compounds (Minimum inhibitory concentrations in μg/mL)

| Compound | ATCC 29213 | ATCC 13709 | ATCC 13709[a] | ATCC 13709 + 50% Mouse Serum | ATCC 13709 + 50% Human Serum | ATCC 13709 + 50% Rat Serum |
|---|---|---|---|---|---|---|
| Rifabutin (15) | 0.0156 | 0.03125 | — | 0.0625 | 0.03125 | 0.03125 |
| 18 | 0.125 | 0.125 | >128 | 0.125 | 0.125 | 0.0156 |
| 19 | 0.25 | 0.25 | >128 | 0.0625 | 0.125 | 0.0156 |
| 28 | 0.5 | 0.5 | >128 | 2 | 0.25 | 0.0625 |
| 36 | 2 | 2 | >128 | 1 | 2 | 0.0625 |
| 42 | 0.25 | 0.125 | >128 | 0.125 | 0.0625 | 0.03125 |
| 48a | 2 | 2 | >128 | 2 | 8 | 0.25 |
| 48b | 0.5 | 0.25 | >128 | 0.25 | 0.5 | 0.0625 |
| 52 | 8 | 4 | >128 | 2 | 16 | 0.5 |
| 59 | 0.125 | 0.125 | >128 | 0.03125 | 0.0625 | 0.008 |
| 66 | 4 | 4 | >128 | 0.125 | 4 | 0.008 |
| 71 | 8 | 4 | >128 | 8 | 16 | 1 |
| 79a | 16 | 16 | >128 | >128 | >128 | 64 |
| 79b | 64 | 64 | >128 | 64 | 128 | 8 |
| 89 | 4 | 4 | >128 | 0.0625 | 16 | 0.0156 |
| 95 | 4 | 4 | >128 | 0.0625 | 16 | 0.0156 |
| 102 | 2 | 4 | >128 | 0.0625 | 16 | 0.0156 |
| 110 | 8 | 8 | >128 | 0.125 | 8 | 0.0156 |
| 118 | 8 | 8 | >128 | 0.25 | 2 | 0.0625 |
| 128 | >128 | >128 | >128 | >128 | >128 | >128 |
| 138 | >128 | >128 | >128 | >128 | >128 | >128 |
| 140 | 16 | 16 | >128 | 32 | 128 | 4 |
| 142a | 16 | 16 | >128 | 16 | 128 | 2 |
| 142b | 0.0625 | 0.125 | >128 | 0.0625 | 0.5 | 0.008 |
| 147 | 128 | 128 | >128 | 2 | 16 | 32 |
| 150 | 64 | 64 | >128 | 128 | >128 | 16 |
| 155 | 128 | 32 | >128 | >128 | 128 | 8 |
| 164 | 4 | 4 | >128 | 2 | 8 | 0.25 | a: Novobiocin and Rifampicin resistant variant.

From this data, it can be broadly deduced that the bisphosphonated prodrugs possess antibacterial activities which are weaker than the parent drug. In fact, the near complete loss of activity in the cases of 79(a-b), 128, 138, 147 and 155 suggests the introduction of a bisphosphonated moiety to be detrimental to the antibacterial nature of the molecules. Prodrugs 18, 19, 28, 42, 48b, 59 and 142b yielded very low MICs whether in the absence or in the presence of serum, and this activity suggests that the bisphosphonated moieties are chemically labile and liberation of the active parental antibacterial agent during the course of the experiment is at least not dependent on biomolecular catalysis. On the other hand, compounds 36, 48a, 52, 66, 71, 89, 95, 102, 110, 118 and 164 all show a significant increase in antibacterial activity in serum which at least suggests that enzymatic degradation of the prodrug to the parent drug occurs. Compounds 140 and 142a are in an intermediate position whereby the weak antibacterial activity does not show a serum dependence. This suggests that there is only a very slow chemical process releasing the drug.

The lack of activity of all the prodrugs against rifampicin resistant *S. aureus* strongly suggests that any activity relies on the same mechanism of action and therefore on the rifamycin portion.

Example 3

Binding of Compounds to Bone Powder In Vitro and Subsequent Regeneration of the Parent Drug Bone Powder Binding The ability of the molecules from Example 1 to bind to bone powder was established using a microbiological assay for detection. An individual compound was dissolved in PBS and resuspended at a concentration of 1 mg/ml in a slurry of bone meal powder (Now Foods, Bloomingdale, Ill., USA) in PBS at 10 mg/ml. The suspension of drug/prodrug in bone meal powder was incubated at 37° C. for 1 h to allow for binding, and centrifuged at 13 000 rpm for 2 min, before recovering the supernatant. The bone meal powder pellet was then washed three times with 1 ml of PBS+2% DMSO. The supernatants were assessed for the amount of prodrug by microbiological assay measurements as follows: Isolated colonies of the indicator strain (*Staphylococcus aureus* K1758) were resuspended in 0.85% saline to $OD_{600}$=0.1 and streaked on Cation-adjusted Miller Hinton agar (CAMHA) plates. Known volumes of the supernatants were applied to discs and dried. The discs were then placed on the seeded CAMHA plates. The plates were incubated at 37° C. for 18 hrs after which the diameters of the zone of inhibition generated by the discs were measured. The amount of prodrug was deduced from standard curves of known amounts that were used as reference for each experiment.

When applied to compounds 18, 19, 28, 36, 89, 95, 102, 118 and 142b the in vitro binding experiment showed that >95% of each compound was bound to the bone meal powder, as shown in Table 2.

This confirms that the bisphosphonated prodrugs are very efficiently removed from solution by osseous matter. The results also undeniably lend credence to the use of bisphosphonates as mediators for bone delivery. It is reasonable to believe that a portion of the unbound material detected by this method was not bisphosphonated prodrug but rather contaminating or regenerated parent drug. Nevertheless, it is also probable that the extent of binding to the osseous matter is reflective of the kinetics of bone absorption/adsorption.

Regeneration of Drug from Bone Powder-Bound Prodrug

The ability of the prodrug to release the active entity at the site of infection is paramount for use in vivo. This can be predicted by measuring the release of the drug from prodrug bound to osseous matter in vitro.

Amounts of parent drug "regenerated" from the phosphonated prodrug were measured as follows. Washed bone powder-bound prodrugs from the above experiment were resuspended in 400 μL PBS+2% DMSO or in 400 μL 50% (v/v in PBS+2% DMSO) human or rat serum. The suspension was incubated overnight at 37° C., centrifuged at 13,000 rpm for 2 min and the supernatant was recovered. The amount of regenerated parent drug in the supernatant was determined by measurements using the microbiological assay that was previously described for the prodrugs themselves. The amount of prodrug was deduced from standard curves of known amounts of parent drug that were used as reference for each experiment. The amount of regenerated drug assessed by this bioassay was corroborated by MIC determination. The percentage of drug regenerated in PBS or serum after the overnight incubation (Table 2) was deduced from the difference between the amount of bound prodrug and the amount of regenerated drug (not shown).

TABLE 2

Bone binding and Conversion of bisphosphonated Rifamycin prodrugs to parent drugs after binding to bone (expressed as % prodrug converted after 24 h incubation)

| Compound | % Bone binding | Medium | % Conversion |
|---|---|---|---|
| 18 | 98.4 | PBS | 0.66 ± 0.03 |
| | | 50% Rat Serum | 0.95 ± 0.40 |
| | | 50% Heat Inactivated Rat Serum | 0.55 ± 0.20 |
| 19 | 99.6 | PBS | 0.14 |
| | | 50% Rat Serum | 0.14 |
| | | 50% Heat Inactivated Rat Serum | 0.14 |
| 28 | 99.7 | PBS | 0.06 ± 0.01 |
| | | 50% Rat Serum | 0.06 ± 0.01 |
| | | 50% Heat Inactivated Rat Serum | 0.07 ± 0.02 |
| 36 | 99.7 | PBS | 0.07 |
| | | 50% Rat Serum | 0.07 |
| | | 50% Heat Inactivated Rat Serum | 0.07 |
| 89 | 99.8 | PBS | 0.02 |
| | | 50% Rat Serum | 0.18 |
| | | 50% Heat Inactivated Rat Serum | 0.16 ± 0.04 |
| 95 | 99.8 | PBS | 0.02 |
| | | 50% Rat Serum | 0.14 ± 0.06 |
| | | 50% Heat Inactivated Rat Serum | 0.13 |
| 102 | 99.8 | PBS | 0.03 |
| | | 50% Rat Serum | 0.1 |
| | | 50% Heat Inactivated Rat Serum | 0.12 ± 0.02 |
| 118 | 99.9 | PBS | 0.01 |
| | | 50% Rat Serum | 0.08 |
| | | 50% Heat Inactivated Rat Serum | 0.11 ± 0.03 |
| 142b | 98.9 | PBS | 0.37 ± 0.08 |
| | | 50% Rat Serum | 0.22 ± 0.06 |
| | | 50% Heat Inactivated Rat Serum | 0.24 ± 0.04 |

This data shows that compounds 18, 19, 28, 36 and 142b release significant amounts of the parent rifabutin once bound to bone powder, regardless of the presence of serum. On the other hand, for prodrugs 89, 95, 102 and 118, the regeneration is clearly accelerated by the presence of serum. This is consistent with the observation that the antibacterial activities of 18, 19, 28, 36 and 142b are not dependent on serum, while for 89, 95, 102 and 118, the antibacterial activity is heightened in the presence of serum. These data are also consistent with the notion that the degradation of 18, 19, 28, 36 and 142b is not dependent on serum enzymes, while that of 89, 95, 102 and 118 is likely at least accelerated by them.

Example 4

Comparisons of the Prophylactic Efficacy of Rifamycin Antibacterials and their Bisphosphonated Prodrugs in Rat Models of Bone Infections To determine the in vivo activity of bisphosphonated prodrugs of Rifamycin derived antibacterials in comparison to their non-bisphosphonated parents, compounds 18, 19, 48a, 59, 66, 89, 95, 102, 110, 142b and 164 and their parent drug rifabutin were used as prophylactic therapeutics in an animal model of infection. Specifically, a spontaneous Novobiocin resistant mutant strain of *S. aureus* ATCC 13709 (a clinical osteomyelitis isolate), was grown overnight at 37° C. in brain heart infusion broth (BHIB). After 16 h of growth, cells were subcultured into fresh BHIB and incubated for 4 to 5 h at 37° C. The cells were washed twice with phosphate-buffered saline (PBS) and resuspended in BHIB supplemented with 10% (vol./vol.) fetal bovine serum at a density of approximately $10^{10}$ colony forming units (CFU)/ml (based upon turbidimetry). The suspension was aliquoted and a portion was used to check the CFU count. The culture was stored frozen (−80° C.) and was used without subculture. For use as an inoculum the culture was thawed, diluted in PBS and kept in an ice bath until it was used.

Animals were infected as described by O'Reilly et al. (Antimicrobial Agents and Chemotherapy (1992), 36(12): 2693-97) to generate the bone infection. Female CD rats (age, 57 to 70 days; n=5/group; Charles River, St-Constant, Canada) were anaesthetized by isofluorane before and during the surgery. Following complete induction of anesthesia, the rat was placed ventral side up and hair was shaved from the surgical site. The skin over the leg was cleaned and disinfected (proviodine-ethanol 70%). A longitudinal incision below the knee joint was made in the sagital plane. The incision was made over the bone below the "knee joint" (tibia head or condyle) but not completely extending to the ankle. A high speed drill fitted with a 2 mm bulb bit was used to drill a hole into the medullar cavity of the tibia. Rats were injected intra-tibially with 0.05 ml 5% sodium morrhuate (sclerosing agent) and then with 0.05 ml of *S. aureus* suspension (ca. $2 \times 10^7$ CFU/rat). The hole was sealed by applying a small amount of dry dental cement which immediately absorbs fluids and adheres to the site. The wound was closed using 3 metal skin clips. Moxifloxacin (as a positive control) was injected once at 10 mg/kg intravenously 1 h postinfection in saline, while the Rifabutin derived prodrugs (prepared in 0.9% saline) were injected at the dose indicated in Table 3 as a single intravenous bolus at different time points prior to the infection.

Infected rats were sacrificed by $CO_2$ asphyxiation 24 h postinfection to monitor the bacterial CFU count. Infected tibiae were removed, dissected free of soft tissue, and weighed. The bones were ground, 50 mg of charcoal were added and the powder was resuspended in 5 ml 0.9% NaCl, serially diluted and processed for quantitative cultures. Treatment efficacy was measured in terms of Log viable bacteria (Log CFU per gram of bone). The results obtained for each group of rats were evaluated by calculating the mean Log CFU and standard deviation. The limit of detection is 2 Log CFU. Statistical comparisons of viable bacterial counts for the different treated and untreated groups were performed with the Dunnett's multiple-comparison test. Differences were considered significant when the P value was <0.05 when comparing treated infected animals to the untreated infected ones. The doses used, the amount of time separating the treatment from the time of infection and the treatment outcomes are shown in Table 3.

TABLE 3

Retrieved bacterial titers following prophylactic treatment in rat model of *S. aureus* bone infection

| Compound No. | Dose (mg/kg) parent drug equivalent) | Time of administration (days prior to infection) | Measured bacterial titer (Log CFU/g of bone) | | |
|---|---|---|---|---|---|
| | | | Untreated | Positive control | Parent drug | Test compound |
| 18 | 20 | 1 | 7.03 ± 0.35 | 3.22 ± 0.65 | 2.03 ± 0.07 | 2.08 ± 0.02 |
| | | 5 | 5.27 ± 0.8 | 2.62 ± 0.37 | 2.75 ± 0.94 | 2.91 ± 1.33 |
| 19 | 20 | 1 | 7.03 ± 0.35 | 3.22 ± 0.65 | 2.03 ± 0.07 | 2.55 ± 0.69 |
| | | 5 | 5.27 ± 0.8 | 2.62 ± 0.37 | 2.75 ± 0.94 | 3.69 ± 1.45 |
| 48a | 20 | 1 | 5.79 ± 0.51 | 2.27 ± 0.21 | 2.09 ± 0.06 | 2.53 ± 0.94 |
| | | 5 | 4.79 ± 0.88 | 2.63 ± 0.65 | 4.27 ± 1.91 | 2.65 ± 0.85 |
| 59 | 20 | 1 | 5.89 ± 0.64 | 2.06 ± 0.10 | 2.03 ± 0.09 | 1.95 ± 0.06 |
| | | 5 | — | — | — | — |
| 66 | 20 | 1 | 5.89 ± 0.64 | 2.06 ± 0.10 | 2.03 ± 0.09 | 1.97 ± 0.05 |
| | | 5 | — | — | — | — |
| 89 | 20 | 1 | 5.79 ± 0.51 | 2.27 ± 0.21 | 2.09 ± 0.06 | 2.05 ± 0.07 |
| | | 5 | 5.87 ± 0.63 | 2.95 ± 1.07 | 4.34 ± 0.79 | 3.45 ± 1.36 |
| 95 | 20 | 1 | 5.79 ± 0.51 | 2.27 ± 0.21 | 2.09 ± 0.06 | 2.3 ± 0.57 |
| | | 5 | 4.79 ± 0.88 | 2.63 ± 0.65 | 4.27 ± 1.91 | 3.75 ± 0.54 |
| 102 | 20 | 1 | 4.87 ± 0.83 | 2.2 ± 0.28 | 2.07 ± 0.09 | 2.89 ± 1.13 |
| | | 5 | 6.57 ± 0.37 | 3.01 ± 0.74 | 4.71 ± 1.05 | 5.38 ± 0.83 |
| 110 | 20 | 1 | 5.89 ± 0.64 | 2.06 ± 0.10 | 2.03 ± 0.09 | 1.94 ± 0.04 |
| | | 5 | — | — | — | — |
| 142b | 20 | 1 | 4.87 ± 0.83 | 2.2 ± 0.28 | 2.07 ± 0.09 | 2.14 ± 0.08 |
| | | 5 | 6.57 ± 0.37 | 3.01 ± 0.74 | 4.71 ± 1.05 | 4.79 ± 1.40 |
| 164 | 20 | 1 | 5.87 ± 0.63 | 2.95 ± 1.07 | 2.35 ± 1.12 | 5.48 ± 0.64 |
| | | 5 | — | — | — | — |

Three classes of compounds are available in this case: the compounds which are ineffective at 1 day (164), the compounds which are active at 1 day and display activity similar to rifabutin at 5 days (18, 19, 89, 95 and 102), and the compounds which are more potent than rifabutin at 5 days (48a). Inactivity at 1 day suggests the compound not to decompose to rifabutin in vivo, or only marginally. Compounds which behave as rifabutin does at both 1 day and 5 days prior to infection can be categorized in two groups: those which bind to bone in vivo and release rifabutin rapidly and those which decompose to rifabutin prior to reaching the bone. Compounds which are still active 5 days prior to infection demonstrate an ability to release rifabutin over an extended period of time These results and the in vitro regeneration data strongly support the notion that the active bisphosphonated prodrugs are targeted to the osseous matter in vivo, where they are able to release their bioactive moieties at concentrations above those needed for antibacterial activity.

It is understood that the examples and embodiments described herein are for illustrative purposes only and that various modifications or changes in light thereof will be suggested to persons skilled in the art and are to be included within the spirit and purview of this application and scope of the appended claims.

All documents, including but not limited to publications, patents, published patent applications, books, manuals, articles, papers, abstracts, and posters, and other materials referenced herein are expressly incorporated herein by reference in their entireties.

What is claimed is:

1. A compound of Formula (I) or a pharmaceutically acceptable salt, metabolite, solvate or prodrug thereof:

wherein:

A is a Rifamycin;

L is a cleavable linker for coupling A to B;

B is a phosphonated group selected from the group consisting of:

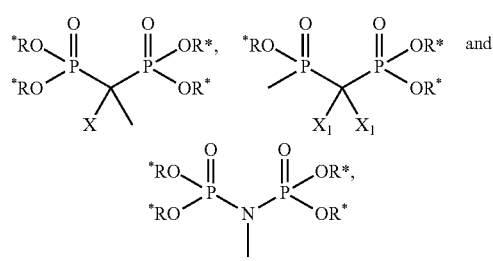

wherein:

each R* is independently selected from the group consisting of H, lower alkyl, cycloalkyl, aryl and heteroaryl, with the proviso that at least two R* are H;

X is H, OH, $NH_2$, or a halo group; and $X_1$ are both H, or each; and n is 1, 2, 3, 4, 5, 6 or 7, wherein each B-L- is independently selected from the group consisting of:

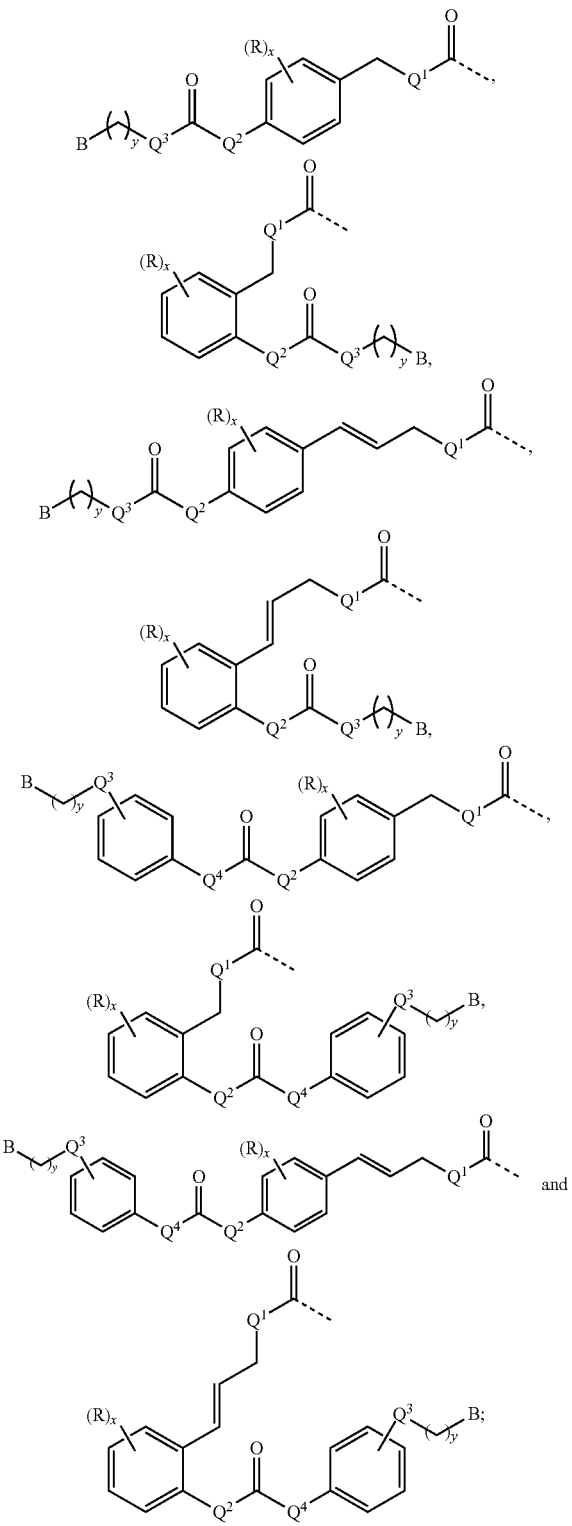

wherein, $Q^1$ is —O— or —S—;

$Q^2$ is —O—, —S— or —N($R_L$)—;

$Q^3$ is —O—, —S—, —N($R_L$)— or —$CH_2$—;

$Q^4$ is —O—, —S—, —N($R_L$)—, —CH$_2$— or a covalent bond;

each R is independently selected from the group consisting of chloro, bromo, fluoro, iodo, nitro, trifluoromethyl and $C_mH_l$, where m is an integer such that $0 \leq m \leq 6$ and l is an integer $\leq 2m+1$;

each $R_L$ is $C_mH_l$, where m is an integer such that $0 \leq m \leq 6$ and l is an integer $\leq 2m+1$;

x is 1, 2, 3 or 4; and y is an integer <10.

2. A compound of Formula (I) or a pharmaceutically acceptable salt, metabolite, solvate or prodrug thereof:

$$A\text{—}[L\text{—}B]_n \quad (I)$$

wherein:
A is a Rifamycin;
L is a cleavable linker for coupling A to B;
B is a phosphonated group selected from the group consisting of:

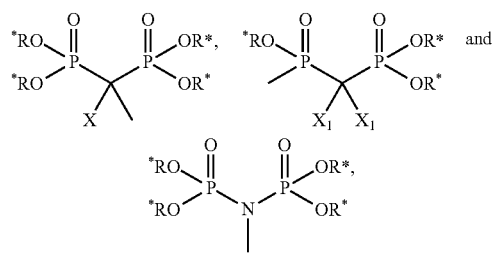

wherein:
each R* is independently selected from the group consisting of H, lower alkyl, cycloalkyl, aryl and heteroaryl, with the proviso that at least two R* are
X is H, OH, NH$_2$, or a halo group; and
$X_1$ are both H, or each; and
n is 1, 2, 3, 4, 5, 6 or 7,
wherein each B-L- is independently represented by the following Formula (BL$_1$):

$$T^1\text{—}R^2\text{—}\underset{\|}{\overset{O}{C}}\text{—}R^1\text{—}\underset{\|}{\overset{O}{C}}\text{----} \quad (BL_1)$$

wherein
each

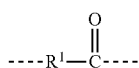

and

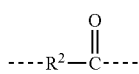

is independently selected from the group consisting of:

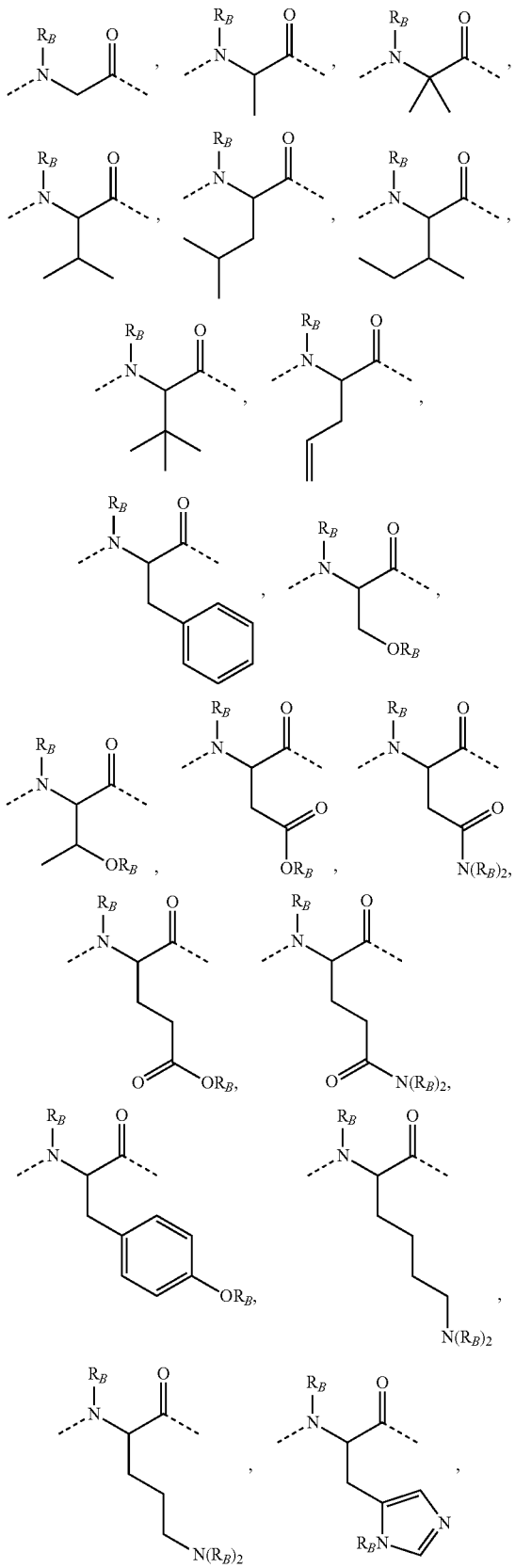

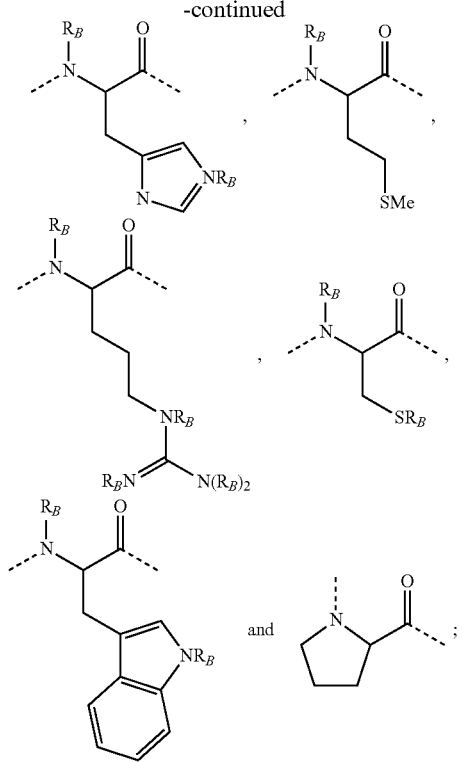
T¹ is selected from the group consisting of:
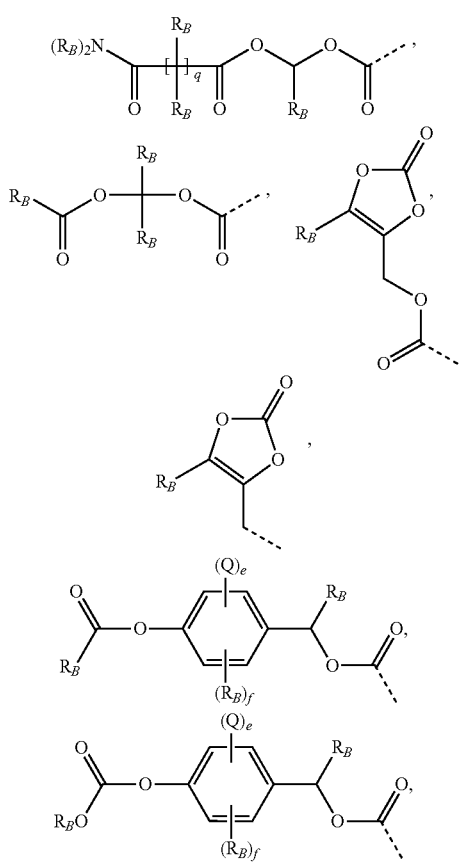
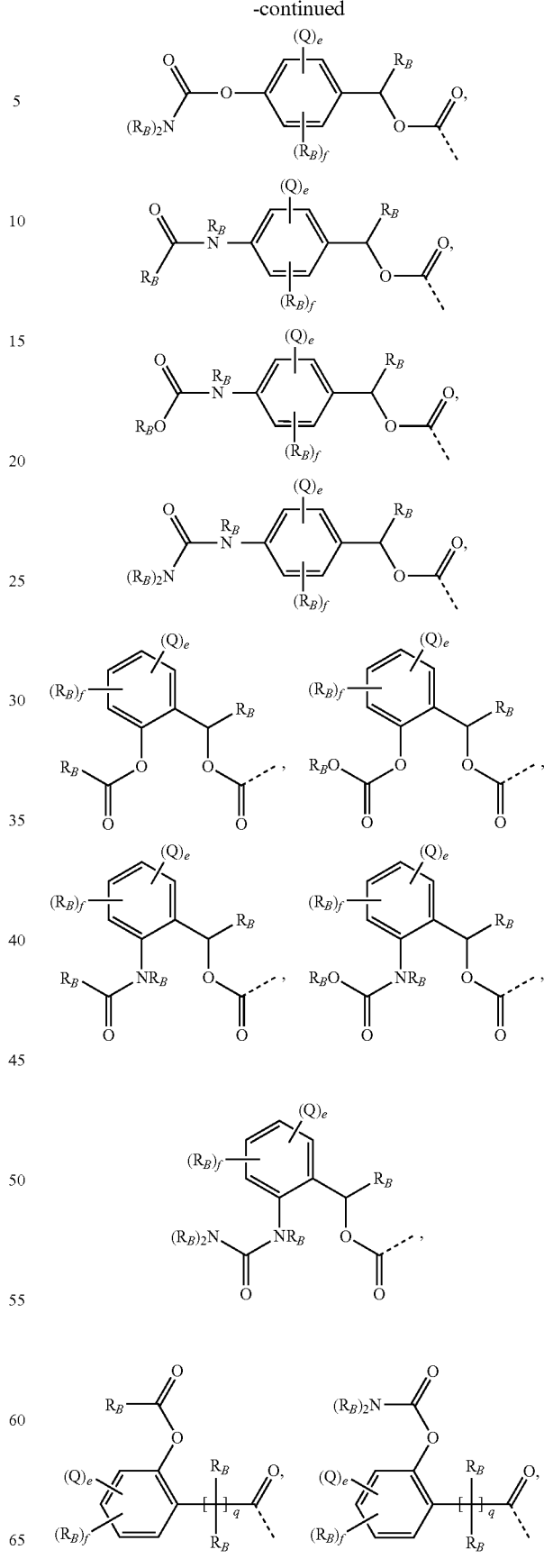

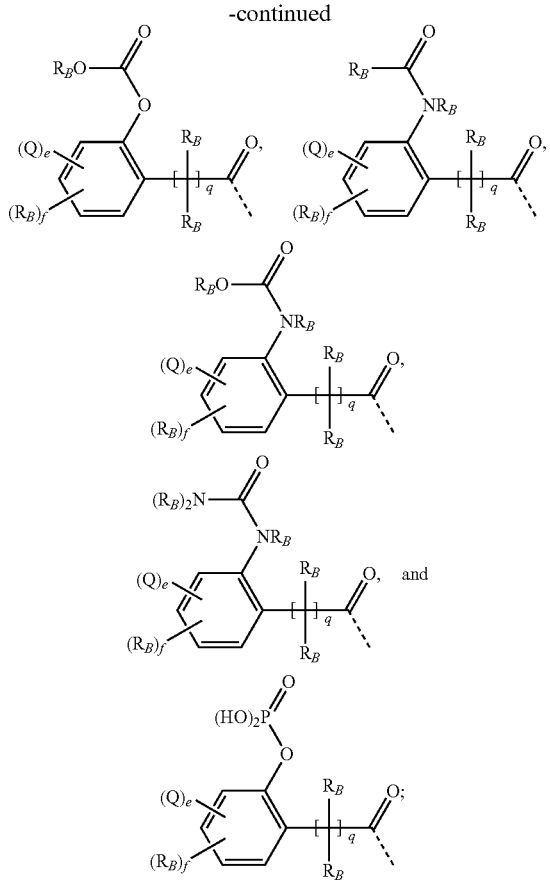

each $R_B$ is independently selected from the group consisting of hydrogen,

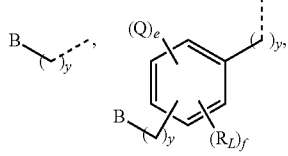

and $C_mH_l$, where m is an integer such that $0 \leq m \leq 6$ and l is an integer $\leq 2m+1$;

each Q is independently nitro, chloro, bromo, iodo or fluoro;

each $R_L$ is $C_mH_l$, where m is an integer such that $0 \leq m \leq 6$ and l is an integer $\leq 2m+1$;

q is 2 or 3;

y is an integer $\leq 10$; and e and f are integers $\geq 0$ such that e+f=4.

3. A compound of Formula (I) or a pharmaceutically acceptable salt, metabolite, solvate or prodrug thereof:

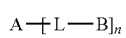 (I)

wherein:

A is a Rifamycin;

L is a cleavable linker for coupling A to B;

B is a phosphorated group selected from the group consisting of:

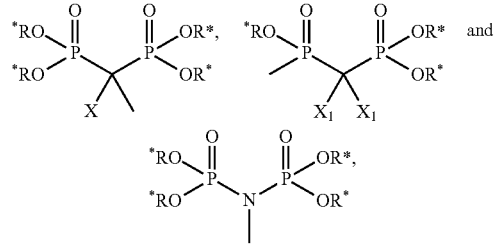

wherein:
each R* is independently selected from the group consisting of H, lower alkyl, cycloalkyl, aryl and heteroaryl, with the proviso that at least two R* are H;

X is H, OH, $NH_2$, or a halo group; and $X_1$ are both H, or each; and n is 1, 2, 3, 4, 5, 6 or 7, wherein each B-L- is independently represented by the following Formula ($BL_2$):

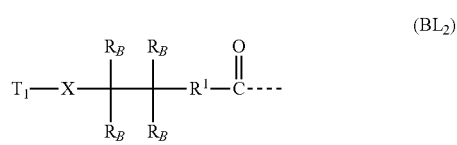 ($BL_2$)

wherein

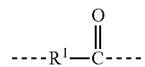

is selected from the group consisting of:

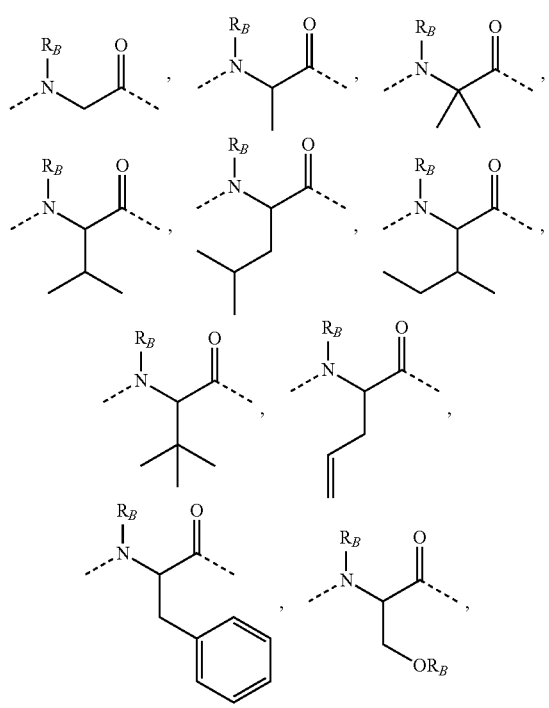

237
-continued
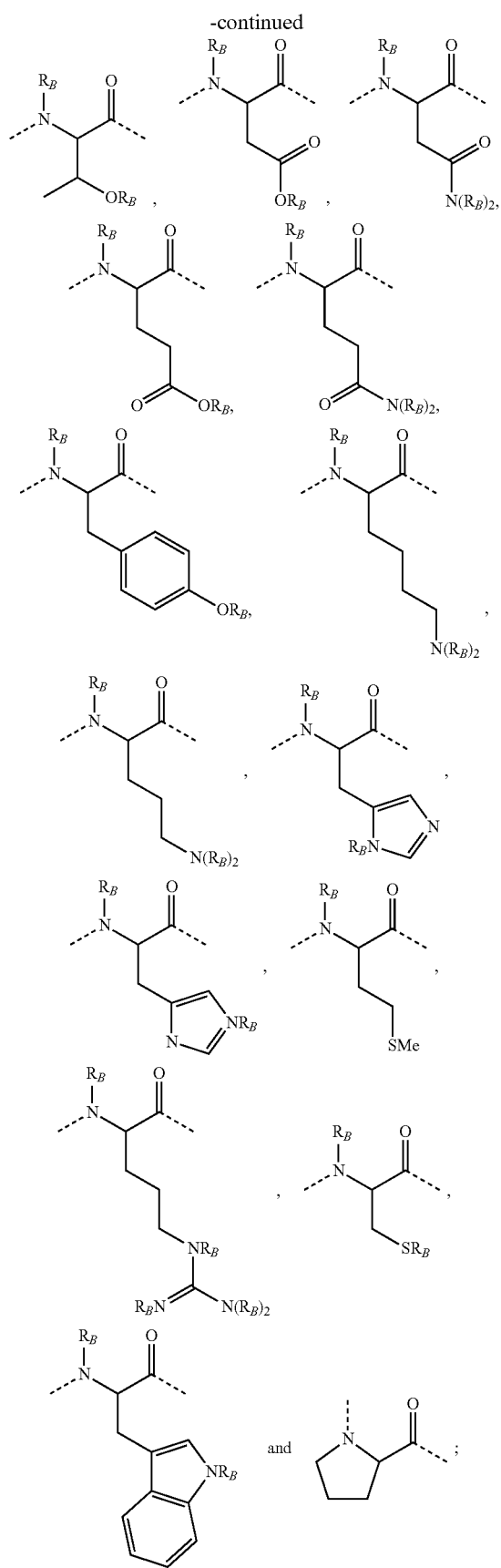
238
$T_1$ is selected from the group consisting of:
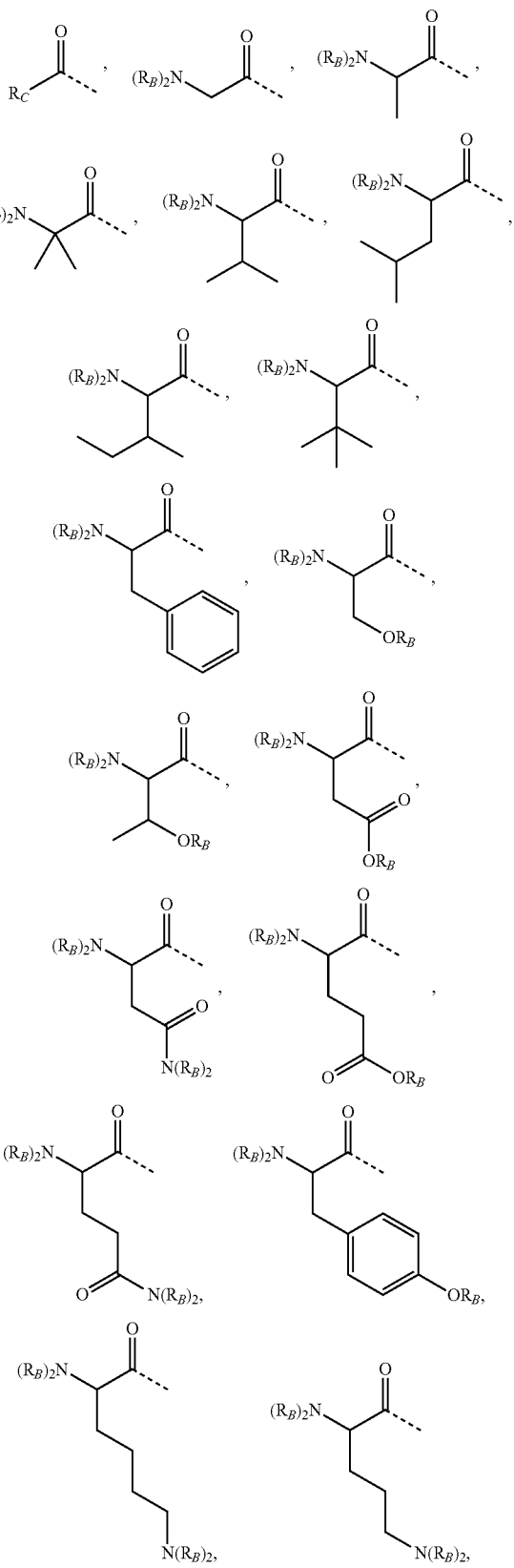

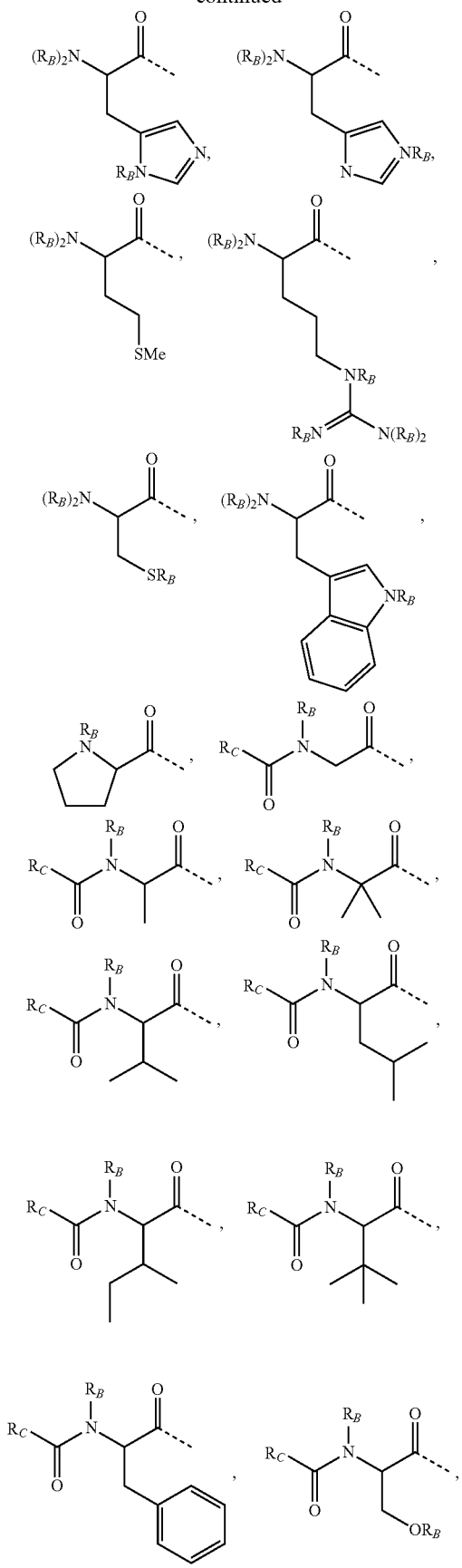
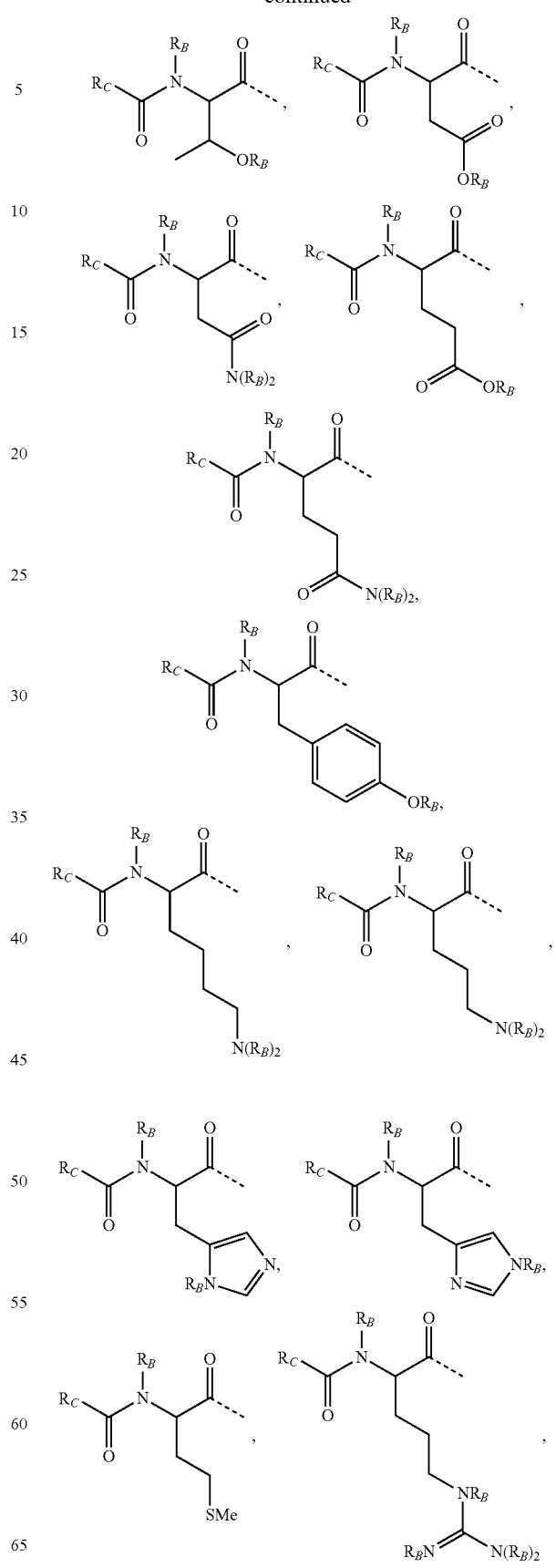

-continued

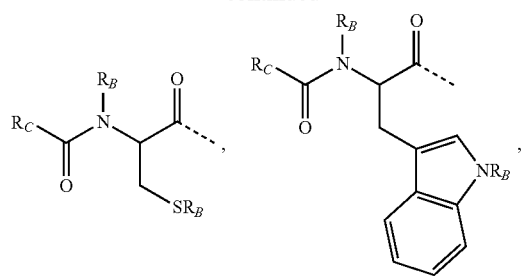

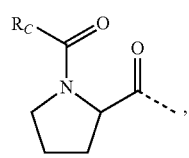

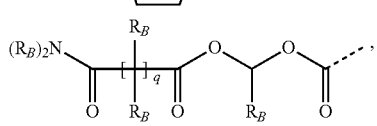

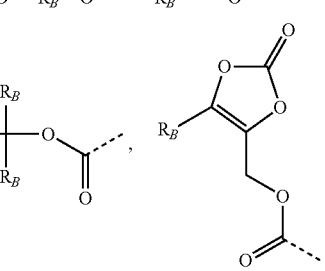

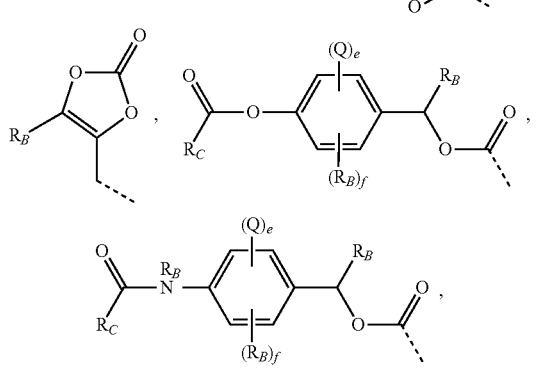

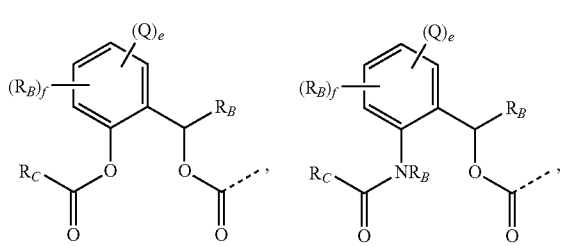

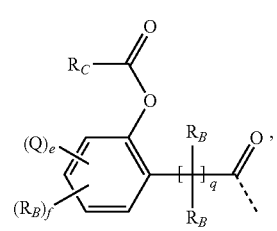

-continued

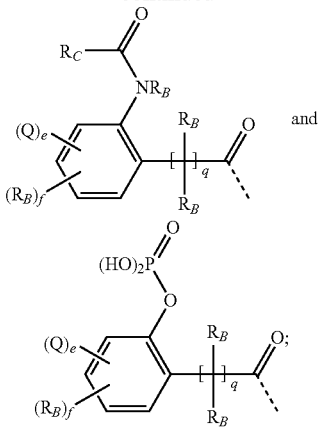

$R_C$ is $R_B$, $OR_B$ or $N(R_B)_2$;
X is —O—, —S— or —N($R_B$)—;
each $R_B$ is independently selected from the group consisting of hydrogen,

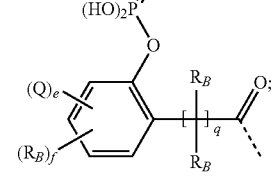

and $C_mH_l$, where m is an integer such that $0 \leq m \leq 6$ and l is an integer $\leq 2m+1$;
each Q is independently nitro, chloro, bromo, iodo or fluoro;
each $R_L$ is $C_mH_l$, where m is an integer such that $0 \leq m \leq 6$ and l is an integer $\leq 2m+1$;
q is 2 or 3;
y is an integer $\leq 10$; and
e and f are integers $\geq 0$ such that e+f=4.

4. A compound of Formula (I) or a pharmaceutically acceptable salt, metabolite, solvate or prodrug thereof:

wherein:
A is a Rifamycin;
L is a cleavable linker for coupling A to B;
B is a phosphonated group selected from the group consisting of:

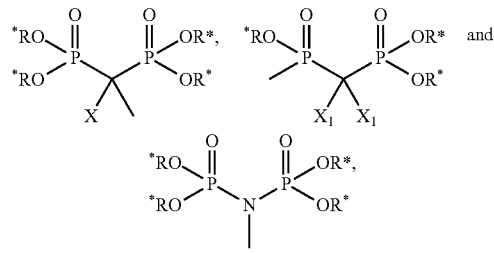

wherein:

each R* is independently selected from the group consisting of H, lower alkyl, cycloalkyl, aryl and heteroaryl, with the proviso that at least two R* are H;

X is H, OH, NH$_2$, or a halo group; and

X$_t$ are both H, or each; and n is 1, 2, 3, 4, 5, 6 or 7, wherein each B-L- is independently represented by the following Formula (BL$_3$):

$$\overset{Y^1}{\underset{\|}{X^2-Y^2-X^1-R^1-C}}\overset{O}{\underset{\|}{-}}--- \quad (BL_3)$$

wherein $$----R^1-\overset{O}{\underset{\|}{C}}----$$

is independently selected from the group consisting of:

[structures of amino acid residues with R$_B$ groups: glycine, alanine, aminoisobutyric, valine, leucine, isoleucine, tert-leucine, phenylalanine, serine (OR$_B$), threonine (OR$_B$), aspartate (OR$_B$), asparagine (N(R$_B$)$_2$)]

-continued

[structures: glutamate (OR$_B$), glutamine (N(R$_B$)$_2$), tyrosine (OR$_B$), lysine (N(R$_B$)$_2$), ornithine (N(R$_B$)$_2$), histidine, histidine (NR$_B$), methionine (SMe), arginine (R$_B$N, N(R$_B$)$_2$), cysteine (SR$_B$), tryptophan (NR$_B$), and proline];

X$^1$ is —O—, —S— or —N(R$_B$)—;

$$\overset{Y^1}{\underset{\|}{----Y^2}}--- \text{ is } ----\overset{O}{\underset{\|}{C}}----, ----\overset{NR_D}{\underset{\|}{C}}----, ----\overset{O}{\underset{\|}{S}}---- \text{ or}$$

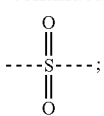

$X^2$ is —$N(R_D)_2$, —$OR_D$ or —$SR_D$;

$R_D$ is hydrogen, $R_B$ or is selected from the group consisting of:

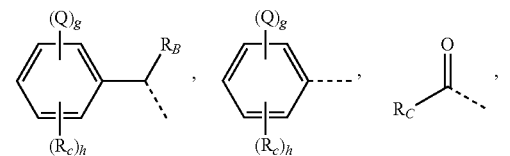

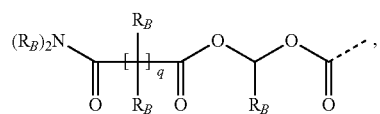

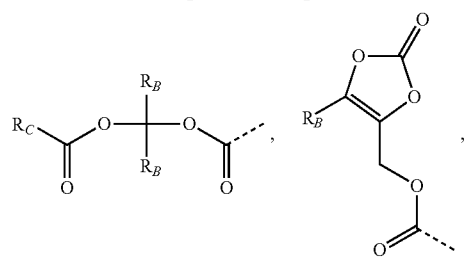

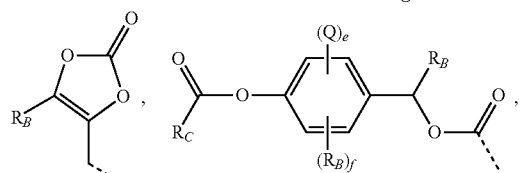

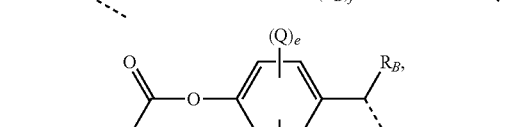

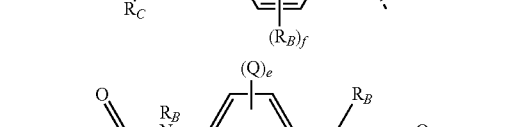

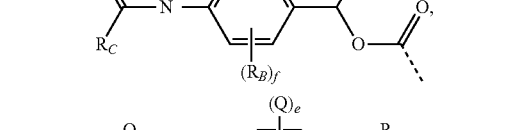

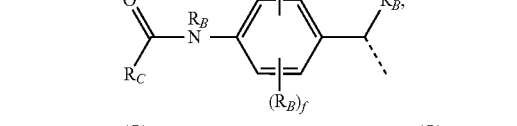

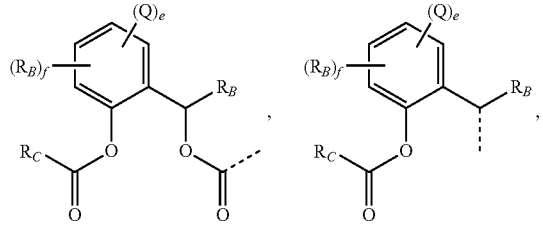

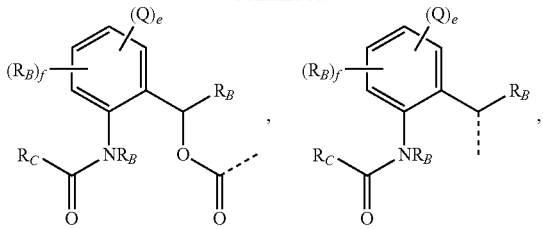

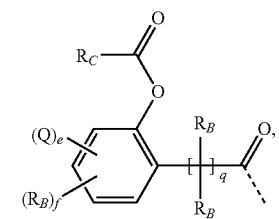

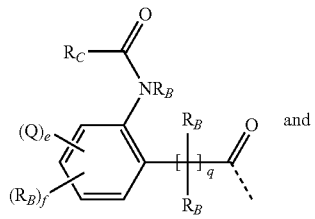

and

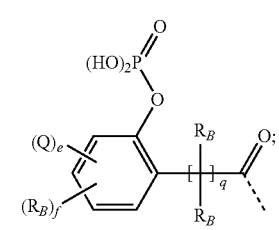

$R_C$ is $R_B$, $OR_B$ or $N(R_B)_2$;

each $R_B$ is independently selected from the group consisting of hydrogen,

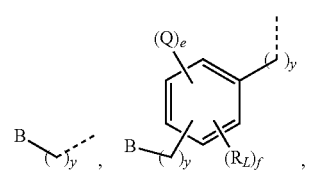

and $C_mH_l$, where m is an integer such that $0 \leq m \leq 6$ and l is an integer $\leq 2m+1$;

each Q is independently —$SR_c$, —$S(O)R_c$, —$S(O)_2R_c$, —$COR_c$, nitro, chloro, bromo, iodo or fluoro;

each $R_L$ is $C_mH_l$, where m is an integer such that $0 \leq m \leq 6$ and l is an integer $\leq 2m+1$;

q is 2 or 3;

y is an integer $\leq 10$;

e and f are integers $\geq 0$ such that e+f=4; and g and h are integers $\geq 0$ such that g+h=5.

5. The compound of any one of claims 1-4, wherein said Rifamycin A has a structure represented by the following Formula (IA):

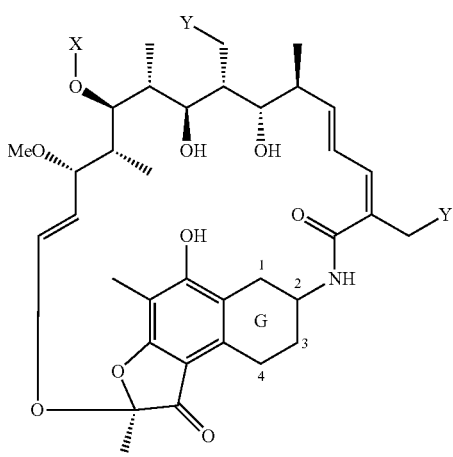

(IA)

wherein:

X is H— or $R_1CO$—, wherein $R_1$ is a substituted or unsubstituted alkyl chain of 1-6 carbons;

each Y is independently selected from the group consisting of H— and RO—, wherein R is H—, $R_1$—, or $R_1CO$—, with $R_1$ defined as above;

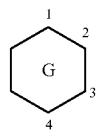

is selected from the group consisting of Formulae IA1-IA9:

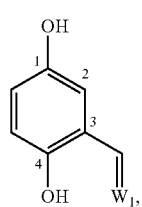

IA1

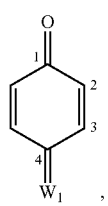

IA2

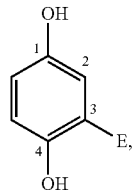

IA3

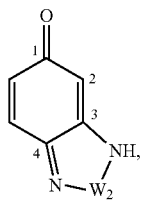

IA4

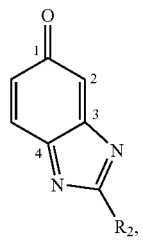

IA5

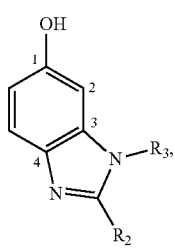

IA6

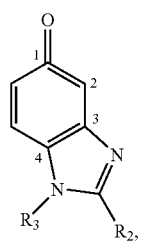

IA7

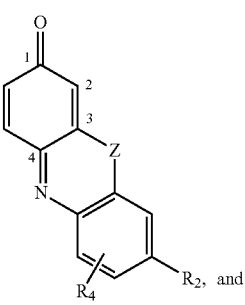

IA8

, and

-continued (IA9)

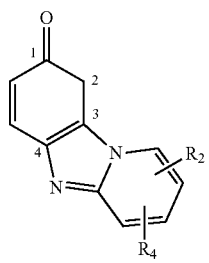

wherein

R₂ is H—, a substituted or unsubstituted alkyl chain of 1-10 carbons, or a dialkyl amino group, wherein said dialkyl amino group may be a substituted piperidine, a substituted morpholine or a substituted piperazine;

R₃ is H— or a substituted or unsubstituted alkyl chain of 1-7 carbons;

R₄ is a hydroxyl group, a sulfhydryl group or a substituted or unsubstituted alkyl chain of 1-3 carbons;

W₁ is oxygen or —NR₂ with R₂ defined as above;

W₂ is a substituted or unsubstituted methylene, including:

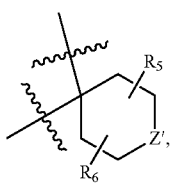

wherein R₅ and R₆ are independently H— or a substituted or unsubstituted alkyl chain of 1-5 carbons, and Z' is an oxygen atom, a sulfur atom, a substituted methylene, a carbonyl, —NR₁ or —N(O)R₁ where R₁ is defined as above;

E is a halogen or R₂, where R₂ is defined as above; and

Z is O, S or NR₃, where R₃ is defined as above.

6. The compound of any one of claims 1-4, wherein A has a structure selected from the group consisting of Formula (IB), Formula (IC), Formula (ID), Formula (IE) and Formula (IF):

(IB)

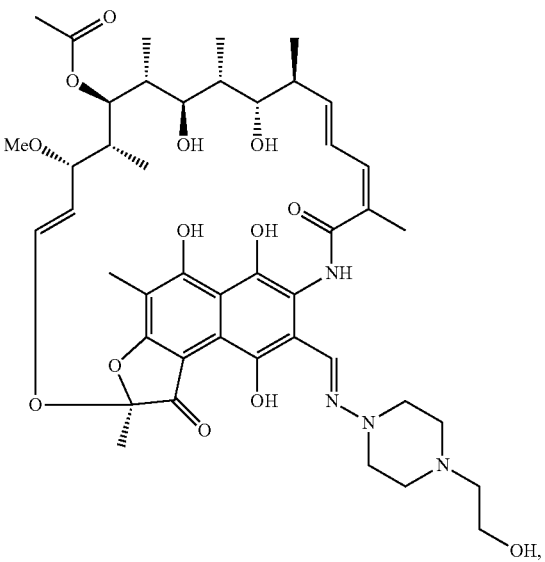

(IC)

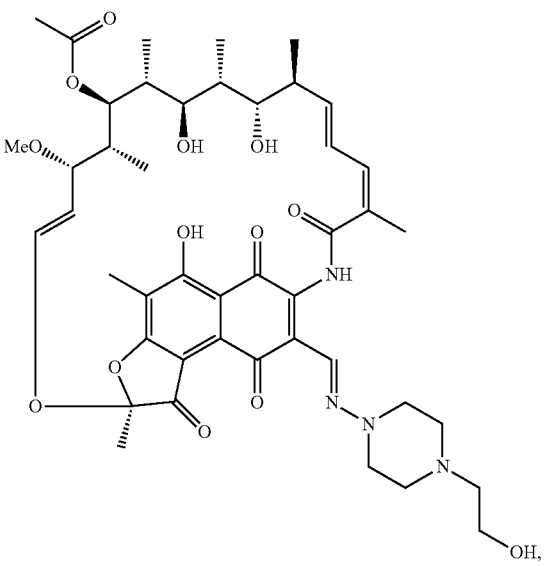

251
-continued (ID)
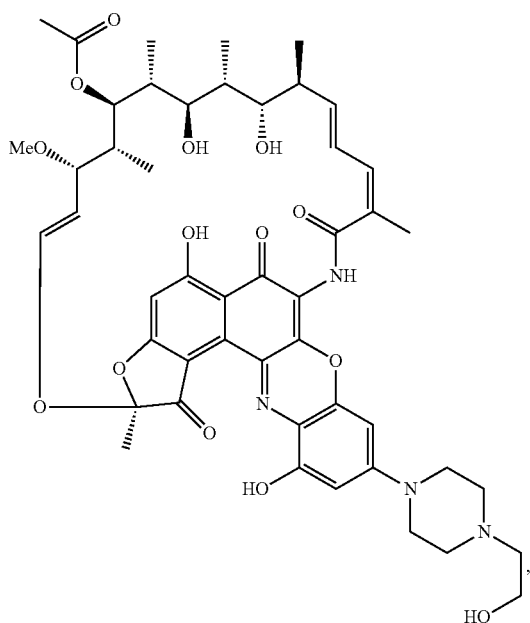

(IE)
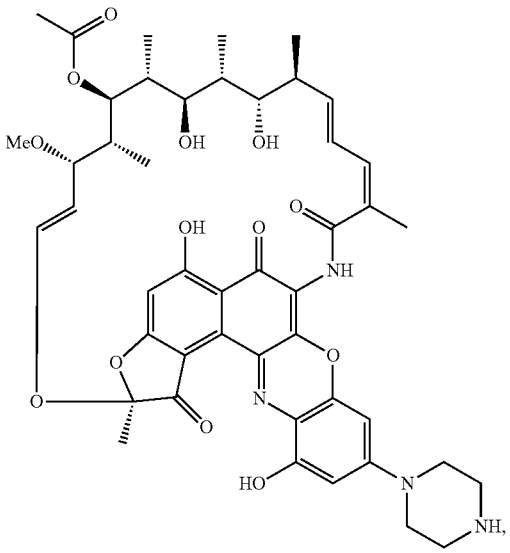

252
-continued (IF)
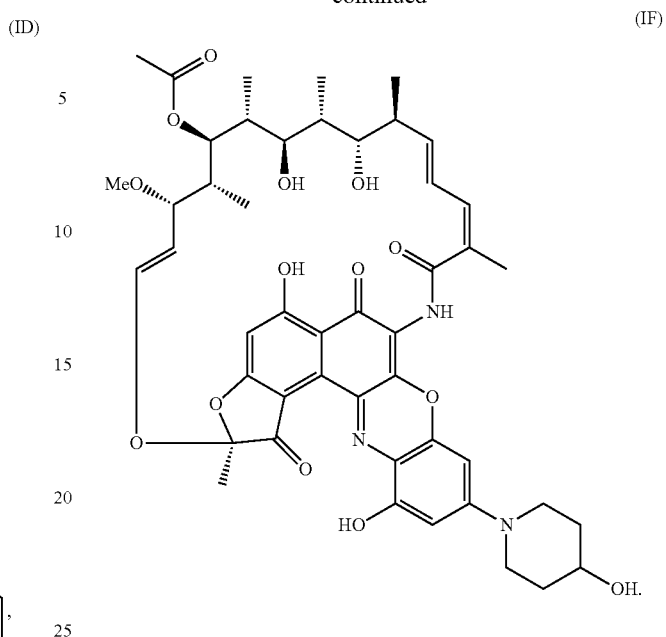

7. The compound of any one of claims 1-4, wherein A is selected from the group consisting of Rifampicin, Rifapentin, Rifabutin, Rifalazil, Rifaximin and Rifandin.

8. A compound represented by Formula (II) or a pharmaceutically acceptable salt, metabolite, solvate or prodrug thereof:

(II)
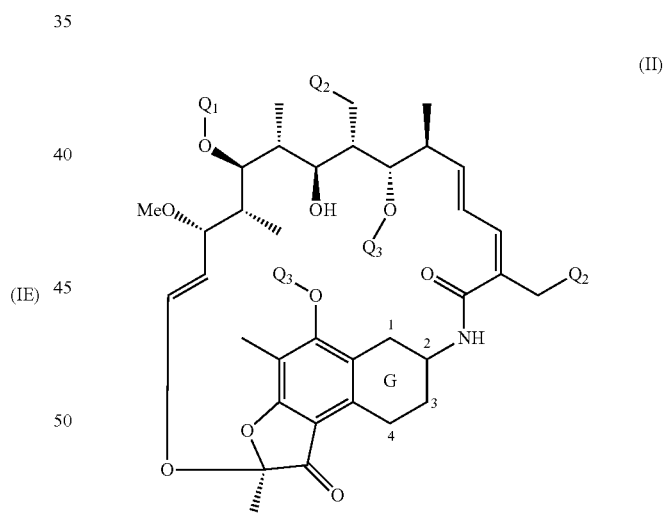

wherein:
$Q_1$ is H—, $R_1$CO— or $L_1$-, wherein $R_1$ is a substituted or unsubstituted alkyl chain of 1-6 carbons;

each $Q_2$ is independently selected from the group consisting of H—, $R_x$O— and $L_2$O—, wherein $R_x$ is H—, $R_1$— or $R_1$CO—, with $R_1$ defined as above;

each $Q_3$ is independently selected from the group consisting of H— and $L_3$-;

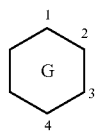

is selected from the group consisting of Formulae IA1-IA9:

IA1
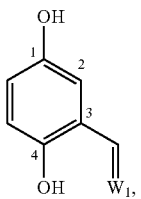

IA2
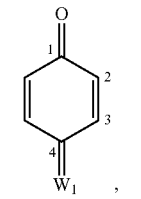

IA3
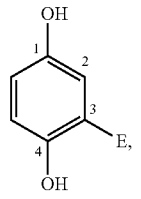

IA4
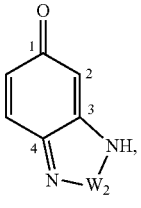

IA5
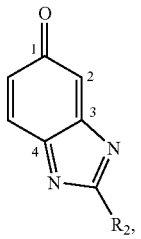

IA6
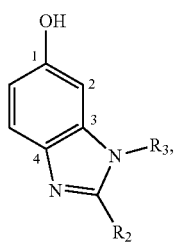

IA7
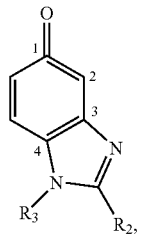

IA8

[structure with Z, N, $R_4$, $R_2$]

IA9
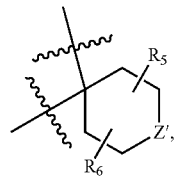

wherein
  $R_2$ is H—, a substituted or unsubstituted alkyl chain of 1-10 carbons or a dialkyl amino group, wherein said dialkyl amino group may be a substituted piperidine, a substituted morpholine or a substituted piperazine, wherein the substituent is one member selected from the group consisting of $L_4O$—, $L_5S$— and $L_6NR_7$—, wherein $R_7$ is a substituted or unsubstituted alkyl chain of 1-7 carbons;
  $R_3$ is H—, a substituted or unsubstituted alkyl chain of 1-7 carbons or $L_7$-;
  $R_4$ is a hydroxyl group, a sulfhydryl group or a substituted or unsubstituted alkyl chain of 1-3 carbons, $L_8O$— or $L_9S$—;
  $W_1$ is oxygen or —$NR_2$, with $R_2$ defined as above;
  $W_2$ is a substituted or unsubstituted methylene, including

[structure with $R_5$, $R_6$, Z']

wherein $R_5$ and $R_6$ are independently H— or a substituted or unsubstituted alkyl chain of 1-5 carbons, and Z' is an oxygen atom, a sulfur atom, a substituted methylene, a carbonyl, —$NR_1$ or —$N(O)R_1$ where $R_1$ is defined as above;
  E is a halogen or $R_2$, where $R_2$ is defined as above;
  Z is O, S or $NR_3$, where $R_3$ is defined as above;

each $L_1$, $L_2$, $L_3$, $L_4$, $L_5$, $L_6$, $L_7$, $L_8$ and $L_9$ is a group of Formula (Ia):

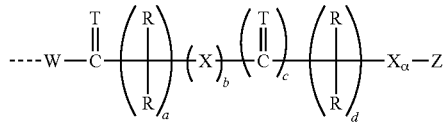
(Ia)

wherein:
  each T is independently oxygen or sulfur;
  each R is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, substituted aryloxy, and $-R^a-Y-R^b-Y-R^b-B$;
  W is a covalent bond or is selected from the group of

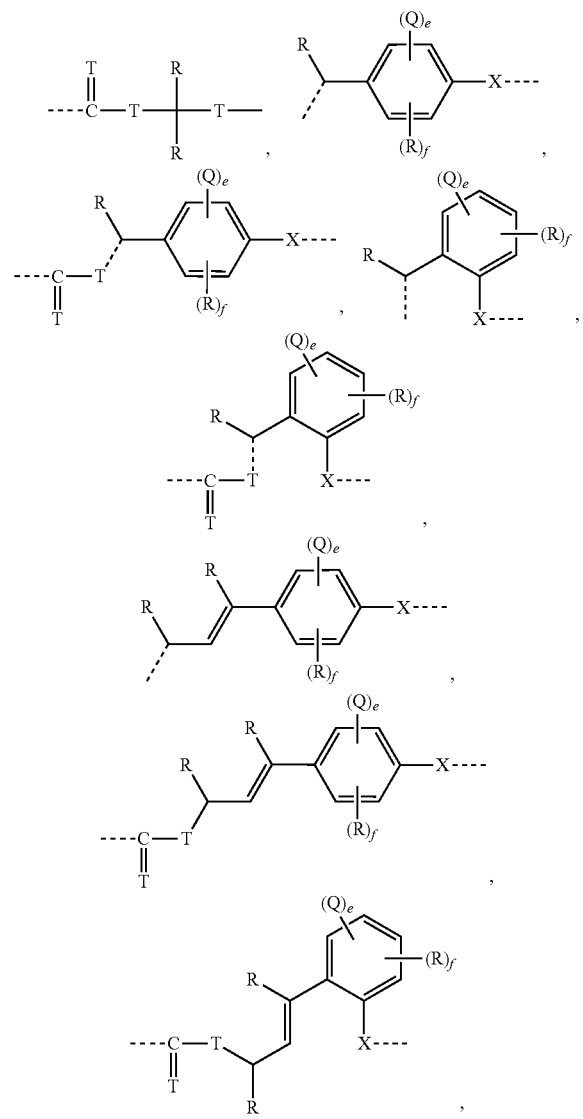

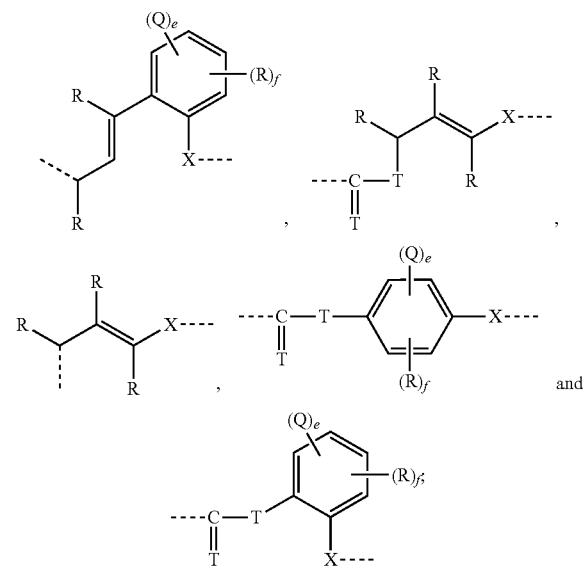

each X is independently —O—, —S— or —N(R)—;
each Q is independently nitro, chloro, bromo, iodo or fluoro;
Z is selected from the group consisting of hydrogen, acyl, substituted acyl, aroyl, substituted aroyl, alkoxycarbonyl, substituted alkoxycarbonyl, aryloxycarbonyl, substituted aryloxycarbonyl,

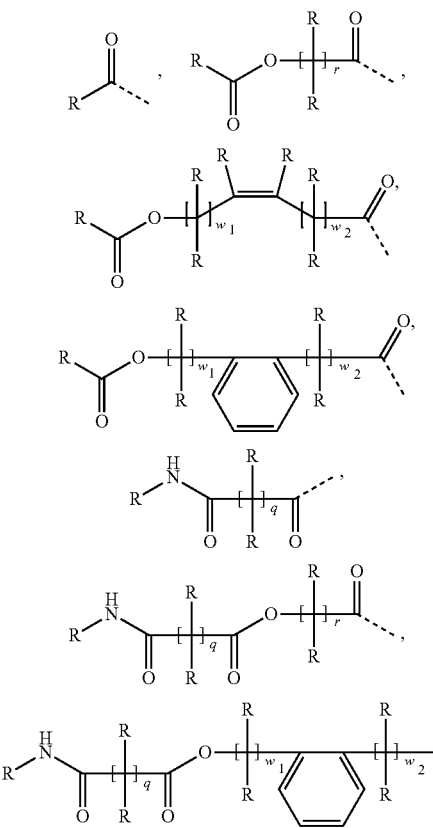

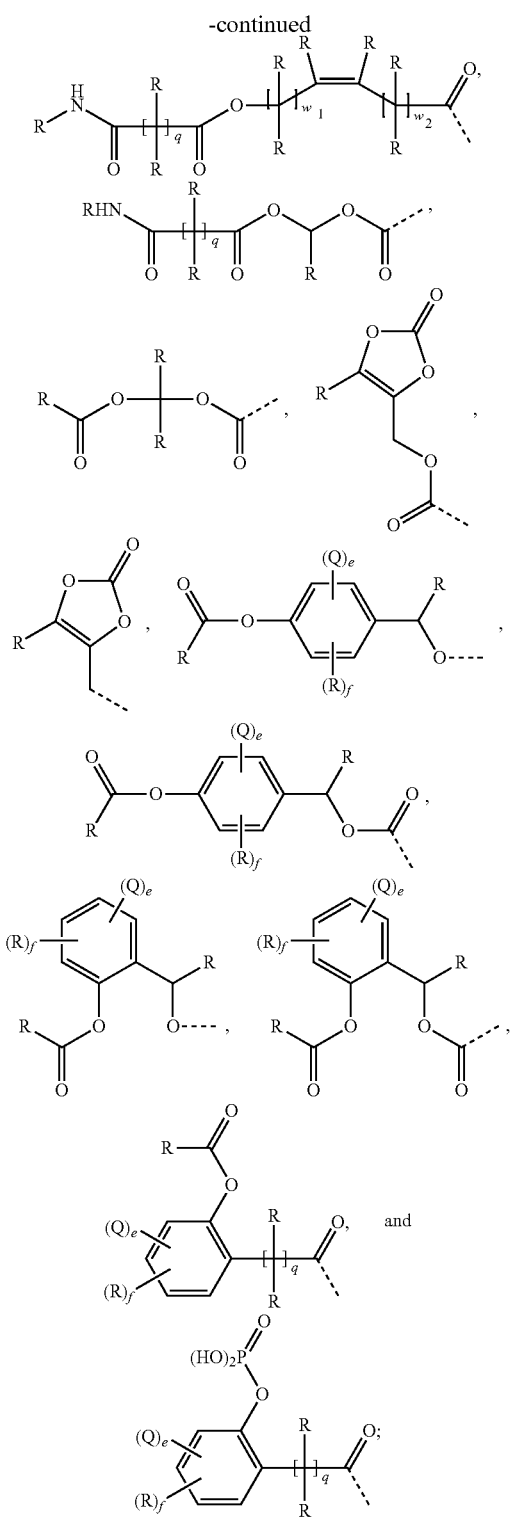

each $R^a$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each $R^b$ is independently selected from the group consisting of a covalent bond, alkylene, substituted alkylene, alkenylene, substituted alkenylene, alkynylene, substituted alkynylene, arylene and substituted arylene;

each Y is independently selected from the group consisting of a covalent bond, —$CH_2$—, —O—, —S—, —S—S—, —$NR^c$—, —S(O)—, —$SO_2$—, —$NR^cC(O)$—, —$OSO_2$—, —OC(O)—, —$N(R^c)SO_2$—, —$C(O)NR^c$—, —C(O)O—, —$SO_2NR^c$—, —$SO_2O$—, —$P(O)(OR^c)O$—, —$P(O)(OR^c)NR^c$—, —OP(O)$(OR^c)O$—, —OP(O)$(OR^c)NR^c$—, —OC(O)O—, —$NR^c(O)O$—, —$NR^c(O)NR^c$—, —$OC(O)NR^c$—, —C(O)—, and —$N(W)SO_2NR^c$—;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$C(O)R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

q is 2 or 3;

r is 1, 2, 3, 4 or 5;

$w_1$ and $w_2$ are each integers $\geq 0$ such that their sum ($w_1 + w_2$) is 1, 2 or 3;

a, b, c, d are each integers >0 such that a+b+c+d<7;

e and f are each integers >0 such that e+f=4;

α is 0 or 1; and

B is a phosphonated group selected from the group consisting of:

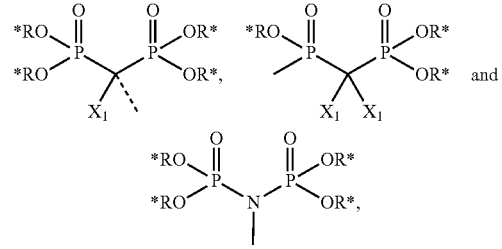

wherein:

each R* is independently selected from the group consisting of H, lower alkyl, cycloalkyl, aryl and heteroaryl, with the proviso that at least two R* are H;

each $X_1$ is independently selected from the group consisting of H, OH, $NH_2$, and a halo group;

with the proviso that at least one of R in Formula (Ia) is —$R^a$—Y—$R^b$—Y—$R^b$—B;

with the further proviso that at least one of $L_1$, $L_2$, $L_3$, $L_4$, $L_5$, $L_6$, $L_7$, $L_8$ and $L_9$ is present; and with the additional proviso that none of $L_1$, $L_2$, $L_3$, $L_4$, $L_5$, $L_6$, $L_7$, $L_8$ and $L_9$ is one of the following structures:

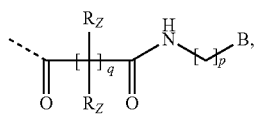

-continued
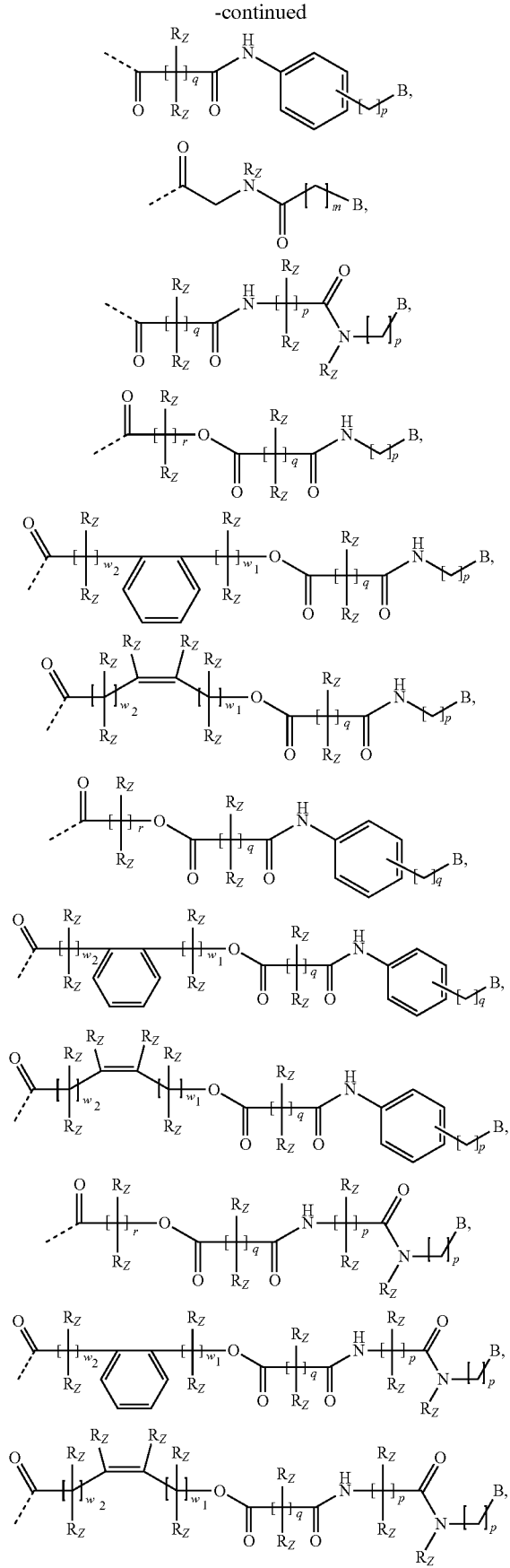
-continued
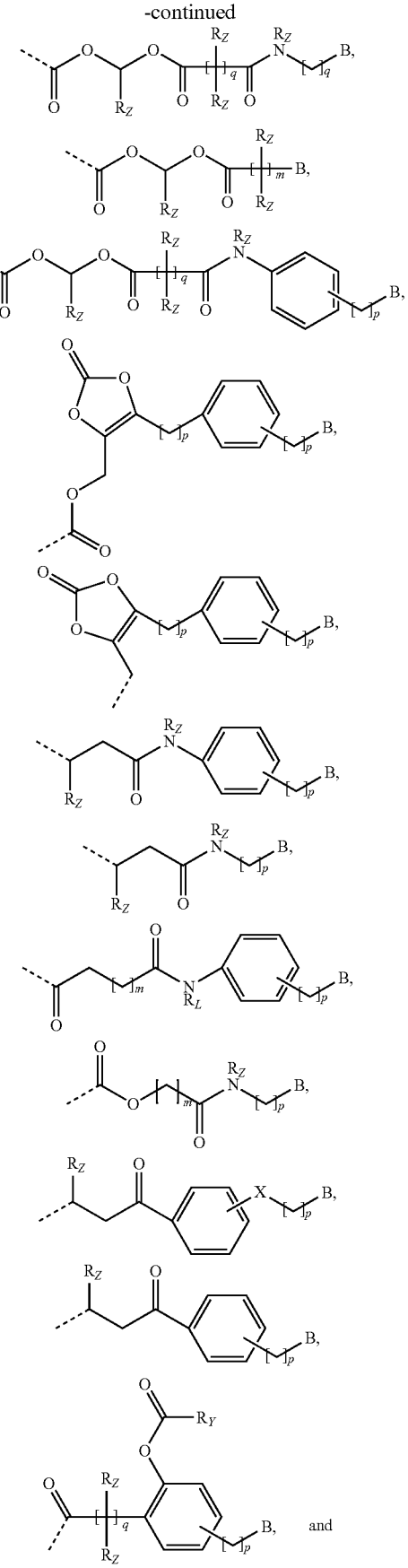

-continued
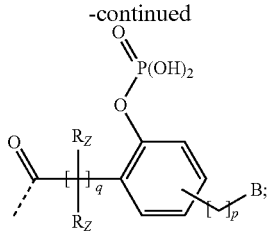
wherein:
X, B, q, r, $w_1$ and $w_2$ are defined as above;
each p is independently 0 or an integer $\leq 10$;
each $R_L$ independently H, ethyl or methyl;
each $R_z$ is independently H, ethyl or methyl;
$R_y$ is represented by $C_iH_j$, where i is an integer $\leq 20$ and j is an integer $\leq 2i+1$; and
m is an integer <10.
9. A compound selected from the group consisting of:
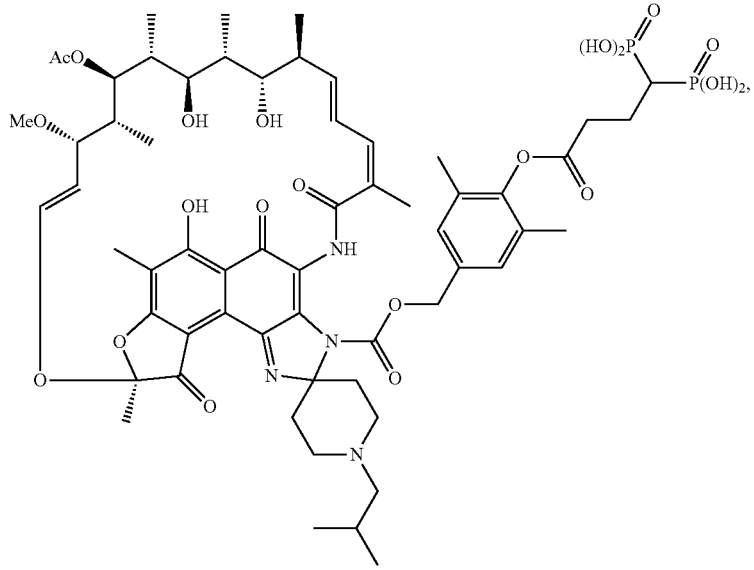
(19)
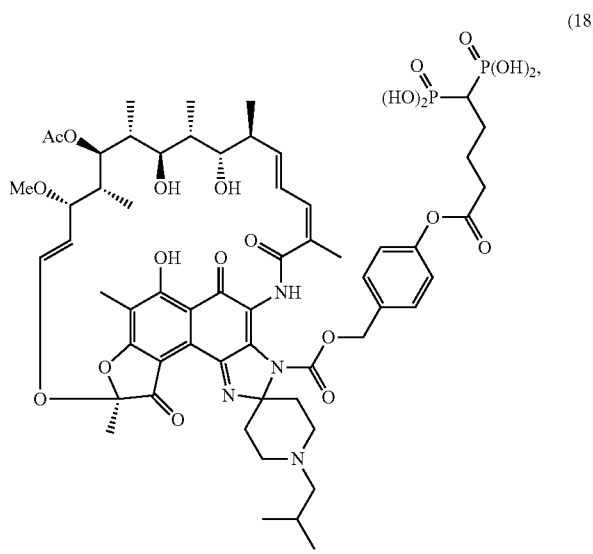
(18)
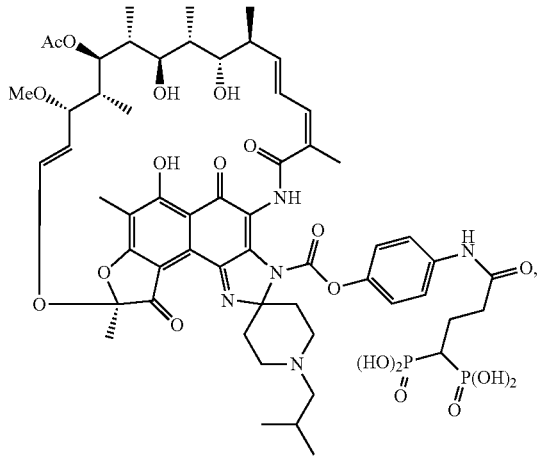
(28)

-continued
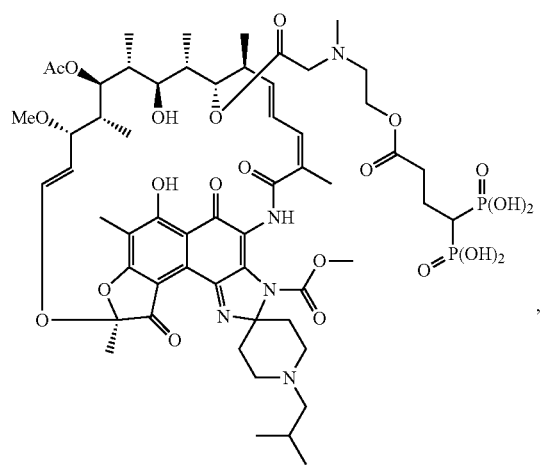
(36)
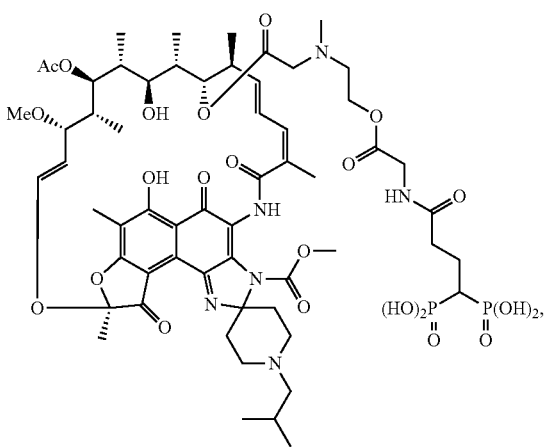
(42)
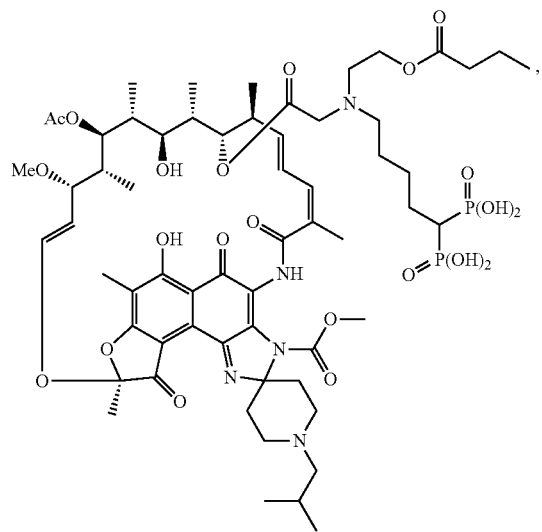
(48a)
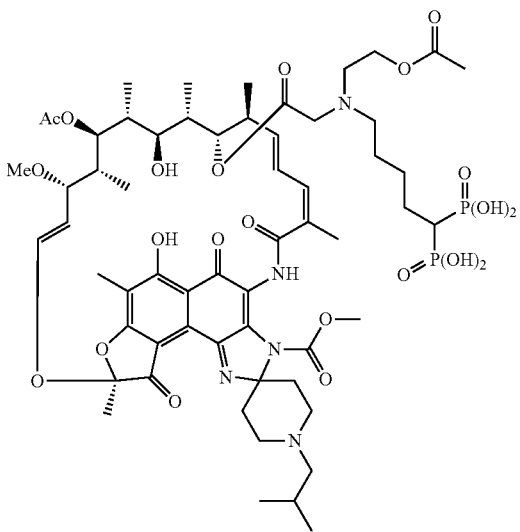
(48b)
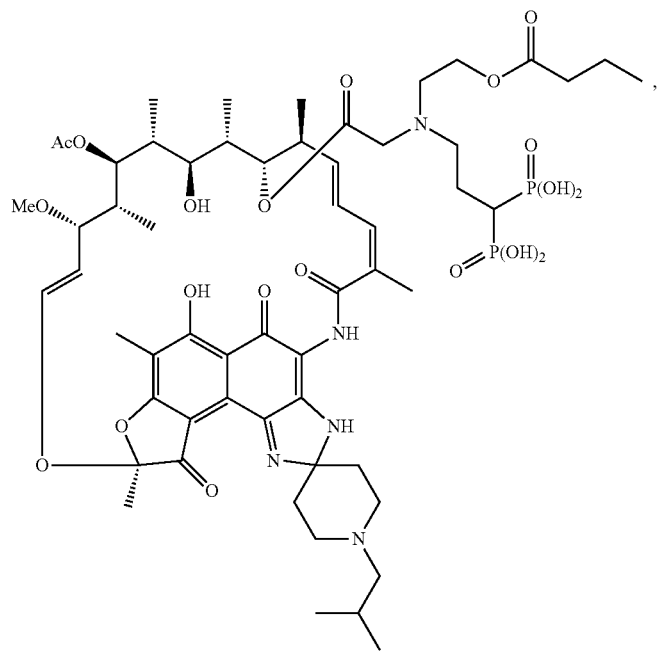
(52)

-continued
(59)
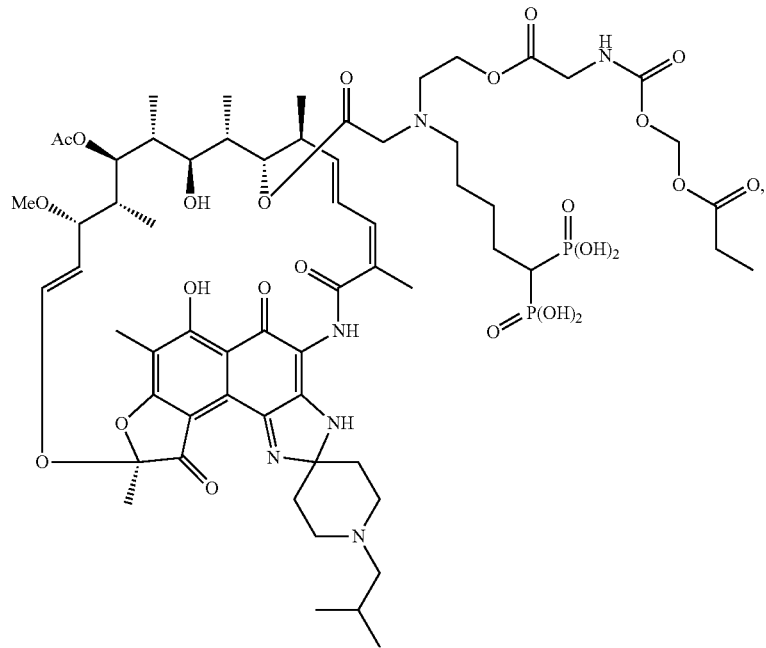
(66)
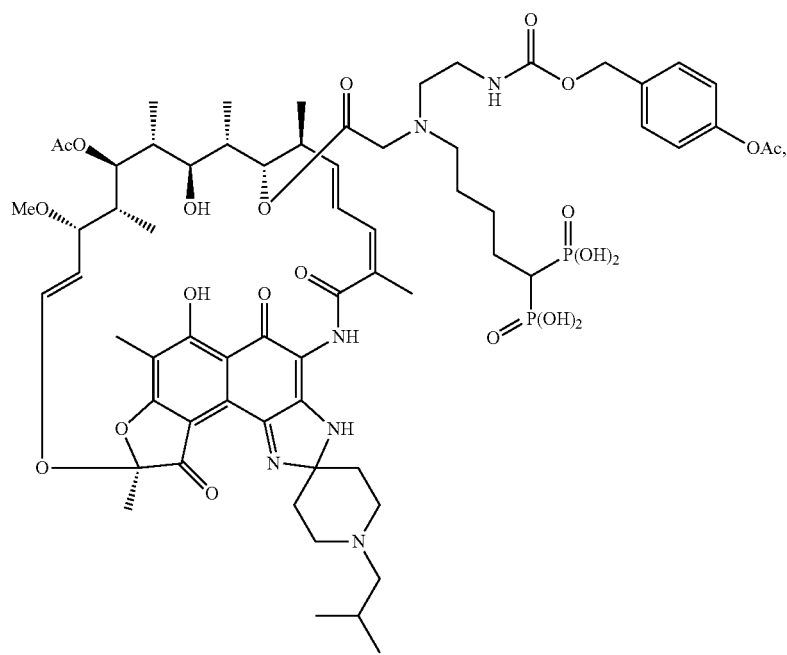

-continued
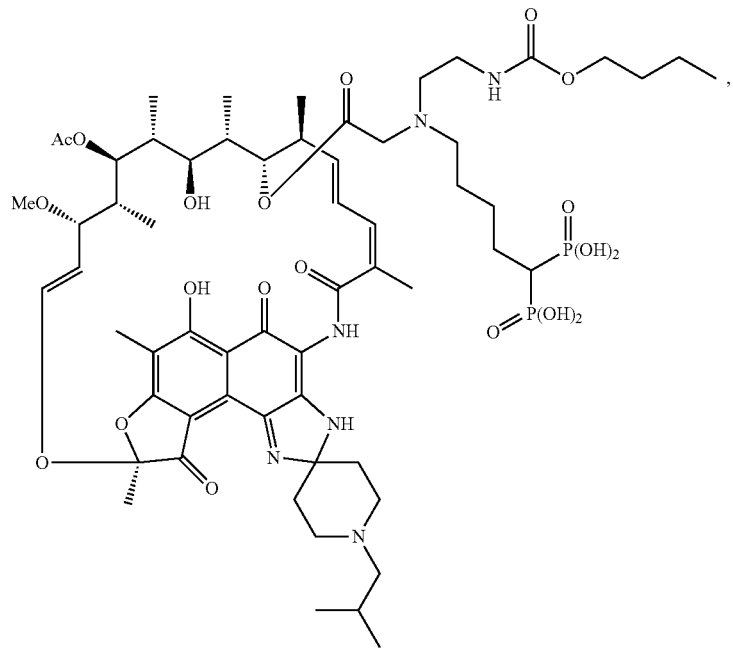
(71)
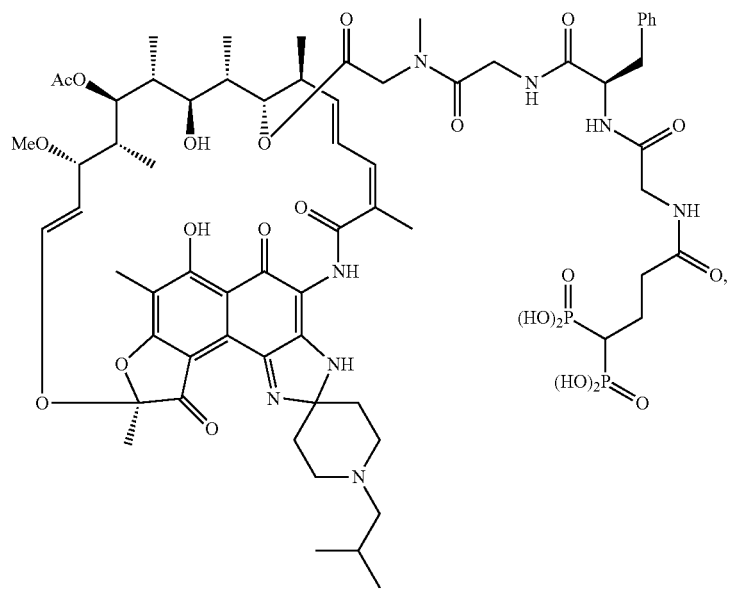
(79a)

-continued (79b)

(89)

(95)

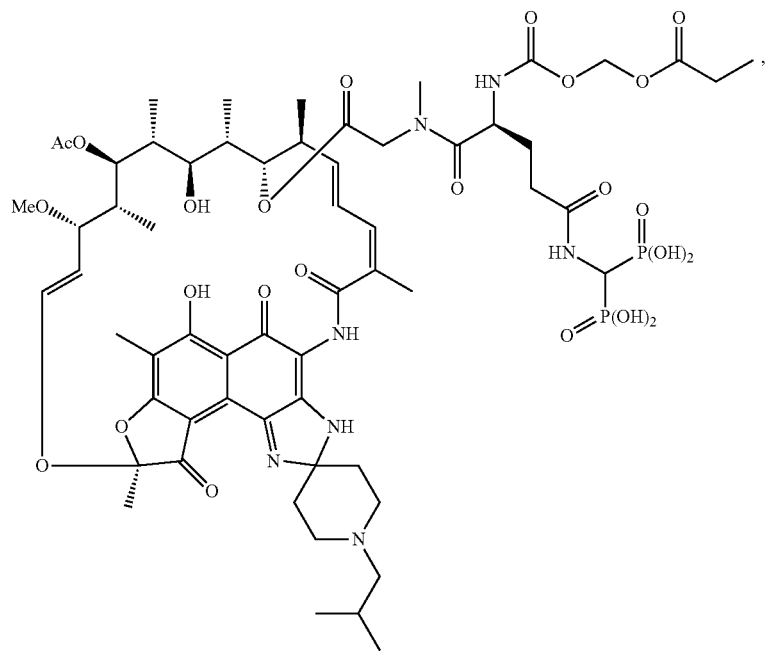
(102)
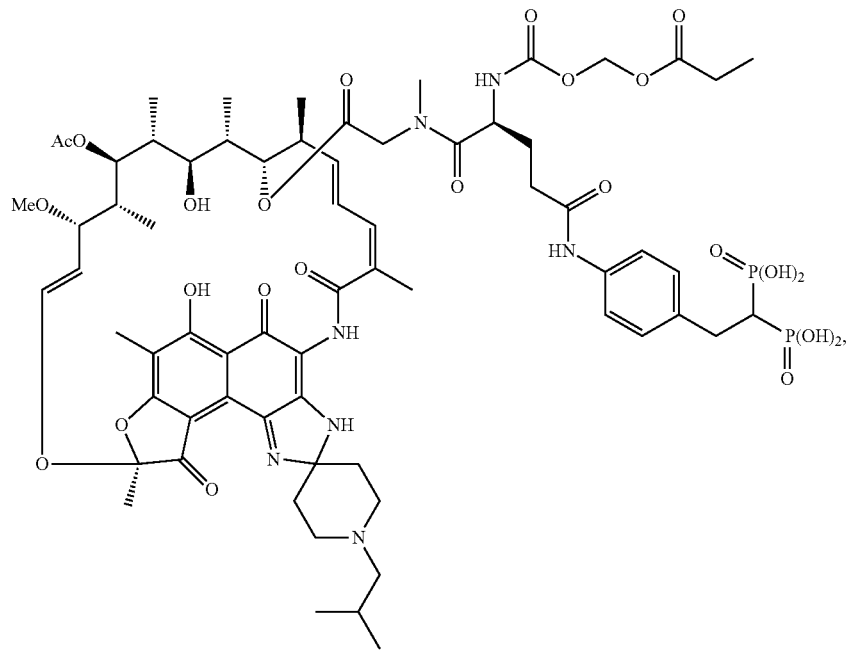
(110)

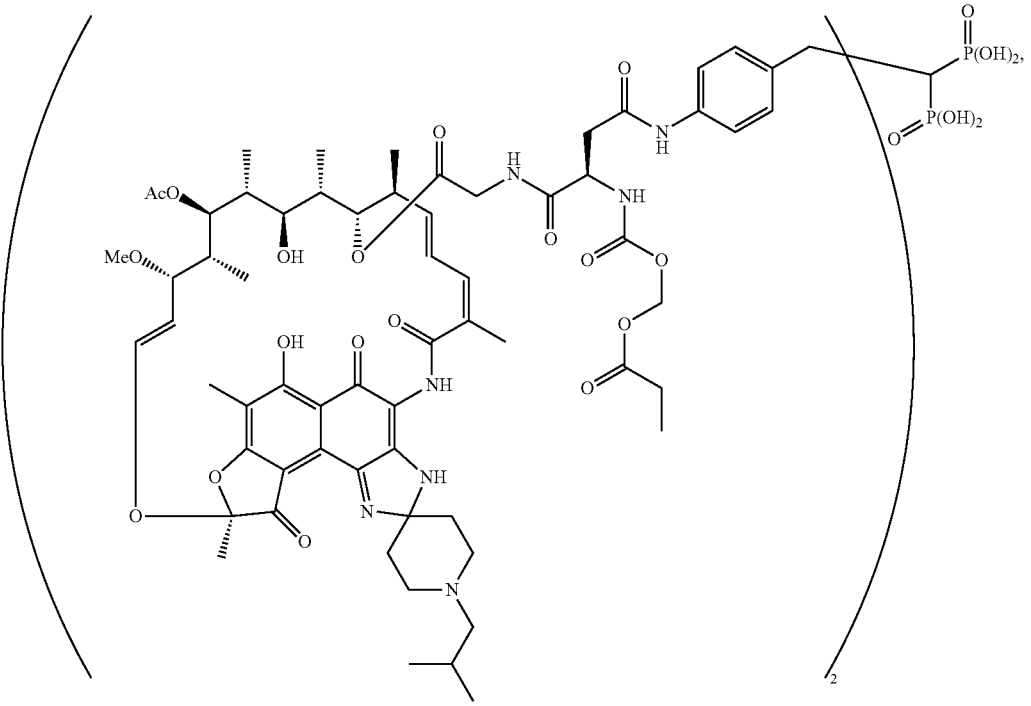
(118)
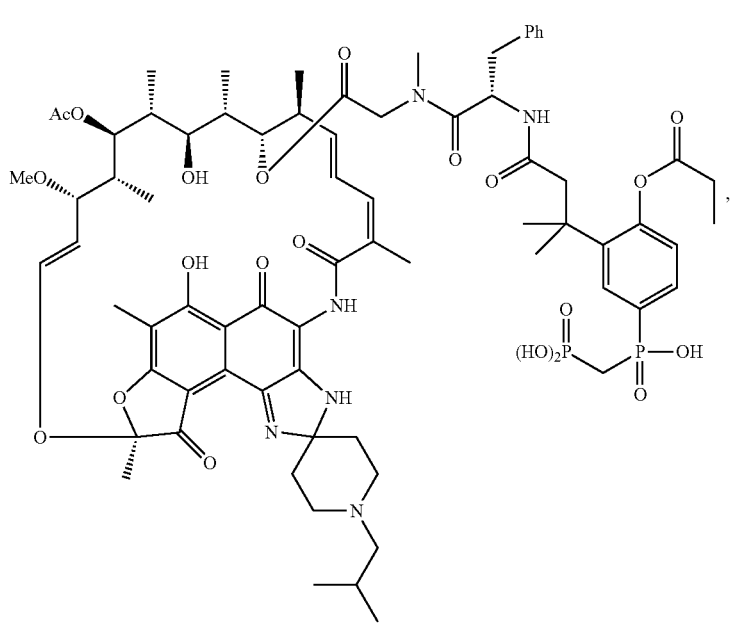
(128)

-continued
(138)
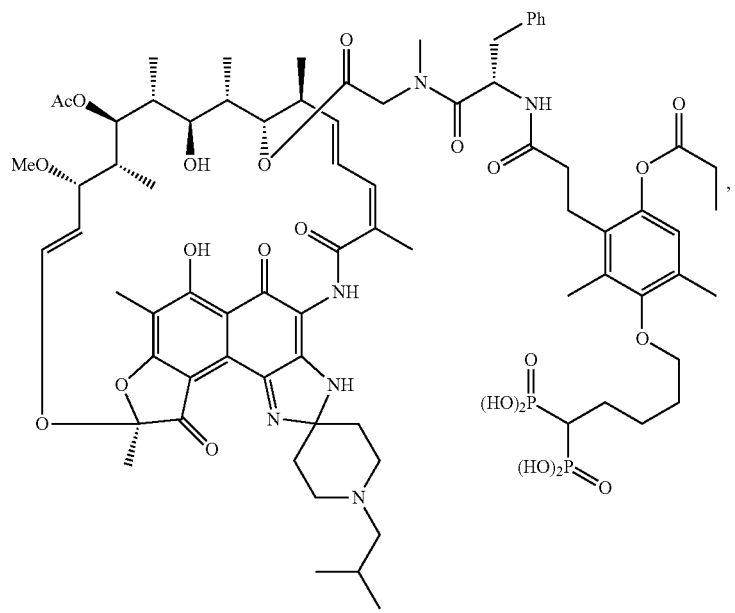
(140)
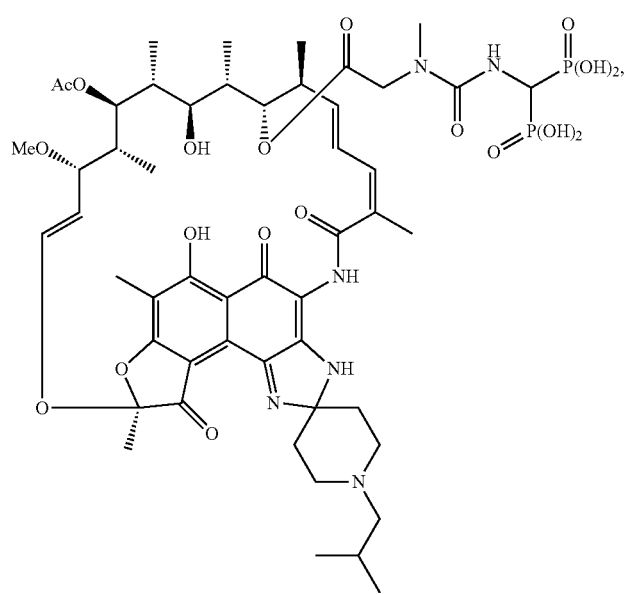

-continued
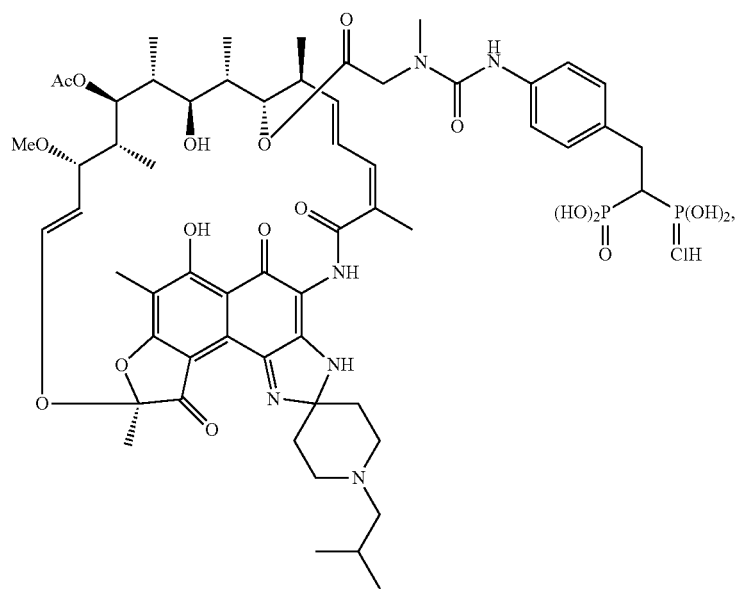
(142b)
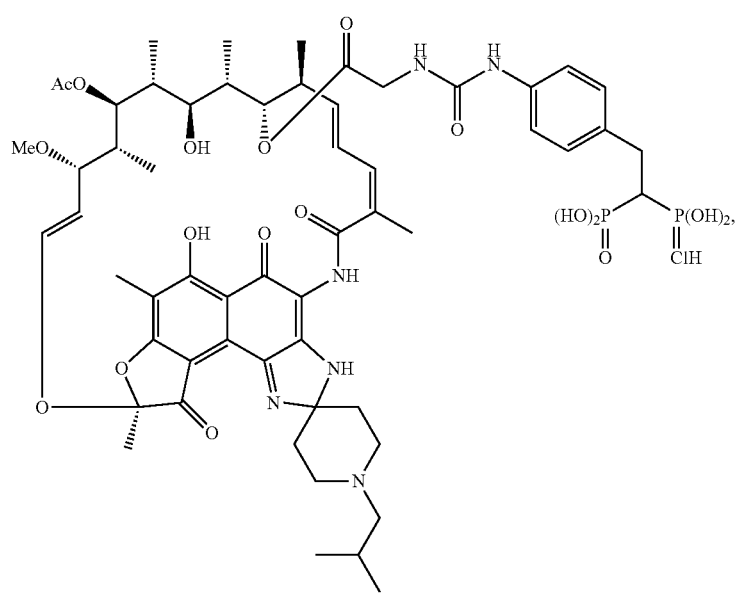
(142a)

-continued (147)
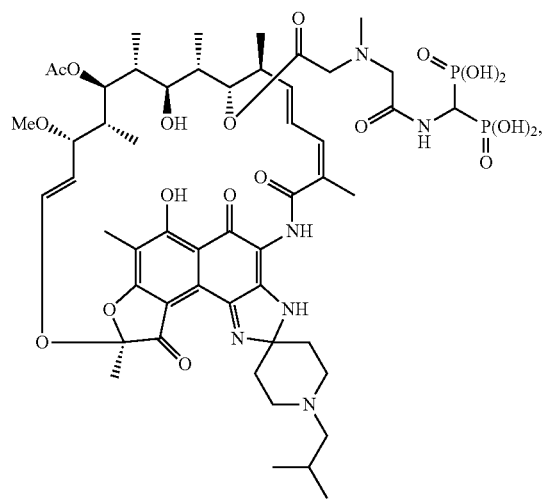

(150)
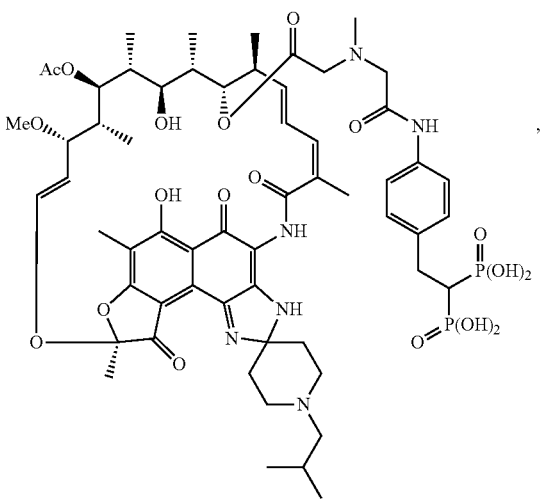

(155)
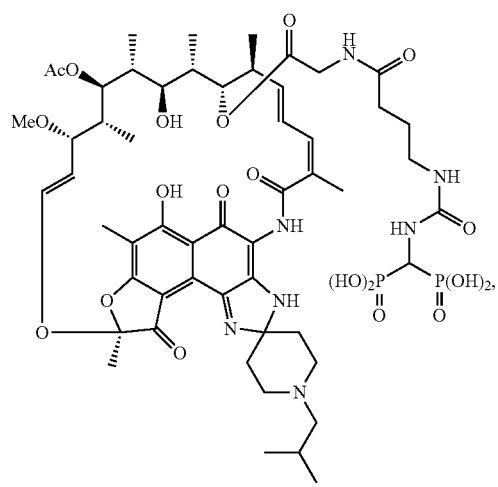

(164)
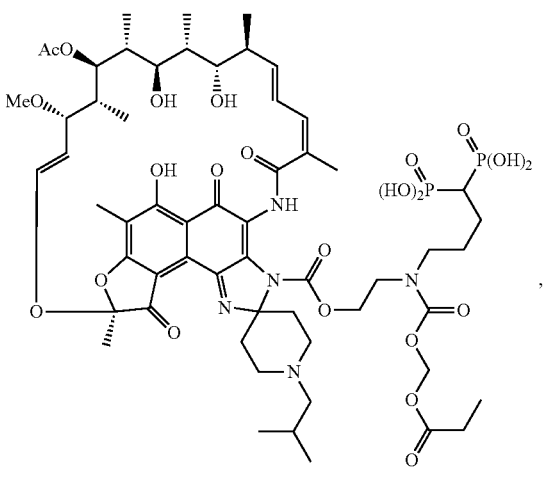

and a pharmaceutically acceptable salt, metabolite, solvate or prodrug thereof.

10. A pharmaceutical composition comprising a compound as defined in any one of claims 1-4, 8 or 9, and a pharmaceutically acceptable carrier or excipient.

11. A method for treating a bacterial infection in a subject, comprising administering to a subject in need of treatment a pharmaceutically effective amount of a pharmaceutical composition according to claim 10, thereby treating a bacterial infection in a subject.

12. A method of providing prophylaxis for a bacterial infection in a subject, comprising administering to a subject in need of prophylaxis a prophylactically effective amount of a pharmaceutical composition according to claim 10, thereby providing prophylaxis for a bacterial infection in a subject.

13. The method of claim 12, wherein said pharmaceutical composition is administered to said subject prior to, during, or after an invasive medical treatment.

14. The method of claim 11, wherein said subject is a human.

15. The method of claim 12, wherein said subject is a human.

16. The method of claim 11, further comprising administering a second therapeutic agent concurrent with administration of said pharmaceutical composition.

17. The method of claim 16, wherein second therapeutic agent is selected from the group consisting of tetracycline, a tetracycline derived antibacterial agent, glycylcycline, a glycylcycline derived antibacterial agent, minocycline, aminocycline derived antibacterial agent, an oxazolidinone antibacterial agent, an aminoglycoside antibacterial agent, a quinolone antibacterial agent, vancomycin, a vancomycin derived antibacterial agent, a teicoplanin, a teicoplanin derived antibacterial agent, eremomycin, an eremomycin derived antibacterial agent, chloroeremomycin, a chloroeremomycin derived antibacterial agent, oritavancin, an oritavancin derived antibacterial agents, daptomycin, a daptomycin derived antibacterial agent, rifamycin and a rifamycin derived antibacterial agent.

18. A method for accumulating a Rifamycin in a bone of a subject, comprising administering to a subject in need of treatment a pharmaceutically effective amount of a pharmaceutical composition according to claim 10, thereby accumulating a Rifamycin in a bone of a subject.

19. The compound of any one of claims 1-4, wherein n is an integer of 1 to 3.

* * * * *

UNITED STATES PATENT AND TRADEMARK OFFICE
CERTIFICATE OF CORRECTION

PATENT NO.       : 8,524,691 B2                                           Page 1 of 1
APPLICATION NO. : 13/058518
DATED            : September 3, 2013
INVENTOR(S)      : Dietrich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 268 days.

Signed and Sealed this

Fifteenth Day of September, 2015

Michelle K. Lee
*Director of the United States Patent and Trademark Office*